US008604069B2

(12) United States Patent
Maeba et al.

(10) Patent No.: US 8,604,069 B2
(45) Date of Patent: Dec. 10, 2013

(54) AMIDE COMPOUND AND MEDICINAL USE THEREOF

(75) Inventors: Takaki Maeba, Osaka (JP); Katsuya Maeda, Osaka (JP); Masayuki Kotoku, Osaka (JP); Kazayuki Hirata, Osaka (JP); Noriyoshi Seki, Osaka (JP); Hiroshi Yamanaka, Osaka (JP); Takayuki Sakai, Osaka (JP); Shintaro Hirashima, Osaka (JP); Shingo Obika, Osaka (JP); Makoto Shiozaki, Osaka (JP); Masahiro Yokota, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 13/457,844

(22) Filed: Apr. 27, 2012

(65) Prior Publication Data

US 2012/0322837 A1 Dec. 20, 2012

Related U.S. Application Data

(60) Provisional application No. 61/482,418, filed on May 4, 2011.

(30) Foreign Application Priority Data

Apr. 28, 2011 (JP) ................................ 2011-100331

(51) Int. Cl.
*A61K 31/42* (2006.01)
*C07D 261/08* (2006.01)

(52) U.S. Cl.
USPC .......................................... 514/378; 548/247

(58) Field of Classification Search
None
See application file for complete search history.

(56) References Cited

U.S. PATENT DOCUMENTS

| | | | |
|---|---|---|---|
| 5,059,614 | A | 10/1991 | Lepage et al. |
| 5,258,397 | A | 11/1993 | Lepage et al. |
| 5,464,860 | A | 11/1995 | Lepage et al. |
| 5,585,357 | A | 12/1996 | Dolle et al. |
| 5,677,283 | A | 10/1997 | Dolle et al. |
| 6,319,939 | B1 | 11/2001 | Mabire et al. |
| 6,936,626 | B2 | 8/2005 | Mabire et al. |
| 7,179,825 | B2 | 2/2007 | Mabire et al. |
| 7,579,352 | B2 | 8/2009 | Mabire et al. |
| 7,750,160 | B2 | 7/2010 | Milanov et al. |
| 7,767,670 | B2 | 8/2010 | Mehta et al. |
| 2002/0115653 | A1 | 8/2002 | Mabire et al. |
| 2005/0148605 | A1 | 7/2005 | Grotzfeld et al. |
| 2005/0165018 | A1 | 7/2005 | Mabire et al. |
| 2005/0165024 | A1 | 7/2005 | Milanov et al. |
| 2005/0165031 | A1 | 7/2005 | Grotzfeld et al. |
| 2005/0165074 | A1 | 7/2005 | Grotzfeld et al. |
| 2005/0171171 | A1 | 8/2005 | Mehta et al. |
| 2005/0171172 | A1 | 8/2005 | Lai et al. |
| 2005/0192314 | A1 | 9/2005 | Mehta et al. |
| 2005/0197371 | A1 | 9/2005 | Milanov et al. |
| 2005/0261315 | A1 | 11/2005 | Mehta et al. |
| 2005/0267182 | A1 | 12/2005 | Milanov et al. |
| 2007/0105858 | A1 | 5/2007 | Mabire et al. |
| 2008/0058334 | A1 | 3/2008 | Mabire et al. |
| 2010/0173917 | A1 | 7/2010 | Grotzfeld et al. |
| 2011/0230477 | A1 | 9/2011 | Hoveyda et al. |
| 2012/0108639 | A1 | 5/2012 | Suzuki et al. |

FOREIGN PATENT DOCUMENTS

| | | | |
|---|---|---|---|
| EP | 0371876 | B1 | 11/1993 |
| EP | 0644198 | A1 | 3/1995 |
| FR | 2639636 | A1 | 6/1990 |
| GB | 768840 | B | 2/1957 |
| JP | 07-089951 | A | 4/1995 |
| WO | WO 99/29674 | A1 | 6/1999 |
| WO | WO 03/057215 | A1 | 7/2003 |
| WO | WO 2005/048953 | A1 | 6/2005 |
| WO | WO 2010/004972 | A1 | 1/2010 |
| WO | WO 2010/066682 | A1 | 6/2010 |

OTHER PUBLICATIONS

Japanese Patent Office, International Search Report in International Patent Application No. PCT/JP2012/061352 (Jun. 5, 2012).
Maloney et al., *J. Med. Chem.*, 43(16): 2971-2974 (2000).
Wang et al., J. Org. Chem., 75(20): 6994-6997 (2010).

*Primary Examiner* — Alicia L Otton
(74) *Attorney, Agent, or Firm* — Leydig, Voit & Mayer, Ltd.

(57) ABSTRACT

A compound of formula [I-W]:

[I-W]

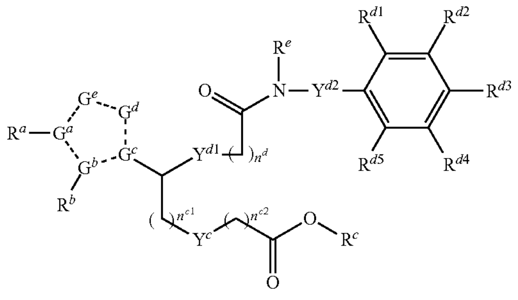

wherein each symbol is as defined in the description, or a pharmaceutically acceptable salt thereof.

50 Claims, 48 Drawing Sheets

Fig. 1

| Example | Structure | NMR | MS | | Stereochemistry of AUX-H |
|---|---|---|---|---|---|
| | | | M+H | M-H | |
| A-1 | 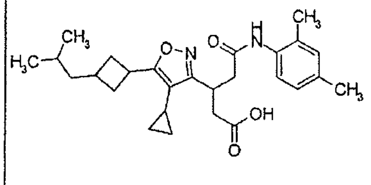 | (400 MHz, CDCl3) 0.36 - 0.55 (m, 2H), 0.76 - 0.92 (m, 2H), 0.86 (d, J=6.68Hz, 6H), 1.29 - 1.45 (m, 3H), 1.47 - 1.61 (m, 1H), 1.85 - 2.05 (m, 2H), 2.08 (s, 3H), 2.25 (s, 3H), 2.28 - 2.43 (m, 3H), 2.71 (dd, J=15.20, 8.40Hz, 1H), 2.87 (dd, J=15.20, 4.40Hz, 1H), 2.97 (dd, J=14.00, 4.80Hz, 1H), 3.06 (dd, J=14.00, 9.20Hz, 1H), 3.41 - 3.57 (m, 1H), 3.89 - 4.02 (m, 1H), 6.90 - 6.99 (m, 2H), 7.49 (dd, J=8.40, 2.40Hz, 1H), 7.81 (brs, 1H) | 453 | 451 | (S) |
| A-2 | 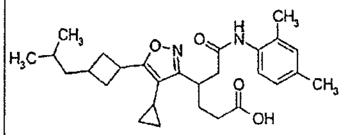 | (400 MHz, DMSO-d6) 0.80 - 0.88 (m, 1H), 0.95 (d, J=6.45Hz, 7H), 1.10 (d, J=7.25Hz, 2H), 1.90 (s, 1H), 2.00 - 2.08 (m, 1H), 2.12 (d, J=2.42Hz, 3H), 2.24 (s, 3H), 2.77 (d, J=6.85Hz, 2H), 2.99 (d, J=3.63Hz, 3H), 3.40 - 3.80 (m, 7H), 6.79 (s, 1H), 6.98 (d, J=10.07Hz, 1H), 7.03 (s, 1H), 7.26 (s, 1H), 9.69 (s, 1H) | 467 | 465 | (R) |
| A-3 | 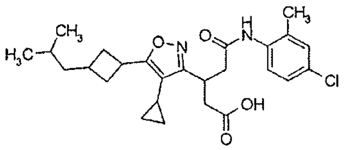 | (400 MHz, DMSO-d6) 0.47 (t, J=4.43Hz, 2H), 0.77 - 0.82 (m, 2H), 0.85 (q, J=3.49Hz, 6H), 1.30 (t, J=6.85Hz, 2H), 1.45 (t, J=5.64Hz, 1H), 1.51 (dd, J=13.30, 6.85Hz, 1H), 1.82 (t, J=9.27Hz, 2H), 2.08 (s, 3H), 2.37 (dt, J=19.61, 6.45Hz, 3H), 2.69 (dtd, J=49.36, 16.92, 7.32Hz, 4H), 3.53 (t, J=8.66Hz, 1H), 3.77 (t, J=7.25Hz, 1H), 7.18 (dd, J=8.66, 2.22Hz, 1H), 7.27 (d, J=2.01Hz, 1H), 7.35 (d, J=8.46Hz, 1H), 9.35 (s, 1H), 12.21 (s, 1H) | 473 | 471 | (S) |
| A-4 | 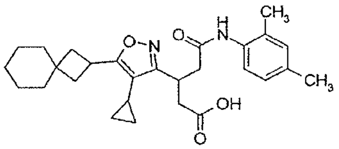 | (400 MHz, CDCl3) 0.46 (d, J=14.91Hz, 2H), 0.87 (d, J=8.87Hz, 2H), 1.38 (d, J=12.89Hz, 5H), 1.47 (s, 4H), 1.58 (d, J=5.24Hz, 2H), 2.05 (ddd, J=28.51, 16.62, 7.35Hz, 8H), 2.26 (s, 3H), 2.76 (t, J=7.86Hz, 1H), 2.97 (ddd, J=37.68, 20.75, 8.46Hz, 3H), 3.61 (t, J=9.07Hz, 1H), 3.94 (s, 1H), 6.98 (d, J=15.72Hz, 2H), 7.52 (t, J=4.43Hz, 1H), 7.73 (s, 1H) | 465 | 463 | (S) |

Fig. 2

| Example | Structure | NMR | MS | | Stereochemistry of AUX-H |
|---|---|---|---|---|---|
| | | | M+H | M-H | |
| A-5 | 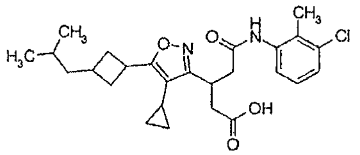 | (400 MHz, CDCl3) 0.41 - 0.46 (m, 2H), 0.86 (d, J=6.80Hz, 6H), 1.30 - 1.33 (m, 3H), 1.49 - 1.56 (m, 1H), 1.88 - 1.99 (m, 3H), 2.16 (s, 3H), 2.29 - 2.39 (m, 3H), 2.65 - 2.72 (m, 2H), 2.85 - 2.96 (m, 2H), 3.07 - 3.13 (m, 1H), 3.44 - 3.50 (m, 1H), 3.88 - 3.95 (m, 1H), 7.03 (dd, J=8.00Hz, 1H), 7.15 (d, J=8.00Hz, 1H), 7.50 (d, J=8.00Hz, 1H), 8.19 (s, 1H) | 473 | 471 | (S) |
| A-6 | 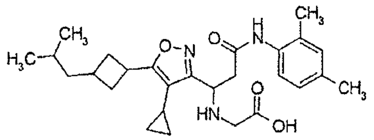 | (400 MHz, DMSO-d6) 0.38 - 0.56 (m, 2H), 0.74 - 0.90 (m, 2H), 0.85 (d, J=6.40Hz, 6H), 1.27 - 1.35 (m, 2H), 1.45 - 1.58 (m, 2H), 1.76 - 1.92 (m, 2H), 2.07 (s, 3H), 2.23 (s, 3H), 2.29 - 2.45 (m, 3H), 2.79 (dd, J=15.20, 6.40Hz, 1H), 2.88 (dd, J=15.20, 8.00Hz, 1H), 3.49 - 3.61 (m, 1H), 4.36 - 4.35 (m, 1H), 6.93 (d, J=8.00Hz, 1H), 6.98 (s, 1H), 7.26 (d, J=8.00Hz, 1H), 9.55 (s, 1H) | 468 | 466 | without using AUX-H |
| A-7 | 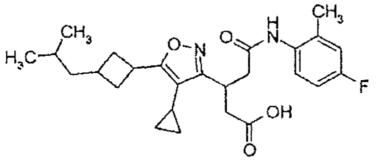 | (400 MHz, CDCl3) 0.38 - 0.57 (m, 2H), 0.77 - 0.92 (m, 2H), 0.87 (d, J=6.80Hz, 6H), 1.27 - 1.45 (m, 3H), 1.47 - 1.62 (m, 1H), 1.84 - 2.05 (m, 2H), 2.12 (s, 3H), 2.30 - 2.44 (m, 3H), 2.74 (dd, J=15.20, 8.00Hz, 1H), 2.88 (dd, J=15.20, 5.20Hz, 1H), 2.97 (dd, J=14.00, 5.20Hz, 1H), 3.08 (dd, J=14.00, 9.20Hz, 1H), 3.44 - 3.57 (m, 1H), 3.91 - 4.03 (m, 1H), 6.81 - 6.89 (m, 2H), 7.49 - 7.58 (m, 1H), 7.87 (s, 1H) | 457 | 455 | (S) |
| A-8 | 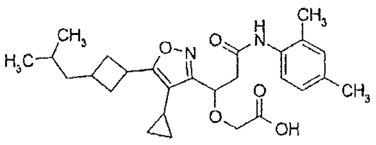 | (400 MHz, DMSO-d6) 0.41 - 0.48 (m, 1H), 0.54 - 0.61 (m, 1H), 0.77 - 0.89 (m, 8H), 1.26 - 1.35 (m, 2H), 1.47 - 1.57 (m, 2H), 1.83 - 1.90 (m, 2H), 2.04 (s, 3H), 2.22 (s, 3H), 2.30 - 2.46 (m, 3H), 2.91 (dd, J=14.96, 6.38Hz, 1H), 3.12 (dd, J=15.07, 7.88Hz, 1H), 3.52 - 3.58 (m, 1H), 3.89 (d, J=16.00Hz, 1H), 4.00 (d, J=16.23Hz, 1H), 5.12 (t, J=7.07Hz, 1H), 6.92 (d, J=8.58Hz, 1H), 6.98 (s, 1H), 7.13 (d, J=8.12Hz, 1H), 9.59 (s, 1H), 12.64 (s, 1H) | 469 | 467 | without using AUX-H |

Fig. 3
| Example | Structure | NMR | MS | | Stereochemistry of AUX-H |
|---|---|---|---|---|---|
| | | | M+H | M-H | |
| A-9 | 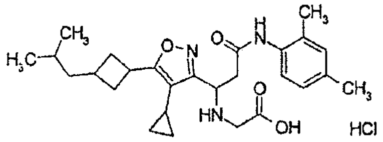 | (400 MHz, DMSO-d6) 0.40 - 0.61 (m, 2H), 0.76 - 0.89 (m, 2H), 0.86 (d, J=6.40Hz, 6H), 1.27 - 1.34 (m, 2H), 1.38 - 1.58 (m, 2H), 1.76 - 1.91 (m, 2H), 1.95 (s, 3H), 2.22 (s, 3H), 2.30 - 2.47 (m, 4H), 3.52 - 3.65 (m, 1H), 3.86 (brs, 2H), 4.87 - 5.00 (m, 1H), 6.93 (d, J=8.00Hz, 1H), 6.98 (s, 1H), 7.08 (d, J=8.00Hz, 1H), 9.61 (s, 1H) | 468 | 466 | without using AUX-H |
| A-10 | 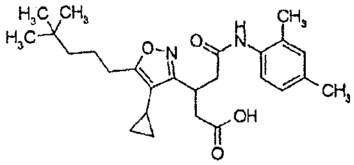 | (400 MHz,CDCl3) 0.49 (m, 1H), 0.54 - 0.61 (m, 1H), 0.88 (s, 9H), 0.84 - 0.93 (m, 2H), 1.20 - 1.27 (m, 2H), 1.41 - 1.47 (m, 1H), 1.62 (tt, J=9.16, 4.52Hz, 2H), 2.13 (s, 3H), 2.28 (s, 3H), 2.71 (dt, J=25.43, 7.71Hz, 3H), 2.99 (ddt, J=50.24, 25.35, 8.46Hz, 3H), 3.97 (dd, J=8.46, 4.99Hz, 1H), 6.96 (d, J=4.87Hz, 2H), 7.52 (m, 1H), 7.83 (s, 1H) | 441 | 439 | (S) |
| A-11 | 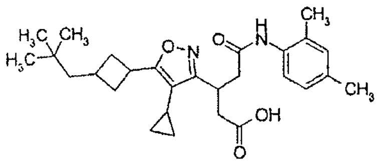 | (400 MHz, CDCl3) 0.47 (dt, J=19.07, 7.76Hz, 2H), 0.87 (s, 12H), 1.38 (d, J=5.64Hz, 2H), 2.00 (dd, J=25.59, 10.28Hz, 2H), 2.11 (s, 3H), 2.26 (s, 3H), 2.39 (dd, J=13.70, 8.06Hz, 3H), 2.75 (dd, J=14.71, 8.26Hz, 1H), 2.88 - 3.03 (m, 3H), 3.50 (d, J=9.67Hz, 1H), 3.94 (s, 1H), 6.98 (d, J=16.12Hz, 2H), 7.51 (d, J=7.66Hz, 1H), 7.71 (s, 1H) | 467 | 465 | (S) |
| A-12 | 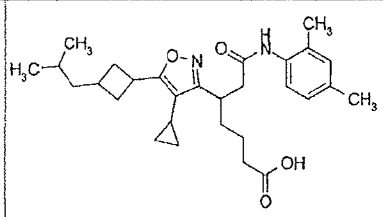 | (400 MHz, CDCl3) 0.31 - 0.40 (m, 1H), 0.44 - 0.53 (m, 1H), 0.79 - 0.91 (m, 8H), 1.30 - 1.38 (m, 2H), 1.39 - 1.93 (m, 8H), 1.97 - 2.07 (m, 1H), 2.02 (s, 3H), 2.25 (s, 3H), 2.30 - 2.44 (m, 4H), 2.71 - 2.80 (m, 1H), 2.92 - 3.02 (m, 1H), 3.45 - 3.62 (m, 2H), 6.92 - 6.97 (m, 2H), 7.43 (d, J=8.82Hz, 1H), 7.51 (s, 1H) | 481 | 479 | (R) |

Fig. 4

| Example | Structure | NMR | MS | | Stereochemistry of AUX-H |
|---|---|---|---|---|---|
| | | | M+H | M-H | |
| A-13 | 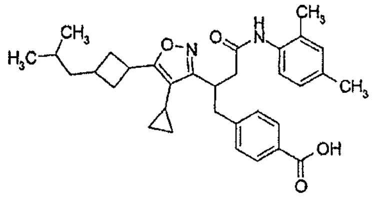 | (400 MHz, CDCl3) 0.30 (dd, J=9.81, 4.96Hz, 1H), 0.53 (dd, J=9.92, 4.85Hz, 1H), 0.80 - 0.85 (m, 2H), 0.87 (dd, J=13.23, 6.62Hz, 6H), 1.18 (td, J=8.82, 4.34Hz, 1H), 1.36 (t, J=6.62Hz, 2H), 1.52 - 1.59 (m, 1H), 1.91 (d, J=9.48Hz, 1H), 2.03 - 2.06 (m, 1H), 2.04 (brs, 3H), 2.23 (s, 3H), 2.37 (td, J=14.00, 7.13Hz, 3H), 2.78 (dd, J=13.89, 4.41Hz, 1H), 2.99 - 3.06 (m, 2H), 3.15 (dd, J=13.34, 6.51Hz, 1H), 3.50 (dd, J=18.31, 8.38Hz, 1H), 3.95 (dd, J=11.14, 4.96Hz, 1H), 6.92 - 6.94 (m, 2H), 7.13 (d, J=8.16Hz, 2H), 7.41 (d, J=8.38Hz, 1H), 7.86 (brs, 1H), 7.91 (d, J=8.16Hz, 2H) | 529 | 527 | (S) |
| A-14 | 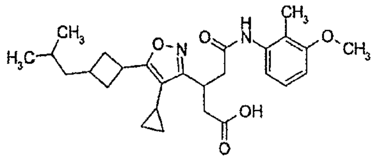 | (400 MHz, DMSO-d6) 0.41 - 0.52 (m, 2H), 0.74 - 0.83 (m, 2H), 0.85 (d, J=6.80Hz, 6H), 1.27 - 1.35 (m, 2H), 1.39 - 1.57 (m, 2H), 1.75 - 1.93 (m, 2H), 1.88 (s, 3H), 2.27 - 2.42 (m, 3H), 2.56 - 2.69 (m, 2H), 2.69 - 2.83 (m, 2H), 3.47 - 3.60 (m, 1H), 3.68 - 3.83 (m, 1H), 3.76 (s, 3H), 6.78 (d, J=8.00Hz, 1H), 6.86 (d, J=8.00Hz, 1H), 7.08 (dd, J=8.00, 8.00Hz, 1H), 9.33 (s, 1H), 12.19 (brs, 1H) | 469 | 467 | (S) |
| A-15 | 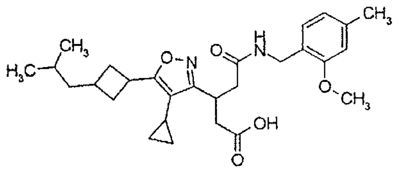 | (400 MHz, DMSO-d6) 0.39 - 0.51 (m, 2H), 0.72 - 0.81 (m, 2H), 0.85 (d, J=6.40Hz, 6H), 1.26 - 1.34 (m, 2H), 1.37 - 1.47 (m, 1H), 1.47 - 1.58 (m, 1H), 1.76 - 1.88 (m, 2H), 2.27 (s, 3H), 2.31 - 2.42 (m, 3H), 2.42 - 2.62 (m, 3H), 2.67 (dd, J=16.00, 8.80Hz, 1H), 3.47 - 3.59 (m, 1H), 3.66 - 3.79 (m, 1H), 3.75 (s, 3H), 4.13 (t, J=6.00Hz, 2H), 6.65 (d, J=8.00Hz, 1H), 6.77 (s, 1H), 6.89 (d, J=8.00Hz, 1H), 8.14 (t, J=6.00Hz, 1H), 12.14 (brs, 1H) | 483 | 481 | (S) |
| A-16 | 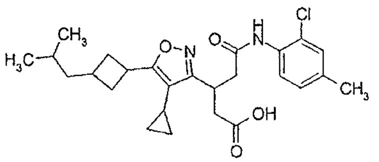 | (400 MHz, DMSO-d6) 0.44 - 0.49 (m, 2H), 0.79 (ddd, J=9.22, 5.16, 3.07Hz, 2H), 0.85 (d, J=6.49Hz, 6H), 1.30 (dd, J=6.72, 6.72Hz, 2H), 1.39 - 1.47 (m, 1H), 1.51 (t, J=6.72Hz, 1H), 1.79 - 1.87 (m, 2H), 2.27 (s, 3H), 2.29 - 2.43 (m, 3H), 2.66 - 2.75 (m, 4H), 3.53 (dt, J=20.41, 6.96Hz, 1H), 3.71 - 3.80 (m, 1H), 7.10 (dd, J=8.58, 1.39Hz, 1H), 7.29 (s, 1H), 7.45 (d, J=8.12Hz, 1H), 9.47 (s, 1H), 12.22 (brs, 1H) | 473 | 471 | (S) |

Fig. 5
| Example | Structure | NMR | MS | | Stereochemistry of AUX-H |
|---|---|---|---|---|---|
| | | | M+H | M-H | |
| A-17 | 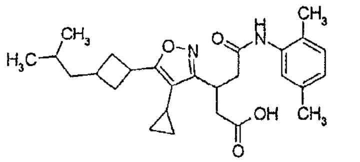 | (400 MHz, DMSO-d6) 0.47 - 0.48 (m, 2H), 0.78 - 0.81 (m, 2H), 0.85 (d, J=6.72Hz, 6H), 1.30 (dd, J=6.84, 6.84Hz, 2H), 1.40 - 1.55 (m, 2H), 1.77 - 1.88 (m, 2H), 2.02 (s, 3H), 2.22 (s, 3H), 2.30 - 2.42 (m, 3H), 2.57 - 2.79 (m, 4H), 3.51 - 3.56 (m, 1H), 3.73 - 3.81 (m, 1H), 6.87 (d, J=8.81Hz, 1H), 7.04 (d, J=7.88Hz, 1H), 7.11 (s, 1H), 9.26 (s, 1H), 12.23 (brs, 1H) | 453 | 451 | (S) |
| A-18 | 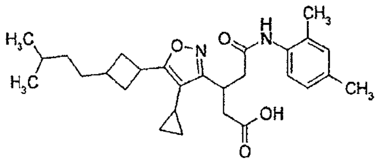 | (400 MHz, DMSO-d6) 0.43 - 0.52 (m, 2H), 0.76 - 0.82 (m, 2H), 0.85 (d, J=6.72Hz, 6H), 0.87 (s, 3H), 1.04 - 1.12 (m, 2H), 1.34 - 1.42 (m, 2H), 1.43 - 1.54 (m, 2H), 1.76 - 1.86 (m, 2H), 2.21 - 2.24 (m, 1H), 2.22 (s, 3H), 2.31 - 2.41 (m, 2H), 2.57 - 2.68 (m, 2H), 2.69 - 2.79 (m, 2H), 3.48 - 3.57 (m, 1H), 3.73 - 3.80 (m, 1H), 6.92 (d, J=8.35Hz, 1H), 6.98 (s, 1H), 7.13 (d, J=8.12Hz, 1H), 9.23 (s, 1H), 12.21 (brs, 1H) | 467 | 465 | (S) |
| A-19 | 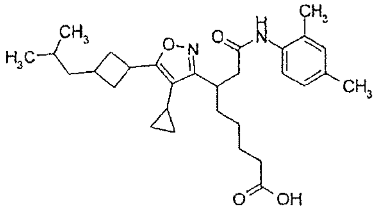 | (400 MHz, CDCl3) 0.35 - 0.39 (m, 1H), 0.45 - 0.51 (m, 1H), 0.79 - 0.90 (m, 8H), 1.32 - 1.37 (m, 3H), 1.41 - 1.43 (m, 2H), 1.52 - 1.58 (m, 1H), 1.63 - 2.00 (m, 5H), 2.03 (s, 3H), 2.26 (s, 3H), 2.34 - 2.40 (m, 6H), 2.72 (dd, J=13.57, 4.52Hz, 1H), 2.96 (dd, J=13.68, 10.67Hz, 1H), 3.47 - 3.58 (m, 2H), 6.92 - 6.98 (m, 2H), 7.43 - 7.52 (m, 2H) | 495 | 493 | (R) |
| A-20 | 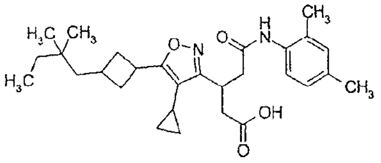 | (400 MHz, DMSO-d6) 0.44 - 0.50 (m, 2H), 0.76 - 0.81 (m, 11H), 1.19 (q, J=7.50Hz, 2H), 1.32 (d, J=6.03Hz, 2H), 1.41 - 1.48 (m, 1H), 1.79 - 1.91 (m, 2H), 2.02 (s, 3H), 2.22 (s, 3H), 2.32 - 2.42 (m, 3H), 2.58 - 2.66 (m, 2H), 2.70 - 2.78 (m, 2H), 3.51 - 3.56 (m, 1H), 3.73 - 3.80 (m, 1H), 6.92 (d, J=8.12Hz, 1H), 6.97 (s, 1H), 7.13 (d, J=8.12Hz, 1H), 9.22 (s, 1H), 12.20 (brs, 1H) | 481 | 479 | (S) |

Fig. 6
| Example | Structure | NMR | MS | | Stereochemistry of AUX-H |
|---|---|---|---|---|---|
| | | | M+H | M-H | |
| A-21 | 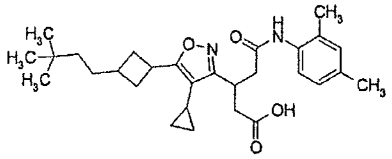 | (400 MHz, CDCl3) 0.43 - 0.54 (m, 2H), 0.84 - 0.92 (m, 11H), 1.04 - 1.11 (m, 2H), 1.23 - 1.30 (m, 1H), 1.35 - 1.44 (m, 2H), 1.88 - 2.00 (m, 2H), 2.13 (s, 3H), 2.15 - 2.24 (m, 1H), 2.28 (s, 3H), 2.31 - 2.43 (m, 2H), 2.77 (dd, J=15.31, 8.12Hz, 1H), 2.89 - 2.99 (m, 2H), 3.04 (dd, J=14.03, 8.70Hz, 1H), 3.46 - 3.56 (m, 1H), 3.92 - 3.99 (m, 1H), 6.96 - 7.00 (m, 2H), 7.53 (d, J=8.58Hz, 1H), 7.68 (s, 1H) | 481 | 479 | (S) |
| A-22 | 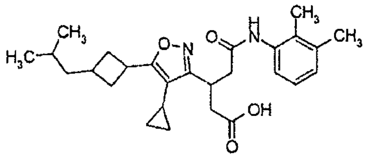 | (400 MHz, DMSO-d6) 0.43 - 0.53 (m, 2H), 0.75 - 0.82 (m, 2H), 0.85 (d, J=6.80Hz, 6H), 1.27 - 1.34 (m, 2H), 1.39 - 1.58 (m, 2H), 1.75 - 1.90 (m, 2H), 1.94 (s, 3H), 2.22 (s, 3H), 2.29 - 2.43 (m, 3H), 2.58 - 2.70 (m, 2H), 2.70 - 2.82 (m, 2H), 3.49 - 3.60 (m, 1H), 3.72 - 3.83 (m, 1H), 6.95 - 7.07 (m, 3H), 9.35 (s, 1H), 12.19 (brs, 1H) | 453 | 451 | (S) |
| A-23 | 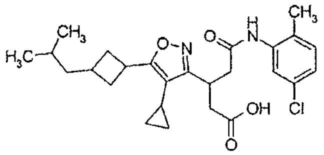 | (400 MHz, DMSO-d6) 0.42 - 0.52 (m, 2H), 0.76 - 0.89 (m, 2H), 0.84 (d, J=6.40Hz, 6H), 1.26 - 1.34 (m, 2H), 1.38 - 1.59 (m, 2H), 1.75 - 1.89 (m, 2H), 2.09 (s, 3H), 2.27 - 2.43 (m, 3H), 2.56 - 2.89 (m, 4H), 3.48 - 3.61 (m, 1H), 3.71 - 3.84 (m, 1H), 7.10 (dd, J=8.40, 2.00Hz, 1H), 7.20 (d, J=8.40Hz, 1H), 7.47 (d, J=2.00Hz, 1H), 9.36 (s, 1H), 12.22 (brs, 1H) | 473 | 471 | (S) |
| A-24 | 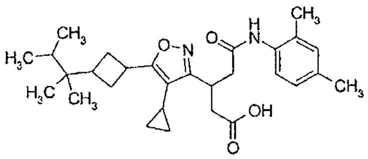 | (400 MHz, DMSO-d6) 0.46 - 0.52 (m, 2H), 0.77 - 0.83 (m, 2H), 0.80 (d, J=6.85Hz, 6H), 1.33 - 1.40 (m, 1H), 1.42 - 1.49 (m, 1H), 1.95 - 2.14 (m, 4H), 2.02 (s, 3H), 2.22 (s, 3H), 2.31 - 2.40 (m, 1H), 2.58 - 2.67 (m, 2H), 2.70 - 2.78 (m, 2H), 3.40 - 3.49 (m, 1H), 3.73 - 3.80 (m, 1H), 6.92 (d, J=8.06Hz, 1H), 6.98 (s, 1H), 7.13 (d, J=8.06Hz, 1H), 9.22 (s, 1H), 12.21 (brs, 1H) | 481 | 479 | (S) |

Fig. 7

| Example | Structure | NMR | MS | | Stereochemistry of AUX-H |
|---|---|---|---|---|---|
| | | | M+H | M-H | |
| A-25 | 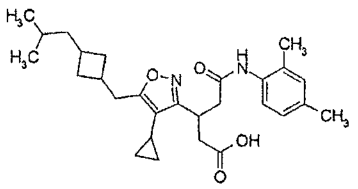 | (400 MHz, DMSO-d6) 0.46 - 0.58 (m, 2H), 0.75 - 0.85 (m, 2H), 0.80 (d, J=6.62Hz, 6H), 1.16 - 1.35 (m, 4H), 1.40 - 1.54 (m, 2H), 2.04 (s, 3H), 2.05 - 2.17 (m, 3H), 2.22 (s, 3H), 2.27 - 2.42 (m, 1H), 2.56 - 2.82 (m, 6H), 3.71 - 3.84 (m, 1H), 6.91 (d, J=7.94Hz, 1H), 6.97 (s, 1H), 7.13 (d, J=7.94Hz, 1H), 9.21 (brs, 1H), 12.23 (brs, 1H) | 467 | 465 | (S) |
| A-26 | 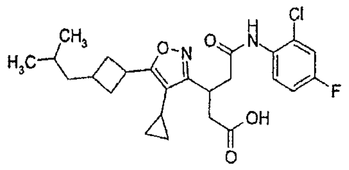 | (400 MHz, DMSO-d6) 0.42 - 0.52 (m, 2H), 0.74 - 0.90 (m, 2H), 0.85 (d, J=6.80Hz, 6H), 1.25 - 1.35 (m, 2H), 1.39 - 1.58 (m, 2H), 1.75 - 1.89 (m, 2H), 2.26 - 2.43 (m, 3H), 2.59 - 2.88 (m, 4H), 3.47 - 3.60 (m, 1H), 3.70 - 3.83 (m, 1H), 7.19 (ddd, J=8.40, 6.00, 2.80Hz, 1H), 7.47 (dd, J=8.80, 2.80Hz, 1H), 7.57 (dd, J=8.80, 6.00Hz, 1H), 9.59 (s, 1H), 12.22 (brs, 1H) | 477 | 475 | (S) |
| A-27 | 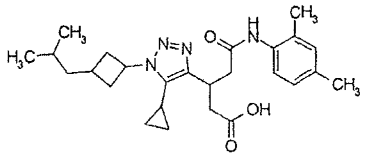 | (400 MHz, CDCl3) 0.64 - 0.65 (m, 1H), 0.81 - 0.83 (m, 1H), 0.89 (d, J=6.84Hz, 6H), 0.98 (d, J=10.59Hz, 2H), 1.42 (t, J=6.69Hz, 2H), 1.50 - 1.58 (m, 2H), 1.94 (s, 3H), 2.22 - 2.24 (m, 2H), 2.23 (s, 3H), 2.36 (q, J=9.56Hz, 1H), 2.75 (q, J=137.18Hz, 5H), 3.06 (dd, J=24.92, 14.34Hz, 1H), 3.97 (dd, J=10.03, 5.40Hz, 1H), 4.74 - 4.83 (m, 1H), 6.90 - 6.94 (m, 2H), 7.30 (t, J=8.60Hz, 1H), 7.99 (brs, 1H) | 453 | 451 | (S) |
| A-28 | 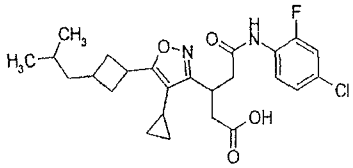 | (400 MHz, DMSO-d6) 0.39 - 0.54 (m, 2H), 0.72 - 0.91 (m, 2H), 0.84 (d, J=6.40Hz, 6H), 1.23 - 1.35 (m, 2H), 1.37 - 1.58 (m, 2H), 1.73 - 1.89 (m, 2H), 2.25 - 2.43 (m, 3H), 2.59 (dd, J=16.40, 6.40Hz, 1H), 2.65 - 2.79 (m, 2H), 2.85 (dd, J=15.60, 7.20Hz, 1H), 3.46 - 3.60 (m, 1H), 3.68 - 3.85 (m, 1H), 7.16 - 7.29 (m, 1H), 7.40 - 7.52 (m, 1H), 7.80 - 7.93 (m, 1H), 9.85 (s, 1H), 12.22 (brs, 1H) | 477 | 475 | (S) |

Fig. 8

| Example | Structure | NMR | MS M+H | MS M-H | Stereochemistry of AUX-H |
|---|---|---|---|---|---|
| A-29 | 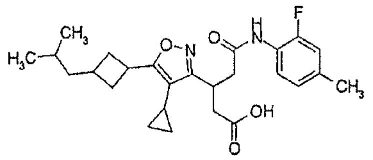 | (400 MHz, DMSO-d6) 0.41 - 0.52 (m, 2H), 0.75 - 0.88 (m, 2H), 0.84 (d, J=6.80Hz, 6H), 1.25 - 1.34 (m, 2H), 1.38 - 1.60 (m, 2H), 1.74 - 1.89 (m, 2H), 2.27 (s, 3H), 2.29 - 2.42 (m, 3H), 2.59 (dd, J=16.00, 6.40Hz, 1H), 2.63 - 2.86 (m, 3H), 3.46 - 3.60 (m, 1H), 3.68 - 3.83 (m, 1H), 6.93 (d, J=8.40Hz, 1H), 7.04 (d, J=12.00Hz, 1H), 7.55 - 7.67 (m, 1H), 9.63 (s, 1H), 12.20 (brs, 1H) | 457 | 455 | (S) |
| A-30 | 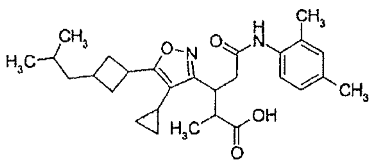 | (400 MHz, DMSO-d6) 0.56 - 0.62 (m, 1H), 0.73 - 0.81 (m, 2H), 0.82 - 0.86 (m, 6H), 1.00 (d, J=6.72Hz, 3H), 1.27 - 1.31 (m, 2H), 1.36 - 1.43 (m, 1H), 1.46 - 1.54 (m, 1H), 1.74 - 1.86 (m, 2H), 1.90 (s, 3H), 2.20 (s, 3H), 2.29 - 2.43 (m, 4H), 2.58 - 2.69 (m, 2H), 2.81 - 2.88 (m, 1H), 3.50 - 3.56 (m, 1H), 3.62 - 3.70 (m, 1H), 6.88 (d, J=8.12Hz, 1H), 6.93 (s, 1H), 7.02 (d, J=8.12Hz, 1H), 9.31 (s, 1H), 12.43 (brs, 1H) | 467 | 465 | (S) |
| A-31 | 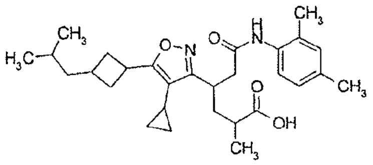 | (400 MHz, CDCl3) 0.37 (t, J=5.64Hz, 1H), 0.48 (t, J=5.24Hz, 1H), 0.82 (dt, J=8.33, 2.12Hz, 1H), 0.87 (t, J=5.84Hz, 7H), 1.25 (q, J=3.63Hz, 4H), 1.32 - 1.38 (m, 3H), 1.51 - 1.58 (m, 2H), 1.74 (dd, J=13.50, 5.44Hz, 1H), 1.95 (dd, J=34.25, 8.87Hz, 2H), 2.04 (s, 3H), 2.25 (s, 3H), 2.34 (ddd, J=27.40, 14.71, 6.45Hz, 3H), 2.64 (d, J=5.64Hz, 1H), 2.83 (dd, J=13.90, 5.04Hz, 1H), 2.96 (dd, J=13.90, 9.87Hz, 1H), 3.49 (t, J=8.87Hz, 1H), 3.69 (s, 1H), 6.94 (d, J=5.64Hz, 2H), 7.42 (d, J=8.87Hz, 1H), 7.60(s, 1H) | 481 | 479 | (R) |
| A-32 | 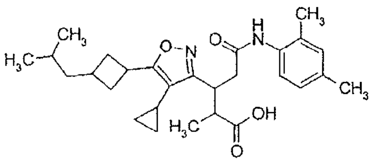 | (400 MHz, DMSO-d6) 0.41 - 0.46 (m, 1H), 0.49 - 0.55 (m, 1H), 0.74 - 0.80 (m, 2H), 0.82 - 0.86 (m, 7H), 1.08 (d, J=6.96Hz, 3H), 1.29 (t, J=6.84Hz, 2H), 1.38 - 1.44 (m, 1H), 1.47 - 1.55 (m, 1H), 1.74 - 1.89 (m, 2H), 1.96 (s, 3H), 2.20 (s, 3H), 2.32 - 2.37 (m, 2H), 2.51 - 2.59 (m, 1H), 2.74 - 2.89 (m, 2H), 3.47 - 3.56 (m, 1H), 3.82 - 3.88 (m, 1H), 6.89 (d, J=8.58Hz, 1H), 6.94 (s, 1H), 7.07 (d, J=8.12Hz, 1H), 9.19 (s, 1H), 12.30 (s, 1H) | 467 | 465 | (S) |

Fig. 9
| Example | Structure | NMR | MS | | Stereochemistry of AUX-H |
|---|---|---|---|---|---|
| | | | M+H | M-H | |
| A-33 | 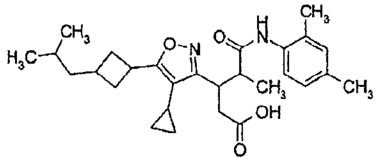 | (400 MHz, CDCl3) 0.42-0.51 (m, 2H), 0.79 - 0.89 (m, 9H), 1.29 - 1.43 (m, 5H), 1.48 - 1.56 (m, 1H), 1.83 - 1.98 (m, 1H), 2.08 (s, 3H), 2.24 - 2.39 (m, 4H), 2.25 (s, 3H), 2.80 - 2.94 (m, 2H), 3.01 - 3.12 (m, 1H), 3.44 - 3.52 (m, 1H), 3.73 - 3.81 (m, 1H), 6.92 - 6.97 (m, 2H), 7.36 (d, J=10.80Hz, 1H), 7.51 (s, 1H) | 467 | 465 | (S) |
| A-34 | 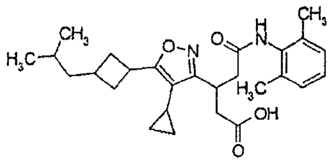 | (400 MHz, DMSO-d6) 0.39 - 0.54 (m, 2H), 0.73 - 0.81 (m, 2H), 0.85 (d, J=6.80Hz, 6H), 1.26 - 1.34 (m, 2H), 1.41 - 1.58 (m, 2H), 1.74 - 1.89 (m, 2H), 1.97 (s, 6H), 2.26 - 2.43 (m, 3H), 2.62 (dd, J=16.00, 6.80Hz, 1H), 2.65 (dd, 1H, J=14.80, 6.80Hz, 1H), 2.72 (dd, J=16.00, 8.00Hz, 1H), 2.80 (dd, J=14.80, 8.40Hz, 1H), 3.48 - 3.59 (m, 1H), 3.71 - 3.83 (m, 1H), 6.97 - 7.04 (m, 3H), 9.25 (s, 1H), 12.23 (brs, 1H) | 453 | 451 | (S) |
| A-35 | 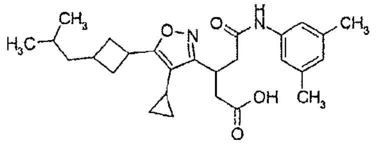 | (400 MHz, DMSO-d6) 0.42 - 0.52 (m, 2H), 0.75 - 0.87 (m, 2H), 0.83 (d, J=6.40Hz, 6H), 1.22 - 1.33 (m, 2H), 1.37 - 1.57 (m, 2H), 1.73 - 1.87 (m, 2H), 2.20 (s, 6H), 2.26 - 2.41 (m, 3H), 2.55 (dd, J=16.40, 6.80Hz, 1H), 2.61 (dd, 1H, J=15.20, 7.20Hz, 1H), 2.70 (dd, J=16.40, 8.00Hz, 1H), 2.75 (dd, J=15.20, 7.60Hz, 1H), 3.46 - 3.58 (m, 1H), 3.70 - 3.82 (m, 1H), 6.66 (s, 1H), 7.16 (s, 2H), 9.78 (s, 1H), 12.22 (brs, 1H) | 453 | 451 | (S) |
| A-36 | 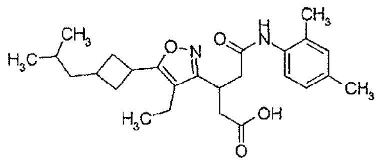 | (400 MHz, DMSO-d6) 0.84 (d, J=6.40Hz, 6H), 1.02 (t, J=7.20Hz, 3H), 1.25 - 1.34 (m, 2H), 1.44 - 1.58 (m, 1H), 1.73 - 1.88 (m, 2H), 2.00 (s, 3H), 2.21 (s, 3H), 2.26 - 2.42 (m, 5H), 2.55 - 2.74 (m, 4H), 3.40 - 3.52 (m, 1H), 3.52 - 3.64 (m, 1H), 6.91 (d, J=8.40Hz, 1H), 6.97 (s, 1H), 7.11 (s, 1H), 9.23 (s, 1H), 12.24 (brs, 1H) | 441 | 439 | (S) |

Fig. 10

| Example | Structure | NMR | MS | | Stereochemistry of AUX-H |
|---|---|---|---|---|---|
| | | | M+H | M-H | |
| A-37 | 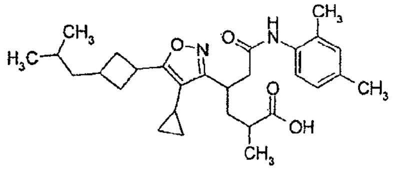 | (400 MHz, CDCl3) 0.40 - 0.47 (m, 2H), 0.79 - 0.85 (m, 1H), 0.88 (dd, J=12.17, 5.45Hz, 7H), 1.25 (d, J=6.96Hz, 4H), 1.33 - 1.43 (m, 3H), 1.52 - 1.58 (m, 1H), 1.87 - 2.03 (m, 2H), 2.05 (d, J=4.87Hz, 3H), 2.12 - 2.20 (m, 1H), 2.26 (s, 3H), 2.32 - 2.42 (m, 3H), 2.53 (dt, J=5.02, 1.80Hz, 1H), 2.79 (dd, J=13.57, 5.22Hz, 1H), 2.89 (dd, J=13.68, 9.97Hz, 1H), 3.49 - 3.51 (m, 1H), 3.64-3.67 (m, 1H), 6.95 (d, J=4.17Hz, 2H), 7.39 (t, J=4.29Hz, 1H), 7.57 (s, 1H) | 481 | 479 | ( R ) |
| A-38 | 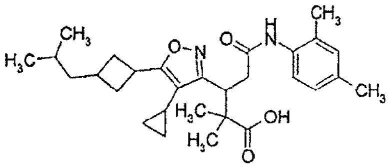 | (400 MHz, CDCl3) 0.33 - 0.40 (m, 1H), 0.67 - 0.76 (m, 1H), 0.80 - 0.91 (m, 9H), 1.27 - 1.39 (m, 2H), 1.30 (s, 3H), 1.36 (s, 3H), 1.48 - 1.58 (m, 1H), 1.81 - 1.93 (m, 1H), 1.95 (s, 3H), 2.00 - 2.09 (m, 1H), 2.25 (s, 3H), 2.29 - 2.43 (m, 3H), 2.88 (dd, J=13.57, 3.13Hz, 1H), 3.10 (t, J=12.99Hz, 1H), 3.49 - 3.58 (m, 1H), 3.86 - 3.95 (m, 1H), 6.90-6.94 (m, 2H), 7.23 (d, J=8.12Hz, 1H), 7.84 (brs, 1H) | 481 | 479 | ( S ) |
| A-39 | 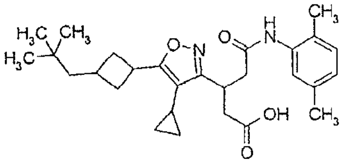 | (400 MHz, CDCl3) 0.46 (s, 2H), 0.88 (d, J=6.45Hz, 10H), 1.38 (d, J=5.64Hz, 3H), 2.00 (dd, J=22.36, 9.47Hz, 2H), 2.12 (s, 3H), 2.28 (s, 4H), 2.39 (t, J=10.48Hz, 3H), 2.77 (d, J=8.46Hz, 1H), 2.93 (t, J=10.28Hz, 2H), 3.04 (d, J=8.06Hz, 1H), 3.50 (d, J=8.06Hz, 1H), 3.94 (s, 1H), 6.86 (d, J=7.66Hz, 1H), 7.02 (d, J=7.66Hz, 1H), 7.55 (s, 1H), 7.75 (s, 1H) | 467 | 465 | ( S ) |
| A-40 | 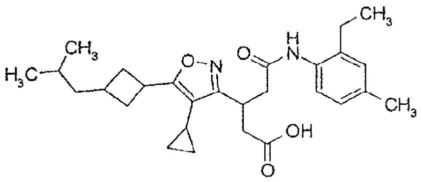 | (400 MHz, DMSO-d6) 0.41 - 0.53 (m, 2H), 0.73 - 0.82 (m, 2H), 0.84 (d, J=6.80Hz, 6H), 1.00 (t, J=7.20Hz, 3H), 1.25 - 1.34 (m, 2H), 1.38 - 1.58 (m, 2H), 1.74 - 1.88 (m, 2H), 2.24 (s, 3H), 2.29 - 2.45 (m, 5H), 2.55 - 2.68 (m, 2H), 2.68 - 2.82 (m, 2H), 3.47 - 3.59 (m, 1H), 3.69 - 3.82 (m, 1H), 6.92 (d, J=8.00Hz, 1H), 6.98 (s, 1H), 7.08 (d, J=8.00Hz, 1H), 9.21 (s, 1H), 12.22 (brs, 1H) | 467 | 465 | ( S ) |

Fig. 11

| Example | Structure | NMR | MS | | Stereochemistry of AUX-H |
|---|---|---|---|---|---|
| | | | M+H | M-H | |
| A-41 | 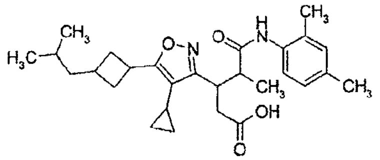 | (400 MHz, CDCl3) 0.39 - 0.46 (m, 1H), 0.50 - 0.55 (m, 1H), 0.83 - 0.89 (m, 9H), 1.25 (d, J=6.96Hz, 3H), 1.32 - 1.44 (m, 3H), 1.49 - 1.60 (m, 1H), 1.93 - 2.04 (m, 2H), 2.21 (s, 3H), 2.29 (s, 3H), 2.31 - 2.43 (m, 2H), 2.81 (dd, J=16.12, 4.99Hz, 1H), 2.91 - 3.05 (m, 2H), 3.45 - 3.57 (m, 1H), 3.69 - 3.77 (m, 1H), 6.98 - 7.02 (m, 2H), 7.46 (s, 1H), 7.68 (d, J=8.81Hz, 1H) | 467 | 465 | (S) |
| A-42 | 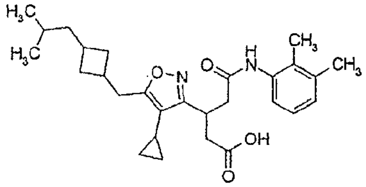 | (400 MHz, $CDCl_3$) 0.44 - 0.61 (m, 2H), 0.83 (d, J=6.72Hz, 6H), 0.87 - 0.94 (m, 2H), 1.19 - 1.37 (m, 4H), 1.39 - 1.55 (m, 2H), 2.02 (s, 3H), 2.07 - 2.23 (m, 3H), 2.26 (s, 3H), 2.35 - 2.46 (m, 1H), 2.68 - 2.78 (m, 3H), 2.88 (dd, J=15.31, 5.33Hz, 1H), 2.98 (dd, J=14.03, 5.10Hz, 1H), 3.07 (dd, J=14.03, 9.39Hz, 1H), 3.95 - 4.05 (m, 1H), 6.98 (d, J=7.65Hz, 1H), 7.04 (t, J=7.65Hz, 1H), 7.34 (d, J=7.65Hz, 1H), 7.88 (brs, 1H) | 467 | 465 | (S) |
| A-43 | 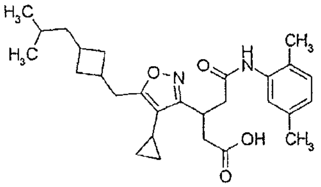 | (400 MHz, $CDCl_3$) 0.46 - 0.60 (m, 2H), 0.83 (d, J=6.72Hz, 6H), 0.87 - 0.93 (m, 2H), 1.24 (t, J=6.96Hz, 2H), 1.31 (t, J=9.86Hz, 2H), 1.39 - 1.54 (m, 2H), 2.10 (s, 3H), 2.11 - 2.23 (m, 3H), 2.28 (s, 3H), 2.36 - 2.45 (m, 1H), 2.68 - 2.78 (m, 3H), 2.89 (dd, J=15.42, 5.22Hz, 1H), 2.97 (dd, J=14.03, 5.10Hz, 1H), 3.07 (dd, J=14.03, 9.16Hz, 1H), 3.97 - 4.01 (m, 1H), 6.86 (d, J=7.65Hz, 1H), 7.02 (d, J=7.65Hz, 1H), 7.52 (s, 1H), 7.85 (brs, 1H) | 467 | 465 | (S) |
| A-44 | 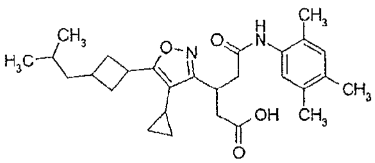 | (400 MHz, DMSO-d6) 0.41 - 0.53 (m, 2H), 0.74 - 0.83 (m, 2H), 0.85 (d, J=6.80Hz, 6H), 1.25 - 1.35 (m, 2H), 1.39 - 1.58 (m, 2H), 1.76 - 1.89 (m, 2H), 1.98 (s, 3H), 2.12 (s, 3H), 2.13 (s, 3H), 2.27 - 2.43 (m, 3H), 2.57 - 2.69 (m, 2H), 2.69 - 2.81 (m, 2H), 3.47 - 3.61 (m, 1H), 3.69 - 3.84 (m, 1H), 6.92 (s, 1H), 7.01 (s, 1H), 9.18 (s, 1H), 12.20 (brs, 1H) | 467 | 465 | (S) |

Fig. 12
| Example | Structure | NMR | MS | | Stereochemistry of AUX-H |
|---|---|---|---|---|---|
| | | | M+H | M-H | |
| A-45 | 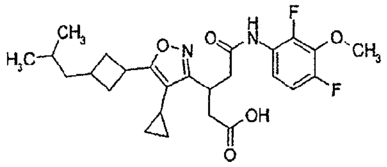 | (400 MHz, DMSO-d6) 0.41 - 0.52 (m, 2H), 0.75 - 0.88 (m, 2H), 0.84 (d, J=6.80Hz, 6H), 1.25 - 1.34 (m, 2H), 1.39 - 1.59 (m, 2H), 1.73 - 1.88 (m, 2H), 2.26 - 2.42 (m, 3H), 2.58 (dd, J=16.60, 6.80Hz, 1H), 2.65 - 2.78 (m, 2H), 2.82 (dd, J=15.20, 7.60Hz, 1H), 3.47 - 3.60 (m, 1H), 3.68 - 3.82 (m, 1H), 3.91 (s, 3H), 7.02 - 7.12 (m, 1H), 7.36 - 7.46 (m, 1H), 9.77 (s, 1H), 12.25 (brs, 1H) | 491 | 489 | (S) |
| A-46 | 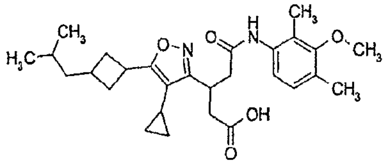 | (400 MHz, DMSO-d6) 0.42 - 0.53 (m, 2H), 0.74 - 0.83 (m, 2H), 0.85 (d, J=6.40Hz, 6H), 1.26 - 1.35 (m, 2H), 1.39 - 1.58 (m, 2H), 1.75 - 1.89 (m, 2H), 1.96 (s, 3H), 2.18 (s, 3H), 2.29 - 2.43 (m, 3H), 2.56 - 2.69 (m, 2H), 2.69 - 2.83 (m, 2H), 3.48 - 3.59 (m, 1H), 3.60 (s, 3H), 3.70 - 3.85 (m, 1H), 6.90 - 6.99 (m, 2H), 9.28 (s, 1H), 12.21 (brs, 1H) | 483 | 481 | (S) |
| A-47 | 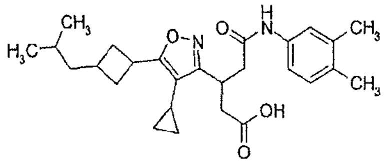 | (400 MHz, DMSO-d6) 0.45 - 0.50 (m, 2H), 0.78 - 0.86 (m, 8H), 1.28 (t, J=6.73Hz, 2H), 1.47 (m, 2H), 1.81 (m, 2H), 2.14 (s, 3H), 2.16 (s, 3H), 2.35 (m, 3H), 2.58 (m, 2H), 2.72 (m, 2H), 3.53 (m, 1H), 3.74 - 3.81 (m, 1H), 7.01 (d, J=8.38Hz, 1H), 7.24 (dd, J=8.16, 1.98Hz, 1H), 7.32 (d, J=1.76Hz, 1H), 9.77 (s, 1H), 12.21 (s, 1H) | 453 | 451 | (S) |
| A-48 | 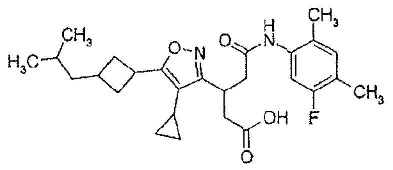 | (400 MHz, CDCl3) 0.45 - 0.52 (m, 2H), 0.87 - 0.89 (m, 2H), 0.87 - 0.89 (br m, 6H), 1.34 (t, J=6.84Hz, 2H), 1.38 - 1.42 (m, 1H), 1.51 - 1.58 (m, 1H), 1.91 - 1.99 (m, 2H), 2.07 (s, 3H), 2.18 (s, 3H), 2.33 - 2.40 (m, 3H), 2.72 - 2.75 (m, 1H), 2.90 - 2.97 (m, 2H), 3.07 - 3.11 (m, 1H), 3.48 - 3.50 (m, 1H), 3.97 - 3.99 (m, 1H), 6.92 (d, J=8.35Hz, 1H), 7.52 (d, J=11.36Hz, 1H), 7.91 (s, 1H) | 471 | 469 | (S) |

Fig. 13

| Example | Structure | NMR | MS M+H | MS M−H | Stereochemistry of AUX-H |
|---|---|---|---|---|---|
| A-49 | 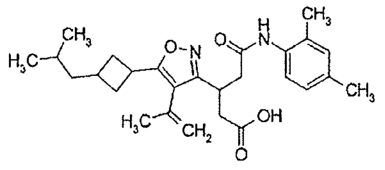 | (400 MHz, CDCl3) 0.84 - 0.88 (m, 6H), 1.25 - 1.27 (m, 2H), 1.31 - 1.37 (m, 2H), 1.49 - 1.58 (m, 1H), 1.93 - 2.04 (m, 4H), 2.14 (s, 3H), 2.27 (s, 3H), 2.30 - 2.40 (m, 2H), 2.69 (dd, J=15.31, 8.35Hz, 1H), 2.84 (dd, J=15.31, 5.33Hz, 1H), 2.92 (dd, J=14.03, 5.22Hz, 1H), 3.03 (dd, J=14.03, 8.46Hz, 1H), 3.35 - 3.45 (m, 1H), 3.79-3.88 (m, 1H), 4.92 (s, 1H), 5.27 (s, 1H), 6.95 - 6.99 (m, 2H), 7.55 (d, J=8.58Hz, 1H), 7.72 (s, 1H) | 453 | 451 | (S) |
| A-50 | 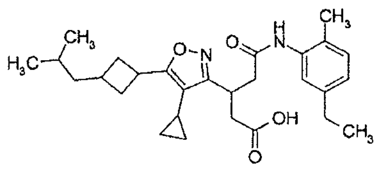 | (400 MHz, DMSO-d6) 0.38 - 0.54 (m, 2H), 0.71 - 0.87 (m, 2H), 0.83 (d, J=6.40Hz, 6H), 1.11 (t, J=7.60Hz, 3H), 1.25 - 1.34 (m, 2H), 1.38 - 1.57 (m, 2H), 1.74 - 1.88 (m, 2H), 2.01 (s, 3H), 2.26 - 2.41 (m, 3H), 2.50 (q, J=7.60Hz, 2H), 2.57 - 2.68 (m, 2H), 2.68 - 2.81 (m, 2H), 3.46 - 3.59 (m, 1H), 3.67 - 3.83 (m, 1H), 6.89 (d, J=8.00Hz, 1H), 7.06 (d, J=8.00Hz, 1H), 7.10 (s, 1H), 9.24 (s, 1H), 12.19 (brs, 1H) | 467 | 465 | (S) |
| A-51 | 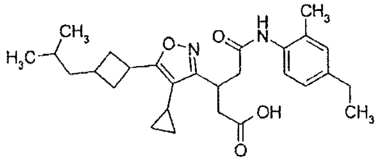 | (400 MHz, DMSO-d6) 0.40 - 0.50 (m, 2H), 0.72 - 0.83 (m, 2H), 0.84 (d, J=6.80Hz, 6H), 1.13 (t, J=7.60Hz, 3H), 1.25 - 1.33 (m, 2H), 1.38 - 1.57 (m, 2H), 1.72 - 1.88 (m, 2H), 2.02 (s, 3H), 2.26 - 2.42 (m, 3H), 2.50 (q, J=7.60Hz, 2H), 2.55 - 2.67 (m, 2H), 2.68 - 2.79 (m, 2H), 3.46 - 3.58 (m, 1H), 3.68 - 3.81 (m, 1H), 6.90 - 6.97 (m, 1H), 6.99 (s, 1H), 7.14 (d, J=8.40Hz, 1H), 9.22 (s, 1H), 12.20 (brs, 1H) | 467 | 465 | (S) |
| A-52 | 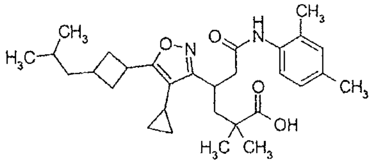 | (400 MHz,CDCl3) 0.37 (m, 1H), 0.52 (m, 1H), 0.76 - 0.84 (m, 2H), 0.86 (dd, J=11.03, 4.41Hz, 6H), 1.21 (s, 3H), 1.27 (s, 3H), 1.30 - 1.43 (m, 4H), 1.52 (td, J=13.34, 6.69Hz, 1H), 1.90 (dq, J=35.95, 8.78Hz, 2H), 2.02 (s, 3H), 2.12 (tt, J=24.15, 8.01Hz, 1H), 2.25 (s, 3H), 2.33 (tt, J=15.22, 5.18Hz, 3H), 2.73 - 2.87 (m, 2H), 3.46 (dd, J=17.75, 8.05Hz, 1H), 3.69 (dd, J=9.37, 5.62Hz, 1H), 6.91 (d, J=5.73Hz, 2H), 7.34 (m, 1H), 7.41 (s, 1H) | 495 | 493 | (R) |

Fig. 14

| Example | Structure | NMR | MS | | Stereochemistry of AUX-H |
|---|---|---|---|---|---|
| | | | M+H | M-H | |
| A-53 | 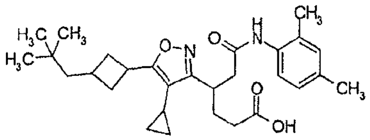 | (400 MHz, CDCl3) 0.36 (dd, J=9.37, 4.74Hz, 1H), 0.48 (dd, J=9.70, 4.85Hz, 1H), 0.80 - 0.82 (m, 2H), 0.87 (s, 9H), 1.34 - 1.37 (m, 1H), 1.39 (d, J=6.55Hz, 2H), 1.93 - 2.09 (m, 3H), 1.93 (s, 3H), 2.14 - 2.17 (m, 1H), 2.25 (s, 3H), 2.35 - 2.43 (m, 5H), 2.75 (dd, J=13.67, 4.85Hz, 1H), 2.95 (dd, J=13.67, 10.59Hz, 1H), 3.49 - 3.51 (m, 1H), 3.65 - 3.67 (m, 1H), 6.93 - 6.94 (m, 2H), 7.39 (d, J=8.60Hz, 1H), 7.57 (s, 1H) | 481 | 479 | (R) |
| A-54 | 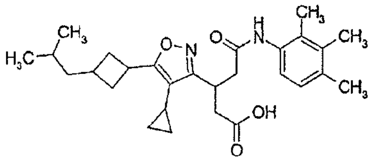 | (400 MHz, CDCl3) 0.47 (m, 2H), 0.79 - 0.89 (m, 8H), 1.23 (td, J=13.34, 6.25Hz, 1H), 1.33 - 1.45 (m, 2H), 1.54 (td, J=13.18, 6.54Hz, 1H), 1.96 (dd, J=17.09, 7.39Hz, 2H), 2.05 (s, 3H), 2.17 (s, 3H), 2.24 (s, 3H), 2.28 - 2.57 (m, 3H), 2.75 (dd, J=15.00, 8.16Hz, 1H), 2.87 - 3.07 (m, 3H), 3.45 - 3.53 (m, 1H), 4.05 (t, J=33.85Hz, 1H), 6.97 (t, J=10.03Hz, 1H), 7.16 (t, J=10.14Hz, 1H), 7.61 (s, 1H) | 467 | 465 | (S) |
| A-55 | 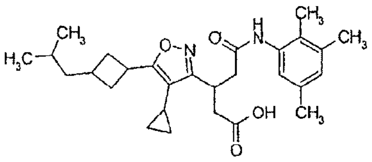 | (400 MHz, CDCl3) 0.47 (m, 2H), 0.87 (m, 8H), 1.39 (dt, J=31.91, 6.89Hz, 3H), 1.51 - 1.58 (m, 1H), 1.97 (dd, J=20.29, 9.48Hz, 5H), 2.23 (s, 3H), 2.25 (s, 3H), 2.38 (d, J=14.11Hz, 3H), 2.78 (dd, J=15.00, 8.16Hz, 1H), 2.98 (tt, J=22.61, 7.02Hz, 3H), 3.50 (dd, J=17.97, 8.49Hz, 1H), 3.94 (t, J=5.62Hz, 1H), 6.83 (s, 1H), 7.22 (t, J=3.86Hz, 1H), 7.65 (s, 1H) | 467 | 465 | (S) |
| A-56 | 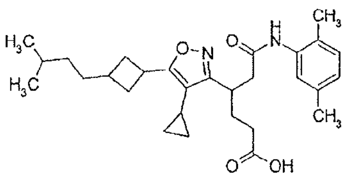 | (400 MHz, CDCl3) 0.37 (t, J=5.18Hz, 1H), 0.49 (t, J=5.29Hz, 1H), 0.82 (d, J=8.38Hz, 2H), 0.88 (t, J=7.72Hz, 6H), 1.06 - 1.11 (m, 2H), 1.37 - 1.44 (m, 3H), 1.51 (td, J=13.12, 6.47Hz, 1H), 1.86 - 2.11 (m, 7H), 2.18 (dt, J=22.13, 7.39Hz, 1H), 2.29 (t, J=8.49Hz, 3H), 2.37 (dt, J=25.44, 9.21Hz, 4H), 2.75 (dd, J=13.45, 4.41Hz, 1H), 2.98 (t, J=12.24Hz, 1H), 3.44 - 3.53 (m, 1H), 3.66 (d, J=5.51Hz, 1H), 6.84 (d, J=7.28Hz, 1H), 7.00 (d, J=7.50Hz, 1H), 7.44 (s, 1H), 7.57 (s, 1H) | 481 | 479 | (R) |

Fig. 15

| Example | Structure | NMR | MS | | Stereochemistry of AUX-H |
|---|---|---|---|---|---|
| | | | M+H | M-H | |
| A-57 | 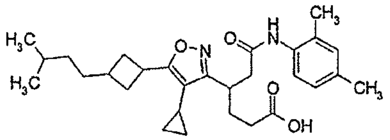 | (400 MHz, CDCl3) 0.36 (t, J=5.29Hz, 1H), 0.48 (t, J=5.18Hz, 1H), 0.82 (d, J=8.38Hz, 2H), 0.89 (t, J=7.72Hz, 6H), 1.09 (dd, J=15.55, 7.39Hz, 2H), 1.36-1.45 (m, 3H), 1.48 - 1.54 (m, 1H), 1.94 (dq, J=36.22, 9.96Hz, 7H), 2.14 - 2.21 (m, 1H), 2.25 (s, 3H), 2.38 (dd, J=22.05, 13.67Hz, 4H), 2.75 (d, J=10.37Hz, 1H), 2.96 (t, J=11.80Hz, 1H), 3.44 - 3.53 (m, 1H), 3.65 (s, 1H), 6.96 (t, J=11.91Hz, 2H), 7.44 (t, J=13.56Hz, 2H) | 481 | 479 | (R) |
| A-58 | 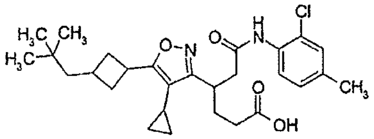 | (400 MHz, CDCl3) 0.37 - 0.40 (m, 1H), 0.44 - 0.49 (m, 1H), 0.77 - 0.90 (m, 2H), 0.77 (s, 9H), 1.33 - 1.37 (m, 1H), 1.35 (d, J=10.00Hz, 2H), 1.96 - 2.18 (m, 4H), 2.26 (s, 3H), 2.36 - 2.39 (m, 5H), 2.75 (dd, J=14.11, 5.07Hz, 1H), 3.00 - 3.03 (m, 1H), 3.45 - 3.51 (m, 1H), 3.63 - 3.66 (m, 1H), 7.01 (d, J=8.38Hz, 1H), 7.12 (s, 1H), 7.84 (s, 1H), 8.03 (d, J=8.16Hz, 1H) | 501 | 499 | (R) |
| A-59 | 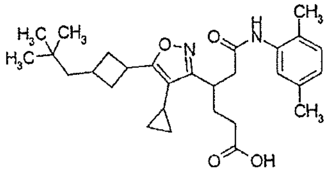 | (400 MHz, CDCl3) 0.36 - 0.37 (m, 1H), 0.48 - 0.50 (m, 1H), 0.81 - 0.82 (m, 2H), 0.87 (s, 9H), 1.37 - 1.38 (m, 1H), 1.37 (d, J=10.00Hz, 2H), 2.00-2.09 (m, 4H), 2.05 (s, 3H), 2.26 (s, 3H), 2.36 - 2.40 (m, 5H), 2.76 (dd, J=13.67, 4.63Hz, 1H), 2.97 (dd, J=12.02, 6.01Hz, 1H), 3.49 - 3.51 (m, 1H), 3.65 - 3.68 (m, 1H), 6.84 (d, J=7.72Hz, 1H), 6.99 (d, J=7.72Hz, 1H), 7.40 (s, 1H), 7.68 (s, 1H) | 481 | 479 | (R) |
| A-60 | 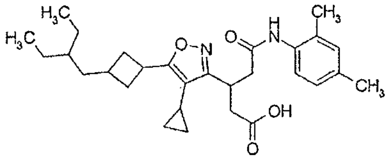 | (400 MHz, CDCl3) 0.53 - 0.38 (m, 2H), 0.84 (t, J=7.25Hz, 6H), 0.89 - 0.79 (m, 2H), 1.20 - 1.11 (m, 1H), 1.32 - 1.20 (m, 4H), 1.43 - 1.33 (m, 3H), 2.04 - 1.87 (m, 2H), 2.10 (s, 3H), 2.25 (s, 3H), 2.43 - 2.28 (m, 3H), 2.79 - 2.65 (m, 1H), 3.01 - 2.84 (m, 2H), 3.11 - 3.01 (m, 1H), 3.55 - 3.42 (m, 1H), 4.00 - 3.90 (m, 1H), 6.98 - 6.91 (m, 2H), 7.50 (d, J=8.46Hz, 1H), 7.78 (s, 1H) | 481 | 479 | (S) |

Fig. 16

| Example | Structure | NMR | MS | | Stereochemistry of AUX-II |
|---|---|---|---|---|---|
| | | | M+H | M-H | |
| A-61 | 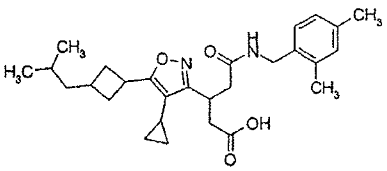 | (400 MHz, DMSO-d6) 0.40 - 0.50 (m, 2H), 0.73 - 0.80 (m, 2H), 0.85 (d, J=6.40Hz, 6H), 1.26 - 1.34 (m, 2H), 1.36 - 1.46 (m, 1H), 1.46 - 1.58 (m, 1H), 1.76 - 1.88 (m, 2H), 2.14 (s, 3H), 2.22 (s, 3H), 2.28 - 2.71 (m, 7H), 3.46 - 3.59 (m, 1H), 3.64 - 3.77 (m, 1H), 4.09 (dd, J=14.80, 5.60Hz, 1H), 4.18 (dd, J=14.80, 5.60Hz, 1H), 6.89 (d, J=8.40Hz, 1H), 6.93 (s, 1H), 6.96 (d, J=8.40Hz, 1H), 8.18 (t, J=5.60Hz, 1H), 12.18 (brs, 1H) | 467 | 465 | (S) |
| A-62 | 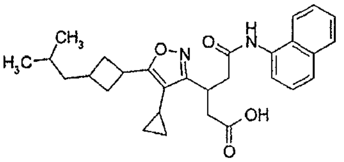 | (400 MHz, CDCl3) 0.40 - 0.49 (m, 2H), 0.82 - 0.86 (m, 2H), 0.85 (d, J=6.62Hz, 6H), 1.27 - 1.30 (m, 2H), 1.37 - 1.39 (m, 1H), 1.48 - 1.54 (m, 1H), 1.85 - 1.96 (m, 2H), 2.32 - 2.33 (m, 3H), 2.77 (dd, J=15.22, 8.16Hz, 1H), 2.92 (dd, J=15.33, 4.96Hz, 1H), 3.10 (dd, J=14.11, 4.85Hz, 1H), 3.23 (dd, J=18.86, 4.74Hz, 1H), 3.45 - 3.47 (m, 1H), 4.04 - 4.06 (m, 1H), 7.39 - 7.43 (m, 3H), 7.64 (d, J=8.16Hz, 1H), 7.77 - 7.79 (m, 3H), 8.60 (s, 1H) | 475 | 473 | (S) |
| A-63 | 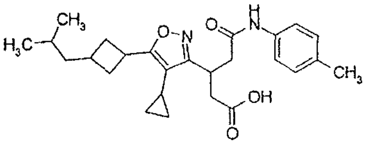 | (400 MHz, DMSO-d6) 0.45 - 0.50 (m, 2H), 0.78 - 0.86 (m, 8H), 1.28 (t, J=6.72Hz, 2H), 1.41 - 1.54 (m, 2H), 1.81 (m, 2H), 2.23 (s, 3H), 2.28 - 2.41 (m, 3H), 2.52 - 2.78 (m, 4H), 3.48 - 3.55 (m, 1H), 3.75 - 3.82 (m, 1H), 7.07 (d, J=8.35Hz, 2H), 7.42 (d, J=8.35Hz, 2H), 9.86 (s, 1H), 12.23 (s, 1H) | 439 | 437 | (S) |
| A-64 | 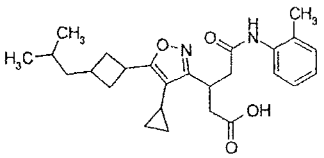 | (400 MHz, DMSO-d6) 0.48 (t, J=2.43Hz, 2H), 0.80 (td, J=4.17, 1.70Hz, 2H), 0.85 (d, J=6.61Hz, 6H), 1.30 (t, J=6.84Hz, 2H), 1.45 - 1.52 (m, 2H), 1.81 - 1.84 (m, 2H), 2.07 (s, 3H), 2.33 - 2.37 (m, 3H), 2.59 - 2.81 (m, 4H), 3.52 - 3.55 (m, 1H), 3.77 - 3.79 (m, 1H), 7.10 - 7.23 (m, 4H), 9.30 (s, 1H), 12.20 (s, 1H) | 439 | 437 | (S) |

Fig. 17

| Example | Structure | NMR | MS | | Stereochemistry of AUX-H |
|---|---|---|---|---|---|
| | | | M+H | M-H | |
| A-65 | 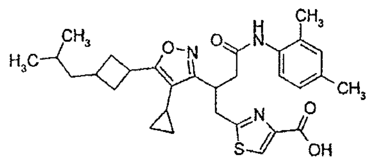 | (400 MHz, CDCl3) 0.38 - 0.28 (m, 1H), 0.61 - 0.52 (m, 1H), 0.87 (d, J=7.25Hz, 6H), 0.89 - 0.83 (m, 4H), 1.37 - 1.29 (m, 4H), 1.58 - 1.49 (m, 1H), 2.04 (s, 3H), 2.09 - 1.90 (m, 3H), 2.23 (s, 3H), 2.44 - 2.29 (m, 5H), 3.03 - 2.93 (m, 1H), 3.21 - 3.09 (m, 1H), 3.59 - 3.38 (m, 3H), 4.20 - 4.09 (m, 1H), 6.92 - 6.90 (m, 2H), 7.36 (d, J=7.66Hz, 1H), 8.02 (s, 1H), 8.07 (s, 1H) | 536 | 534 | (S) |
| A-66 | 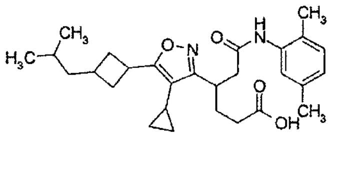 | (400 MHz, DMSO-d6) 0.34 - 0.55 (m, 2H), 0.75 - 0.82 (m, 2H), 0.85 (d, J=6.72Hz, 6H), 1.30 (dd, J=6.84, 6.84Hz, 2H), 1.39 - 1.45 (m, 1H), 1.52 (t, J=40.12Hz, 1H), 1.76 - 1.87 (m, 2H), 1.90 - 1.95 (m, 2H), 2.00 (s, 3H), 2.15 - 2.22 (m, 2H), 2.21 (s, 3H), 2.28 - 2.43 (m, 3H), 2.68 - 2.75 (m, 2H), 3.42 - 3.50 (m, 1H), 3.52 - 3.59 (m, 1H), 6.87 (d, J=7.88Hz, 1H), 7.04 (d, J=7.65Hz, 1H), 7.08 (s, 1H), 9.26 (s, 1H), 12.13 (brs, 1H) | 467 | 465 | (R) |
| A-67 | 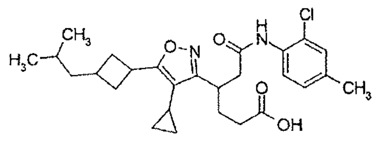 | (400 MHz, DMSO-d6) 0.32 - 0.54 (m, 2H), 0.76 - 0.83 (m, 2H), 0.85 (d, J=6.51Hz, 6H), 1.30 (dd, J=6.73, 6.73Hz, 2H), 1.38 - 1.45 (m, 1H), 1.47 - 1.57 (m, 1H), 1.75 - 2.04 (m, 4H), 2.10 - 2.22 (m, 2H), 2.26 (s, 3H), 2.30 - 2.43 (m, 3H), 2.68 - 2.85 (m, 2H), 3.39 - 3.58 (m, 2H), 7.09 (dd, J=8.38, 1.10Hz, 1H), 7.28 (s, 1H), 7.43 (d, J=8.16Hz, 1H), 9.46 (s, 1H), 12.14 (brs, 1H) | 487 | 485 | (R) |
| A-68 | 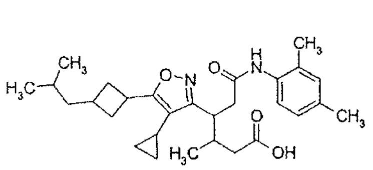 | (400 MHz, CDCl3) 0.32 - 0.39 (m, 1H), 0.46 - 0.54 (m, 1H), 0.78 - 0.84 (m, 2H), 0.85 - 0.88 (m, 6H), 1.14 (d, J=6.84Hz, 3H), 1.32 - 1.38 (m, 3H), 1.49 - 1.59 (m, 1H), 1.88 (d, J=9.48Hz, 1H), 1.97 - 2.06 (m, 4H), 2.15 (dd, J=15.33, 9.15Hz, 1H), 2.24 (s, 3H), 2.29 - 2.43 (m, 3H), 2.47 - 2.60 (m, 2H), 2.68 (dd, J=13.34, 3.20Hz, 1H), 2.93 (t, J=12.68Hz, 1H), 3.45 - 3.54 (m, 1H), 3.58 - 3.71 (m, 1H), 6.90 - 6.97 (m, 2H), 7.31 (s, 1H), 7.39 (d, J=8.82Hz, 1H) | 481 | 479 | (S) |

Fig. 18

| Example | Structure | NMR | MS | | Stereochemistry of AUX-H |
|---|---|---|---|---|---|
| | | | M+H | M-H | |
| A-69 | 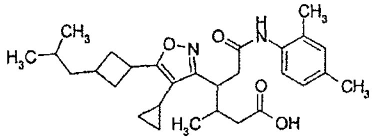 | (400 MHz, CDCl3) 0.33 - 0.39 (m, 1H), 0.46 - 0.54 (m, 1H), 0.78 - 0.89 (m, 8H), 1.01 (d, J=6.84Hz, 3H), 1.32 - 1.39 (m, 3H), 1.48 - 1.60 (m, 1H), 1.83 - 1.91 (m, 1H), 1.96 - 2.06 (m, 4H), 2.24 (s, 3H), 2.27 - 2.43 (m, 4H), 2.50 - 2.70 (m, 3H), 2.98 (t, J=12.46Hz, 1H), 3.45 - 3.55 (m, 1H), 3.63 - 3.70 (m, 1H), 6.91 - 6.95 (m, 2H), 7.39 (d, J=8.82Hz, 1H), 7.46 - 7.50 (m, 1H) | 481 | 479 | (S) |
| A-70 | 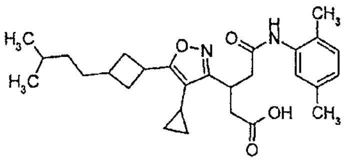 | (400 MHz, CDCl3) 0.43 - 0.53 (m, 2H), 0.88 (d, J=6.8Hz, 6H), 1.06 - 1.12 (m, 2H), 1.37 - 1.45 (m, 3H), 1.48 - 1.55 (m, 1H), 1.88 - 2.02 (m, 2H), 2.11 (s, 3H), 2.18 - 2.27 (m, 2H), 2.29 (s, 3H), 2.33 - 2.40 (m, 2H), 2.75 (dd, J=15.60, 8.00Hz, 2H), 2.94 (ddd, J=18.40, 13.60, 4.80Hz, 2H), 3.07 (dd, J=14.00, 8.80Hz, 1H), 3.46 - 3.55 (m, 1H), 3.92 - 3.98 (m, 1H), 6.87 (d, J=7.60Hz, 1H), 7.03 (d, J=7.60Hz, 1H), 7.55 (s, 1H), 7.80 (s, 1H) | 467 | 465 | (S) |
| A-71 | 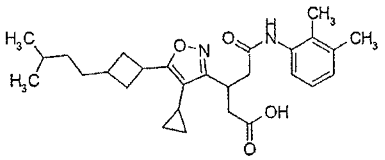 | (400 MHz, CDCl3) 0.44 - 0.54 (m, 2H), 0.88 (d, J=6.40Hz, 6H), 1.04 - 1.13 (m, 2H), 1.37 - 1.46 (m, 3H), 1.48 - 1.56 (m, 1H), 1.89 - 2.00 (m, 2H), 2.03 (s, 3H), 2.17 - 2.23 (m, 2H), 2.27 (s, 3H), 2.35 - 2.41 (m, 2H), 2.75 (dd, J=15.20, 8.40Hz, 2H), 2.94 (ddd, J=28.30, 13.80, 5.20Hz, 2H), 3.08 (dd, J=13.80, 9.20Hz, 1H), 3.47 - 3.56 (m, 1H), 3.94 - 4.00 (m, 1H), 6.99 (d, J=7.60Hz, 1H), 7.06 (dd, J=7.60, 7.60Hz, 1H), 7.36 (d, J=7.60Hz, 1H), 7.85 (s, 1H) | 467 | 465 | (S) |
| A-72 | 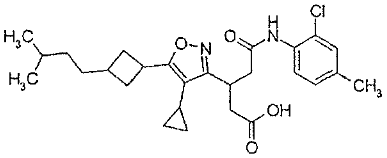 | (400 MHz, CDCl3) 0.48 - 0.49 (m, 2H), 0.87 (d, J=6.80Hz, 6H), 1.06 - 1.12 (m, 2H), 1.37 - 1.45 (m, 3H), 1.48 - 1.56 (m, 1H), 1.90 - 2.03 (m, 2H), 2.17 - 2.26 (m, 2H), 2.29 (s, 3H), 2.31 - 2.40 (m, 2H), 2.80 (dd, J=16.00, 7.60Hz, 2H), 2.93 (ddd, J=15.40, 15.40, 6.40Hz, 2H), 3.04 (dd, J=14.40, 8.40Hz, 1H), 3.45 - 3.54 (m, 1H), 3.92 - 3.99 (m, 1H), 7.04 (d, J=8.20Hz, 1H), 7.16 (s, 1H), 7.92 (s, 1H), 8.11 (d, J=8.20Hz, 1H) | 487 | 485 | (S) |

Fig. 19
| Example | Structure | NMR | MS | | Stereochemistry of AUX-H |
|---|---|---|---|---|---|
| | | | M+H | M-H | |
| A-73 | 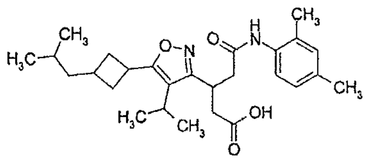 | (400 MHz, CDCl3) 0.83 - 0.90 (m, 6H), 1.12 - 1.23 (m, 6H), 1.35 (t, J=6.72Hz, 2H), 1.49 - 1.59 (m, 1H), 1.92 - 2.06 (m, 2H), 2.08 (d, J=3.48Hz, 3H), 2.26 (s, 3H), 2.29 - 2.42 (m, 3H), 2.65 - 2.86 (m, 3H), 2.89 - 2.96 (m, 1H), 2.97- 3.06 (m, 1H), 3.39 - 3.50 (m, 1H), 3.78 - 3.87 (m, 1H), 6.93 - 6.98 (m, 2H), 7.47 - 7.52 (m, 1H), 7.59 - 7.65 (m, 1H) | 455 | 453 | (S) |
| A-74 | 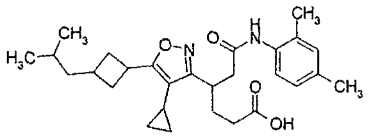 | (400 MHz, DMSO-d6) 0.32 - 0.42 (m, 1H), 0.44 - 0.53 (m, 1H), 0.72 - 0.86 (m, 2H), 0.84 (d, J=6.40Hz, 6H), 1.25 - 1.34 (m, 2H), 1.35 - 1.45 (m, 1H), 1.46 - 1.58 (m, 1H), 1.74 - 1.88 (m, 2H), 1.88 - 1.97 (m, 2H), 2.00 (s, 3H), 2.28 - 2.43 (m, 3H), 2.66 (dd, J=14.40, 7.20Hz, 1H), 2.75 (dd, J=14.40, 8.00Hz, 1H), 3.41 - 3.49 (m, 1H), 3.50 - 3.60 (m, 1H), 6.91 (d, J=8.00Hz, 1H), 6.96 (s, 1H), 7.09 (d, J=8.00Hz, 1H), 9.23 (s, 1H), 12.10 (brs, 1H) | 467 | 465 | (S) |
| A-75 | 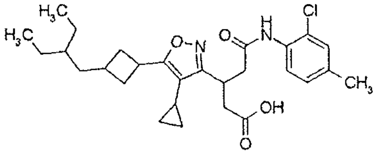 | (400 MHz, CDCl3) 0.50 - 0.45 (m, 2H), 0.83 (t, J=7.25Hz, 6H), 0.89 - 0.82 (m, 2H), 1.20 - 1.10 (m, 1H), 1.29 - 1.23 (m, 4H), 1.41 - 1.35 (m, 3H), 2.03 - 1.92 (m, 2H), 2.28 (s, 3H), 2.39 - 2.30 (m, 3H), 2.79 (dd, J=15.72, 7.25Hz, 1H), 2.97 - 2.89 (m, 2H), 3.03 (dd, J=14.91, 8.46Hz, 1H), 3.53 - 3.44 (m, 1H), 3.99 - 3.92 (m, 1H), 7.02 (d, J=8.06Hz, 1H), 7.14(s, 1H), 7.91 (s, 1H), 8.10 (d, J=8.06Hz, 1H) | 501 | 499 | (S) |
| A-76 | 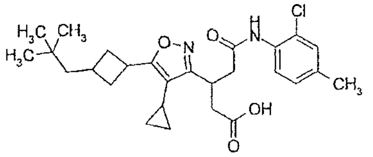 | (400 MHz, DMSO-d6) 0.44 - 0.50 (m, 2H), 0.79 (m, 2H), 0.88 (s, 9H), 1.34 (m, 2H), 1.44 (dd, J=9.97, 8.12Hz, 1H), 1.88 (dd, J=12.52, 8.58Hz, 2H), 2.27 (s, 3H), 2.37 - 2.43 (m, 3H), 2.59 - 2.83 (m, 4H), 3.52 - 3.57 (m, 1H), 3.72 - 3.80 (m, 1H), 7.10 (d, J=7.88Hz, 1H), 7.29 (s, 1H), 7.45 (d, J=8.35Hz, 1H), 9.47 (s, 1H), 12.26 (s, 1H). | 487 | 485 | (S) |

Fig. 20
| Example | Structure | NMR | MS | | Stereochemistry of AUX-H |
|---|---|---|---|---|---|
| | | | M+H | M-H | |
| A-77 | 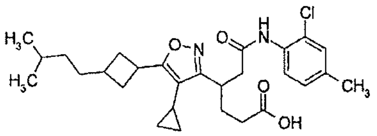 | (400 MHz, CDCl3) 0.41 - 0.37 (m, 1H), 0.49 - 0.44 (m, 1H), 0.87 (d, J=6.04Hz, 6H), 0.90 - 0.81 (m, 2H), 1.11 - 1.06 (m, 2H), 1.54 - 1.33 (m, 4H), 2.03 - 1.89 (m, 2H), 2.23 - 2.07 (m, 2H), 2.27 (s, 3H), 2.44 - 2.31 (m, 4H), 2.74 (dd, J=14.51, 5.24Hz, 1H), 3.01 (dd, J=14.91, 9.27Hz, 1H), 3.53 - 3.44 (m, 1H), 3.67 - 3.60 (m, 1H), 7.02 (d, J=8.46Hz, 1H), 7.14 (s, 1H), 7.76 (s, 1H), 8.07 (d, J=7.66Hz, 1H) | 501 | 499 | (R) |
| A-78 | 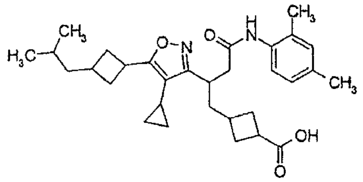 | (400 MHz, CDCl3) 0.36 - 0.37 (m, 1H), 0.47 - 0.48 (m, 1H), 0.79 - 0.90 (m, 2H), 0.87 (d, J=6.62Hz, 6H), 1.31 - 1.35 (m, 3H), 1.52 - 1.55 (m, 1H), 1.85 - 1.97 (m, 6H), 2.00 (s, 3H), 2.25 (s, 3H), 2.31 - 2.39 (m, 6H), 2.69 (dd, J=13.56, 4.30Hz, 1H), 2.88 - 2.99 (m, 2H), 3.46 - 3.50 (m, 2H), 6.93 - 6.94 (m, 2H), 7.41 - 7.43 (m, 1H), 7.51 (s, 1H) | 507 | 505 | (R) |
| A-79 | 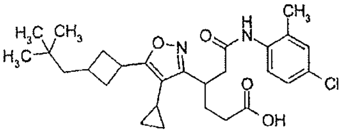 | (400 MHz, CDCl3) 0.35 - 0.40 (m, 1H), 0.45 - 0.49 (m, 1H), 0.80 - 0.83 (m, 2H), 0.87 (s, 9H), 1.33 - 1.37 (m, 1H), 1.37 (d, J=5.95Hz, 2H), 1.92 (dd, J=21.28, 11.14Hz, 1H), 2.00 - 2.21 (m, 3H), 2.03 (s, 3H), 2.32 - 2.45 (m, 5H), 2.77 (dd, J=13.89, 4.63Hz, 1H), 2.97 (dd, J=13.67, 10.81Hz, 1H), 3.46 - 3.55 (m, 1H), 3.66 - 3.71 (m, 1H), 7.08 - 7.10 (m, 2H), 7.53 (d, J=9.15Hz, 1H), 7.86 (s, 1H) | 501 | 499 | (R) |
| A-80 | 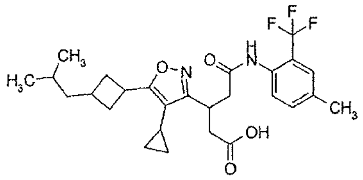 | (400 MHz, DMSO-d6) 0.42 - 0.51 (m, 2H), 0.75 - 0.82 (m, 2H), 0.85 (d, J=6.40Hz, 6H), 1.26 - 1.35 (m, 2H), 1.39 - 1.58 (m, 2H), 1.76 - 1.91 (m, 2H), 2.29 - 2.43 (m, 3H), 2.36 (s, 3H), 2.55 - 2.83 (m, 4H), 3.48 - 3.61 (m, 1H), 3.68 - 3.81 (m, 1H), 7.26 (d, J=8.40Hz, 1H), 7.45 (d, J=8.40Hz, 1H), 7.51 (s, 1H), 9.53 (s, 1H), 12.20 (brs, 1H) | 507 | 505 | (S) |

Fig. 21
| Example | Structure | NMR | MS | | Stereochemistry of AUX-H |
|---|---|---|---|---|---|
| | | | M+H | M-H | |
| A-81 | 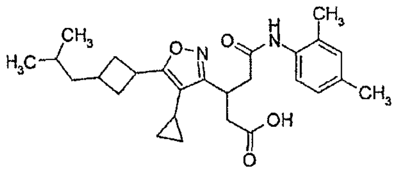 | (400 MHz, DMSO-d6) 0.46 - 0.47 (m, 2H), 0.77 - 0.80 (m, 2H), 0.84 (s, 6H), 1.29 (t, J=6.72Hz, 2H), 1.43 - 1.51 (m, 2H), 1.81 - 1.84 (m, 2H), 2.01 (s, 3H), 2.22 (s, 3H), 2.29 - 2.40 (m, 3H), 2.57 - 2.77 (m, 4H), 3.50 - 3.54 (m, 1H), 3.72 - 3.79 (m, 1H), 6.91 (d, J=8.12Hz, 1H), 6.97 (s, 1H), 7.13 (d, J=8.12Hz, 1H), 9.23 (s, 1H), 12.22 (s, 1H) | 453 | 451 | (S) |
| A-82 | 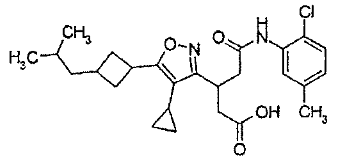 | (400 MHz, DMSO-d6) 0.41 - 0.52 (m, 2H), 0.74 - 0.89 (m, 2H), 0.84 (d, J=6.40Hz, 6H), 1.24 - 1.34 (m, 2H), 1.37 - 1.58 (m, 2H), 1.75 - 1.89 (m, 2H), 2.26 (s, 3H), 2.28 - 2.43 (m, 3H), 2.55 - 2.87 (m, 4H), 3.45 - 3.61 (m, 1H), 3.68 - 3.83 (m, 1H), 6.99 (d, J=8.40, 1H), 7.32 (d, J=8.40Hz, 1H), 7.44 (s, 1H), 9.46 (s, 1H), 12.22 (brs, 1H) | 473 | 471 | (S) |
| A-83 | 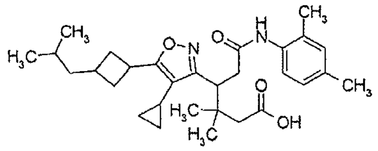 | (400 MHz, CDCl3) 0.29 - 0.34 (m, 1H), 0.58 - 0.64 (m, 1H), 0.78 - 0.83 (m, 2H), 0.86 - 0.90 (m, 6H), 1.16 (s, 3H), 1.23 (s, 3H), 1.27 - 1.39 (m, 3H), 1.50 - 1.59 (m, 1H), 1.82 - 1.91 (m, 1H), 1.92 (s, 3H), 2.00 - 2.08 (m, 1H), 2.25 (s, 3H), 2.30 - 2.48 (m, 5H), 2.78 - 2.93 (m, 2H), 3.47 - 3.56 (m, 1H), 3.70 (dd, J=11.71, 4.06Hz, 1H), 6.90 - 6.93 (m, 2H), 7.06 (s, 1H), 7.21 - 7.25 (m, 1H) | 495 | 493 | (S) |
| B-1 | 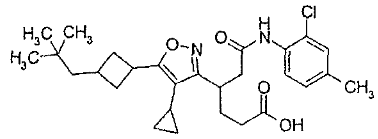 | (400 MHz, CDCl3) 0.31 - 0.49 (m, 2H), 0.79 - 0.84 (m, 2H), 0.87 (s, 9H), 1.31 - 1.40 (m, 1H), 1.44 (d, J=6.84Hz, 2H), 2.02 - 2.23 (m, 4H), 2.27 (s, 3H), 2.33 - 2.50 (m, 4H), 2.67 - 2.77 (m, 2H), 3.03 (dd, J=14.34, 9.04Hz, 1H), 3.69 - 3.60 (m, 2H), 7.02 (d, J=8.38Hz, 1H), 7.13 (s, 1H), 7.78 (s, 1H), 8.09 (d, J=8.38Hz, 1H) | 501 | 499 | (R) |

Fig. 22
| Example | Structure | NMR | MS | | Stereochemistry of AUX-H |
|---|---|---|---|---|---|
| | | | M+H | M-H | |
| B-2 | 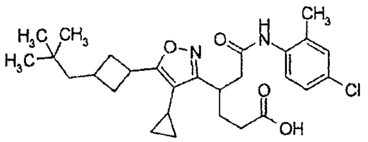 | (400 MHz, CDCl3) 0.30 - 0.49 (m, 2H), 0.76 - 0.85 (m, 2H), 0.87 (s, 9H), 1.31 - 1.41 (m, 2H), 1.45 (d, J=6.75Hz, 2H), 1.99 - 2.13 (m, 5H), 2.13 - 2.24 (m, 1H), 2.28 - 2.51 (m, 4H), 2.62 - 2.73 (m, 1H), 2.78 (dd, J=13.72, 4.42Hz, 1H), 3.00 (dd, J=13.37, 10.82Hz, 1H), 3.60 - 3.72 (m, 2H), 7.10 (d, J=1.86Hz, 2H), 7.58 (d, J=9.07Hz, 1H), 7.75 (s, 1H) | 501 | 499 | (R) |
| A-84 | 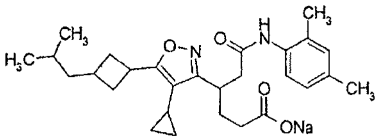 | (400 MHz, DMSO-d6) 0.37 - 0.49 (m, 2H), 0.75 - 0.80 (m, 2H), 0.84 (d, J=6.80Hz, 6H), 1:30 (t, J=6.80Hz, 2H), 1.37 - 1.44 (m, 1H), 1.47 - 1.56 (m, 1H), 1.76 - 1.89 (m, 6H), 2.02 (s, 3H), 2.21 (s, 3H), 2.28 - 2.41 (m, 3H), 2.61 - 2.72 (m, 2H), 3.36 - 3.40 (m, 2H), 3.48 - 3.56 (m, 1H), 6.90 (d, J=8.00Hz, 1H), 6.95 (s, 1H), 7.11 (d, J=8.40Hz, 1H), 9.55 (s, 1H) | 467 | 465 | (R) |
| A-85 | 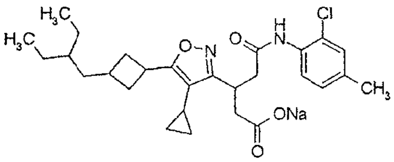 | (400 MHz, DMSO-d6) 0.43 - 0.48 (m, 2H), 0.73 - 0.77 (m, 2H), 0.80 (t, J=7.60Hz, 6H), 1.10 - 1.17 (m, 1H), 1.20 - 1.27 (m, 3H), 1.33 (t, J=6.40Hz, 2H), 1.38 - 1.45 (m, 1H), 1.77 - 1.86 (m, 2H), 2.12 - 2.18 (m, 1H), 2.25 (s, 3H), 2.29 - 2.38 (m, 3H), 2.66 - 2.73 (m, 1H), 2.83 (dd, J=14.60, 4.80Hz, 1H), 3.25 - 3.40 (m, 2H), 3.47 - 3.54 (m, 1H), 3.59 - 3.67 (m, 1H), 7.06 (d, J=6.80Hz, 1H), 7.25 (s, 1H), 7.49 (d, J=8.00Hz, 1H), 10.21 (brs, 1H) | 501 | 499 | (S) |

Fig. 23

| Example | Structure | NMR | MS | | Stereochemistry of AUX-H | Materials or Stereochemistry |
|---|---|---|---|---|---|---|
| | | | M+H | M-H | | |
| A-86 | 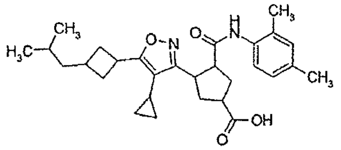 | (400 MHz, CDCl3) 0.37 - 0.42 (m, 2H), 0.79 - 0.85 (m, 2H), 0.85 - 0.90 (m, 6H), 1.32 - 1.38 (m, 3H), 1.50 - 1.59 (m, 1H), 1.88 - 1.96 (m, 1H), 1.96 - 2.05 (m, 1H), 2.05 - 2.08 (m, 3H), 2.23 - 2.28 (m, 3H), 2.32 - 2.49 (m, 5H), 2.57 - 2.70 (m, 1H), 2.72 - 2.84 (m, 1H), 3.08 - 3.19 (m, 2H), 3.41 - 3.66 (m, 2H), 6.91 - 6.95 (m, 1H), 6.95 - 7.00 (m, 1H), 7.69 - 7.75 (m, 1H), 7.89 - 7.94 (m, 1H) | 479 | 477 | Without using AUX-H | Dimethyl 4-oxo-cyclopentane-trans-1,2-dicarboxylate was used as a material. |
| A-87 | 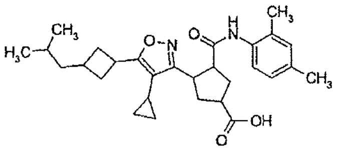 | (400 MHz, CDCl3) 0.37 - 0.42 (m, 2H), 0.79 - 0.85 (m, 2H), 0.85 - 0.90 (m, 6H), 1.32 - 1.38 (m, 3H), 1.50 - 1.59 (m, 1H), 1.88 - 1.96 (m, 1H), 1.96 - 2.05 (m, 1H), 2.05 - 2.08 (m, 3H), 2.23 - 2.28 (m, 3H), 2.32 - 2.49 (m, 5H), 2.57 - 2.70 (m, 1H), 2.72 - 2.84 (m, 1H), 3.08 - 3.19 (m, 2H), 3.41 - 3.66 (m, 2H), 6.91 - 6.95 (m, 1H), 6.95 - 7.00 (m, 1H), 7.69 - 7.75 (m, 1H), 7.89 - 7.94 (m, 1H) | 479 | 477 | Without using AUX-H | Dimethyl 4-oxo-cyclopentane-trans-1,2-dicarboxylate was used as a material. · Enantiomer of A-86 |
| A-88 | 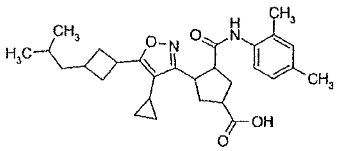 | (400 MHz, CDCl3) 0.37 - 0.42 (m, 2H), 0.75 - 0.85 (m, 2H), 0.85 - 0.90 (m, 6H), 1.32 - 1.38 (m, 3H), 1.51 - 1.58 (m, 1H), 1.88 - 1.97 (m, 1H), 1.97 - 2.03 (m, 1H), 2.04 - 2.08 (m, 3H), 2.23 - 2.27 (m, 3H), 2.32 - 2.44 (m, 5H), 2.60 - 2.71 (m, 1H), 2.71 - 2.85 (m, 1H), 3.14 - 3.25 (m, 1H), 3.38 - 3.57 (m, 2H), 3.57 - 3.69 (m, 1H), 6.91 - 6.95 (m, 1H), 6.95 - 6.99 (m, 1H), 7.69 - 7.75 (m, 1H), 7.89 - 7.94 (m, 1H) | 479 | 477 | Without using AUX-H | Dimethyl 4-oxo-cyclopentane-trans-1,2-dicarboxylate was used as a material. Diastereomer of A-86 |
| A-89 | 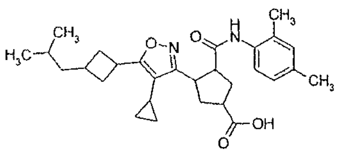 | (400 MHz, CDCl3) 0.37 - 0.42 (m, 2H), 0.75 - 0.85 (m, 2H), 0.85 - 0.90 (m, 6H), 1.32 - 1.38 (m, 3H), 1.51 - 1.58 (m, 1H), 1.88 - 1.97 (m, 1H), 1.97 - 2.03 (m, 1H), 2.04 - 2.08 (m, 3H), 2.23 - 2.27 (m, 3H), 2.32 - 2.44 (m, 5H), 2.60 - 2.71 (m, 1H), 2.71 - 2.85 (m, 1H), 3.14 - 3.25 (m, 1H), 3.38 - 3.57 (m, 2H), 3.57 - 3.69 (m, 1H), 6.91 - 6.95 (m, 1H), 6.95 - 6.99 (m, 1H), 7.69 - 7.75 (m, 1H), 7.89 - 7.94 (m, 1H) | 479 | 477 | Without using AUX-H | Dimethyl 4-oxo-cyclopentane-trans-1,2-dicarboxylate was used as a material. Diastereomer of A-86 |

Fig. 24

| Example | Structure | NMR | MS M+H | MS M-H | Stereochemistry of AUX-H | Materials or Stereochemistry |
|---|---|---|---|---|---|---|
| B-3 | 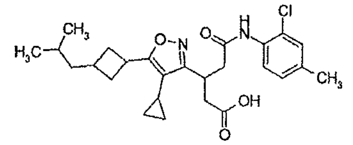 | (400 MHz, CDCl3) 0.41 - 0.50 (m, 2H), 0.83 - 0.88 (m, 2H), 0.87 (d, J=6.62Hz, 6H), 1.32 - 1.43 (m, 3H), 1.55 (m, 1H), 1.95 - 2.04 (m, 2H), 2.28 (s, 3H), 2.34 - 2.59 (m, 3H), 2.78 - 3.07 (m, 4H), 3.64 - 3.72 (m, 1H), 3.93 - 4.00 (m, 1H), 7.03 (dd, J=8.27, 1.65Hz, 1H), 7.15 (s, 1H), 7.89 (s, 1H), 8.12 (d, J=8.38Hz, 1H) | 473 | 471 | (S) | – |
| B-4 | 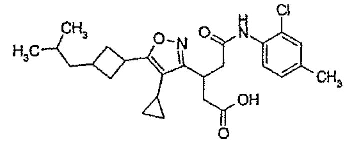 | (400 MHz, CDCl3) 0.43 - 0.49 (m, 2H), 0.84 - 0.88 (m, 2H), 0.87 (d, J=6.62Hz, 6H), 1.38 - 1.43 (m, 3H), 1.94 - 2.04 (m, 2H), 2.28 (s, 3H), 2.37 - 2.50 (m, 2H), 2.50 - 2.62 (m, 1H), 2.80 - 3.06 (m, 4H), 3.64 - 3.73 (m, 1H), 3.92 - 3.99 (m, 1H), 7.04 (dd, J=8.16, 1.32Hz, 1H), 7.16 (s, 1H), 7.86 (s, 1H), 8.13 (d, J=8.16Hz, 1H) | 473 | 471 | (R) | – |
| C-1 | 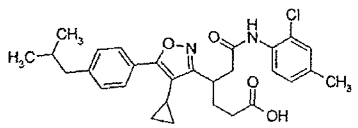 | (400 MHz, CDCl3) 0.27 - 0.38 (m, 1H), 0.47 - 0.58 (m, 1H), 0.84 - 1.03 (m, 2H), 0.92 (d, J=6.40Hz, 6H), 1.59 - 1.70 (m, 1H), 1.84 - 1.97 (m, 1H), 2.08 - 2.32 (m, 2H), 2.27 (s, 3H), 2.39 - 2.57 (m, 2H), 2.52 (d, J=7.20Hz, 2H), 2.80 (dd, J=14.40, 5.20Hz, 1H), 3.09 (dd, J=14.40, 9.60Hz, 1H), 3.74 - 3.85 (m, 1H), 7.02 (d, J=8.40Hz, 1H), 7.12 (s, 1H), 7.23 (d, J=8.40Hz, 2H), 7.73 (d, J=8.40Hz, 2H), 7.80 (brs, 1H), 8.08 (d, J=8.40Hz, 1H) | 509 | 507 | (R) | – |
| C-2 | 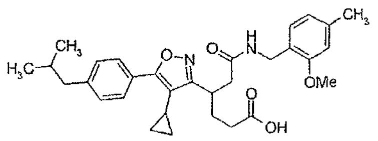 | (400 MHz, CDCl3) 0.18 - 0.27 (m, 1H), 0.39 - 0.49 (m, 1H), 0.82 - 1.02 (m, 2H), 0.94 (d, J=7.20Hz, 6H), 1.50 - 1.60 (m, 1H), 1.85 - 1.98 (m, 1H), 1.99 - 2.22 (m, 2H), 2.17 (s, 3H), 2.34 - 2.47 (m, 2H), 2.54 (d, J=7.20Hz, 2H), 2.61 (dd, J=14.00, 5.60Hz, 1H), 2.75 (dd, J=14.00, 10.00Hz, 1H), 3.66 - 3.83 (m, 1H), 3.78 (s, 3H), 4.24 (dd, J=14.40, 5.60Hz, 1H), 4.34 (dd, J=14.40, 6.40Hz, 1H), 6.20 - 6.28 (m, 1H), 6.53 - 6.57 (m, 1H), 6.54 (s, 1H), 6.95 (d, J=8.00Hz, 1H), 7.24 (d, J=8.00Hz, 2H), 7.73 (d, J=8.00Hz, 2H) | 519 | 517 | (R) | – |

Fig. 25

| Example | Structure | NMR | MS M+H | MS M-H | Stereochemistry of AUX-H | Materials or Stereochemistry |
|---|---|---|---|---|---|---|
| D-1 | 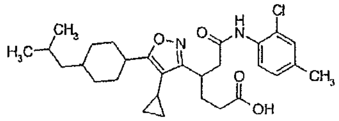 | (400 MHz, CDCl3) 0.38 - 0.44 (m, 1H), 0.46 - 0.54 (m, 1H), 0.78 - 0.89 (m, 2H), 0.86 (d, J=6.52Hz, 6H), 1.19 (t, J=7.00Hz, 2H), 1.33 - 1.40 (m, 1H), 1.40 - 1.66 (m, 8H), 1.76 - 1.90 (m, 2H), 2.03 - 2.22 (m, 2H), 2.25 (s, 3H), 2.36 - 2.45 (m, 2H), 2.73 (dd, J=14.00, 5.36Hz, 1H), 2.95 - 3.07 (m, 2H), 3.60 - 3.68 (m, 1H), 7.00 (d, J=8.00Hz, 1H), 7.11 (s, 1H), 7.71 (brs, 1H), 8.06 (d, J=8.00Hz, 1H) | 515 | 513 | (R) | – |
| D-2 | 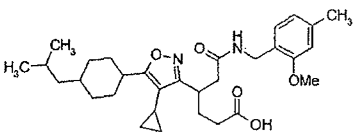 | (400 MHz, CDCl3) 0.33 - 0.41 (m, 1H), 0.45 - 0.53 (m, 1H), 0.80 - 0.92 (m, 2H), 0.88 (d, J=6.80Hz, 6H), 1.19 (t, J=7.20Hz, 2H), 1.32 - 1.40 (m, 1H), 1.41 - 1.70 (m, 8H), 1.78 - 1.91 (m, 2H), 1.95 - 2.16 (m, 2H), 2.28 - 2.42 (m, 2H), 2.32 (s, 3H), 2.54 (dd, J=14.40, 6.00Hz, 1H), 2.70 (dd, J=14.40, 8.40Hz, 1H), 2.96 - 3.05 (m, 1H), 3.55 - 3.66 (m, 1H), 3.81 (s, 3H), 4.24 - 4.37 (m, 2H), 6.20 (dd, J=5.60, 5.60Hz, 1H), 6.64 (s, 1H), 6.66 (d, J=7.60Hz, 1H), 7.01 (d, J=7.60Hz, 1H) | 525 | 523 | (R) | – |
| A-90 | 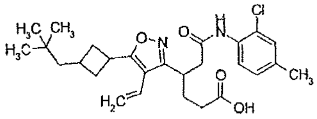 | (400 MHz, CDCl3) 0.87 (s, 9H), 1.39 (d, J=6.18Hz, 2H), 2.06 - 2.14 (m, 4H), 2.27 (s, 3H), 2.32 - 2.46 (m, 5H), 2.74 (dd, J=14.45, 5.62Hz, 1H), 3.02 (dd, J=14.45, 8.93Hz, 1H), 3.44 - 3.61 (m, 2H), 5.35 (ddd, J=14.56, 8.38, 1.21Hz, 2H), 6.37 (dd, J=17.64, 11.47Hz, 1H), 7.01 (d, J=9.70Hz, 1H), 7.14 (s, 1H), 7.82 (s, 1H), 8.07 (d, J=8.38Hz, 1H) | 487 | 485 | (R) | – |
| A-91 | 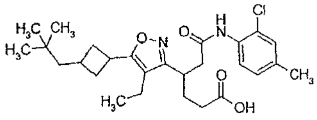 | (400 MHz, CDCl3) 0.87 (s, 9H), 1.03 (t, J=7.28Hz, 3H), 1.40 (d, J=11.69Hz, 2H), 2.04 - 2.11 (m, 4H), 2.26 - 2.39 (m, 10H), 2.75 (dd, J=14.11, 4.52Hz, 1H), 2.98 (dd, J=13.23, 9.70Hz, 1H), 3.31 - 3.49 (m, 2H), 7.01 (d, J=7.94Hz, 1H), 7.13 (s, 1H), 7.81 (s, 1H), 8.03 (d, J=7.94Hz, 1H) | 489 | 487 | (R) | – |

Fig. 26

| Example | Structure | NMR | MS M+H | MS M-H | Stereochemistry of AUX-H | Materials or Stereochemistry |
|---|---|---|---|---|---|---|
| A-92 | 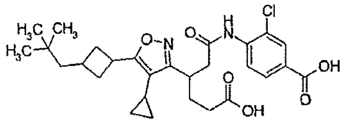 | (400 MHz, DMSO-d6) 0.38 - 0.43 (m, 1H), 0.46 - 0.51 (m, 1H), 0.78 - 0.83 (m, 2H), 0.85 (s, 9H), 1.33 (d, J=6.00Hz, 2H), 1.38 - 1.45 (m, 1H), 1.83 - 1.96 (m, 4H), 2.13 - 2.24 (m, 2H), 2.36 - 2.43 (m, 3H), 2.83 (dd, J=15.20, 6.80Hz, 1H), 2.94 (dd, J=15.40, 8.00Hz, 1H), 3.43 - 3.59 (m, 2H), 7.84 (dd, J=8.40, 2.00Hz, 1H), 7.92 (d, J=8.80Hz, 1H), 7.92 (d, J=2.00Hz, 1H), 9.65 (s, 1H) | 531 | 529 | (R) | – |
| A-93 | 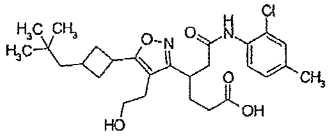 | (400 MHz, CDCl3) 0.87 (s, 9H), 1.03 (t, J=7.28Hz, 3H), 1.40 (d, J=11.69Hz, 2H), 2.04 - 2.11 (m, 4H), 2.26 - 2.39 (m, 10H), 2.75 (dd, J=14.11, 4.52Hz, 1H), 2.98 (dd, J=13.23, 9.70Hz, 1H), 3.31 - 3.49 (m, 2H), 7.01 (d, J=7.94Hz, 1H), 7.13 (s, 1H), 7.81 (s, 1H), 8.03 (d, J=7.94Hz, 1H) | 505 | 503 | (R) | – |
| A-94 | 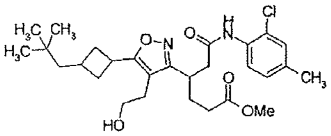 | (400 MHz, CDCl3) 0.87 (s, 9H), 1.38 (d, J=5.96Hz, 2H), 2.02 - 2.09 (m, 4H), 2.27 (s, 3H), 2.35 - 2.41 (m, 5H), 2.51 - 2.61 (m, 2H), 2.77 (dd, J=14.89, 4.74Hz, 1H), 3.06 (dd, J=14.78, 10.37Hz, 1H), 3.34 - 3.38 (m, 1H), 3.48 - 3.50 (m, 1H), 3.48 (s, 3H), 3.63 - 3.72 (m, 2H), 7.00 (d, J=8.38Hz, 1H), 7.14 (s, 1H), 7.67 (s, 1H), 8.03 (d, J=8.38Hz, 1H) | 519 | 517 | (R) | – |
| D-3 | 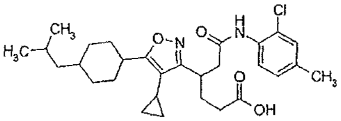 | (400 MHz, DMSO-d6) 0.37 - 0.46 (m, 1H), 0.49 - 0.58 (m, 1H), 0.77 - 0.90 (m, 2H), 0.85 (d, J=6.40Hz, 6H), 0.91 - 1.11 (m, 2H), 1.07 (t, J=7.20Hz, 2H), 1.29 - 1.85 (m, 9H), 1.87 - 1.99 (m, 2H), 2.09 - 2.31 (m, 2H), 2.27 (s, 3H), 2.65 - 2.89 (m, 3H), 3.42 - 3.54 (m, 1H), 7.09 (d, J=8.00Hz, 1H), 7.28 (s, 1H), 7.42 (d, J=8.00Hz, 1H), 9.45 (s, 1H), 12.08 (brs, 1H) | 515 | 513 | (R) | – |

Fig. 27

| Example | Structure | NMR | MS M+H | MS M-H | Stereochemistry of AUX-H | Materials or Stereochemistry |
|---|---|---|---|---|---|---|
| D-4 | 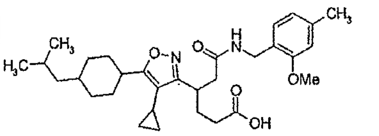 | (400 MHz, DMSO-d6) 0.34 - 0.44 (m, 1H), 0.47 - 0.56 (m, 1H), 0.73 - 0.91 (m, 2H), 0.86 (d, J=6.40Hz, 6H), 0.91 - 1.13 (m, 2H), 1.07 (t, J=7.20Hz, 2H), 1.30 - 1.46 (m, 2H), 1.46 - 1.92 (m, 9H), 2.06 - 2.22 (m, 2H), 2.27 (s, 3H), 2.43 - 2.62 (m, 2H), 2.77 - 2.88 (m, 1H), 3.20 - 3.47 (m, 1H), 3.75 (s, 3H), 4.06 - 4.19 (m, 2H), 6.64 (d, J=7.20Hz, 1H), 6.76 (s, 1H), 6.89 (d, J=7.20Hz, 1H), 8.14 (dd, J=6.00, 6.00Hz, 1H), 12.06 (brs, 1H) | 525 | 523 | (R) | – |
| C-3 | 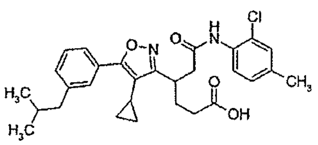 | (400 MHz, DMSO-d6) 0.15 - 0.28 (m, 1H), 0.41 - 0.51 (m, 1H), 0.81 - 0.99 (m, 2H), 0.89 (d, J=7.20Hz, 6H), 1.71 - 1.82 (m, 1H), 1.82 - 2.07 (m, 3H), 2.17 - 2.36 (m, 2H), 2.27 (s, 3H), 2.54 (d, J=7.20Hz, 2H), 2.80 (dd, J=14.80, 6.40Hz, 1H), 2.92 (dd, J=14.80, 8.00Hz, 1H), 3.56 - 3.68 (m, 1H), 7.09 (d, J=7.20Hz, 1H), 7.25 - 7.33 (m, 1H), 7.28 (s, 1H), 7.40 - 7.50 (m, 2H), 7.58 - 7.66 (m, 2H), 9.51 (s, 1H), 12.12 (brs, 1H) | 509 | 507 | (R) | – |
| C-4 | 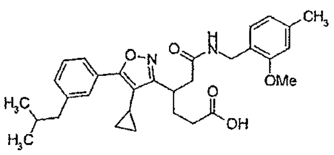 | (400 MHz, DMSO-d6) 0.13 - 0.23 (m, 1H), 0.40 - 0.51 (m, 1H), 0.83 - 0.99 (m, 2H), 0.90 (d, J=7.20Hz, 6H), 1.67 - 1.78 (m, 1H), 1.83 - 2.00 (m, 3H), 2.16 - 2.30 (m, 2H), 2.21 (s, 3H), 2.46 - 2.62 (m, 1H), 2.55 (d, J=6.80Hz, 2H), 2.69 (dd, J=14.40, 9.20Hz, 1H), 3.53 - 3.63 (m, 1H), 3.75 (s, 3H), 4.07 (dd, J=15.60, 6.00Hz, 1H), 4.18 (dd, J=15.60, 6.00Hz, 1H), 6.50 (d, J=7.20Hz, 1H), 6.74 (s, 1H), 6.79 (d, J=7.60Hz, 1H), 7.31 (d, J=7.60Hz, 1H), 7.42 - 7.50 (m, 1H), 7.58 - 7.67 (m, 2H), 8.20 (dd, J=6.00, 6.00Hz, 1H), 12.11 (brs, 1H) | 519 | 517 | (R) | – |
| A-95 | 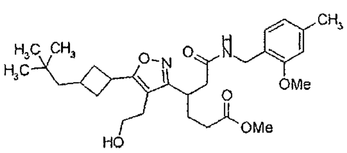 | (400 MHz, CDCl3) 0.87 (s, 9H), 1.39 (d, J=6.18Hz, 2H), 1.95 - 2.02 (m, 4H), 2.27 - 2.46 (m, 4H), 2.27 (s, 3H), 2.50 - 2.55 (m, 3H), 2.75 (dd, J=14.67, 10.48Hz, 1H), 3.30 - 3.44 (m, 2H), 3.58 - 3.61 (m, 1H), 3.58 (s, 1H), 3.71 (dd, J=10.81, 5.51Hz, 1H), 3.81 (s, 3H), 4.22 - 4.33 (m, 2H), 6.07 (s, 1H), 6.07 (t, J=5.62Hz, 1H), 6.65 - 6.68 (m, 2H), 6.67 (s, 1H), 6.98 (d, J=7.50Hz, 1H) | 529 | 527 | (R) | – |

Fig. 28

| Example | Structure | NMR | MS M+H | MS M-H | Stereochemistry of AUX-H | Materials or Stereochemistry |
|---|---|---|---|---|---|---|
| A-96 | 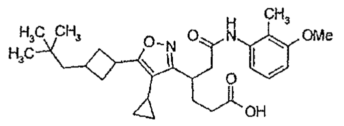 | (400 MHz, CDCl3) 0.35 - 0.40 (m, 1H), 0.45 - 0.50 (m, 1H), 0.79 - 0.87 (m, 2H), 0.87 (s, 9H), 1.33 - 1.39 (m, 1H), 1.38 (d, J=5.95Hz, 2H), 1.92 (s, 3H), 1.92 - 2.21 (m, 4H), 2.33 - 2.50 (m, 5H), 2.76 (dd, J=13.56, 4.52Hz, 1H), 2.98 (dd, J=13.56, 10.70Hz, 1H), 3.46 - 3.55 (m, 1H), 3.63 - 3.70 (m, 1H), 3.79 (s, 3H), 6.66 (d, J=8.16Hz, 1H), 7.09 (t, J=8.16Hz, 1H), 7.20 (d, J=8.16Hz, 1H), 7.56 (brs, 1H) | 497 | 495 | (R) | – |
| A-97 | 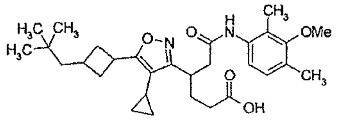 | (400 MHz, DMSO-d6) 0.32 - 0.43 (m, 1H), 0.45 - 0.55 (m, 1H), 0.73 - 0.92 (m, 2H), 0.86 (s, 9H), 1.30 - 1.35 (m, 1H), 1.32 (d, J=5.60Hz, 2H), 1.79 - 2.00 (m, 4H), 1.94 (s, 3H), 2.13 - 2.25 (m, 2H), 2.18 (s, 3H), 2.32 - 2.46 (m, 3H), 2.67 (dd, J=14.40Hz, 6.80Hz, 1H), 2.75 (dd, J=14.40, 8.40Hz, 1H), 3.39 - 3.66 (m, 2H), 3.60 (s, 3H), 6.88 - 6.98 (m, 2H), 9.29 (s, 1H), 12.08 (brs, 1H) | 511 | 509 | (R) | – |
| A-98 | 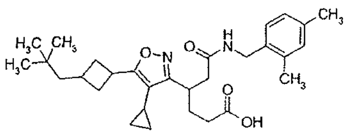 | (400 MHz, DMSO-d6) 0.31 - 0.41 (m, 1H), 0.44 - 0.53 (m, 1H), 0.69 - 0.93 (m, 2H), 0.86 (s, 9H), 1.30 - 1.43 (m, 1H), 1.36 (d, J=6.00Hz, 2H), 1.78 - 1.97 (m, 4H), 2.05 - 2.25 (m, 2H), 2.13 (s, 3H), 2.22 (s, 3H), 2.32 - 2.54 (m, 4H), 2.59 (dd, J=14.40, 8.40Hz, 1H), 3.13 - 3.48 (m, 1H), 3.48 - 3.63 (m, 1H), 4.07 (dd, J=14.80, 5.60Hz, 1H), 4.20 (dd, J=14.80, 5.60Hz, 1H), 6.85 - 6.97 (m, 2H), 6.93 (s, 1H), 8.17 (dd, J=5.60, 5.60Hz, 1H), 12.07 (brs, 1H) | 495 | 493 | (R) | – |
| A-99 | 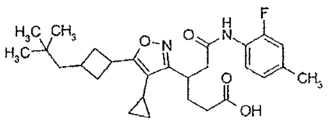 | (400 MHz, DMSO-d6) 0.33 - 0.56 (m, 2H), 0.71 - 0.95 (m, 2H), 0.85 (s, 9H), 1.28 - 1.47 (m, 1H), 1.34 (d, J=6.00Hz, 2H), 1.78 - 1.99 (m, 4H), 2.08 - 2.31 (m, 2H), 2.26 (s, 3H), 2.31 - 2.45 (m, 3H), 2.72 (dd, J=14.80, 7.20Hz, 1H), 2.81 (dd, J=14.80, 8.00Hz, 1H), 3.16 - 3.62 (m, 2H), 6.93 (d, J=8.00Hz, 1H), 7.04 (d, J=11.4Hz, 1H), 7.61 (dd, J=8.00, 8.00Hz, 1H), 9.63 (s, 1H), 12.08 (brs, 1H) | 485 | 483 | (R) | – |

Fig. 29

| Example | Structure | NMR | MS M+H | MS M-H | Stereochemistry of AUX-H | Materials or Stereochemistry |
|---|---|---|---|---|---|---|
| A-100 | 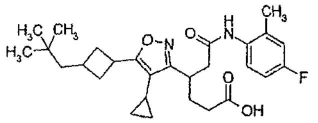 | (400 MHz, CDCl3) 0.37 (dd, J=9.59, 4.52Hz, 1H), 0.49 (dd, J=9.70, 4.63Hz, 1H), 0.82 (dd, J=8.27, 4.74Hz, 2H), 0.87 (s, 9H), 1.33 - 1.38 (m, 1H), 1.37 (d, J=5.73Hz, 2H), 1.98 - 2.12 (m, 7H), 2.38 - 2.42 (m, 5H), 2.77 (dd, J=13.78, 4.74Hz, 1H), 2.96 (dd, J=13.78, 10.70Hz, 1H), 3.50 - 3.52 (m, 1H), 3.67 - 3.69 (m, 1H), 6.81 - 6.83 (m, 2H), 7.41 (dd, J=8.49, 6.06Hz, 1H), 7.76 (s, 1H) | 485 | 483 | (R) | – |
| A-101 | 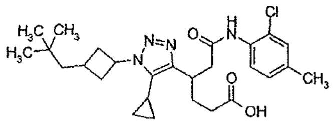 | (400 MHz, CDCl3) 0.48 - 0.50 (m, 1H), 0.81 (d, J=5.29Hz, 1H), 0.90 (s, 9H), 0.95 - 0.96 (m, 2H), 1.47 (dd, J=12.90, 7.39Hz, 3H), 2.13 (s, 2H), 2.31 - 2.34 (m, 8H), 2.62 (t, J=14.78Hz, 2H), 2.79 (dd, J=13.45, 4.63Hz, 1H), 3.06 (dd, J=13.34, 10.70Hz, 1H), 3.54 - 3.57 (m, 1H), 4.77 - 4.79 (m, 1H), 6.97 (d, J=8.38Hz, 1H), 7.08 (s, 1H), 7.83 (d, J=8.38Hz, 1H), 7.90 (s, 1H) | 501 | 499 | (R) | – |
| A-102 | 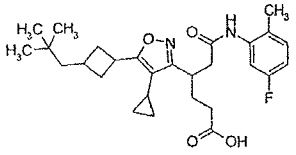 | (400 MHz, CDCl3) 0.43 - 0.46 (m, 2H), 0.84 - 0.87 (m, 1H), 0.86 (s, 9H), 1.34 - 1.36 (m, 3H), 1.91 - 2.19 (m, 8H), 2.36 - 2.42 (m, 5H), 2.78 (dd, J=13.78, 4.52Hz, 1H), 3.00 (dd, J=13.56, 10.70Hz, 1H), 3.46 - 3.55 (m, 1H), 3.65 - 3.67 (m, 1H), 6.70 - 6.72 (m, 1H), 7.04 (t, J=7.28Hz, 1H), 7.58 (dd, J=10.81, 2.43Hz, 1H), 7.81 (s, 1H) | 485 | 483 | (R) | – |
| D-5 | 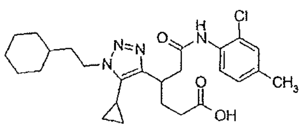 | (400 MHz, CDCl3) 0.53 - 0.56 (m, 1H), 0.88 - 0.97 (m, 5H), 1.15 - 1.18 (m, 4H), 1.52 - 1.54 (m, 1H), 1.68 - 1.71 (m, 7H), 2.12 - 2.14 (m, 2H), 2.26 - 2.31 (m, 5H), 2.80 (dd, J=13.78, 4.74Hz, 1H), 3.05 (dd, J=13.23, 10.81Hz, 1H), 3.58 (s, 1H), 4.30 (t, J=7.94Hz, 2H), 6.97 (d, J=8.38Hz, 1H), 7.08 (s, 1H), 7.89 (d, J=7.72Hz, 2H) | 487 | 485 | (R) | – |

Fig. 30

| Example | Structure | NMR | MS M+H | MS M-H | Stereochemistry of AUX-H | Materials or Stereochemistry |
|---|---|---|---|---|---|---|
| D-6 | 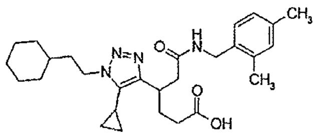 | (400 MHz, CDCl3) 0.45 - 0.46 (m, 1H), 0.86 - 1.02 (m, 5H), 1.19 - 1.30 (m, 4H), 1.44 - 1.51 (m, 1H), 1.65 - 1.78 (m, 7H), 2.02 - 2.10 (m, 5H), 2.15 - 2.33 (m, 5H), 2.63 - 2.81 (m, 2H), 3.51 (t, J=5.51Hz, 1H), 4.06 (dd, J=14.67, 4.96Hz, 1H), 4.22 - 4.29 (m, 3H), 6.64 (t, J=5.62Hz, 1H), 6.76 (d, J=7.72Hz, 1H), 6.84 - 6.87 (m, 2H) | 481 | 479 | (R) | – |
| A-103 | 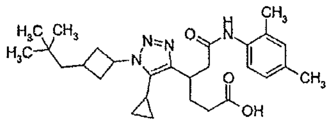 | (400 MHz, CDCl3) 0.51 (s, 1H), 0.87 - 0.89 (m, 10H), 0.96 (d, J=8.38Hz, 2H), 1.44 - 1.49 (m, 3H), 1.87 (s, 3H), 2.06 - 2.09 (m, 2H), 2.27 - 2.38 (m, 8H), 2.62 - 2.63 (m, 2H), 2.81 (dd, J=13.23, 4.63Hz, 1H), 3.03 (t, J=12.35Hz, 1H), 3.58 - 3.60 (m, 1H), 4.75 - 4.84 (m, 1H), 6.86 - 6.87 (m, 2H), 7.16 (d, J=8.82Hz, 1H), 8.05 (s, 1H) | 481 | 479 | (R) | – |
| A-104 | 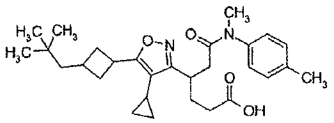 | (400 MHz, CDCl3) 0.31 - 0.37 (m, 1H), 0.49 - 0.55 (m, 1H), 0.80 (dd, J=8.40, 1.90Hz, 2H), 0.85 (s, 9H), 1.28 - 1.38 (m, 3H), 1.89 - 2.04 (m, 4H), 2.25 (t, J=7.80Hz, 2H), 2.31 - 2.40 (m, 7H). 2.61 (dd, J=16.20, 7.10Hz, 1H), 3.20 (s, 3H), 3.46 (t, J=6.50Hz, 1H), 3.58 (t, J=7.00Hz, 1H), 7.04 (d, J=8.10Hz, 2H), 7.19 (d, J=8.10Hz, 2H) | 481 | 479 | (R) | – |
| A-105 | 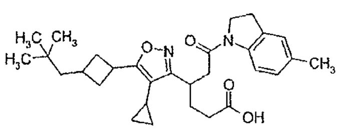 | (400MHz, CDCl3) 0.36 - 0.43 (m, 1H), 0.51 - 0.60 (m, 1H), 0.79 - 0.90 (m, 2H), 0.84 (s, 9H), 1.36 (d, J=5.60Hz, 2H), 1.37 - 1.43 (m, 1H), 1.99 (t, J=10.10Hz, 2H), 2.07 - 2.16 (m, 2H), 2.27 (s, 3H), 2.30 - 2.43 (m, 5H), 2.69 (dd, J=16.00, 6.50Hz, 1H), 3.01 (dd, J=16.00, 7.20Hz, 1H), 3.11 (td, J=8.40, 0.10Hz, 2H), 3.43 - 3.54 (m, 1H), 3.75 (t, J=6.90Hz, 1H), 3.99 - 4.13 (m, 2H), 6.94 (d, J=8.80Hz, 2H), 8.03 (d, J=8.10Hz, 1H) | 493 | 491 | (R) | – |

Fig. 31

| Example | Structure | NMR | MS M+H | MS M-H | Stereochemistry of AUX-H | Materials or Stereochemistry |
|---|---|---|---|---|---|---|
| A-106 | 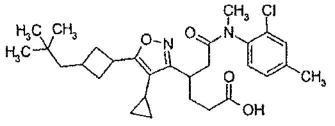 | (400 MHz, CDCl3) 0.32 - 0.58 (m, 2H), 0.80 - 0.89 (m, 11H), 1.23 - 1.38 (m, 3H), 1.90 - 2.04 (m, 4H), 2.20 - 2.60 (m, 10H), 3.13 (s, 2H), 3.18 (s, 1H), 3.41 - 3.52 (m, 1H), 3.56 - 3.66 (m, 1H), 7.09 - 7.14 (m, 2H), 7.26 - 7.30 (m, 1H) | 515 | 513 | (R) | – |
| A-107 | 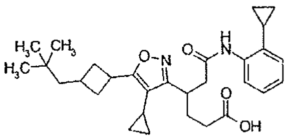 | (400 MHz, CDCl3) 0.35 - 0.71 (m, 4H), 0.80 - 1.02 (m, 13H), 1.33 - 1.37 (m, 3H), 1.59 (s, 1H), 1.90 - 2.19 (m, 4H), 2.35 - 2.42 (m, 5H), 2.78 (dd, J=13.78, 4.74Hz, 1H), 3.01 (dd, J=13.56, 10.26Hz, 1H), 3.43 - 3.52 (m, 1H), 3.66 - 3.67 (m, 1H), 6.98 - 7.07 (m, 2H), 7.16 (t, J=7.61Hz, 1H), 7.97 (d, J=7.94Hz, 1H), 8.02 (s, 1H) | 493 | 491 | (R) | – |
| A-108 | 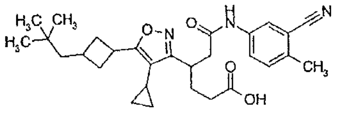 | (400 MHz, CDCl3) 0.37 - 0.43 (m, 1H), 0.46 - 0.52 (m, 1H), 0.79 - 0.89 (m, 2H), 0.85 (s, 9H), 1.33 - 1.38 (m, 1H), 1.35 (d, J=6.00Hz, 2H), 1.89 - 2.12 (m, 3H), 2.19 (dd, J=14.10, 7.10Hz, 1H), 2.31 - 2.44 (m, 5H), 2.44 (s, 3H), 2.76 (dd, J=14.30, 4.80Hz, 1H), 2.91 (dd, J=14.30, 10.10Hz, 1H), 3.44 - 3.54 (m, 1H), 3.71 (dd, J=9.50, 5.10Hz, 1H), 7.15 (d, J=8.40Hz, 1H), 7.48 (d, J=8.60Hz, 1H), 7.76 (s, 1H), 8.44 (br d, J=14.20Hz, 1H) | 492 | 490 | (R) | – |
| A-109 | 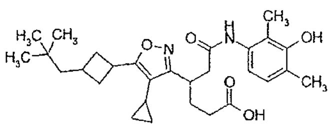 | (400 MHz, DMSO-d6) 0.31 - 0.42 (m, 1H), 0.46 - 0.5 6 (m, 1H), 0.72 - 0.91 (m, 2H), 0.86 (s, 9H), 1.29 - 1.46 (m, 1H), 1.35 (d, J=5. 6Hz, 2H), 1.79 - 1.97 (m, 4H), 1.85 (s, 3H), 2.08 - 2 .23 (m, 2H), 2.11 (s, 3H), 2.31 - 2.46 (m, 3H), 2.64 (dd, J=14.40, 6.80Hz, 1H), 2.73 (dd, J=14.40, 8.40Hz 1H), 3.17 - 3.62 (m, 2H), 6.60 (d, J=8.00Hz, 1H), 6 81 (d, J=8.00Hz, 1H), 8.1 5 (brs, 1H), 9.24 (s, 1H), 12.08 (brs, 1H) | 497 | 495 | (R) | – |

Fig. 32

| Example | Structure | NMR | MS | | Stereochemistry of AUX-H | Materials or Stereochemistry |
|---|---|---|---|---|---|---|
| | | | M+H | M-H | | |
| A-110 | 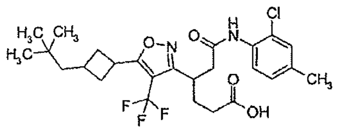 | (400 MHz, CDCl3) 0.85 (s, 9H), 1.37 (d, J=6.30Hz, 2H), 2.02 - 2.17 (m, 4H), 2.26 (s, 3H), 2.37 - 2.47 (m, 5H), 2.73 (dd, J=14.40, 5.80Hz, 1H), 2.99 (dd, J=15.20, 8.50Hz, 1H), 3.56 - 3.66 (m, 2H), 7.02 (d, J=8.10Hz, 1H), 7.14 (s, 1H), 7.61 (s, 1H), 8.11 (d, J=8.40Hz, 1H) | 529 | 527 | (R) | – |
| A-111 | 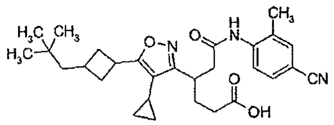 | (400 MHz, CDCl3) 0.34 - 0.39 (m, 1H), 0.40 - 0.45 (m, 1H), 0.78 - 0.83 (m, 2H), 0.86 (s, 9H), 1.29 - 1.36 (m, 1H), 1.36 (d, J=4.40Hz, 2H), 1.90 (dd, J=20.20, 10.50Hz, 1H), 2.03 (dt, J=20.30, 6.40Hz, 2H), 2.15 (s, 3H), 2.19 (t, J=7.10Hz, 1H), 2.38 (tt, J=23.80, 7.60Hz, 5H), 2.78 (dd, J=13.60, 3.80Hz, 1H), 3.03 (dd, J=14.40, 10.90Hz, 1H), 3.49 (tt, J=9.70, 4.10Hz, 1H) 3.62 (td, J=10.40, 5.90Hz 1H), 7.39 (s, 1H), 7.43 (d, J=8.60Hz, 1H), 8.05 (d, J=5.30Hz, 2H) | 492 | 490 | (R) | – |
| A-112 | 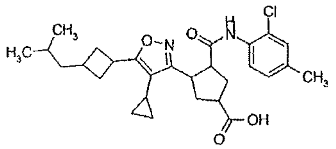 | (400 MHz, DMSO-d6) 0.35 - 0.44 (m, 2H), 0.72 - 0.82 (m, 2H), 0.83 (t, J=7.83 Hz, 6H), 1.30 (t, J=6.73Hz, 2H), 1.36 - 1.43 (m, 1H), 1.48 - 1.55 (m, 1H), 1.79 - 1.89 (m, 2H), 1.96 (dd, J=22.05, 11.25Hz, 1H), 2.10 (dt, J=15.88, 6.45Hz, 1H), 2.26 (s, 3H), 2.30 - 2.44 (m, 4H), 2.45 - 2.47 (m, 1H), 2.95 - 3.05 (m, 1H), 3.31 - 3.33 (m, 1H), 3.40 (q, J=8.67Hz, 1H), 3.51 - 3.61 (m, 2H), 7.09 (dd, J=8.60, 1.54Hz, 1H), 7.28 (d, J=1.10Hz, 1H), 7.46 (d, J=8.16Hz, 1H), 9.44 (s, 1H) | 499 | 497 | AUX-H Without using | Dimethyl 4-oxo-cyclopentane-trans-1,2-dicarboxylate was used as a material. |
| A-113 | 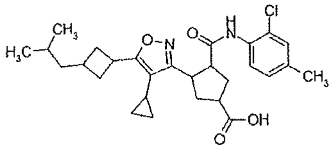 | (400 MHz, DMSO-d6) 0.40 (d, J=3.09 Hz, 2H), 0.78 (dd, J=8.16, 1.76Hz, 2H), 0.85 (dd, J=6.51, 4.08Hz, 6H), 1.30 (t, J=6.84Hz, 2H), 1.41 (td, J=9.32, 5.15Hz, 1H), 1.48 - 1.55 (m, 1H), 1.83 (t, J=10.59Hz, 2H), 2.02 (dt, J=30.80, 8.66Hz, 2H), 2.27 (d, J=6.62Hz, 3H), 2.37 (tt, J=17.53, 6.40Hz, 4H), 2.98 (t, J=7.83Hz, 1H), 3.38 (t, J=9.26Hz, 2H), 3.51 - 3.63 (m, 2H), 7.10 (d, J=7.94Hz, 1H), 7.28 (s, 1H), 7.47 (d, J=6.62Hz, 1H), 9.46 (s, 1H) | 499 | 497 | AUX-H Without using | Dimethyl 4-oxo-cyclopentane-trans-1,2-dicarboxylate was used as a material<br>Diastereomer of A-112 |

Fig. 33

| Example | Structure | NMR | MS M+H | MS M-H | Stereochemistry of AUX-H | Materials or Stereochemistry |
|---|---|---|---|---|---|---|
| C-5 | 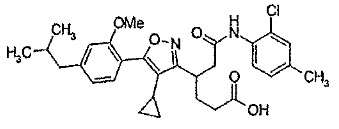 | (400 MHz, CDCl3) 0.12 - 0.20 (m, 1H), 0.25 - 0.33 (m, 1H), 0.61 - 0.75 (m, 2H), 0.93 (d, J=6.80Hz, 6H), 1.51 - 1.62 (m, 1H), 1.84 - 1.98 (m, 1H), 2.10 - 2.34 (m, 2H), 2.27 (s, 3H), 2.44 - 2.56 (m, 2H), 2.51 (d, J=7.20Hz, 2H), 2.81 (dd, J=14.40, 5.60Hz, 1H), 3.10 (dd, J=14.40, 9.20Hz, 1H), 3.69 - 3.82 (m, 1H), 3.77 (s, 3H), 6.73 (s, 1H), 6.79 (d, J=8.00, 1H), 7.02 (d, J=8.40Hz, 1H), 7.14 (s, 1H), 7.27 (d, J=8.00Hz, 1H), 7.89 (s, 1H), 8.09 (d, J=8.40Hz, 1H) | 539 | 537 | ( R ) | – |
| C-6 | 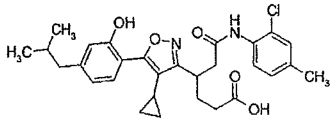 | (400 MHz, CDCl3) 0.25 - 0.35 (m, 1H), 0.44 - 0.54 (m, 1H), 0.82 - 0.99 (m, 2H), 0.92 (d, J=6.80Hz, 6H), 1.58 - 1.69 (m, 1H), 1.83 - 1.96 (m, 1H), 2.12 - 2.32 (m, 2H), 2.27 (s, 3H), 2.40 - 2.53 (m, 2H), 2.46 (d, J=6.80Hz, 2H), 2.81 (dd, J=14.40, 5.20Hz, 1H), 3.09 (dd, J=14.40, 9.20Hz, 1H), 3.76 - 3.87 (m, 1H), 6.78 (d, J=8.00Hz, 1H), 6.81 (s, 1H), 7.02 (d, J=8.40Hz, 1H), 7.14 (s, 1H), 7.50 (d, J=8.40Hz, 1H), 7.78 (s, 1H), 8.08 (d, J=8.80Hz, 1H) | 525 | 523 | ( R ) | – |
| A-114 | 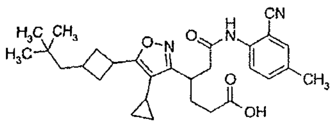 | (400 MHz, CDCl3) 0.38 - 0.46 (m, 1H), 0.49 - 0.56 (m, 1H), 0.80 - 0.85 (m, 2H), 0.86 (s, 9H), 1.38 (d, J=5.10Hz, 2H), 1.41 (tt, J=6.50, 1.70Hz, 1H), 1.96 - 2.23 (m, 4H), 2.32 (s, 3H), 2.35 - 2.45 (m, 5H), 2.79 (dd, J=14.80, 5.70Hz, 1H), 3.03 (dd, J=15.00, 8.80Hz, 1H), 3.51 (ddd, J=18.00, 10.10, 7.30Hz, 1H), 3.66 (dt, J=14.70, 6.50Hz, 1H), 7.33 (dd, J=7.50, 2.00Hz, 1H), 7.35 (d, J=1.80Hz, 1H), 7.96 (s, 1H), 8.05 (d, J=8.20Hz, 1H) | 492 | 490 | ( R ) | – |
| A-115 | 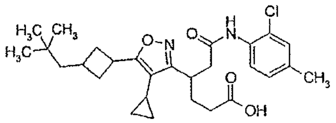 | (400 MHz, CDCl3) 0.35 - 0.42 (m, 1H), 0.44 - 0.49 (m, 1H), 0.78 - 0.91 (m, 11H), 1.31 - 1.40 (m, 3H), 1.91 - 2.22 (m, 4H), 2.27 (s, 3H), 2.31 - 2.46 (m, 5H), 2.74 (dd, J=14.19, 5.12Hz, 1H), 2.95 - 3.06 (m, 1H), 3.45 - 3.54 (m, 1H), 3.60 - 3.67 (m, 1H), 7.02 (d, J=8.37Hz, 1H), 7.13 (s, 1H), 7.78 (s, 1H), 8.06 (d, J=8.37Hz, 1H) | 501 | 499 | ( S ) | – |

Fig. 34

| Example | Structure | NMR | MS M+H | MS M-H | Stereochemistry of AUX-H | Materials or Stereochemistry |
|---|---|---|---|---|---|---|
| B-5 | 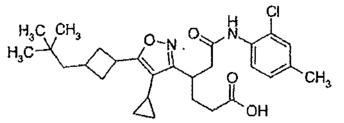 | (400 MHz, CDCl3) 0.31 - 0.38 (m, 1H), 0.40 - 0.48 (m, 1H), 0.78 - 0.89 (m, 11H), 1.31 - 1.39 (m, 1H), 1.44 (d, J=6.98Hz, 2H), 2.00 - 2.22 (m, 4H), 2.27 (s, 3H), 2.32 - 2.51 (m, 4H), 2.63 - 2.80 (m, 2H), 2.97 - 3.08 (m, 1H), 3.59 - 3.69 (m, 2H), 7.02 (d, J=8.37Hz, 1H), 7.13 (s, 1H), 7.80 (s, 1H), 8.07 (d, J=8.37Hz, 1H) | 501 | 499 | (S) | − |
| C-7 | 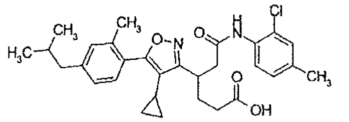 | (400 MHz, CDCl3) 0.10 - 0.20 (m, 1H), 0.22 - 0.32 (m, 1H), 0.65 - 0.79 (m, 2H), 0.92 (d, J=7.20Hz, 6H), 1.49 - 1.60 (m, 1H), 1.82 - 1.96 (m, 1H), 2.10 - 2.38 (m, 2H), 2.21 (s, 3H), 2.28 (s, 3H), 2.41 - 2.57 (m, 2H), 2.48 (d, J=8.00Hz, 2H), 2.83 (dd, J=14.00, 5.60Hz, 1H), 3.09 (dd, J=14.00, 9.20Hz, 1H), 3.70 - 3.81 (m, 1H), 6.98 - 7.07 (m, 3H), 7.14 (s, 1H), 7.23 (d, J=7.60Hz, 1H), 7.86 (s, 1H), 8.09 (d, J=8.40Hz, 1H) | 523 | 521 | (R) | − |
| A-116 | 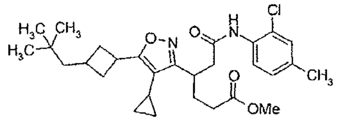 | (400 MHz, CDCl3) 0.36 - 0.41 (m, 1H), 0.44 - 0.49 (m, 1H), 0.80 - 0.85 (m, 2H), 0.87 (s, 9H), 1.32 - 1.39 (m, 3H), 1.94 - 2.18 (m, 4H), 2.27 (s, 3H), 2.32 - 2.44 (m, 5H), 2.72 (dd, J=14.40, 5.60Hz, 1H), 3.00 (dd, J=14.40, 9.60Hz, 1H), 3.45 - 3.54 (m, 1H), 3.56 - 3.63 (m, 1H), 3.65 (s, 3H), 7.02 (dd, J=8.40, 1.60Hz, 1H), 7.14 (d, J=1.20Hz, 1H), 7.73 (s, 1H), 8.09 (d, J=8.40Hz, 1H) | 515 | 513 | (R) | − |
| A-117 | 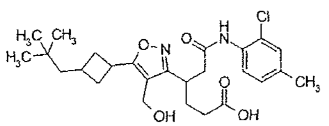 | (400 MHz, CDCl3) 0.85 (s, 9H), 1.37 (d, J=6.40Hz, 2H), 2.00 - 2.07 (m, 3H), 2.18 (dt, J=20.10, 6.90Hz, 1H), 2.26 (s, 3H), 2.32 - 2.49 (m, 5H), 2.87 (dd, J=14.40, 4.50Hz, 1H), 3.02 (dd, J=15.10, 10.90Hz, 1H), 3.43 - 3.52 (m, 1H), 3.55 - 3.62 (m, 1H), 4.45 (dd, J=20.00, 12.90Hz, 2H), 6.98 (d, J=8.60Hz, 1H), 7.12 (s, 1H), 7.71 (s, 1H), 7.91 (d, J=8.40Hz, 1H) | 491 | 489 | (R) | − |

Fig. 35

| Example | Structure | NMR | MS M+H | MS M-H | Stereochemistry of AUX-H | Materials or Stereochemistry |
|---|---|---|---|---|---|---|
| A-118 | 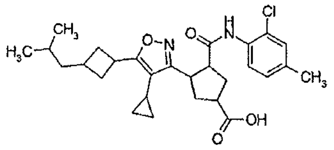 | (400 MHz, DMSO-d6) 0.39 (s, 2H), 0.78 (dd, J=8.27, 2.10Hz, 2H), 0.85 (dd, J=6.51, 4.08Hz, 6H), 1.30 (t, J=6.84Hz, 2H), 1.39 (t, J=5.29Hz, 1H), 1.48 - 1.55 (m, 1H), 1.82 - 1.87 (m, 2H), 1.98 - 2.09 (m, 2H), 2.27 (d, J=6.84Hz, 3H), 2.33 - 2.41 (m, 4H), 2.97 - 3.01 (m, 1H), 3.38 - 3.42 (m, 2H), 3.51 - 3.59 (m, 2H), 7.08 - 7.11 (m, 1H), 7.28 (s, 1H), 7.46 - 7.48 (m, 1H), 9.44 (s, 1H), 12.27 (brs, 1H) | 499 | 497 | AUX-H Without using | Dimethyl 4-oxo-cyclopentane-trans-1,2-dicarboxylate was used as a material<br>Mixture of Enantiomer of A-112 and Enantiomer of A-113 |
| A-119 | 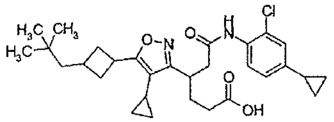 | (400 MHz, CDCl3) 0.36 - 0.47 (m, 2H), 0.60 - 0.64 (m, 2H), 0.80 - 0.95 (m, 13H), 1.32 - 1.39 (m, 3H), 1.77 - 1.84 (m, 1H), 1.96 - 2.16 (m, 4H), 2.36 - 2.39 (m, 5H), 2.74 (dd, J=14.22, 5.18Hz, 1H), 3.01 (dd, J=14.11, 9.70Hz, 1H), 3.47 - 3.52 (m, 1H), 3.64 (s, 1H), 6.91 (dd, J=8.60, 1.98Hz, 1H), 7.02 (d, J=1.98Hz, 1H), 7.82 (s, 1H), 8.03 (d, J=8.60Hz, 1H) | 527 | 525 | ( R ) | – |
| A-120 | 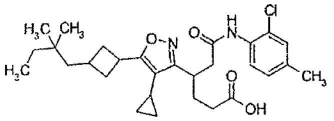 | (400 MHz, DMSO-d6) 0.34 - 0.42 (m, 1H), 0.42 - 0.54 (m, 1H), 0.67 - 0.86 (m, 13H), 1.13 - 1.22 (m, 2H), 1.28 -1.36 (m, 2H), 1.36 - 1.46 (m, 1H), 1.78 - 1.97 (m, 2H), 2.11 - 2.23 (m, 2H), 2.23 - 2.29 (m, 3H), 2.29 - 2.42 (m, 2H), 2.61 - 2.88 (m, 3H), 3.40 - 3.47 (m, 1H), 3.47 - 3.59 (m, 1H), 7.07 (d, J=52.34Hz, 1H), 7.27 (brs, 1H), 7.42 (d, J=40.01Hz, 1H), 9.42 (brs, 1H), 12.03 (brs, 1H) | 515 | 513 | ( R ) | – |
| A-121 | 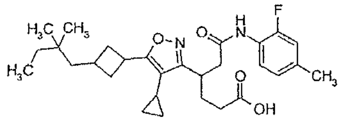 | (400 MHz, DMSO-d6) 0.33 - 0.44 (m, 1H), 0.44 - 0.55 (m, 1H), 0.71 - 0.86 (m, 11H), 1.12 - 1.24 (m, 2H), 1.27 - 1.35 (m, 2H), 1.35 - 1.47 (m, 1H), 1.80 - 1.95 (m, 4H), 2.12 - 2.22 (m, 2H), 2.22 - 2.30 (m, 3H), 2.29 - 2.44 (m, 3H), 2.62 - 2.89 (m, 2H), 3.38 - 3.63 (m, 2H), 6.87 - 6.98 (m, 1H), 7.00 - 7.09 (m, 1H), 7.53 - 7.66 (m, 1H), 9.66 (brs, 1H) | 499 | 497 | ( R ) | – |

Fig. 36

| Example | Structure | NMR | MS M+H | MS M-H | Stereochemistry of AUX-H | Materials or Stereochemistry |
|---|---|---|---|---|---|---|
| A-122 | 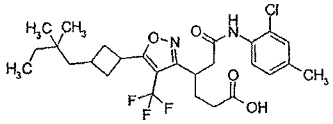 | (400 MHz, DMSO-d6) 0.71 - 0.85 (m, 9H), 1.12 - 1.22 (m, 2H), 1.29 - 1.38 (m, 2H), 1.84 - 2.02 (m, 4H), 2.14 - 2.24 (m, 2H), 2.24 - 2.30 (m, 3H), 2.37 - 2.48 (m, 3H), 2.76 - 2.88 (m, 2H), 3.40 - 3.51 (m, 1H), 3.62 - 3.79 (m, 1H), 7.06 - 7.14 (m, 1H), 7.29 (brs, 1H), 7.40 - 7.48 (m, 1H), 9.53 (brs, 1H), 12.13 (brs 1H) | 543 | 541 | ( R ) | − |
| A-123 | 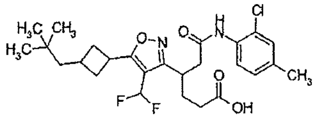 | (400 MHz, CDCl3) 0.85 (s, 9H), 1.37 (d, J=6.30Hz, 2H), 2.01 - 2.21 (m, 4H), 2.26 (s, 3H), 2.31 - 2.50 (m, 5H), 2.76 (dd, J=15.10, 5.30Hz, 1H), 2.96 (dd, J=14.07, 8.80Hz, 1H), 3.48 - 3.62 (m, 2H), 6.66 (t, J=54.70Hz, 1H), 7.01 (d, J=8.80Hz, 1H), 7.13 (s, 1H), 7.61 (s, 1H), 8.07 (d, J=8.10Hz, 1H) | 511 | 509 | ( R ) | − |
| A-124 | 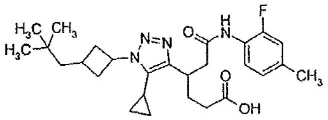 | (400 MHz, CDCl3) 0.50 - 0.51 (m, 1H), 0.83 - 0.85 (m, 1H), 0.87 (s, 9H), 0.96 - 0.98 (m, 2H), 1.46 - 1.51 (m, 3H), 2.12 - 2.14 (m, 2H), 2.21 - 2.45 (m, 8H), 2.58 - 2.68 (m, 2H), 2.80 (dd, J=13.56, 4.74Hz, 1H), 3.00 - 3.06 (m, 1H), 3.56 - 3.57 (m, 1H), 4.75 - 4.79 (m, 1H), 6.79 (t, J=10.37 Hz, 2H), 7.76 (t, J=8.16Hz, 1H), 8.08 (s, 1H) | 485 | 483 | ( R ) | − |
| C-8 | 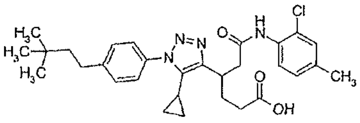 | (400 MHz, CDCl3) 0.29 - 0.40 (m, 1H), 0.60 - 0.70 (m, 1H), 0.75 - 0.92 (m, 2H), 0.98 (s, 9H), 1.48 - 1.58 (m, 2H), 1.63 - 1.73 (m, 1H), 2.09 - 2.32 (m, 2H), 2.26 (s, 3H), 2.32 - 2.49 (m, 2H), 2.59 - 2.70 (m, 2H), 2.85 (dd, J=14.00, 4.80 Hz, 1H), 3.12 (dd, J=14.00, 10.00Hz, 1H), 3.58 - 3.68 (m, 1H), 7.00 (d, J=8.40 Hz, 1H), 7.11 (s, 1H), 7.29 (d, J=8.40Hz, 2H), 7.38 (d, J=8.40Hz, 2H), 7.75 (s, 1H), 7.97 (d, J=8.40Hz, 1H) | 537 | 535 | ( R ) | − |

Fig. 37
| Example | Structure | NMR | MS M+H | MS M-H | Stereochemistry of AUX-H | Materials or Stereochemistry |
|---|---|---|---|---|---|---|
| C-9 | 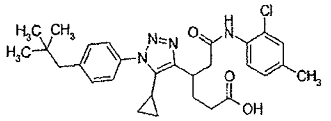 | (400 MHz, CDCl3) 0.30 - 0.39 (m, 1H), 0.60 - 0.69 (m, 1H), 0.74 - 0.98 (m, 2H), 0.93 (s, 9H), 1.64 - 1.75 (m, 1H), 2.11 - 2.31 (m, 2H), 2.26 (s, 3H), 2.32 - 2.49 (m, 2H), 2.57 (s, 2H), 2.86 (dd, J=13.60, 4.80Hz, 1H), 3.12 (dd, J=13.60, 10.00Hz, 1H), 3.58 - 3.70 (m, 1H), 7.00 (d, J=8.00Hz, 1H), 7.11 (s, 1H), 7.23 (d, J=8.00Hz, 2H), 7.38 (d, J=8.00Hz, 2H), 7.76 (s, 1H), 7.97 (d, J=8.00Hz, 1H) | 523 | 521 | (R) | – |
| A-125 | 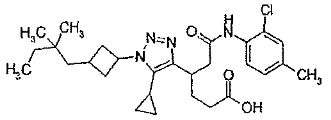 | (400 MHz, DMSO-d6) 0.41 - 0.55 (m, 1H), 0.74 - 0.86 (m, 11H), 0.86 - 0.99 (m, 2H), 1.16 - 1.25 (m, 2H), 1.35 - 1.43 (m, 2H), 1.47 - 1.61 (m, 1H), 1.82 - 1.96 (m, 2H), 2.00 - 2.19 (m, 5H), 2.19 - 2.30 (m, 3H), 2.56 - 2.85 (m, 4H), 4.79 - 4.97 (m, 1H), 7.02 - 7.12 (m, 1H), 7.22 - 7.28 (m, 1H), 7.32 - 7.39 (m, 1H), 9.20 - 9.40 (m, 1H), 11.86 - 12.09 (m, 1H) | 515 | 513 | (R) | – |
| A-126 | 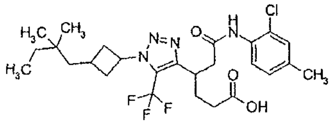 | (400 MHz, DMSO-d6) 0.72 - 0.84 (m, 11H), 1.16 - 1.28 (m, 2H), 1.35 - 1.43 (m, 2H), 1.87 - 2.01 (m, 2H), 2.01 - 2.12 (m, 1H), 2.18 - 2.37 (m, 5H), 2.59 - 2.73 (m, 2H), 2.73 - 2.98 (m, 2H), 3.42 - 3.55 (m, 1H), 4.80 - 5.00 (m, 1H), 7.03 - 7.10 (m, 1H), 7.23 - 7.28 (m, 1H), 7.32 - 7.42 (m, 1H), 9.38 - 9.54 (m, 1H), 12.05 (brs, 1H) | 543 | 541 | (R) | – |
| A-127 | 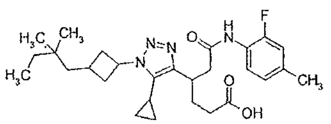 | (400 MHz, DMSO-d6) 0.42 - 0.56 (m, 1H), 0.73 - 0.83 (m, 13H), 0.88 - 0.97 (m, 1H), 1.14 - 1.26 (m, 2H), 1.34 - 1.41 (m, 2H), 1.50 - 1.61 (m, 2H), 1.77 - 1.92 (m, 1H), 1.96 - 2.09 (m, 1H), 2.09 - 2.18 (m, 2H), 2.18 - 2.26 (m, 3H), 2.55 - 2.81 (m, 5H), 4.78 - 4.93 (m, 1H), 6.83 - 6.94 (m, 1H), 6.94 - 7.03 (m, 1H), 7.44 - 7.60 (m, 1H), 9.49 (brs, 1H), 11.98 (brs, 1H) | 499 | 497 | (R) | – |

Fig. 38
| Example | Structure | NMR | MS M+H | MS M-H | Stereochemistry of AUX-H | Materials or Stereochemistry |
|---|---|---|---|---|---|---|
| A-128 | 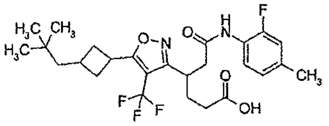 | (400 MHz, CDCl3) 0.85 (s, 9H), 1.35 (d, J=6.30Hz, 2H), 1.97 - 2.14 (m, 4H), 2.26 (s, 3H), 2.33 (t, J=7.40 Hz, 2H), 2.37 - 2.48 (m, 3H), 2.72 (dd, J=15.00, 5.90 Hz, 1H), 2.94 (dd, J=14.90, 8.60Hz, 1H), 3.52 - 3.65 (m, 2H), 6.83 (d, J=5.60Hz, 1H), 6.85 (s, 1H), 7.53 (s, 1H), 7.99 (t, J=8.10Hz, 1H) | 513 | 511 | ( R ) | – |
| A-129 | 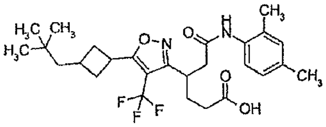 | (400 MHz, CDCl3) 0.86 (s, 9H), 1.37 (d, J=6.00Hz, 2H), 2.00 - 2.20 (m, 4H), 2.13 (s, 3H), 2.25 (s, 3H), 2.37 - 2.48 (m, 5H), 2.71 (dd, J=14.20, 6.00Hz, 1H), 2.95 (dd, J=14.20, 9.10Hz, 1H), 3.56 - 3.68 (m, 2H), 6.87 (s, 1H), 6.88 (d, J=8.80Hz, 1H), 7.13 (s, 1H), 7.49 (d, J=8.80Hz, 1H) | 509 | 507 | ( R ) | – |
| A-130 | 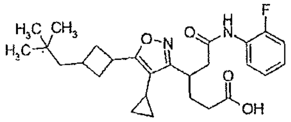 | (400 MHz, CDCl3) 0.35 - 0.41 (m, 1H), 0.44 - 0.50 (m, 1H), 0.80 - 0.84 (m, 2H), 0.85 (s, 9H), 1.37 (d, J=5.80Hz, 2H), 1.93 - 2.21 (m, 4H), 2.30 - 2.44 (m, 5H), 2.74 (dd, J=14.20, 5.30Hz, 1H), 2.98 (dd, J=14.40, 9.30Hz, 1H), 3.49 (ddd, J=18.40, 9.60, 6.30Hz, 1H), 3.64 (ddd, J=14.30, 7.00, 5.60Hz, 1H), 6.97 - 7.09 (m, 3H), 7.72 (s, 1H), 8.17 (t, J=7.70Hz, 1H) | 471 | 469 | ( R ) | – |

Fig. 39
| Example | Structure | NMR | MS M+H | MS M-H | Stereochemistry of AUX-H | Materials or Stereochemistry |
|---|---|---|---|---|---|---|
| A-131 | 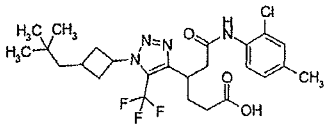 | (400 MHz, DMSO-d6) 0.80 - 0.92 (m, 9H), 1.34 - 1.46 (m, 2H), 1.81 - 2.02 (m, 2H), 2.02 - 2.17 (m, 2H), 2.17 - 2.38 (m, 6H), 2.59 - 2.76 (m, 2H), 2.76 - 2.94 (m, 2H), 3.39 - 3.55 (m, 1H), 4.80 - 5.01 (m, 1H), 7.02 - 7.13 (m, 1H), 7.21 - 7.30 (m, 1H), 7.32 - 7.41 (m, 1H), 9.32 - 9.54 (m, 1H), 11.92 - 12.23 (m, 1H) | 529 | 527 | ( R ) | – |
| A-132 | 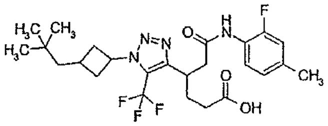 | (400 MHz, DMSO-d6) 0.80 - 0.89 (m, 9H), 1.84 - 1.98 (m, 2H), 2.03 - 2.15 (m, 2H), 2.18 - 2.34 (m, 6H), 2.58 - 2.68 (m, 2H), 2.79 - 2.86 (m, 2H), 3.36 - 3.50 (m, 3H), 4.83 - 4.94 (m, 1H), 6.84 - 6.93 (m, 1H), 6.97 - 7.05 (m, 1H), 7.36 - 7.65 (m, 1H), 9.45 - 9.73 (m, 1H), 11.94 - 12.15 (m, 1H) | 513 | 511 | ( R ) | – |
| A-133 | 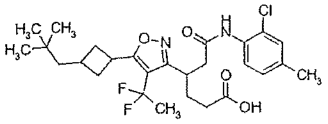 | (400 MHz, CDCl3) 0.85 (s, 9H), 1.36 (d, J=6.00Hz, 2H), 1.86 (t, J=18.50Hz, 3H), 1.97 - 2.17 (m, 4H), 2.26 (s, 3H), 2.34 - 2.46 (m, 5H), 2.71 (dd, J=14.70, 5.30Hz, 1H), 3.00 (dd, J=14.07, 9.10Hz, 1H), 3.50 - 3.60 (m, 2H), 7.00 (d, J=7.90Hz, 1H), 7.13 (s, 1H), 7.58 (brs, 1H), 8.06 (d, J=8.60Hz, 1H) | 525 | 523 | ( R ) | – |

Fig. 40
| Example | Structure | NMR | MS | | Stereochemistry of AU X-H | Materials or Stereochemistry |
|---|---|---|---|---|---|---|
| | | | M+H | M-H | | |
| A-134 | 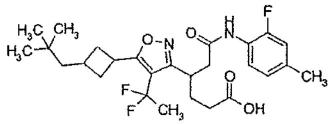 | (400 MHz, CDCl3) 0.85 (s, 9H), 1.36 (d, J=5.30Hz, 2H), 1.87 (t, J=18.50Hz, 3H), 1.97 - 2.16 (m, 4H), 2.27 (s, 3H), 2.34 - 2.46 (m, 5H), 2.71 (dd, J=14.80, 5.20Hz, 1H), 2.97 (dd, J=14.70, 9.50Hz, 1H), 3.50 - 3.61 (m, 2H), 6.83 - 6.87 (m, 2H), 7.38 (brs, 1H), 7.98 (t, J=8.50Hz, 1H) | 509 | 507 | ( R ) | – |
| A-135 | 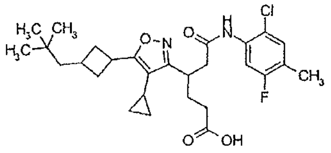 | (400 MHz, CDCl3) 0.37 - 0.49 (m, 2H), 0.81 - 0.87 (m, 2H), 0.81 (s, 9H), 1.31 - 1.36 (m, 1H), 1.38 (d, J=7.50Hz, 2H), 2.02 - 2.15 (m, 7H), 2.37 - 2.42 (m, 5H), 2.75 (dd, J=14.34, 5.07Hz, 1H), 3.02 (dd, J=14.34, 9.48Hz, 1H), 3.45 - 3.52 (m, 1H), 3.62 - 3.63 (m, 1H), 7.12 (d, J=7.50Hz, 1H), 7.86 (s, 1H), 8.03 (d, J=11.47Hz, 1H) | 519 | 517 | ( R ) | – |
| A-136 | 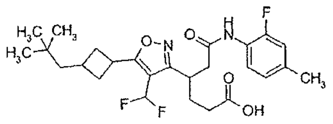 | (400 MHz, CDCl3) 0.85 (s, 9H), 1.38 (d, J=6.40Hz, 2H), 2.04 - 2.12 (m, 4H), 2.28 (s, 3H), 2.37 - 2.48 (m, 5H), 2.78 (dd, J=15.00, 5.51Hz, 1H), 2.95 (dd, J=14.89, 9.15Hz, 1H), 3.55 - 3.59 (m, 2H), 6.71 (t, J=56.59Hz, 1H), 6.83 - 6.87 (m, 2H), 7.56 (brs, 1H), 7.98 (t, J=8.38Hz, 1H) | 495 | 493 | ( R ) | – |

Fig. 41
| Example | Structure | NMR | MS | | Stereochemistry of AU X-H | Materials or Stereochemistry |
|---|---|---|---|---|---|---|
| | | | M+H | M-H | | |
| A-137 | 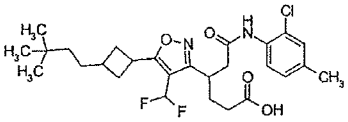 | (400 MHz, CDCl3) 0.85 (s, 9H), 1.03 - 1.07 (m, 2H), 1.34 - 1.40 (m, 2H), 1.92 - 2.02 (m, 2H), 2.05 - 2.20 (m, 3H), 2.26 (s, 3H), 2.34 - 2.45 (m, 4H), 2.76 (dd, J=15.10, 5.30Hz, 1H), 2.97 (dd, J=15.20, 8.50Hz, 1H), 3.48 - 3.61 (m, 2H), 6.67 (t, J=54.50Hz, 1H), 7.01 (d, J=8.40Hz, 1H), 7.13 (s, 1H), 7.62 (s, 1H), 8.07 (d, J=8.40Hz, 1H) | 525 | 523 | ( R ) | – |
| A-138 | 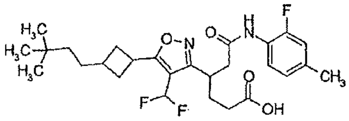 | (400 MHz, CDCl3) 0.85 (s, 9H), 1.03 - 1.07 (m, 2H), 1.34 - 1.40 (m, 2H), 1.93 - 2.22 (m, 5H), 2.27 (s, 3H), 2.36 - 2.46 (m, 4H), 2.75 (dd, J=14.90, 5.60Hz, 1H), 2.93 (dd, J=15.00, 9.00Hz, 1H), 3.49 - 3.63 (m, 2H), 6.67 (t, J=54.50Hz, 1H), 6.77 (s, 1H), 6.86 (d, J=16.70Hz, 1H), 7.41 (s, 1H), 8.00 (t, J=8.30Hz, 1H) | 509 | 507 | ( R ) | – |

Fig. 42

| Example | in vitro EC50(μM) | |
|---|---|---|
| | LUC | |
| | Human | Mouse |
| A-1 | 0.024 | 0.024 |
| A-2 | 0.053 | 0.042 |
| A-3 | 0.055 | 0.051 |
| A-4 | 0.058 | 0.044 |
| A-5 | 0.13 | 0.11 |
| A-6 | 0.25 | 0.14 |
| A-7 | 0.064 | 0.041 |
| A-8 | 0.33 | 0.20 |
| A-9 | 0.39 | 0.23 |
| A-10 | 0.033 | 0.025 |
| A-11 | 0.029 | 0.032 |
| A-12 | 0.094 | 0.060 |
| A-13 | 0.018 | 0.016 |
| A-14 | 0.088 | 0.067 |
| A-15 | 0.32 | 0.41 |
| A-16 | 0.055 | 0.040 |
| A-17 | 0.064 | 0.054 |
| A-18 | 0.072 | 0.046 |
| A-19 | 0.037 | 0.018 |
| A-20 | 0.020 | 0.039 |
| A-21 | 0.034 | 0.049 |
| A-22 | 0.088 | 0.096 |
| A-23 | 0.079 | 0.064 |
| A-24 | 0.020 | 0.032 |
| A-25 | 0.098 | 0.054 |
| A-26 | 0.065 | 0.039 |
| A-27 | 0.094 | 0.098 |
| A-28 | 0.097 | 0.050 |

Fig. 43

| Example | in vitro EC50(μM) | |
|---|---|---|
| | LUC | |
| | Human | Mouse |
| A-29 | 0.060 | 0.030 |
| A-30 | 0.16 | 0.097 |
| A-31 | 0.26 | 0.21 |
| A-32 | 0.046 | 0.042 |
| A-33 | 0.78 | 0.72 |
| A-34 | >3.2 | 0.48 |
| A-35 | 1.8 | 1.1 |
| A-36 | 0.063 | 0.039 |
| A-37 | 0.10 | 0.076 |
| A-38 | 0.26 | 0.083 |
| A-39 | 0.021 | 0.036 |
| A-40 | 0.23 | 0.095 |
| A-41 | >3.2 | 2.0 |
| A-42 | 0.25 | 0.098 |
| A-43 | 0.088 | 0.057 |
| A-44 | 0.12 | 0.12 |
| A-45 | 0.42 | 0.14 |
| A-46 | 0.092 | 0.087 |
| A-47 | 0.27 | 0.12 |
| A-48 | 0.064 | 0.049 |
| A-49 | 1.2 | 0.23 |
| A-50 | 0.17 | 0.12 |
| A-51 | 0.11 | 0.069 |
| A-52 | 0.54 | 0.53 |
| A-53 | 0.033 | 0.037 |
| A-54 | 0.065 | 0.086 |
| A-55 | 0.063 | 0.094 |
| A-56 | 0.092 | 0.056 |

Fig. 44

| Example | in vitro EC50(μM) | |
|---|---|---|
| | LUC | |
| | Human | Mouse |
| A-57 | 0.044 | 0.028 |
| A-58 | 0.024 | 0.034 |
| A-59 | 0.029 | 0.034 |
| A-60 | 0.024 | 0.040 |
| A-61 | 0.96 | 0.95 |
| A-62 | 0.081 | 0.080 |
| A-63 | 0.21 | 0.056 |
| A-64 | 0.077 | 0.027 |
| A-65 | 0.11 | 0.15 |
| A-66 | 0.053 | 0.036 |
| A-67 | 0.043 | 0.026 |
| A-68 | 0.077 | 0.055 |
| A-69 | 0.17 | 0.13 |
| A-70 | 0.10 | 0.076 |
| A-71 | 0.39 | 0.14 |
| A-72 | 0.058 | 0.049 |
| A-73 | 0.66 | 0.18 |
| A-74 | 1.1 | 0.50 |
| A-75 | 0.027 | 0.039 |
| A-76 | 0.045 | 0.043 |
| A-77 | 0.057 | 0.031 |
| A-78 | 0.030 | 0.016 |
| A-79 | 0.041 | 0.050 |
| A-80 | 0.16 | 0.13 |
| A-81 | 1.1 | 0.84 |
| A-82 | 0.071 | 0.065 |
| A-83 | 0.53 | 0.19 |
| B-1 | 0.025 | 0.037 |

Fig. 45

| Example | in vitro EC50(μM) | |
|---|---|---|
| | LUC | |
| | Human | Mouse |
| B-2 | 0.087 | 0.14 |
| A-84 | 0.052 | 0.040 |
| A-85 | 0.029 | 0.047 |

Fig. 46

| Example | in vitro EC50(μM) | |
|---|---|---|
| | LUC | |
| | Human | Mouse |
| A-86 | 0.089 | 0.089 |
| A-87 | 0.60 | 0.71 |
| A-88 | >3.2<br>(82%) | 2.9 |
| A-89 | 0.65 | 0.12 |
| B-3 | 0.048 | 0.060 |
| B-4 | 0.32 | 0.34 |
| C-1 | 0.044 | 0.032 |
| C-2 | 0.27 | 0.26 |
| D-1 | 0.073 | 0.052 |
| D-2 | 0.21 | 0.31 |
| A-90 | 0.026 | 0.032 |
| A-91 | 0.017 | 0.026 |
| A-92 | >20<br>(85%) | >20<br>(99%) |
| A-93 | 0.024 | 0.024 |
| A-94 | 0.018 | 0.011 |
| D-3 | 0.091 | 0.056 |
| D-4 | 0.22 | 0.18 |
| C-3 | 0.68 | 0.11 |
| C-4 | 0.12 | 0.24 |
| A-95 | 0.035 | 0.026 |
| A-96 | 0.021 | 0.028 |
| A-97 | 0.029 | 0.047 |
| A-98 | 0.39 | 0.50 |
| A-99 | 0.019 | 0.026 |
| A-100 | 0.029 | 0.042 |

Fig. 47

| Example | in vitro EC50(μM) | |
|---|---|---|
| | LUC | |
| | Human | Mouse |
| A-101 | 0.017 | 0.025 |
| A-102 | 0.027 | 0.037 |
| D-5 | 0.032 | 0.022 |
| D-6 | 0.21 | 0.39 |
| A-103 | 0.022 | 0.048 |
| A-104 | >8 (79%) | >8 (82%) |
| A-105 | 3.2 | 0.92 |
| A-106 | >8 (82%) | >8 (92%) |
| A-107 | 0.10 | 0.054 |
| A-108 | 0.17 | 0.16 |
| A-109 | 0.13 | 0.12 |
| A-110 | 0.065 | 0.045 |
| A-111 | 0.022 | 0.031 |
| A-112 | >8 (62%) | 1.9 |
| A-113 | 0.076 | 0.11 |
| C-5 | 5.6 | 1.6 |
| C-6 | 0.23 | 0.078 |
| A-114 | 0.021 | 0.025 |
| A-115 | 1.2 | 0.36 |
| B-5 | 2.4 | 0.40 |
| C-7 | 2.0 | 0.82 |
| A-116 | 0.024 | 0.018 |
| A-117 | 0.067 | 0.040 |
| A-118 | 0.48 | 0.19 |
| A-119 | 0.061 | 0.072 |

Fig. 48

| Example | in vitro EC50(μM) | |
|---|---|---|
| | LUC | |
| | Human | Mouse |
| A-120 | 0.014 | 0.022 |
| A-121 | 0.011 | 0.017 |
| A-122 | 0.028 | 0.030 |
| A-123 | 0.024 | 0.020 |
| A-124 | 0.019 | 0.022 |
| C-8 | 0.25 | 0.059 |
| C-9 | 0.020 | 0.019 |
| A-125 | 0.0099 | 0.017 |
| A-126 | 0.014 | 0.018 |
| A-127 | 0.013 | 0.021 |
| A-128 | 0.11 | 0.046 |
| A-129 | 0.051 | 0.038 |
| A-130 | 0.019 | 0.014 |
| A-131 | 0.022 | 0.021 |
| A-132 | 0.053 | 0.030 |
| A-133 | not tested | not tested |
| A-134 | not tested | not tested |
| A-135 | not tested | not tested |
| A-136 | not tested | not tested |
| A-137 | not tested | not tested |
| A-138 | not tested | not tested |

AMIDE COMPOUND AND MEDICINAL USE THEREOF

CROSS-REFERENCE TO A RELATED APPLICATION

This patent application claims the benefit of U.S. Provisional Patent Application No. 61/482,418, filed May 4, 2011.

TECHNICAL FIELD

The present invention relates to amide compounds and medicinal use thereof.

In particular, the present invention relates to compounds which can inhibit retinoid-related orphan receptor gamma (RORγ), thereby the differentiation and activation of T helper 17 (Th17) cells can be inhibited, and the production of interleukin-17 (IL-17) can be inhibited.

Specifically, the present invention relates to compounds for preventing or treating a disease related to Th17 cells, for example, autoimmune disease such as rheumatoid arthritis, psoriasis, inflammatory bowel disease such as Crohn's disease and ulcerative colitis, multiple sclerosis, systemic lupus erythematosus (SLE), ankylosing spondylitis, uveitis, polymyalgia rheumatica, and type I diabetes; allergic disease such as asthma; dry eye; fibrosis such as pulmonary fibrosis and primary biliary cirrhosis; and metabolic disease such as diabetes and medicinal use thereof.

BACKGROUND ART

RORγ is a nuclear receptor which is important for the differentiation and activation of Th17 cells. RORγt is also known as a splice variant of RORγ. RORγ and RORγt differ only in their N-terminal domains, and share the same ligand-binding domain and DNA-binding domain. It is reported that RORγ is expressed in other tissues besides Th17 cells. By inhibiting RORγ, the differentiation and activation of Th17 cells can be inhibited. IL-17 produced in Th17 cells is involved in the induction of a variety of chemokines, cytokines, metalloproteases and other inflammatory mediators, and the migration of neutrophil, hence, the inhibition of IL-17 may lead to the inhibition of such induction and migration. RORγ in adipose tissues is related to the regulation of adipogenesis, and by inhibiting RORγ, insulin resistance can be improved.

It is known that Th17 cells are involved in autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease; dry eye; and fibrosis such as pulmonary fibrosis and primary biliary cirrhosis.

As for rheumatoid arthritis, for example, it is reported that the administration of anti-IL-17 antibody can improve swelling and joint destruction associated with collagen-induced arthritis. Moreover, it is reported that swelling and joint destruction associated with collagen-induced arthritis can be improved in IL-17-deficient mice.

As for psoriasis, it is reported that in a clinical trial, the administration of anti-IL-17 antibody is effective in treating psoriasis.

As for inflammatory bowel disease such as Crohn's disease and ulcerative colitis, in a colitis model induced by the adaptive transfer of naive T-cells, the adaptive transfer of naive T-cells derived from RORγ-KO mice does not increase IL-17 in the mucosa, thereby the onset of colitis can be suppressed.

As for multiple sclerosis, the disease state of mouse experimental autoimmune encephalomyelitis model which is an animal model of multiple sclerosis can be suppressed in RORγt-KO mice.

As for systemic lupus erythematosus, it is reported that the onset of GBM nephritis model which is an animal model of glomerulonephritis can be inhibited in RORγt-KO mice. Nephritis associated with SLE may also be suppressed.

As for ankylosing spondylitis, it is reported that the administration of anti-IL-17 antibody is effective in treating ankylosing spondylitis.

As for uveitis, it is reported that the administration of anti-IL-17 antibody is effective in treating uveitis associated with Behcet's disease, sarcoidosis and Harada disease.

As for polymyalgia rheumatica, an efficacy of anti-IL-antibody in treatment of polymyalgia rheumatica is currently tested in a clinical trial.

As for type I diabetes, the disease state of NOD mice which is a type I diabetes model can be suppressed by the administration of anti-IL-17 antibody.

As for allergic disease such as asthma, in OVA-sensitized model, the attenuated eosinophilic pulmonary inflammation, the reduced numbers of CD4+ lymphocytes, and the decrease of Th2 cytokines/chemokines level are exhibited in RORγ-KO mice, that is, the allergenic reaction can be inhibited in RORγ-KO mice.

As for dry eye, it is reported that the Th17 cells increases in an animal model of dry eye, and an efficacy of anti-IL-17 antibody in dry eye patient is currently tested in a clinical trial.

As for fibrosis, in a bleomycin-induced pulmonary fibrosis model which is an animal model of pulmonary fibrosis, the administration of anti-IL-17 antibody can inhibit inflammation and fibrosis in lung and can increase survival of the animal.

As for primary biliary cirrhosis, it is reported that Th17 cells in the lesion area of a patient with a primary biliary cirrhosis increase, and an efficacy of an antibody to IL-23 which activates Th17 cells is currently tested in a clinical trial.

As for metabolic disease, the insulin resistance which is induced by feeding a high-fat diet can be suppressed in RORγ KO mice.

On the basis of these findings, RORγ antagonists are thought to be useful for preventing or treating autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease such as asthma; dry eye; fibrosis such as pulmonary fibrosis and primary biliary cirrhosis; and metabolic disease such as diabetes.

SUMMARY OF INVENTION

Technical Problem

An object of the present invention is to provide novel RORγ antagonists. Another object of the present invention is to provide medicaments of preventing or treating autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease such as asthma; dry eye; fibrosis such as pulmonary fibrosis and primary biliary cirrhosis; and metabolic disease such as diabetes.

Solution to Problem

The present inventors have found amide compounds which are RORγ antagonists, thereby have completed the present invention.

That is, the present invention provides the following aspects.

[01] A compound of formula [I-W]:

[I-W]

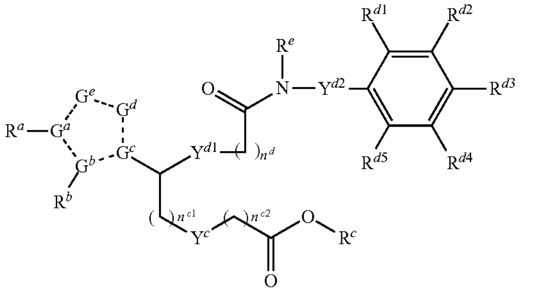

wherein

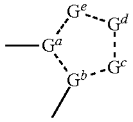
is
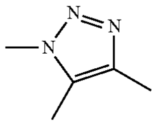
or
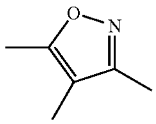
;

$R^a$ is (1) $C_{5-12}$ alkyl group which may be substituted with the same or different 1 to 5 substituents selected from Group A, or (2)

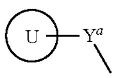

wherein $Y^a$ is (i) single bond, or (ii) $C_{1-6}$ alkylene group, cyclic moiety U is (i) $C_{3-7}$ cycloalkyl group which may be substituted with the same or different 1 to 5 substituents selected from Group A, (ii) spirocyclic cycloalkyl group which may be substituted with the same or different 1 to 5 substituents selected from Group A, or (iii) $C_{6-10}$ aryl group which may be substituted with the same or different 1 to 5 substituents selected from Group A;

$R^b$ is a group selected from the following (1) to (3):

(1) $C_{1-3}$ alkyl group which may be substituted with the same or different 1 to 5 substituents selected from Group A, (2) $C_{2-3}$ alkenyl group which may be substituted with the same or different 1 to 5 substituents selected from Group A, (3) $C_{3-7}$ cycloalkyl group which may be substituted with the same or different 1 to 5 substituents selected from Group A;

$R^c$ is (1) hydrogen atom, or (2) $C_{1-6}$ alkyl group;

$Y^c$ is a group selected from the following (1) to (7):

(1) single bond, (2) $C_{1-6}$ alkylene group which may be substituted with the same or different 1 to 5 substituents selected from Group A, (3) —$NR^{C1}$— wherein $R^{C1}$ is hydrogen atom or $C_{1-6}$ alkyl group, (4) —O—, (5) $C_{3-10}$ cycloalkylene group which may be substituted with the same or different 1 to 5 substituents selected from Group A, (6) $C_{6-10}$ arylene group which may be substituted with the same or different 1 to 5 substituents selected from Group A, (7) monocyclic heteroaromatic group which may be substituted with the same or different 1 to 5 substituents selected from Group A wherein the monocyclic heteroaromatic ring consists of carbon atoms and the same or different 1 to 4 hetero atoms selected from nitrogen atom, oxygen atom and sulfur atom, and is 3 to 7-membered;

$Y^{d1}$ is (1) single bond, or (2) $C_{1-6}$ alkylene group which may be substituted with the same or different 1 to 5 substituents selected from Group A; or alternatively both $Y^c$ and $Y^{d1}$ may be methine and be linked each other directly or via $C_{1-4}$ alkylene group to form $C_{3-7}$ cycloalkyl ring;

$Y^{d2}$ is (1) single bond, or (2) $C_{1-6}$ alkylene group;

$R^{d1}$, $R^{d2}$, $R^{d3}$, $R^{d4}$, and $R^{d5}$ are the same or different group selected from the following (1) to (7):

(1) hydrogen atom (2) halogen atom, (3) $C_{1-6}$ alkyl group which may be substituted with the same or different 1 to 5 substituents selected from Group A, (4) —$OR^{d10}$ wherein $R^{d10}$ is hydrogen atom or $C_{1-6}$ alkyl group which may be substituted with the same or different 1 to 5 substituents selected from Group A, (5) —$COOR^{d11}$ wherein $R^{d11}$ is hydrogen atom or $C_{1-6}$ alkyl group, (6) $C_{3-7}$ cycloalkyl group which may be substituted with the same or different 1 to 5 substituents selected from Group A, (7) cyano group, or alternatively $R^{d1}$ and $R^{d2}$, or $R^{d2}$ and $R^{d3}$ can be taken together to form a $C_{6-10}$ aryl ring fused to the benzene ring to which they are all attached wherein the $C_{6-10}$ aryl ring may be substituted with the same or different 1 to 4 substituents selected from Group A;

$R^e$ is (1) hydrogen atom, or (2) $C_{1-3}$ alkyl group, or alternatively $R^e$ and $R^{d1}$, or $R^e$ and $R^{d5}$ can be taken together to form $C_{1-4}$ alkylene;

$n^{c1}$ is an integer selected from 0 or 1 to 4, $n^{c2}$ is an integer selected from 0 or 1 to 3, $n^d$ is an integer selected from 0 or 1 to 3, Group A is (a) $C_{1-6}$ alkyl group, (b) halogen atom, and (c) —$OR^{A1}$ wherein $R^{A1}$ is hydrogen atom or $C_{1-6}$ alkyl group, or a pharmaceutically acceptable salt thereof.

[02] The compound of formula [I-W] according to [01]:

[I-W]

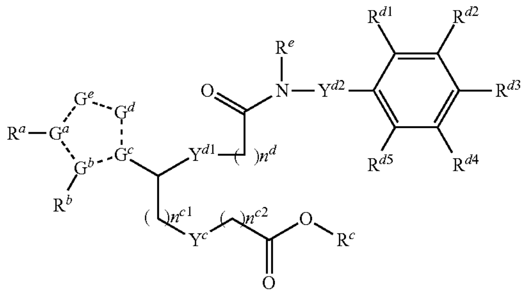

wherein

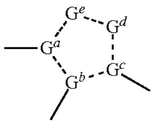 is 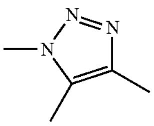 or 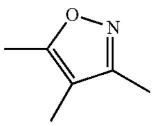 ;

$R^a$ is (1) $C_{5-12}$ alkyl group which may be substituted with the same or different 1 to 5 substituents selected from Group A, or (2)

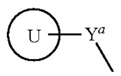

wherein $Y^a$ is (i) single bond, or (ii) $C_{1-6}$ alkylene group, cyclic moiety U is (i) $C_{3-7}$ cycloalkyl group which may be substituted with the same or different 1 to 5 substituents selected from Group A, or (ii) $C_{5-11}$ spirocyclic cycloalkyl group which may be substituted with the same or different 1 to 5 substituents selected from Group A;

$R^b$ is a group selected from the following (1) to (3):

(1) $C_{1-3}$ alkyl group which may be substituted with the same or different 1 to 5 substituents selected from Group A, (2) $C_{2-3}$ alkenyl group which may be substituted with the same or different 1 to 5 substituents selected from Group A, (3) $C_{3-7}$ cycloalkyl group which may be substituted with the same or different 1 to 5 substituents selected from Group A;

$R^c$ is (1) hydrogen atom, or (2) $C_{1-6}$ alkyl group;

$Y^c$ is a group selected from the following (1) to (7):

(1) single bond, (2) $C_{1-6}$ alkylene group which may be substituted with the same or different 1 to 5 substituents selected from Group A, (3) —$NR^{C1}$— wherein $R^{C1}$ is hydrogen atom or $C_{1-6}$ alkyl group, (4) —O—, (5) $C_{3-10}$ cycloalkylene group which may be substituted with the same or different 1 to 5 substituents selected from Group A, (6) $C_{6-10}$ arylene group which may be substituted with the same or different 1 to 5 substituents selected from Group A, (7) monocyclic heteroaromatic group which may be substituted with the same or different 1 to 5 substituents selected from Group A wherein the monocyclic heteroaromatic ring consists of carbon atoms and the same or different 1 to 4 hetero atoms selected from nitrogen atom, oxygen atom and sulfur atom, and is 3 to 7-membered;

$Y^{d1}$ is (1) single bond, or (2) $C_{1-6}$ alkylene group which may be substituted with the same or different 1 to 5 substituents selected from Group A;

$Y^{d2}$ is (1) single bond, or (2) $C_{1-6}$ alkylene group;

$R^{d1}$, $R^{d2}$, $R^{d3}$, $R^{d4}$, and $R^{d5}$ are the same or different group selected from the following (1) to (4):

(1) hydrogen atom (2) halogen atom, (3) $C_{1-6}$ alkyl group which may be substituted with the same or different 1 to 5 substituents selected from Group A, (4) —$OR^{d10}$ wherein $R^{d10}$ is hydrogen atom or $C_{1-6}$ alkyl group which may be substituted with the same or different 1 to 5 substituents selected from Group A, or alternatively $R^{d1}$ and $R^{d2}$, or $R^{d2}$ and $R^{d3}$ can be taken together to form a $C_{6-10}$ aryl ring fused to the benzene ring to which they are all attached wherein the $C_{6-10}$ aryl ring may be substituted with the same or different 1 to 4 substituents selected from Group A;

$n^{c1}$ is an integer selected from 0 or 1 to 3, $n^{c2}$ is an integer selected from 0 or 1 to 3, $n^d$ is an integer selected from 0 or 1 to 3, $R^e$ is hydrogen atom, Group A is (a) $C_{1-6}$ alkyl group, (b) halogen atom, and (c) —$OR^{A1}$ wherein $R^{A1}$ is hydrogen atom or $C_{1-6}$ alkyl group, or a pharmaceutically acceptable salt thereof.

[03] The compound of formula [II] according to [01]:

[II]

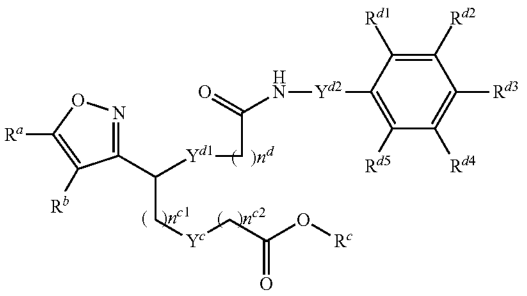

wherein each symbol is as defined in [01], or a pharmaceutically acceptable salt thereof.

[04] The compound of formula [III] according to [03]:

[III]

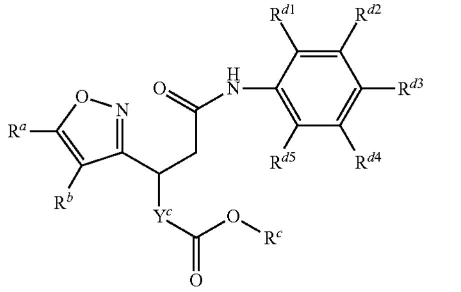

wherein each symbol is as defined in [01],
or a pharmaceutically acceptable salt thereof.

[05] The compound of formula [IV] according to [04]:

[IV]

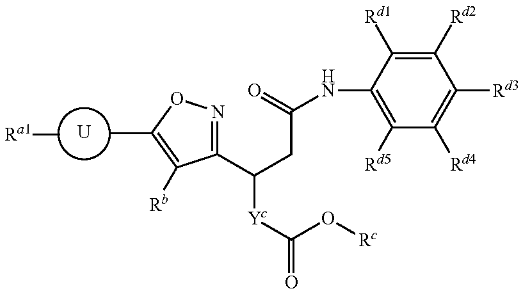

wherein $R^{a1}$ is $C_{1-6}$ alkyl group, and the other symbols are as defined in [01],
or a pharmaceutically acceptable salt thereof.

[06] The compound of formula [V] according to [01]:

[V]

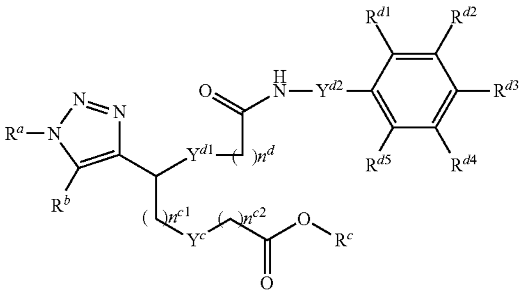

wherein each symbol is as defined in [01],
or a pharmaceutically acceptable salt thereof.

[07] The compound according to any one of [01] to [06] wherein:

$R^b$ is $C_{3-7}$ cycloalkyl group which may be substituted with the same or different 1 to 5 substituents selected from Group A,
or a pharmaceutically acceptable salt thereof.

[08] The compound according to any one of [01] to [07] wherein:

$R^b$ is cyclopropyl group,
or a pharmaceutically acceptable salt thereof.

[09] The compound according to any one of [01] to [08] wherein:

the cyclic moiety U is $C_{3-7}$ cycloalkyl group which may be substituted with the same or different 1 to 5 substituents selected from Group A,
or a pharmaceutically acceptable salt thereof.

[10] The compound according to any one of [01] to [09] wherein:

the cyclic moiety U is cyclobutyl group which may be substituted with the same or different 1 to 5 substituents selected from Group A,
or a pharmaceutically acceptable salt thereof.

[11] The compound according to [01] or [02] which is selected from the group consisting of the following formulas or a pharmaceutically acceptable salt thereof:

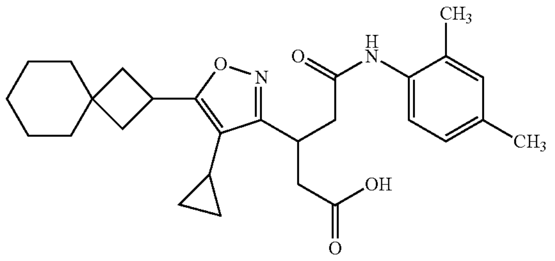

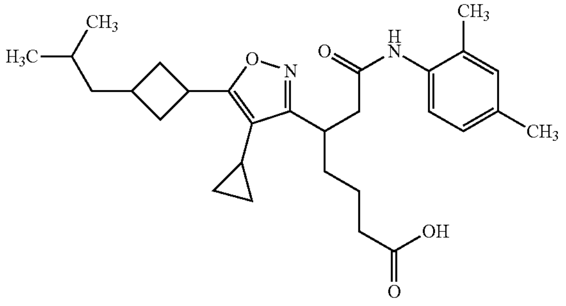

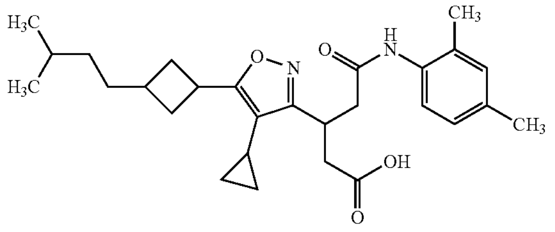

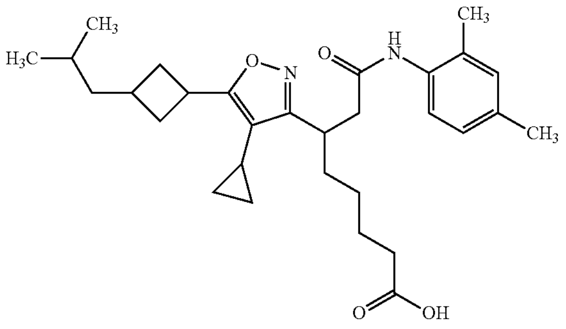

-continued
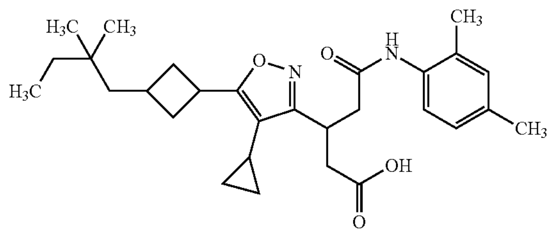
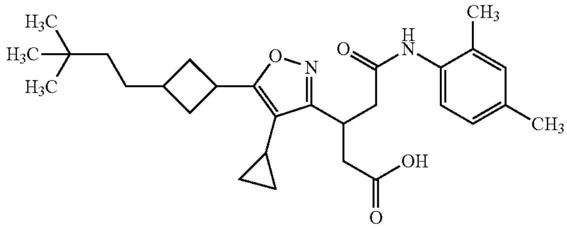
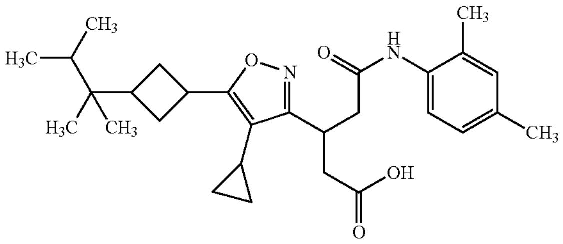
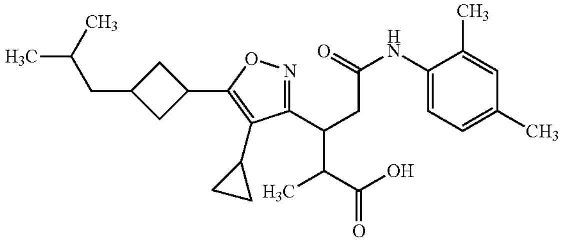
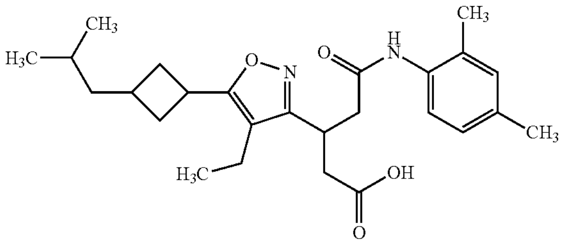
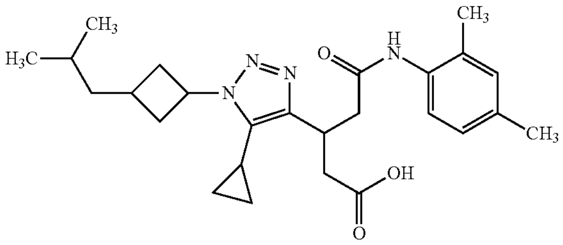
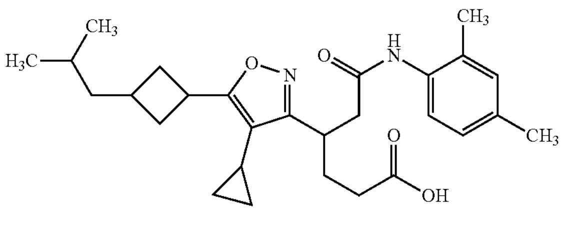
-continued
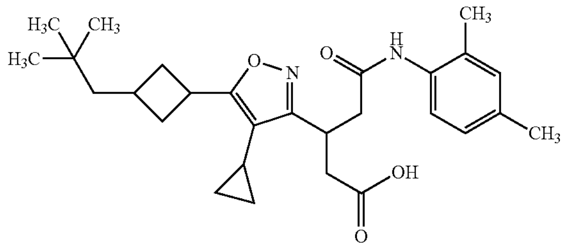
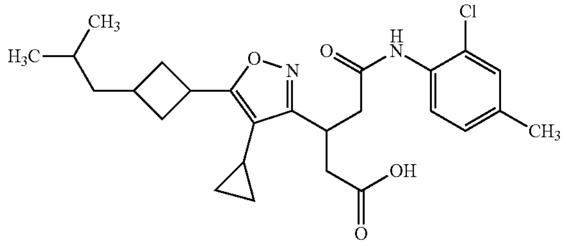
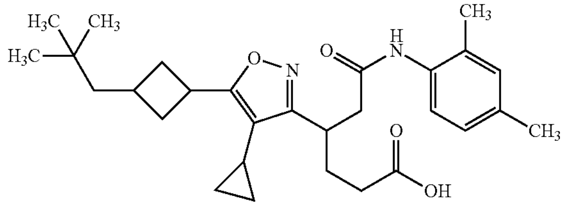
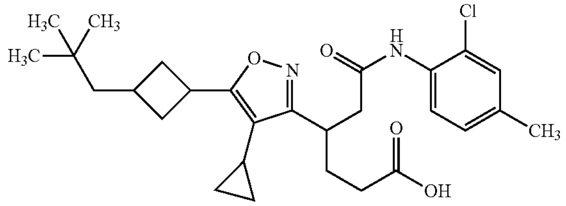
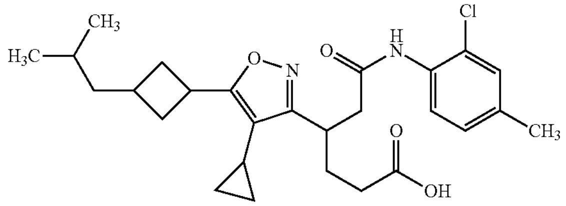
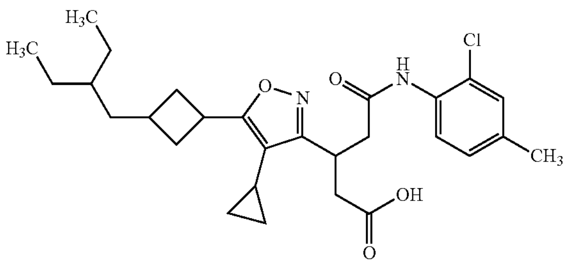
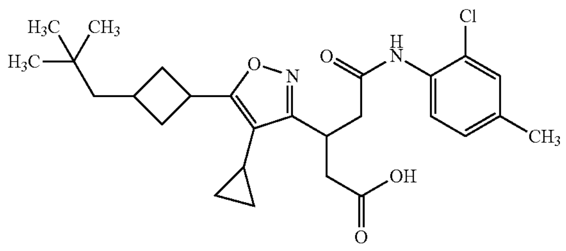

-continued
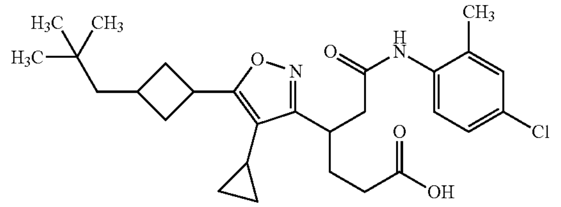
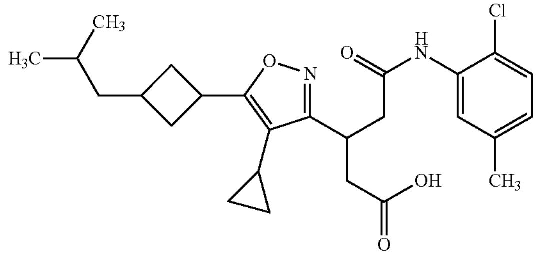
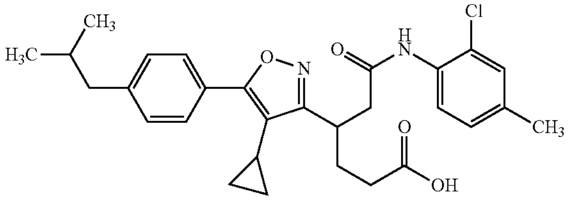
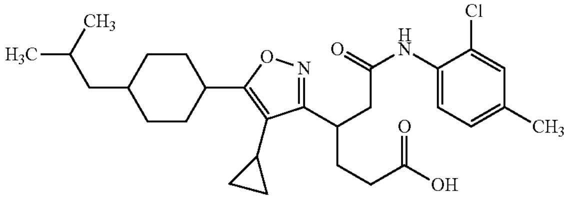
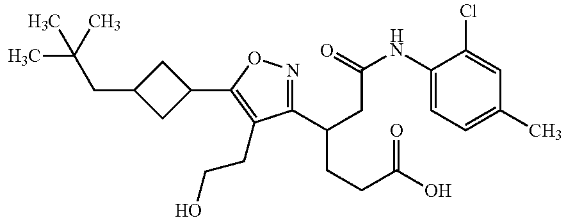
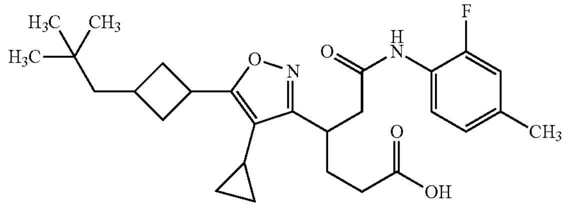
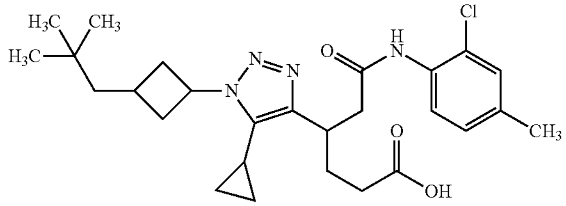
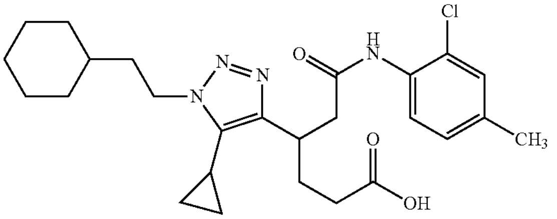
-continued
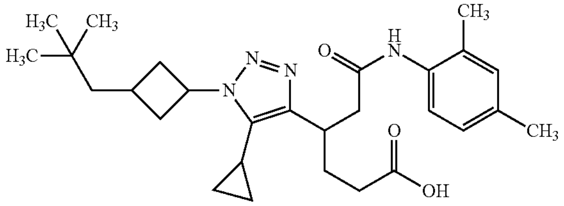
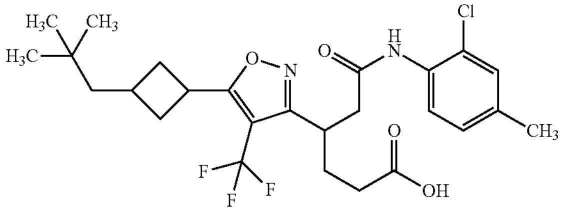
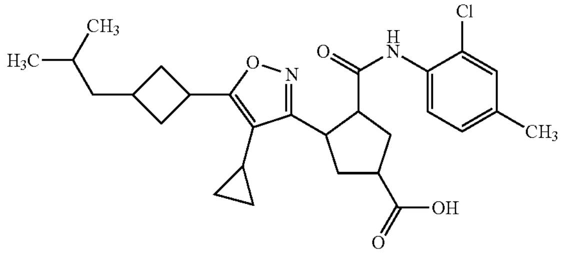
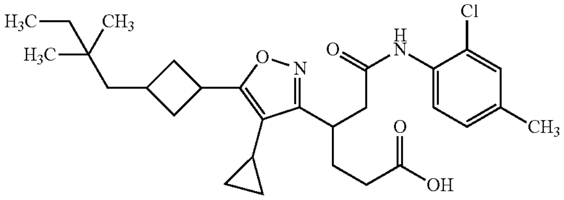
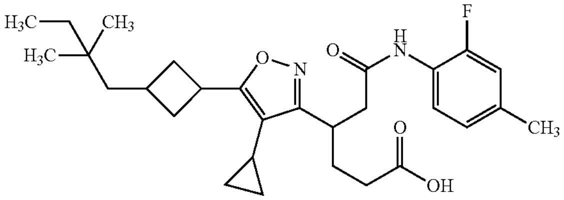
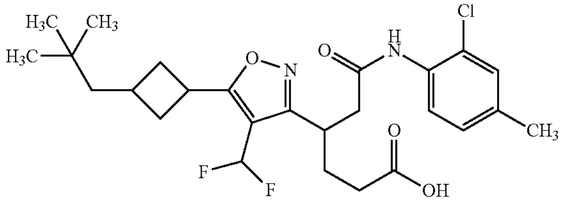
[12] The compound according to [01] or [02] which is selected from the group consisting of the following formulas or a pharmaceutically acceptable salt thereof:
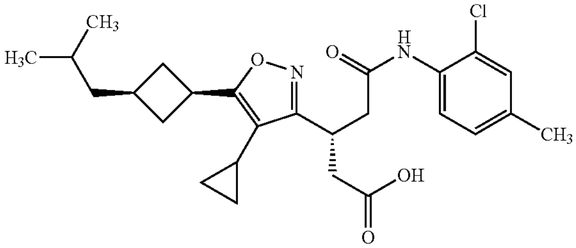

-continued

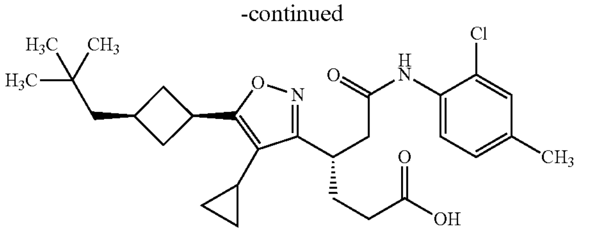

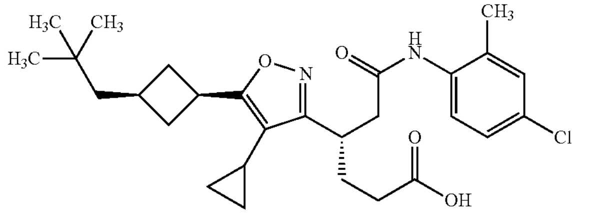

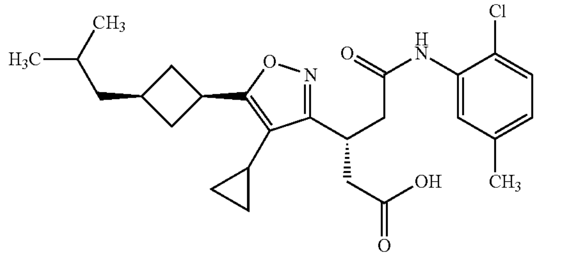

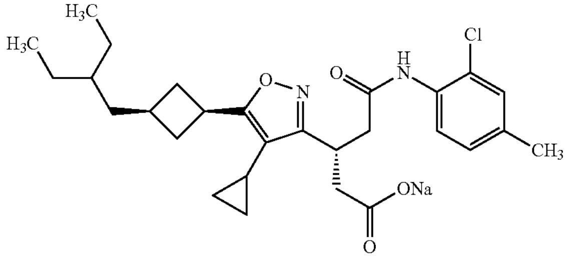

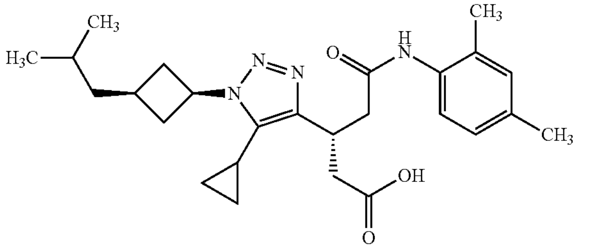

[13] A pharmaceutical composition comprising the compound according to any one of [01] to [12] or a pharmaceutically acceptable salt thereof, and a pharmaceutically acceptable carrier.

[14] A RORγ antagonist comprising the compound according to any one of [01] to [12] or a pharmaceutically acceptable salt thereof.

[15] A medicament for treating or preventing a disease selected from the group consisting of autoimmune disease, allergic disease, and metabolic disease, comprising the compound according to any one of [01] to [12] or a pharmaceutically acceptable salt thereof.

[16] A medicament for treating or preventing a disease selected from the group consisting of autoimmune disease and allergic disease, comprising the compound according to any one of [01] to [12] or a pharmaceutically acceptable salt thereof.

[17] The medicament according to [15] or [16] wherein the autoimmune disease is selected from the group consisting of rheumatoid arthritis, psoriasis, inflammatory bowel disease, multiple sclerosis, systemic lupus erythematosus, ankylosing spondylitis, uveitis, polymyalgia rheumatica, and type I diabetes.

[18] The medicament according to [15] wherein the metabolic disease is diabetes.

[19] A method of inhibiting RORγ in a mammal, comprising administering to said mammal a therapeutically effective amount of the compound according to any one of [01] to [12] or a pharmaceutically acceptable salt thereof.

[20] A method of treating or preventing a disease in a mammal selected from the group consisting of autoimmune disease, allergic disease, and metabolic disease, comprising administering to said mammal a therapeutically effective amount of the compound according to any one of [01] to [12] or a pharmaceutically acceptable salt thereof.

[21] A method of treating or preventing a disease in a mammal selected from the group consisting of autoimmune disease and allergic disease, comprising administering to said mammal a therapeutically effective amount of the compound according to any one of [01] to [12] or a pharmaceutically acceptable salt thereof.

[22] The method according to [20] or [21] wherein the autoimmune disease is selected from the group consisting of rheumatoid arthritis, psoriasis, inflammatory bowel disease, multiple sclerosis, systemic lupus erythematosus, ankylosing spondylitis, uveitis, polymyalgia rheumatica, and type I diabetes.

[23] The method according to [20] wherein the metabolic disease is diabetes.

[24] A pharmaceutical composition for treating or preventing a disease selected from the group consisting of autoimmune disease, allergic disease, and metabolic disease, which comprises:

(a) the compound according to any one of [01] to [12] or a pharmaceutically acceptable salt thereof, and (b) at least one additional medicament for treating or preventing a disease selected from the group consisting of autoimmune disease, allergic disease, and metabolic disease.

[25] A combination drug comprising:

(a) the compound according to any one of [01] to [12] or a pharmaceutically acceptable salt thereof, and (b) at least one additional medicament for treating or preventing a disease selected from the group consisting of autoimmune disease, allergic disease and metabolic disease, wherein the compound of (a) and the additional medicament of (b) may be administered simultaneously, separately or consecutively.

[26] Use of the compound according to any one of [01] to [12] or a pharmaceutically acceptable salt thereof in the manufacture of a RORγ antagonist.

[27] Use of the compound according to any one of [01] to [12] or a pharmaceutically acceptable salt thereof in the manufacture of a medicament for treating or preventing a disease selected from the group consisting of autoimmune disease, allergic disease, and metabolic disease.

[28] The use according to [27] wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes.

[29] The use according to [27] wherein the metabolic disease is diabetes.

[30] The compound according to any one of [01] to [12] or a pharmaceutically acceptable salt thereof for use in treating or preventing a disease selected from the group consisting of autoimmune disease, allergic disease, and metabolic disease.

[31] A commercial package comprising the medicament according to [15], and instructions which explain that the medicament can be used to treat and/or prevent a disease selected from the group consisting of autoimmune disease, allergic disease, and metabolic disease.

[32] The commercial package comprising the combination drug according to [25], and instructions which explain that the combination drug can be used to treat and/or prevent a disease selected from the group consisting of autoimmune disease, allergic disease, and metabolic disease.

[33] A medicament for treating or preventing a disease selected from the group consisting of autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease such as asthma; dry eye; fibrosis such as pulmonary fibrosis and primary biliary cirrhosis; and metabolic disease such as diabetes, comprising the compound according to any one of [01] to [12] or a pharmaceutically acceptable salt thereof.

[34] A pharmaceutical composition for treating or preventing a disease selected from the group consisting of: autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease such as asthma; dry eye; fibrosis such as pulmonary fibrosis and primary biliary cirrhosis; and metabolic disease such as diabetes, comprising:

(a) the compound according to any one of [01] to [12] or a pharmaceutically acceptable salt thereof, and (b) at least one additional medicament for treating or preventing a disease selected from the group consisting of autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease such as asthma; dry eye; fibrosis such as pulmonary fibrosis and primary biliary cirrhosis; and metabolic disease such as diabetes.

[35] A combination drug comprising:

(a) the compound according to any one of [01] to [12] or a pharmaceutically acceptable salt thereof, and (b) at least one an additional medicament for treating or preventing a disease selected from the group consisting of autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease such as asthma; dry eye; fibrosis such as pulmonary fibrosis and primary biliary cirrhosis; and metabolic disease such as diabetes, wherein the compound of (a) and the additional medicament of (b) may be administered simultaneously, separately or consecutively.

Each symbol of the formulas described in the following [102] to [122] has the same meaning as defined in the formula [I] in the following [101].

In particular, $R^a$; $Y^c$ and $Y^{d1}$; $R^{d1}$, $R^{d2}$, $R^{d3}$, $R^{d4}$, and $R^{d5}$ of the formulas described in [102] to [122] have the same meaning as defined in the formula [I] described in [101].

[101] A compound of formula [I]:

[1]

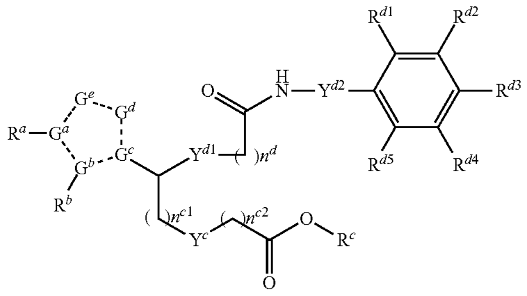

wherein

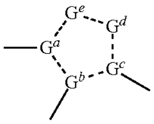 is 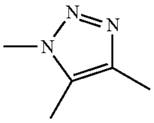 or 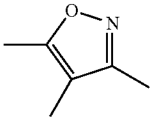 ;

$R^a$ is (1) $C_{5-12}$ alkyl group which may be substituted with the same or different 1 to 5 substituents selected from Group A, or (2)

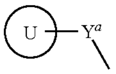

wherein $Y^a$ is (i) single bond, or (ii) $C_{1-6}$ alkylene group, cyclic moiety U is (i) $C_{3-7}$ cycloalkyl group which may be substituted with the same or different 1 to 5 substituents selected from Group A, or (ii) $C_{5-11}$ spirocyclic cycloalkyl group which may be substituted with the same or different 1 to 5 substituents selected from Group A;

$R^b$ is a group selected from the following (1) to (3):

(1) $C_{1-3}$ alkyl group which may be substituted with the same or different 1 to 5 substituents selected from Group A, (2) $C_{2-3}$ alkenyl group which may be substituted with the same or different 1 to 5 substituents selected from Group A, (3) $C_{3-7}$ cycloalkyl group which may be substituted with the same or different 1 to 5 substituents selected from Group A;

$R^c$ is (1) hydrogen atom, or (2) $C_{1-6}$ alkyl group;

$Y^c$ is a group selected from the following (1) to (7):

(1) single bond, (2) $C_{1-6}$ alkylene group which may be substituted with the same or different 1 to 5 substituents selected from Group A, (3) —$NR^{C1}$— wherein $R^{C1}$ is hydrogen atom or $C_{1-6}$ alkyl group, (4) —O—, (5) $C_{3-10}$ cycloalkylene group which may be substituted with the same or different 1 to 5 substituents selected from Group A, (6) $C_{6-10}$ arylene group which may be substituted with the same or different 1 to 5 substituents selected from Group A, (7) monocyclic heteroaromatic group which may be substituted with the same or different 1 to 5 substituents selected from Group A wherein the monocyclic heteroaromatic ring consists of carbon atoms and the same or different 1 to 4 hetero atoms selected from nitrogen atom, oxygen atom and sulfur atom, and is 3 to 7-membered;

$Y^{d1}$ is (1) single bond, or (2) $C_{1-6}$ alkylene group which may be substituted with the same or different 1 to 5 substituents selected from Group A;

$Y^{d2}$ is (1) single bond, or (2) $C_{1-6}$ alkylene group;

$R^{d1}$, $R^{d2}$, $R^{d3}$, $R^{d4}$, and $R^{d5}$ are the same or different group selected from the following (1) to (4):

(1) hydrogen atom (2) halogen atom, (3) $C_{1-6}$ alkyl group which may be substituted with the same or different 1 to 5 substituents selected from Group A, (4) —$OR^{d10}$ wherein $R^{d10}$ is hydrogen atom or $C_{1-6}$ alkyl group which may be substituted with the same or different 1 to 5 substituents selected from Group A, or alternatively $R^{d1}$ and $R^{d2}$, or $R^{d2}$ and $R^{d3}$ can be taken together to form a $C_{6-10}$ aryl ring fused to the benzene ring to which they are all attached wherein the $C_{6-10}$ aryl ring may be substituted with the same or different 1 to 4 substituents selected from Group A;

$n^{c1}$ is an integer selected from 0 or 1 to 3, $n^{c2}$ is an integer selected from 0 or 1 to 3, $n^{d}$ is an integer selected from 0 or 1 to 3, Group A is (a) $C_{1-6}$ alkyl group, (b) halogen atom, and (c) —$OR^{A1}$ wherein $R^{A1}$ is hydrogen atom or $C_{1-6}$ alkyl group, or a pharmaceutically acceptable salt thereof.

[102] The compound of formula [II] according to [101]:

[II]

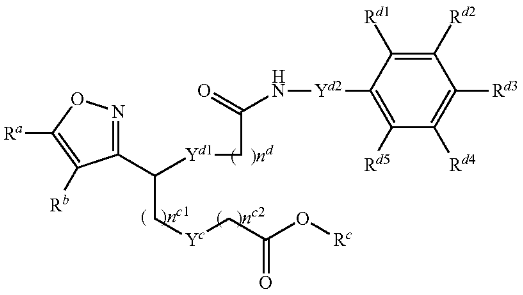

wherein each symbol is as defined in [101], or a pharmaceutically acceptable salt thereof.

[103] The compound of formula [III] according to [101] or [102]:

[III]

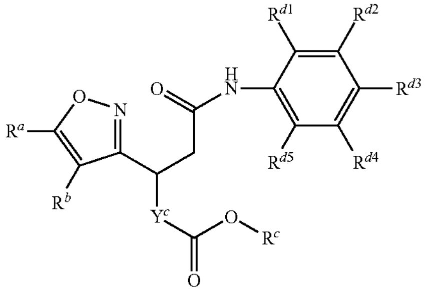

wherein each symbol is as defined in [101], or a pharmaceutically acceptable salt thereof.

[104] The compound of formula [IV] according to [101]:

[IV]

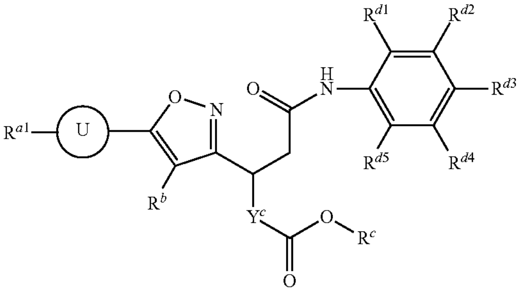

wherein $R^{a1}$ is $C_{1-6}$ alkyl group, and the other symbols are defined in [101], or a pharmaceutically acceptable salt thereof.

[105] The compound of formula [V] according to [101]:

[V]

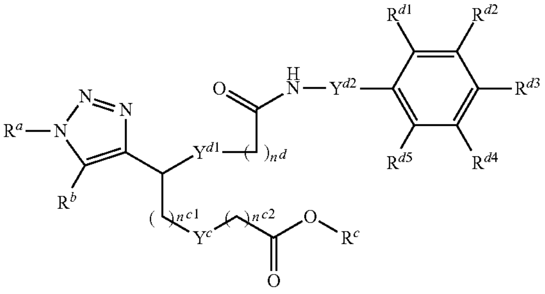

wherein each symbol is as defined in [101], or a pharmaceutically acceptable salt thereof.

[106] The compound according to any one of [101] to [105] wherein:

$R^{b}$ is cyclopropyl group, or a pharmaceutically acceptable salt thereof.

[107] The compound according to any one of [101] to [106] wherein the cyclic moiety U is cyclobutyl group, or a pharmaceutically acceptable salt thereof.

[108] A pharmaceutical composition comprising the compound according to any one of [101] to [107] or a pharmaceutically acceptable salt thereof, and a pharmaceutically acceptable carrier.

[109] A RORγ antagonist comprising the compound according to any one of [101] to [107] or a pharmaceutically acceptable salt thereof.

[110] A medicament for treating or preventing a disease selected from the group consisting of autoimmune disease and allergic disease, comprising the compound according to any one of [101] to [107] or a pharmaceutically acceptable salt thereof.

[111] The medicament according to [110] wherein the autoimmune disease is selected from the group consisting of rheumatoid arthritis, psoriasis, inflammatory bowel disease, multiple sclerosis, and systemic lupus erythematosus.

[112] A pharmaceutical composition for treating or preventing a disease selected from the group consisting of autoimmune disease and allergic disease, comprising (a) the compound according to any one of [101] to [107] or a pharmaceutically acceptable salt thereof, and (b) at least one additional medicament for treating or preventing a disease selected from the group consisting of autoimmune disease and allergic disease.

[113] A combination drug comprising:

(a) the compound according to any one of [101] to [107] or a pharmaceutically acceptable salt thereof, and (b) at least one an additional medicament for treating or preventing a disease selected from the group consisting of autoimmune disease and allergic disease, wherein the compound of (a) and the additional medicament of (b) may be administered simultaneously, separately or consecutively.

[114] A method of inhibiting RORγ in a mammal, comprising administering to said mammal a therapeutically effective amount of the compound according to any one of [101] to [107] or a pharmaceutically acceptable salt thereof.

[115] A method of treating or preventing a disease in a mammal selected from the group consisting of autoimmune disease and allergic disease, comprising administering to said mammal a therapeutically effective amount of the compound according to any one of [101] to [107] or a pharmaceutically acceptable salt thereof.

[116] The method according to [115] wherein the autoimmune disease is selected from the group consisting of rheumatoid arthritis, psoriasis, inflammatory bowel disease, multiple sclerosis, and systemic lupus erythematosus.

[117] Use of the compound according to any one of [101] to [107] or a pharmaceutically acceptable salt thereof in the manufacture of a RORγ antagonist.

[118] Use of the compound according to any one of [101] to [107] or a pharmaceutically acceptable salt thereof in the manufacture of a medicament for treating or preventing a disease selected from the group consisting of autoimmune disease and allergic disease.

[119] The use according to [118] wherein the autoimmune disease is selected from the group consisting of rheumatoid arthritis, psoriasis, inflammatory bowel disease, multiple sclerosis, and systemic lupus erythematosus.

[120] The compound according to any one of [101] to [107] or a pharmaceutically acceptable salt thereof for use in treating or preventing a disease selected from the group consisting of autoimmune disease and allergic disease.

[121] A commercial package comprising the medicament according to [110], and instructions which explain that the medicament can be used to treat and/or prevent a disease selected from the group consisting of autoimmune disease and allergic disease.

[122] A commercial package comprising the combination drug according to [113], and instructions which explain that the combination drug can be used to treat and/or prevent a disease selected from the group consisting of autoimmune disease and allergic disease.

Effects of the Invention

The amide compound of the present invention can inhibit the RORγ activity, thereby the compound is effective as a medicament for treating or preventing a disease such as autoimmune disease such as rheumatoid arthritis, psoriasis, inflammatory bowel disease such as Crohn's disease and ulcerative colitis, multiple sclerosis, and systemic lupus erythematosus; allergic disease; metabolic disease; dry eye; and fibrosis.

BRIEF DESCRIPTION OF DRAWINGS

FIG. 1 Structures, NMR results and the like of Examples A-1 to A-4.

FIG. 2 Structures, NMR results and the like of Examples A-5 to A-8.

Example A-6 was prepared by using L-homoserine as a material without using any chiral auxiliary reagent (AUX-H) according to the preparation methods of A-6 as described below.

Example A-8 was prepared by using L(−)-malic acid as a material without using any chiral auxiliary reagent (AUX-H) according to the preparation methods of A-8 as described below.

FIG. 3 Structures, NMR results and the like of Examples A-9 to A-12.

Example A-9 was prepared by using L-homoserine as a material without using any chiral auxiliary reagent (AUX-H) according to the preparation methods of A-9 as described below.

FIG. 4 Structures, NMR results and the like of Examples A-13 to A-16.

FIG. 5 Structures, NMR results and the like of Examples A-17 to A-20.

FIG. 6 Structures, NMR results and the like of Examples A-21 to A-24.

FIG. 7 Structures, NMR results and the like of Examples A-25 to A-28.

FIG. 8 Structures, NMR results and the like of Examples A-29 to A-32.

FIG. 9 Structures, NMR results and the like of Examples A-33 to A-36.

FIG. 10 Structures, NMR results and the like of Examples A-37 to A-40.

FIG. 11 Structures, NMR results and the like of Examples A-41 to A-44.

FIG. 12 Structures, NMR results and the like of Examples A-45 to A-48.

FIG. 13 Structures, NMR results and the like of Examples A-49 to A-52.

FIG. 14 Structures, NMR results and the like of Examples A-53 to A-56.

FIG. 15 Structures, NMR results and the like of Examples A-57 to A-60.

FIG. 16 Structures, NMR results and the like of Examples A-61 to A-64.

FIG. 17 Structures, NMR results and the like of Examples A-65 to A-68.

FIG. 18 Structures, NMR results and the like of Examples A-69 to A-72.

FIG. 19 Structures, NMR results and the like of Examples A-73 to A-76.

FIG. 20 Structures, NMR results and the like of Examples A-77 to A-80.

FIG. 21 Structures, NMR results and the like of Examples A-81 to A-83 and B-1.

FIG. 22 Structures, NMR results and the like of Examples B-2 and A-84 and A-85.

FIG. 23 Structures, NMR results and the like of Examples A-86 to A-89.

FIG. 24 Structures, NMR results and the like of Examples B-3, B-4 C-1 and C-2.

FIG. 25 Structures, NMR results and the like of Examples D-1, D-2, A-90, and A-91.

FIG. 26 Structures, NMR results and the like of Examples A-92 to A-94 and D-3.

FIG. 27 Structures, NMR results and the like of Examples D-4, C-3, C-4, and A-95.

FIG. 28 Structures, NMR results and the like of Examples A-96 to A-99.

FIG. 29 Structures, NMR results and the like of Examples A-100 to A-102 and D-5.

FIG. 30 Structures, NMR results and the like of Examples D-6 and A-103 to A-105.

FIG. 31 Structures, NMR results and the like of Examples A-106 to A-109.

FIG. 32 Structures, NMR results and the like of Examples A-110 to A-113.

FIG. 33 Structures, NMR results and the like of Examples C-5 to C-6 and A-114 to A-115.

FIG. 34 Structures, NMR results and the like of Examples B-5, C-7 and A-116 to A-117.

FIG. 35 Structures, NMR results and the like of Examples A-118 to A-121.

FIG. 36 Structures, NMR results and the like of Examples A-122 to A-124 and C-8.

FIG. 37 Structures, NMR results and the like of Examples C-9 and A-125 to A-127.

FIG. 38 Structures, NMR results and the like of Examples A-128 to A-130.

FIG. 39 Structures, NMR results and the like of Examples A-131 to A-133.

FIG. 40 Structures, NMR results and the like of Examples A-134 to A-136.

FIG. 41 Structures, NMR results and the like of Examples A-137 and A-138.

The "Stereochemistry of AUX-H" described in FIGS. 1 to 41 is explained as follows.

The stereochemistry of the alpha position from the 5-membered ring (-$G^a$-$G^b$-$G^c$-$G^d$-$G^e$-) can be introduced by using a chiral substituted 2-oxazolidinone as a chiral auxiliary reagent (AUX-H) to obtain optically-active compounds of the present invention stereospecifically or stereoselectively.

For example, the chiral compound of Example "A-1" can be obtained by using (S)-4-benzyl-2-oxazolidinone as an AUX-H.

The above "stereochemistry of the alpha position from the 5-membered ring (-$G^a$-$G^b$-$G^c$-$G^d$-$G^e$-)" means the stereochemistry at the carbon indicated by an arrow in the following formula:

[I]

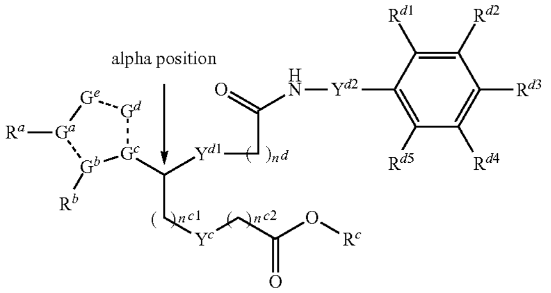

For example, by using the chiral 4-benzyl-2-oxazolidinone as an "AUX-H" in Preparation method 2B (Step 2) or Preparation method 4B (Step 2) described below, the following optically-active Compound [I] can be obtained stereoselectively. The symbol "*" denotes a new chiral point induced by this procedure.

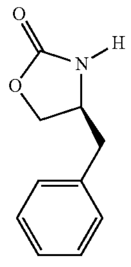

(S)-4-benzyl-2-oxazolidinone

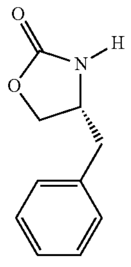

(R)-4-benzyl-2-oxazolidinone

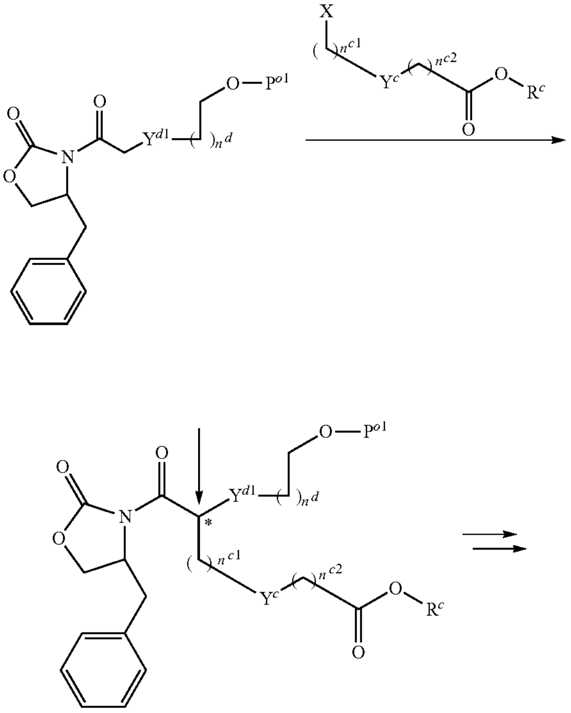

-continued

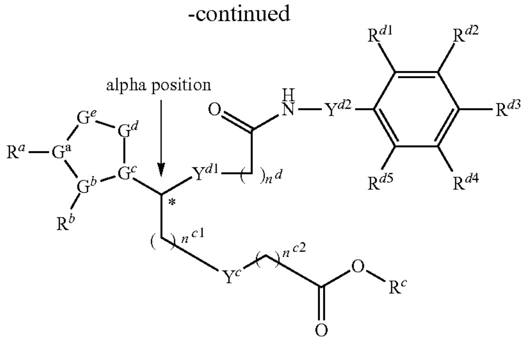

[I]

Besides, by using the chiral 4-benzyl-2-oxazolidinone as an "AUX-H" in Preparation method 3B (Step 3) described below, the following optically-active Compound [I] can be also obtained stereoselectively. The symbol "*" denotes a new chiral point induced by this procedure.

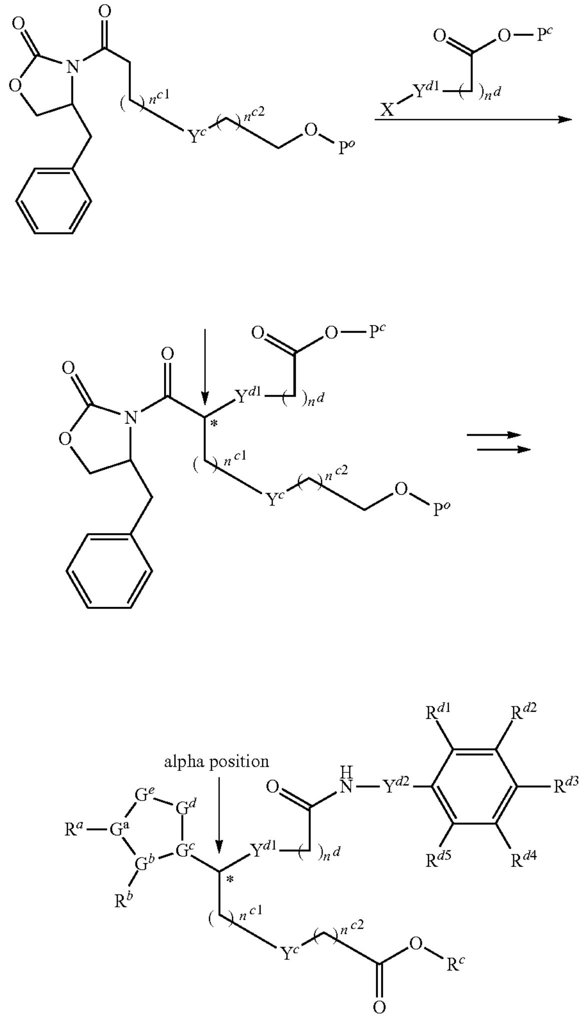

[I]

According to the above procedures, the following optically-active compound [I-C1-W] and [I-C2-W] can be obtained stereoselectively.

[I-C1-W]

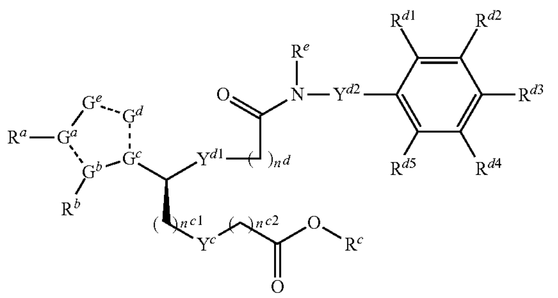

[I-C2-W]

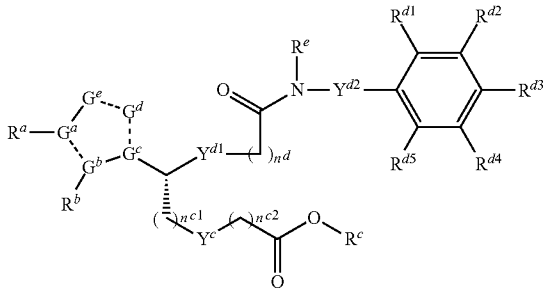

According to the above procedures, for example, the following optically-active compound [IV-C1] and [IV-C2] can be also obtained stereoselectively.

[IV-C1]

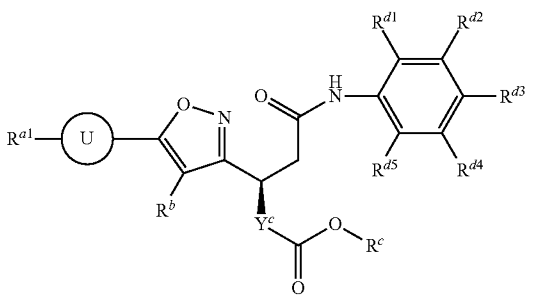

[IV-C2]

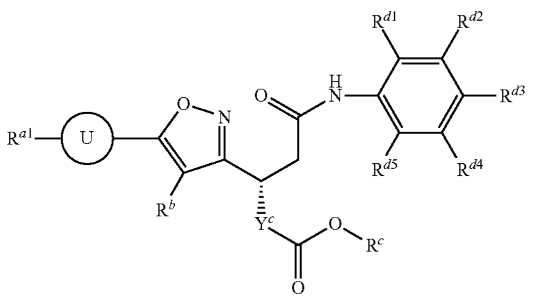

For example, an optically-active compound [IV-C2-001-W] may be obtained by using (R)-4-benzyl-2-oxazolidinone as an AUX-H.

[IV-C2-001-W]

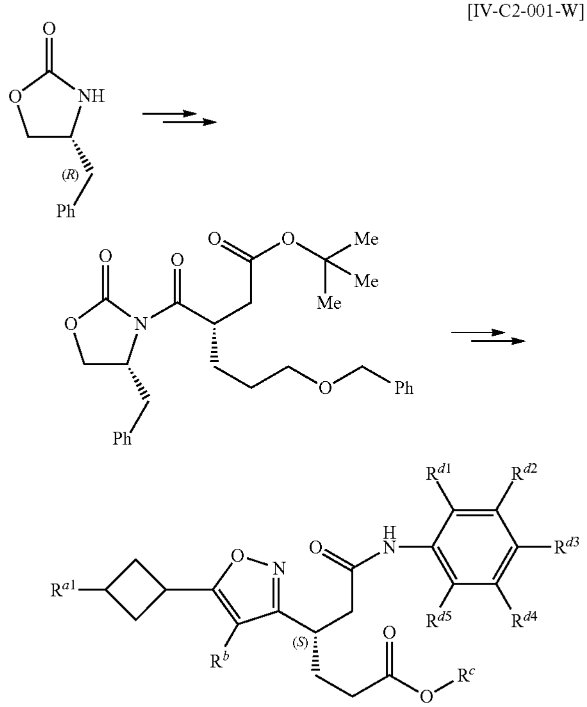

The "Materials or Stereochemistry" described in FIGS. 1 to 41 is explained as follows.

For example, in Examples A-86, A-87, A-88, and A-89, the explanation "Dimethyl 4-oxo-cyclopentane-trans-1,2-dicarboxylate was used as a material" means that these examples were prepared by using dimethyl 4-oxo-cyclopentane-trans-1,2-dicarboxylate as a material without using any chiral auxiliary reagent (AUX-H) in the preparation methods for Examples A-86, A-87, A-88, and A-89 as described below.

Examples listed in FIGS. 1 to 41 whose compound name comprises symbol "A" or "B" are explained as follows.

Examples A-1 to A-85 (excluding Examples A-4 and A-10) were prepared by using 3-substituted cyclobutane-carboxylic acid [X-200A] obtained by the catalytic hydrogenation reaction as showed in the following scheme, according to the preparation methods as described below.

The catalytic hydrogenation reaction was carried out in Step A-82-5 in Example A-82, Step A-53-7 in Example A-53, and Step A-75-7 in Example A-75 as described below.

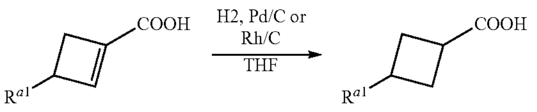

[X-200 A]

Examples B-1 and B-2 were prepared by using 3-substituted cyclobutane-carboxylic acid [X-200B] obtained by the reduction reaction with zinc as showed in the following scheme, according to the preparation methods as described below.

The reduction reaction was carried out in Step B-1-1 in Example B-1 as described below.

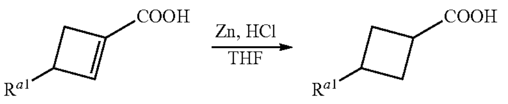

[X-200 B]

The above [X-200B] is a stereoisomer of [X-200A].

By using the 3-substituted cyclobutane-carboxylic acids prepared by the above methods, for example, the following compound [IV-B21] and [IV-B22] can be obtained stereoselectively.

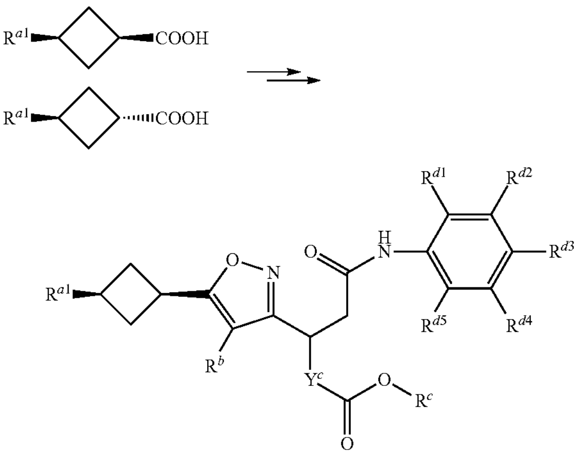

[IV-B21]

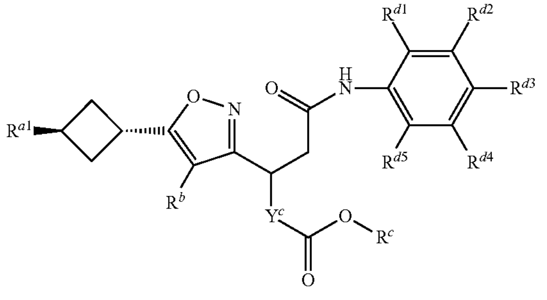

[IV-B22]

For example, the following compound [IV-B21-002-W] (cis-isomer) may be obtained by the catalytic hydrogenation reaction with palladium on activated carbon or rhodium on activated carbon.

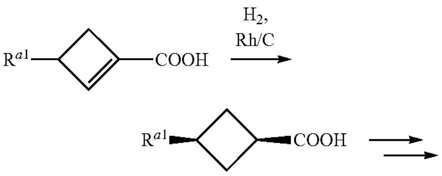

-continued

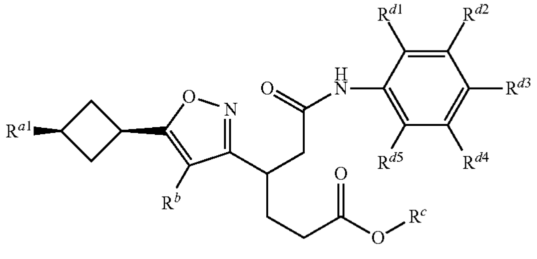

[IV-B21-002-W]

Examples listed in FIGS. 1 to 41 whose compound name comprises symbol "C" or "D" are explained as follows.

Examples C-1 to C-9 were prepared by using an arylcarboxylic acid, according to "Preparation method of Example C series" as described below.

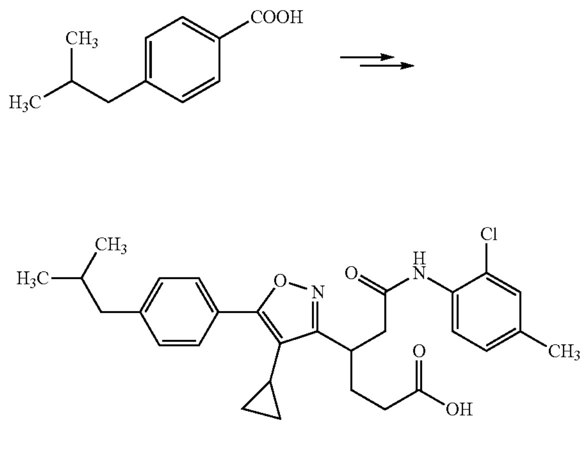

Examples D-1 to D-6 were prepared by using a cyclohexanecarboxylic acid obtained by the reduction reaction of a phenylcarboxylic acid, according to "Preparation method of Example D series".

A mixture of the Weinreb amide intermediates as showed below was separated into cis-isomer and trans-isomer thereof through the purification by silica gel column chromatography.

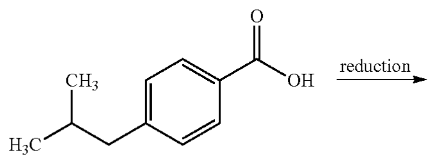

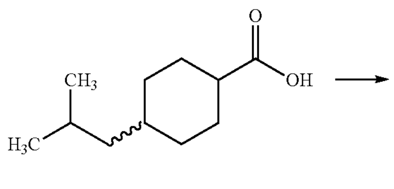

-continued

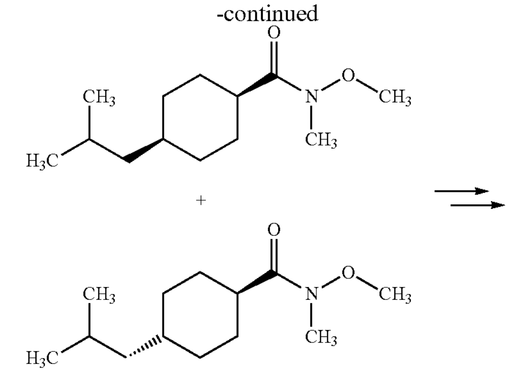

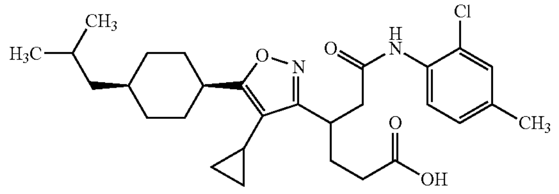

or

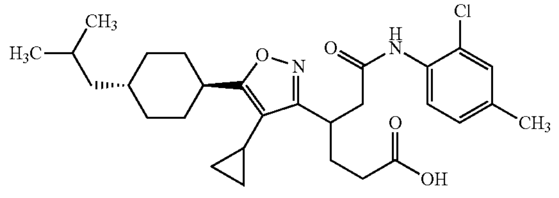

FIG. 42 The results of the biological assay for Examples A-1 to A-28 of the inhibitory effect against RORγ transcriptional activity ($EC_{50}$) in CHO cells co-transfected with pGL5-Luc plasmid and either human or mouse GAL4-RORγ plasmid.

FIG. 43 The results of the biological assay for Examples A-29 to A-56 of the inhibitory effect against RORγ transcriptional activity ($EC_{50}$) in CHO cells co-transfected with pGL5-Luc plasmid and either human or mouse GAL4-RORγ plasmid.

FIG. 44 The results of the biological assay for Examples A-57 to A-83 and B-1 of the inhibitory effect against RORγ transcriptional activity ($EC_{50}$) in CHO cells co-transfected with pGL5-Luc plasmid and either human or mouse GAL4-RORγ plasmid.

FIG. 45 The results of the biological assay for Examples B-2, A-84, and A-85 of the inhibitory effect against RORγ transcriptional activity ($EC_{50}$) in CHO cells co-transfected with pGL5-Luc plasmid and either human or mouse GAL4-RORγ plasmid.

FIG. 46 The results of the biological assay for Examples A-86 to A-100, B-3, B4, C-1 to C-4, and D-1 to D-4 of the inhibitory effect against RORγ transcriptional activity ($EC_{50}$) in CHO cells co-transfected with pGL5-Luc plasmid and either human or mouse GAL4-RORγ plasmid.

FIG. 47 The results of the biological assay for Examples A-101 to A-119, B-5, C-5 to C-7, D-5, and D-6 of the inhibitory effect against RORγ transcriptional activity ($EC_{50}$) in CHO cells co-transfected with pGL5-Luc plasmid and either human or mouse GAL4-RORγ plasmid.

FIG. 48 The results of the biological assay for Examples A-120 to A-138, C-8, and C-9 of the inhibitory effect against RORγ transcriptional activity ($EC_{50}$) in CHO cells co-transfected with pGL5-Luc plasmid and either human or mouse GAL4-RORγ plasmid.

DESCRIPTION OF EMBODIMENTS

The followings are definitions of terms that may be used in the specification.

The phrase "may be substituted" means to be substituted with the given number of given substituent(s) at any replaceable position(s) or not to be substituted (unsubstituted). The phrase "not substituted" herein means that all replaceable positions are occupied with hydrogen atoms.

For example, the phrase "$C_{1-6}$ alkyl group which may be substituted with the same or different 1 to 5 substituents selected from Group A" includes both cases where $C_{1-6}$ alkyl group may be substituted with the same or different 1 to 5 substituents selected from Group A at any replaceable position(s) thereof and where $C_{1-6}$ alkyl group is not substituted (unsubstituted).

The term "halogen atom" includes for example, fluorine atom, chlorine atom, bromine atom, or iodine atom and the like.

The term "alkyl group" refers to a straight- or branched-chain saturated hydrocarbon group, and includes for example, $C_{1-12}$ alkyl group, $C_{1-8}$ alkyl group, $C_{1-6}$ alkyl group, $C_{1-4}$ alkyl group, $C_{1-3}$ alkyl group, $C_{5-42}$ alkyl group, and $C_{5-8}$ alkyl group which have 1 to 12, 1 to 8, 1 to 6, 1 to 4, 1 to 3, 5 to 12, and 5 to 8 carbon atoms, respectively. The preferred examples of alkyl group include "$C_{1-3}$ alkyl group", "$C_{1-6}$ alkyl group", "$C_{5-12}$ alkyl group" and the like. The "$C_{1-3}$ alkyl group" includes, for example, methyl group, ethyl group, propyl group, and isopropyl group. The "$C_{1-6}$ alkyl group" includes, for example, butyl group, isobutyl group, sec-butyl group, tert-butyl group, pentyl group, isopentyl group, neopentyl group, tert-pentyl group, 1-ethylpropyl group, hexyl group, isohexyl group, 1,1-dimethylbutyl group, 2,2-dimethylbutyl group, 3,3-dimethylbutyl group, 2-ethylbutyl group, and 1,1-dimethyl-2-methylpropyl group, besides the above-mentioned examples of $C_{1-3}$ alkyl group. The example of "$C_{5-12}$ alkyl group" includes, heptyl, octyl, nonyl, decyl, undecyl, dodecyl and the like, besides the above-mentioned examples, which may be a straight- or branched-chain.

The term "alkenyl group" refers to a straight- or branched-chain unsaturated hydrocarbon group having one or more double bonds, and includes for example, vinyl group, 1-propenyl group, isopropenyl group, allyl group, methylpropenyl group (1-methyl-1-propenyl group, 2-methyl-1-propenyl group and the like), 1-butenyl group, 2-butenyl group, 3-butenyl group, methylbutenyl group (1-methyl-1-butenyl group, 2-methyl-1-butenyl group, 3-methyl-1-butenyl group and the like), pentenyl group, methylpentenyl group, hexenyl group and the like.

The term "$C_{2-3}$ alkenyl group" refers to a straight- or branched-chain unsaturated hydrocarbon group having 2 to 3 carbon atoms and one double bond, and includes for example, vinyl group, 1-propenyl group, isopropenyl group, allyl group and the like.

The term "alkylene group" refers to a bivalent group derived from a straight- or branched-chain alkyl, and includes for example, "$C_{1-6}$ alkylene group", "$C_{1-4}$ alkylene group" and "$C_{1-3}$ alkylene group". The preferred example of alkylene group includes a bivalent group derived by removing each one hydrogen atom from both terminal carbon atoms of straight-chain alkane, and includes, for example, methylene ($—CH_2—$), ethylene ($—CH_2CH_2—$), trimethylene ($—CH_2CH_2CH_2—$), tetramethylene ($—CH_2CH_2CH_2CH_2—$)$_f$ pentamethylene ($—CH_2CH_2CH_2CH_2CH_2—$), hexamethylene ($—CH_2CH_2CH_2CH_2CH_2CH_2—$) and the like.

The term "alkane" refers to a saturated hydrocarbon.

The term "cycloalkyl ring" refers to a monocyclic saturated hydrocarbon, and includes, for example, $C_{3-7}$ cycloalkyl ring which means a cycloalkyl ring having 3 to 7 carbon atoms. The example of "cycloalkyl ring" includes cyclopropane ring, cyclobutane ring, cyclopentane ring, cyclohexane ring, cycloheptane ring and the like.

The term "cycloalkyl group" refers to a monocyclic saturated hydrocarbon group, and includes for example, $C_{3-7}$ cycloalkyl group which means a cycloalkyl group having 3 to 7 carbon atoms. The example of "cycloalkyl group" includes cyclopropyl group, cyclobutyl group, cyclopentyl group, cyclohexyl group, cycloheptyl group and the like.

The term "cycloalkylene group" refers to a bivalent group derived from the above-mentioned cycloalkyl group, which has any two available ring carbon atoms for binding. The carbons may be the same single carbon atom or different carbon atoms. The example of "cycloalkylene group" includes "$C_{3-10}$ cycloalkylene group" which means a cycloalkylene group having 3 to 10 carbon atoms. The example of "cycloalkylene group" includes for example, cyclopropylene group, cyclobutylene group, cyclopentylene group, cyclohexylene group, cycloheptylene group, cyclooctylene group, cyclononylene group, cyclodecylene group and the like, and specifically, for example, 1,1-cyclopropylene group, 1,2-cyclopropylene group, 1,1-cyclobutylene group, 1,2-cyclobutylene group, 1,3-Cyclobutylene group, 1,3-cyclopentylene group, 1,4-cyclohexylene group, 1,4-cyclopentylene group, 1,5-cyclooctylene group and the like.

The term "$C_{6-10}$ aryl ring" refers to a monocyclic or bicyclic aromatic hydrocarbon having 6 to 10 carbon atoms in the ring and includes for example, benzene ring, and naphthalene ring.

The term "$C_{6-10}$ aryl group" refers to an aromatic hydrocarbon group having 6 to 10 carbon atoms, and includes for example, phenyl group, 1-naphthyl group, 2-naphthyl group and the like.

A specific aspect of the definition "$R^{d1}$ and $R^{d2}$, or $R^{d2}$ and $R^{d3}$ can be taken together to form a $C_{6-10}$ aryl ring fused to the benzene ring to which they are all attached wherein the $C_{6-10}$ aryl ring may be substituted with the same or different 1 to 4 substituents selected from Group A" includes, for example, $C_{10}$ aryl ring (such as naphthalene ring) and the like, as described below:

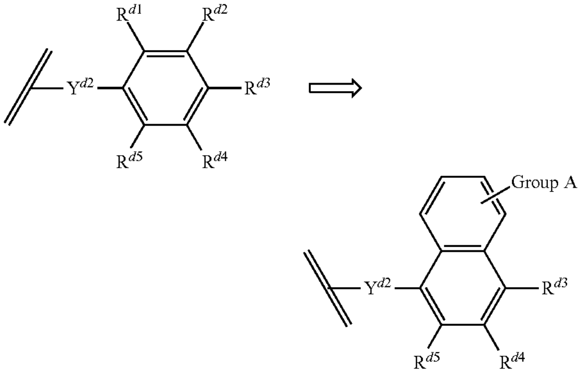

-continued

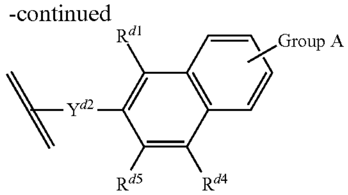

The term "$C_{6-10}$ arylene group" refers to a bivalent monocyclic- or bicyclic-aromatic hydrocarbon group which has 6 to 10 carbon atoms in the ring and has any two available ring carbon atom for binding, and includes, for example, phenylene, naphthylene and the like, preferably phenylene (o-phenylene, m-phenylene, p-phenylene), more preferably p-phenylene.

The term "$C_{5-11}$ spirocyclic cycloalkyl group" includes spiro[4.4]nonanyl group, spiro[4.4]non-1-enyl group, spiro[4.5]decanyl group, spiro[4.5]dec-6-enyl group, spiro[5.5]undecanyl group, spiro[5.5]undec-1-enyl group, spiro[3.5]nonyl group and the like, preferably spiro[3.5]nonyl group.

The term "monocyclic heteroaromatic group" refers to a 3- to 7-membered monocyclic heteroaromatic group which contains the same or different 1 to 4 heteroatoms selected from nitrogen atom, oxygen atom and sulfur atom, besides carbon atoms.

When the term "monocyclic heteroaromatic group" is used as a definition of $Y^c$, the term "monocyclic heteroaromatic group" is a bivalent group which has any two available ring atoms for binding. The monocyclic heteroaromatic group may be attached via any available nitrogen or carbon atom in the ring.

The example of monocyclic heteroaromatic group includes for example, furylene, thienylene, pyrrolinylene, oxazolylene, isooxazolylene, thiazolylene, isothiazolylene, imidazolylene, pyrazolylene, oxadiazolylene (1,2,5-oxadiazolylene, 1,3,4-oxadiazolylene, 1,2,4-oxadiazolylene), thiadiazolylene (1,2,5-thiadiazolylene, 1,3,4-thiadiazolylene, 1,2,4-thiadiazolylene), triazolylene (1,2,3-triazolylene, 1,2,4-triazolylene), tetrazolylene, pyridylene, pyrimidinylene, pyridazinylene, pyrazinylene, triazinylene and the like.

The preferred example of monocyclic heteroaromatic group includes thienylene, oxazolylene, thiazolylene, imidazolylene, pyrazolylene, oxadiazolylene (1,3,4-oxadiazolylene, 1,2,4-oxadiazolylene), triazolylene (1,2,4-triazolylene), tetrazolylene, pyridylene, pyrimidinylene and the like.

The definition "monocyclic heteroaromatic group which may be substituted with the same or different 1 to 5 substituents selected from Group A" means a monocyclic heteroaromatic group which may have the given substituent(s) on carbon atom(s) or on nitrogen atom(s) if it/they exist in the monocyclic heteroaromatic ring.

When nitrogen atom is contained in the monocyclic heteroaromatic ring, the nitrogen atom may be quaternized with a substituent or may be oxidized to form a N-oxide derivative thereof.

The term "autoimmune disease" is a collective term for diseases which relate to conditions wherein own immune system excessively reacts to own healthy cells or tissues and attacks them, and includes for example, rheumatoid arthritis, psoriasis, inflammatory bowel disease such as Crohn's disease and ulcerative colitis, multiple sclerosis, systemic lupus erythematosus, Behcet's disease, ankylosing spondylitis, uveitis, polymyalgia rheumatica, type I diabetes.

The "allergic disease" refers to a disease due to an excessive immune response to a particular antigen, and includes for example, atopic dermatitis, allergic rhinitis such as pollinosis, allergic conjunctivitis, allergic gastroenteritis, bronchial asthma, childhood asthma, food allergy, drug allergy, hives and the like.

The term "metabolic disease" refers to a disease caused by abnormal metabolic turnover or a disease relating to metabolic abnormality, and includes for example, diabetes such as type I diabetes and type II diabetes.

The "RORγ antagonist" refers to a compound which can inhibit a function of retinoid-related orphan receptor γ (RORγ) to make the activity thereof disappear or reduced.

The preferred examples of each substituent in the compounds represented by formula [I-W] or [I] are explained as follows.

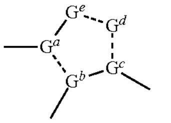

is

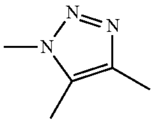

or

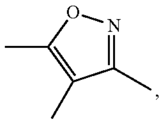

, and the examples of

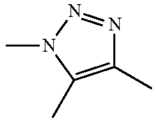

or

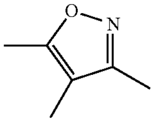

which are substituted with $R^a$ and $R^b$ includes:

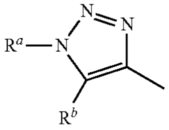

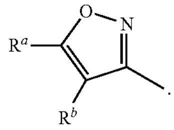

.

In one aspect, $R^a$ is $C_{5-12}$ alkyl group, preferably $C_{5-8}$ alkyl group, which may be substituted with the same or different 1 to 5 substituents selected from Group A.

The preferred $R^a$ includes an unsubstituted-$C_{5-8}$alkyl group, most preferably $(CH_3)_3CCH_2CH_2CH_2$—.

In one aspect, $R^a$ is

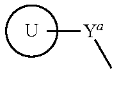

wherein $Y^a$ is (i) single bond, or (ii) $C_{1-6}$ alkylene group, cyclic moiety U is (i) cycloalkyl group which may be substituted with the same or different 1 to 5 substituents selected from Group A, (ii) $C_{5-11}$ spirocyclic cycloalkyl group which may be substituted with the same or different 1 to 5 substituents selected from Group A, or (iii) $C_{6-10}$ aryl group which may be substituted with the same or different 1 to 5 substituents selected from Group A.

In another aspect, $R^a$ is

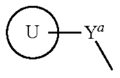

wherein $Y^a$ is (i) single bond, or (ii) $C_{1-6}$ alkylene group, cyclic moiety U is (i) $C_{3-7}$ cycloalkyl group which may be substituted with the same or different 1 to 5 substituents selected from Group A, or (ii) $C_{5-11}$ spirocyclic cycloalkyl group which may be substituted with the same or different 1 to 5 substituents selected from Group A.

The preferred $Y^a$ includes (i) single bond (ii) methylene, ethylene, trimethylene; and the more preferred $Y^a$ includes single bond, methylene and ethylene.

The preferred cyclic moiety U includes cyclobutyl group or cyclohexyl group, which may be substituted with the same or different 1 to 3 substituents selected from Group A;

the more preferred cyclic moiety U includes cyclobutyl group or cyclohexyl group, which may be substituted with the same or different 1 to 3 $C_{1-6}$ alkyl group; and the yet more preferred cyclic moiety U includes cyclobutyl group or cyclohexyl group, which may be substituted with the same or different 1 to 3 substituents selected from $(CH_3)_2CHCH_2$—, $(CH_3)_3CCH_2$—, $(CH_3)_2CHCH_2CH_2$—, $CH_3CH_2C(CH_3)_2CH_2$—, $(CH_3)_3CCH_2CH_2$—, $(CH_3)_2CHC(CH_3)_2$—, and $CH_3CH_2CH(C_2H_5)CH_2$—.

Another preferred cyclic moiety U includes spiro[4.4]nonanyl group, spiro[4.4]non-1-enyl group, spiro[4.5]decanyl group, spiro[4.5]dec-6-enyl group, spiro[5.5]undecanyl group, spiro[5.5]undec-1-enyl group, or spiro[3.5]nonyl group, which may be substituted with the same or different 1 to 5 substituents selected from Group A;

more preferably spiro[3.5]nonyl group which may be substituted with the same or different 1 to 5 substituents selected from Group A.

Another preferred cyclic moiety U includes phenyl group which may be substituted with the same or different 1 to 5 substituents selected from Group A;

more preferably phenyl group which may be substituted with the same or different 1 to 3 $C_{1-6}$ alkyl group;

yet more preferably, phenyl group which may be substituted with 1 to 3 $(CH_3)_2CHCH_2$—.

In another preferred aspect, $R^a$ includes the followings:

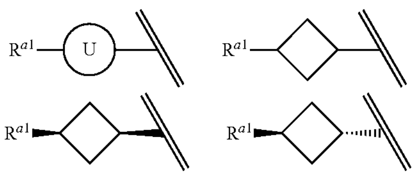

wherein $R^{a1}$ is $C_{1-6}$ alkyl group.

In one preferred aspect, $R^b$ includes $C_{1-3}$ alkyl group such as ethyl group and isopropyl group and the like, which may be substituted with the same or different 1 to 5 substituents selected from Group A; and the more preferred $R^b$ includes an unsubstituted-ethyl group, hydroxyethyl group, trifluoromethyl group, difluoromethyl group, 1,1-difluoro-ethyl group, and an unsubstituted-isopropyl group.

In another preferred aspect, $R^b$ includes $C_{2-3}$ alkenyl group, preferably vinyl group, 1-propenyl group, isopropenyl group, allyl group, which may be substituted with the same or different 1 to 5 substituents selected from Group A; and the more preferred $R^b$ includes an unsubstituted-vinyl group and an unsubstituted-isopropenyl group.

In yet another aspect, $R^b$ includes $C_{3-7}$ cycloalkyl group such as cyclopropyl group, cyclobutyl group, cyclopentyl group, cyclohexyl group, cycloheptyl group and the like, which may be substituted with the same or different 1 to 5 substituents selected from Group A;

the more preferred $R^b$ includes cyclopropyl group which may be substituted with the same or different 1 to 5 substituents selected from Group A; and the yet more preferred $R^b$ includes an unsubstituted-cyclopropyl group.

In one aspect, $R^c$ is (1) hydrogen atom, or (2) $C_{1-6}$ alkyl group, preferably $C_{1-3}$ alkyl group;

the more preferred $R^c$ includes hydrogen atom and methyl group.

In one aspect, $Y^c$ is single bond.

In another aspect, $Y^c$ is $C_{1-6}$ alkylene group which may be substituted with the same or different 1 to 5 substituents selected from Group A;

the preferred $Y^c$ includes $C_{1-6}$ alkylene group which may be substituted with the same or different 1 to 3 $C_{1-3}$ alkyl group; and the more preferred $Y^c$ includes —$CH_2$—, —$CH_2CH_2CH_2CH_2$—, —$CH(CH_3)$—, —$CH_2CH(CH_3)$—, —$C(CH_3)_2$—, —$CH_2C(CH_3)_2$—, —$CH_2CH_2$—, —$CH(CH_3)CH_2$—, —$C(CH_3)_2CH_2$, and —$CH_2CH_2$ $CH_2$—, wherein the symbol "—" located on the terminal sides of these chemical formulae indicates a single bond, and the right and left bonds are linked to right and left moieties adjacent to $Y^c$, respectively.

In another aspect, $Y^c$ is —$NR^{C1}$— wherein $R^{C1}$ is hydrogen atom or $C_{1-6}$ alkyl group;

the preferred example of $R^{C1}$ includes hydrogen atom and $C_{1-3}$ alkyl group; and the more preferred example of $R^{C1}$ includes hydrogen atom.

In another aspect, $Y^c$ is —O—.

In another aspect, $Y^c$ is $C_{3-10}$ cycloalkylene group such as cyclopropylene group, cyclobutylene group, cyclopentylene group, cyclo hexylene group, cycloheptylene group and cyclooctylene group and the like, which may be substituted with the same or different 1 to 5 substituents selected from Group A;

the preferred example of $Y^c$ includes cyclobutylene group which may be substituted with the same or different 1 to 2 substituents selected from Group A; and the most preferred example of $Y^c$ includes an unsubstituted-cyclobutylene group.

In one aspect, $Y^c$ is $C_{6-10}$ arylene group such as phenylene group and naphthylene group and the like, which may be substituted with the same or different 1 to 5 substituents selected from Group A; and the preferred example of $Y^c$ includes unsubstituted-phenylene group.

In one aspect, $Y^c$ is monocyclic heteroaromatic group which may be substituted with the same or different 1 to 5 substituents selected from Group A wherein the monocyclic heteroaromatic ring consists of carbon atoms and the same or different 1 to 4 hetero atoms selected from nitrogen atom, oxygen atom and sulfur atom, and is 3 to 7-membered;

the preferred example of $Y^c$ includes thienylene, oxazolylene, thiazolylene, imidazolylene, pyrazolylene, oxadiazolylene (1,3,4-oxadiazolylene, 1,2,4-oxadiazolylene), triazolylene (1,2,4-triazolylene), tetrazolylene, pyridylene, pyrimidinylene and the like, which may be substituted with the same or different 1 to 3 substituents selected from Group A; and the more preferred example of $Y^C$ includes unsubstituted-thiazolylene.

In one aspect, $Y^{d1}$ is single bond.

In one aspect, $Y^{d1}$ is $C_{1-6}$ alkylene group which may be substituted with the same or different 1 to 5 substituents selected from Group A;

the preferred example of $Y^{d1}$ includes $C_{1-3}$ alkylene group which may be substituted with the same or different 1 to 5 $C_{1-3}$ alkyl group; and the more preferred example of $Y^{d1}$ includes $—CH_2—$ and $—CH(CH_3)—$.

In one aspect, the compound of formula [I-W] wherein both $Y^c$ and $Y^{d1}$ may be methine and be linked each other directly or via $C_{1-4}$ alkylene group to form $C_{3-7}$ cycloalkyl ring includes compounds of the following formula [I-Wc]:

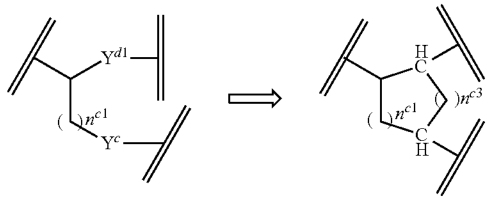

[I-Wc]

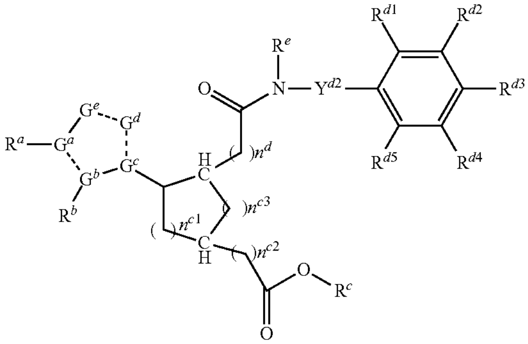

wherein $n^{c3}$ is an integer selected from 0 or 1 to 4, and the other symbols are as defined in [01], provided that a sum of $n^{c1}$ and $n^{c3}$ is an integer selected from 0 or 1 to 4.

In one aspect, the compound of formula [I-W] wherein both $Y^c$ and $Y^{d1}$ may be methine and be linked each other directly or via $C_{1-4}$ alkylene group to form $C_{3-7}$ cycloalkyl ring includes compounds of the following formula [I-Wc5] wherein $Y^c$ and $Y^{d1}$ are connected via methylene to form a cyclopentane moiety:

[I-Wc5]

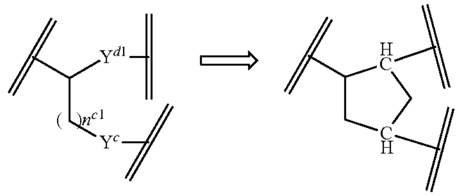

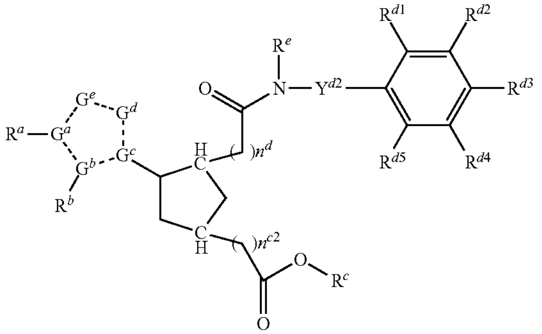

wherein each symbol is as defined in [01].

In one aspect, $Y^{d2}$ is a single bond.

In another aspect, $Y^{d2}$ is $C_{1-6}$ alkylene group, preferably $C_{1-3}$ alkylene group, more preferably $—CH_2—$.

In one aspect, $R^{d1}$, $R^{d2}$, $R^{d3}$, $R^{d4}$, and $R^{d5}$ are the same or different group selected from the following (1) to (7):

(1) hydrogen atom (2) halogen atom, (3) $C_{1-6}$ alkyl group which may be substituted with the same or different 1 to 5 substituents selected from Group A, (4) $—OR^{d10}$ wherein $R^{d10}$ is hydrogen atom or $C_{1-6}$ alkyl group which may be substituted with the same or different 1 to 5 substituents selected from Group A, (5) $—COOR^{d11}$ wherein $R^{d11}$ is hydrogen atom or $C_{1-6}$ alkyl group, (6) $C_{3-7}$ cycloalkyl group which may be substituted with the same or different 1 to 5 substituents selected from Group A, (7) cyano group, or alternatively $R^{d1}$ and $R^{d2}$, or $R^{d2}$ and $R^{d3}$ can be taken together to form a $C_{6-10}$ aryl ring fused to the benzene ring to which they are all attached wherein the $C_{6-10}$ aryl ring is unsubstituted or substituted with the same or different 1 to 4 substituents selected from Group A.

In another aspect, $R^{d1}$, $R^{d2}$, $R^{d3}$, $R^{d4}$, and $R^{d5}$ are the same or different group selected from the following (1) to (4):

(1) hydrogen atom (2) halogen atom, (3) $C_{1-6}$ alkyl group which may be substituted with the same or different 1 to 5 substituents selected from Group A, (4) $—OR^{d10}$ wherein $R^{d10}$ is hydrogen atom or $C_{1-6}$ alkyl group which may be substituted with the same or different 1 to 5 substituents selected from Group A, or alternatively $R^{d1}$ and $R^{d2}$, or $R^{d2}$ and $R^{d3}$ can be taken together to form a $C_{6-10}$ aryl ring fused to the benzene ring to which they are all attached wherein the $C_{6-10}$ aryl ring is unsubstituted or may be substituted with the same or different 1 to 4 substituents selected from Group A.

In the preferred aspect, $R^{d1}$, $R^{d2}$, $R^{d3}$, $R^{d4}$, and $R^{d5}$ are the same or different group selected from the following (1) to (7):

(1) hydrogen atom, (2) fluorine atom or chlorine atom, (3) $C_{1-3}$ alkyl group which may be substituted with the same or different 1 to 5 halogen atoms, wherein the specific example of $R^{d1}$, $R^{d2}$, $R^{d3}$, $R^{d4}$, and $R^{d5}$ includes unsubstituted-methyl, unsubstituted-ethyl, and trifluoromethyl, (4) —$OR^{d10}$ wherein $R^{d10}$ is hydrogen atom or $C_{1-3}$ alkyl group which may be substituted with the same or different 1 to 5 substituents selected from Group A, wherein the specific example of said —$OR^{d11}$ includes methoxy group, (5) —$COOR^{d11}$ wherein $R^{d11}$ is hydrogen atom or $C_{1-6}$ alkyl group, preferably $R^{d11}$ is hydrogen atom, (6) cyclopropyl group, (7) cyano group.

In another preferred aspect $R^{d1}$, $R^{d2}$, $R^{d3}$, $R^{d4}$, and $R^{d5}$ are the same or different group selected from the following (1) to (4):

(1) hydrogen atom, (2) fluorine atom or chlorine atom, (3) $C_{1-3}$ alkyl group which may be substituted with the same or different 1 to 5 halogen atoms, wherein the specific example of $R^{d1}$, $R^{d2}$, $R^{d3}$, $R^{d4}$, and $R^{d5}$ includes unsubstituted-methyl, unsubstituted-ethyl, and trifluoromethyl, (4) —$OR^{d10}$ wherein $R^{d10}$ is hydrogen atom or $C_{1-3}$ alkyl group which may be substituted with the same or different 1 to 5 substituents selected from Group A, wherein the specific example of said —$OR^{d10}$ includes methoxy group.

In another aspect, $R^{d1}$ and $R^{d2}$, or $R^{d2}$ and $R^{d3}$ can be taken together to form a benzene ring fused to another benzene ring to which they are all attached wherein the former benzene ring may be substituted with the same or different 1 to 4 substituents selected from Group A, and for example, the following naphthalene ring moieties are provided:

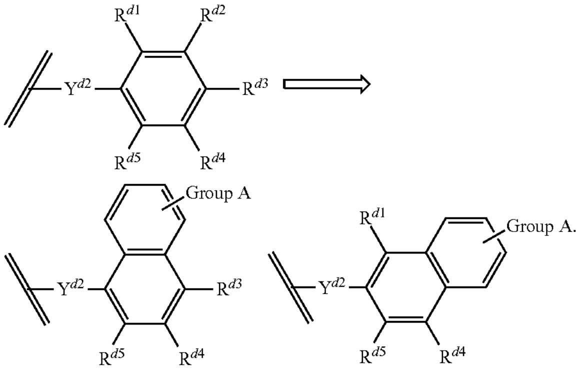

In one aspect, $R^e$ is (1) hydrogen atom, or (2) $C_{1-3}$ alkyl group, or alternatively $R^e$ and $R^{d1}$, or $R^e$ and $R^{d5}$ can be taken together to form alkylene.

The preferred example of $R^e$ includes (1) hydrogen atom, (2) methyl group.

In the preferred aspect, $R^e$ and $R^{d1}$, or $R^e$ and $R^{d5}$ can be taken together to form ethylene, and for example, the following ring moieties are provided:

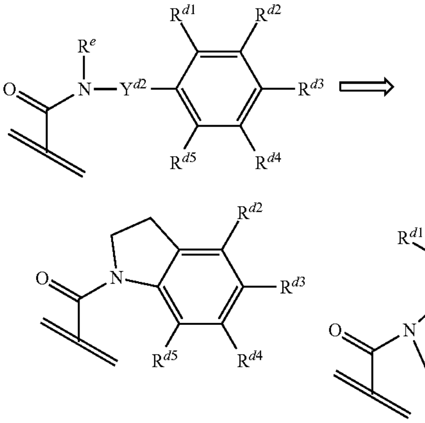

In formula [I-W] or [I], the example of the moiety containing $Y^{d2}$ and the benzene ring to which $Y^{d2}$ is attached includes as follows:

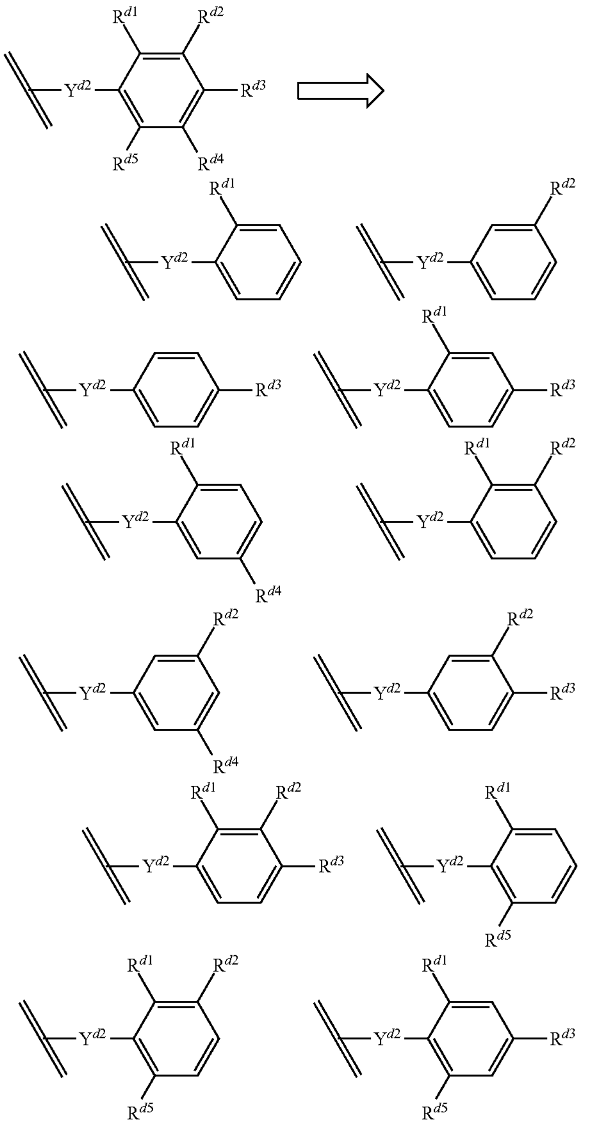

-continued

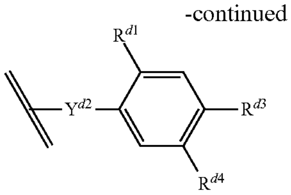

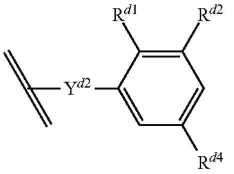

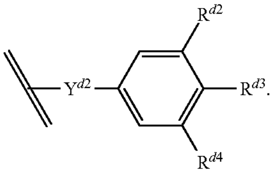

In one aspect, $n^{c1}$ is an integer selected from 0 or 1 to 4, preferably 0 or 1.

In another aspect, $n^{c1}$ is an integer selected from 0 or 1 to 3, preferably 0 or 1.

In one aspect, $n^{c2}$ is an integer selected from 0 or 1 to 3, preferably 0 or 1.

In one aspect, $n^{d}$ is an integer selected from 0 or 1 to 3, preferably 0.

In one aspect, Group A is (a) $C_{1-6}$ alkyl group, (b) halogen atom, and (c) —$OR^{A1}$ wherein $R^{A1}$ is hydrogen atom or $C_{1-6}$ alkyl group.

The preferred Group A includes:

(a) $CH_3$—, $(CH_3)_2CHCH_2$—, $(CH_3)_3CCH_2$—, $(CH_3)_2CHCH_2CH_2$—, $CH_3CH_2C(CH_3)_2CH_2$—, $(CH_3)_3CCH_2CH_2$—, $(CH_3)_2CHO(CH_3)_2$—, and $CH_3CH_2CH(C_2H_5)CH_2$—, (b) fluorine atom and chlorine atom, (c) —OH, and —$OC_{1-3}$ alkyl such as methoxy group.

The preferred aspect of compounds of formula [I-W] includes compounds of the following formula:

[I-A-W]

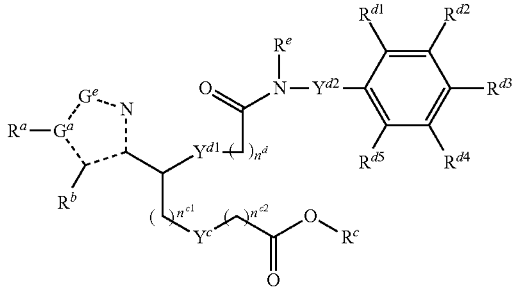

wherein

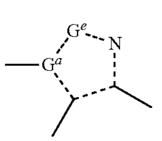

is

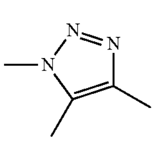

or

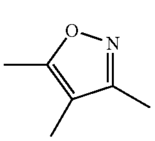

;

the other symbols are as defined in [01].

The preferred aspect of compounds of formula [I-W] includes compounds of the following formulae:

[II-B3-W]

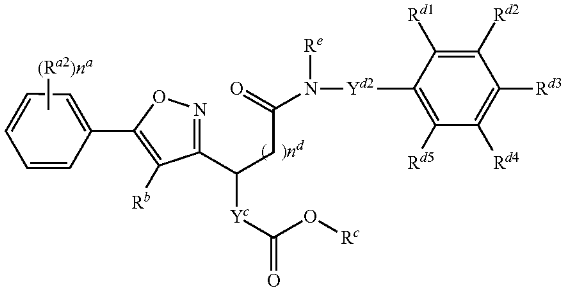

[II-B31-W]

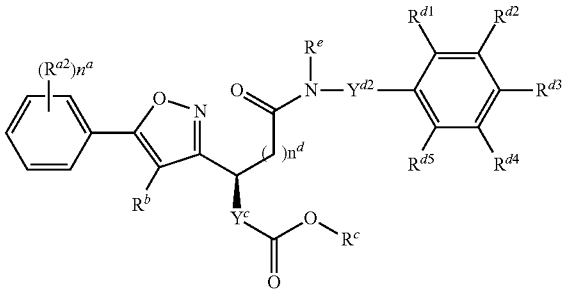

[II-B32-W]

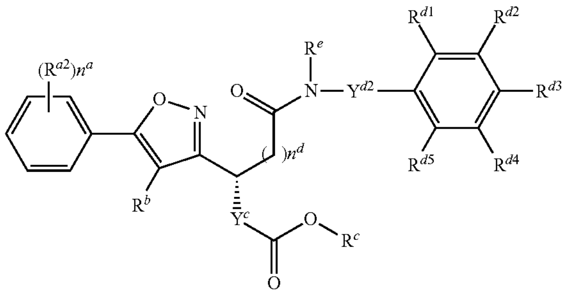

wherein $R^{a2}$ is independently selected from the group consisting of:

(a) $C_{1-6}$ alkyl group, (b) halogen atom, and (c) —$OR^{A1}$ wherein $R^{A1}$ is hydrogen atom or $C_{1-6}$ alkyl group;

$n^{a}$ is an integer selected from 0 or 1 to 5; and the other symbols are as defined in [01].

Another preferred aspect of compounds of formula [I-W] includes compounds of the following formula:

[I-Wc]

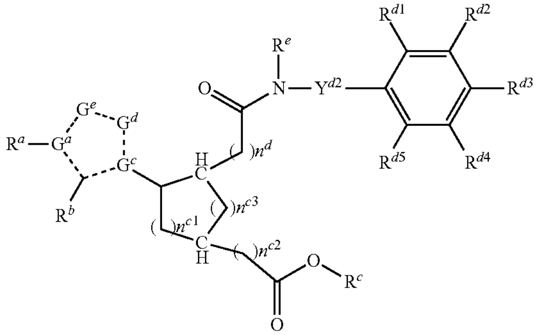

wherein $n^{c3}$ is an integer selected from 0 or 1 to 4; and the other symbols are as defined in [01], provided that a sum of $n^{c1}$ and $n^{c3}$ is an integer selected from 0 or 1 to 4.

Another preferred aspect of compounds of formula [I-W] includes compounds of the following formula:

[I-Wc5]

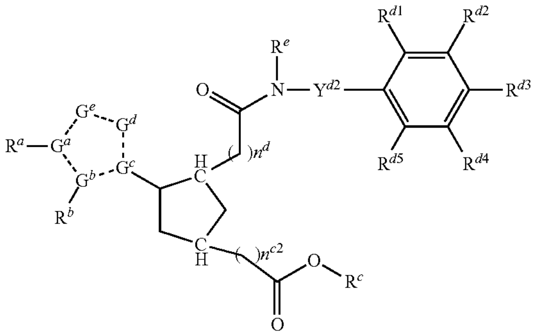

wherein each symbol is as defined in [01]

Another preferred aspect of compounds of formula [I-W] includes compounds of the following formula:

[II-C1-W]

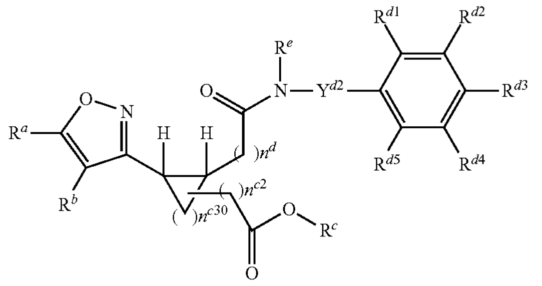

wherein $n^{c30}$ is an integer selected from 1 to 5; and the other symbols are as defined in [01].

Another preferred aspect of compounds of formula [I-W] includes compounds of the following formulae:

[II-C2-W]

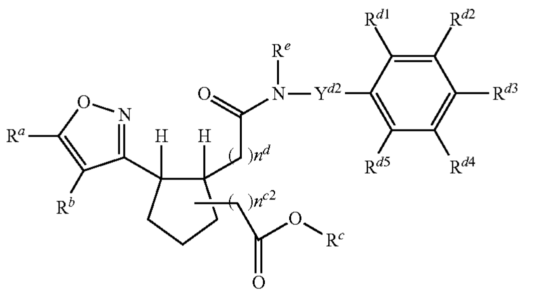

-continued

[II-C3-W]

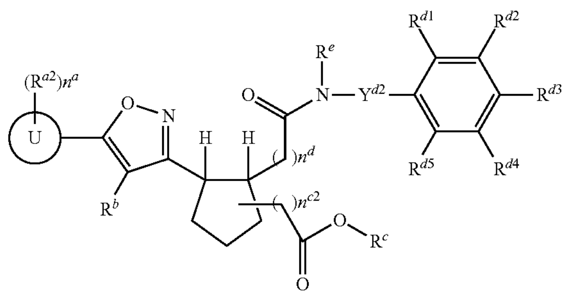

[II-C4-W]

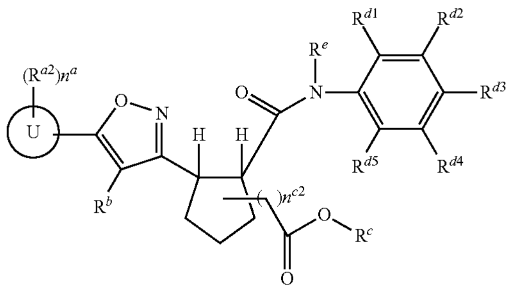

[II-C51-W]

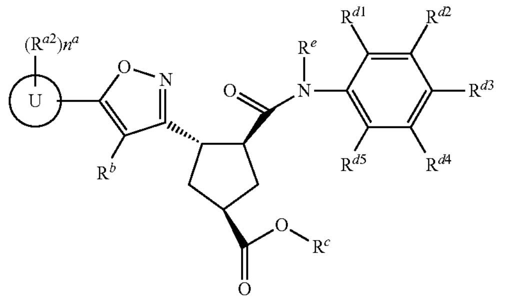

[II-C52-W]

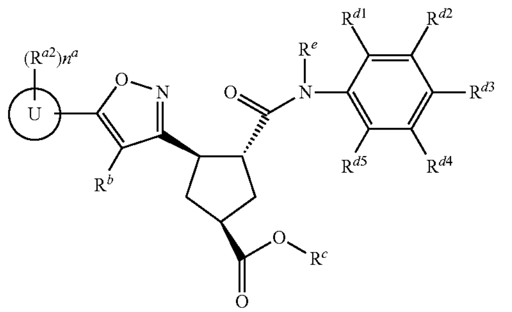

[II-C53-W]

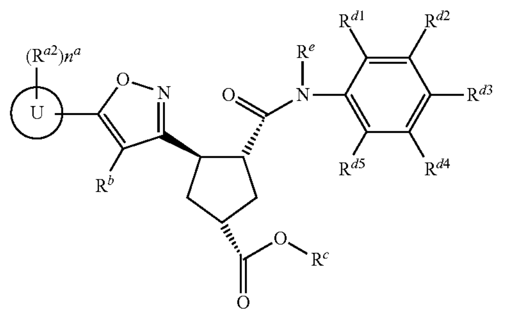

-continued

[II-C54-W]

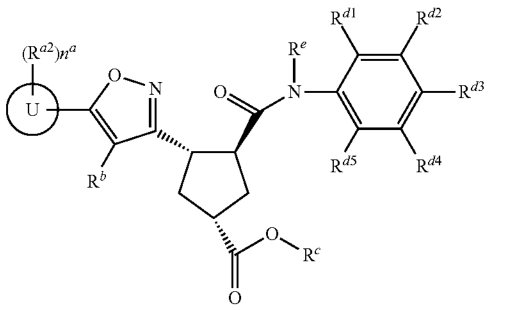

wherein $R^{a2}$ is independently selected from the group consisting of:

(a) $C_{1-6}$ alkyl group, (b) halogen atom, and (c) —$OR^{A1}$ wherein $R^{A1}$ is hydrogen atom or $C_{1-6}$ alkyl group, $n^a$ is an integer selected from 0 or 1 to 5; and the other symbols are as defined in [01].

Another preferred aspect of compounds of formula [I-W] includes compounds of the following formulae:

[I-A10-W]

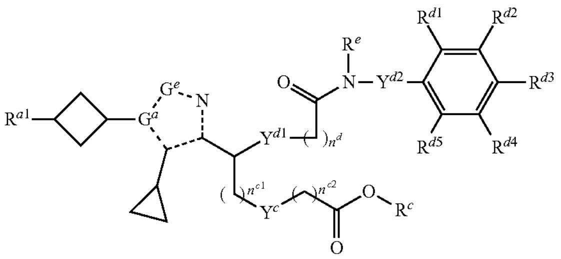

[I-A20-W]

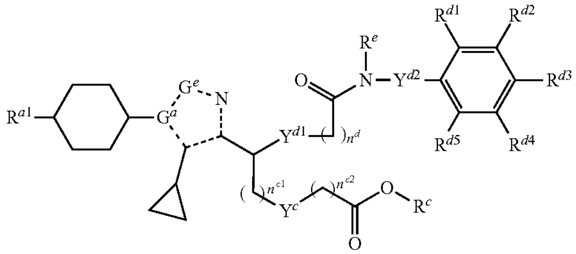

wherein

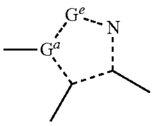 is 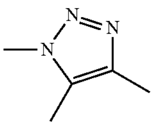 or 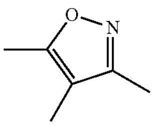 ;

$R^{a1}$ is $C_{1-6}$ alkyl group, and the other symbols are as defined in [01]; and

[I-A30-W]

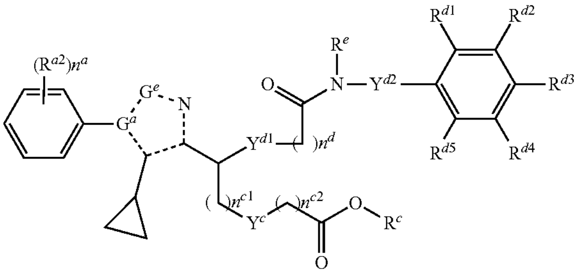

wherein

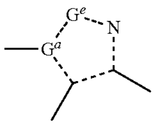 is 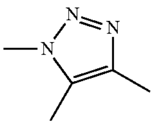 or 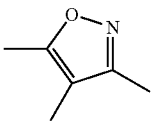 , $R^{a2}$ is independently selected from the group consisting of:

(a) $C_{1-6}$ alkyl group, (b) halogen atom, and (c) —$OR^{A1}$ wherein $R^{A1}$ is hydrogen atom or $C_{1-6}$ alkyl group, $n^a$ is an integer selected from 0 or 1 to 5; and the other symbols are as defined in [01].

The preferred aspect of compounds of formula [I-W] or [I] includes compounds of the following formulae:

[I-A]

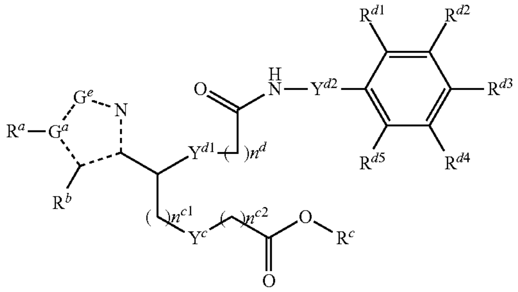

[II]

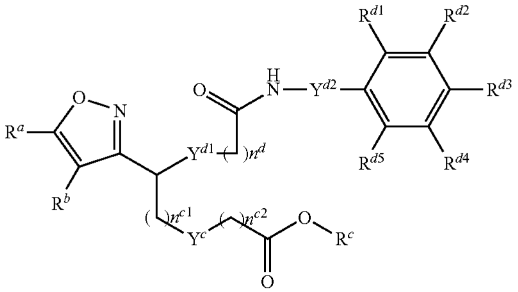

-continued
[III]
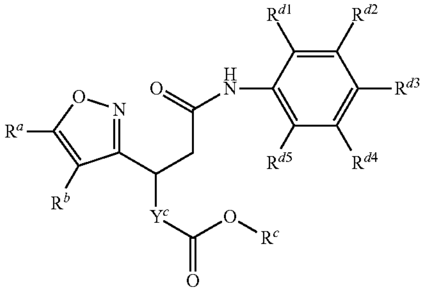
[IV]
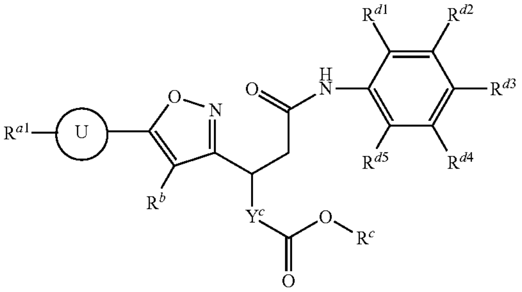
[IV-A1]
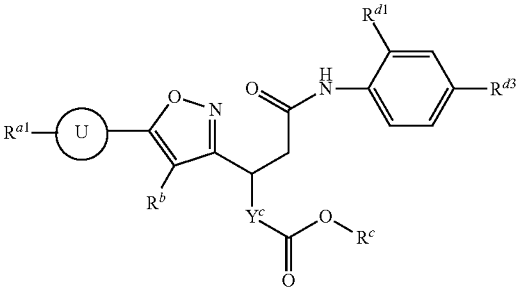
[IV-A2]
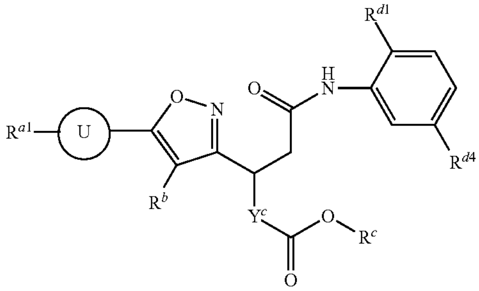
[IV-A3]
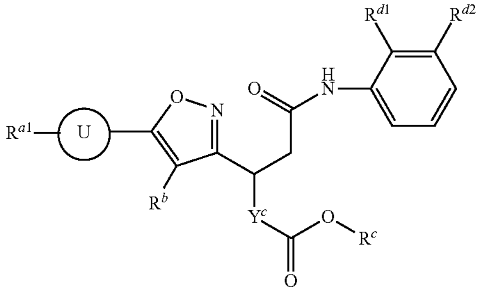
-continued
[IV-A4]
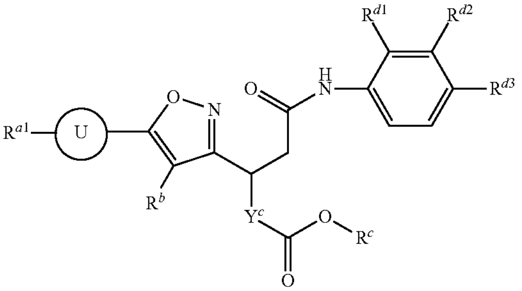
[IV-B1]
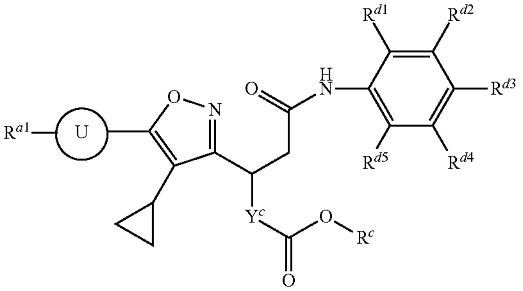
[IV-B2]
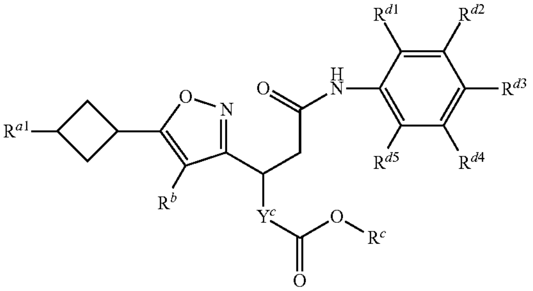
[IV-B21]
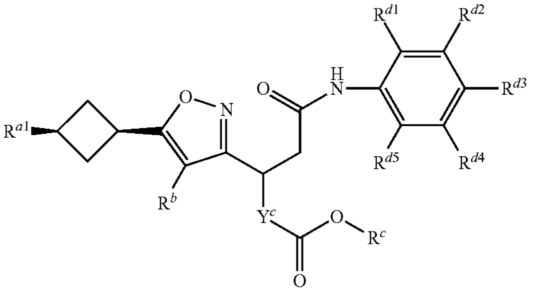
[IV-B22]
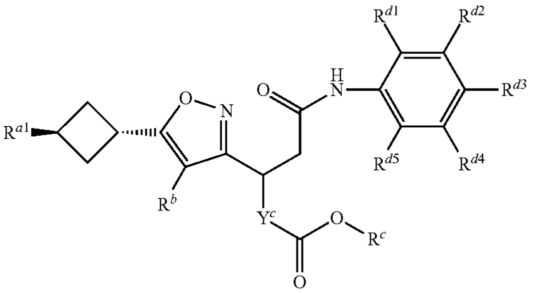

-continued
[IV-C1]
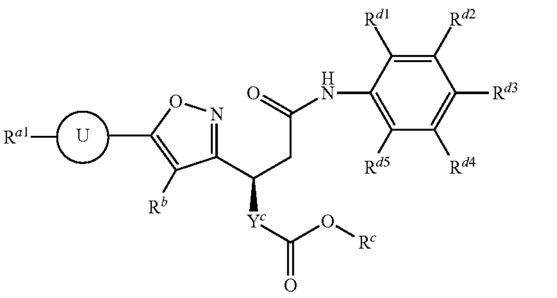
[IV-C2]
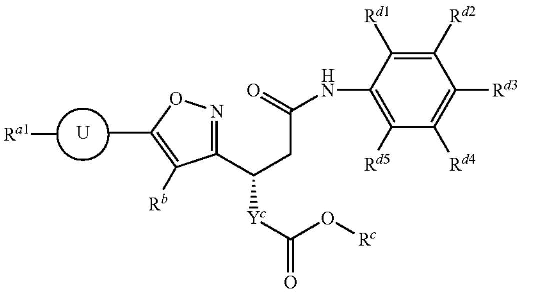
[IV-D1]
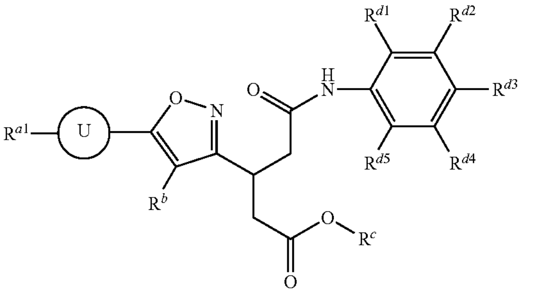
[IV-D2]
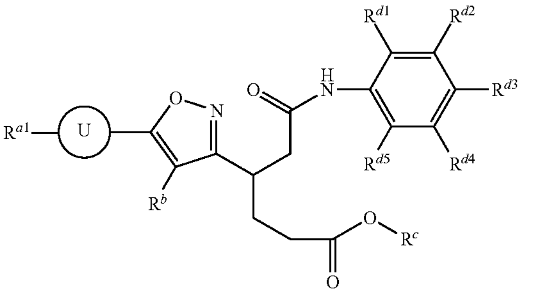
[IV-D3]
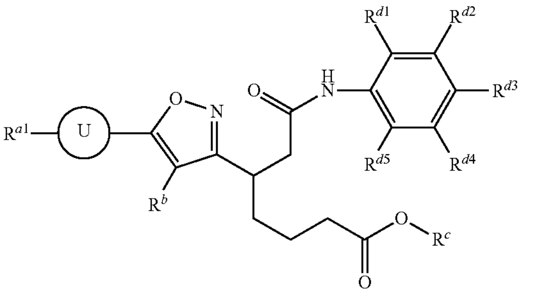
-continued
[IV-D4]
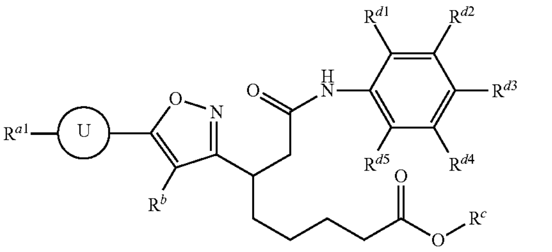
[IV-D5]
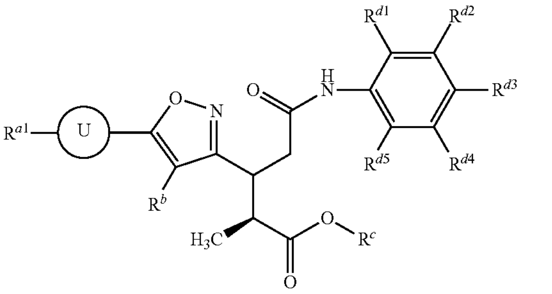
[IV-D6]
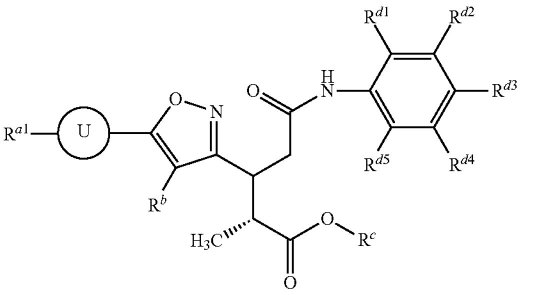
[IV-D7]
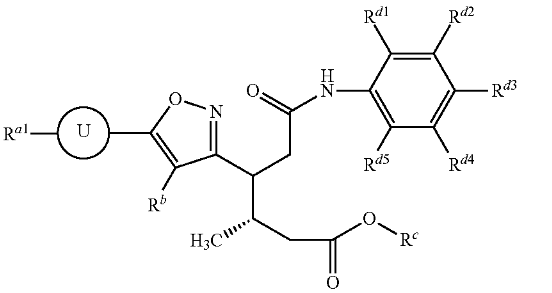
[IV-D8]
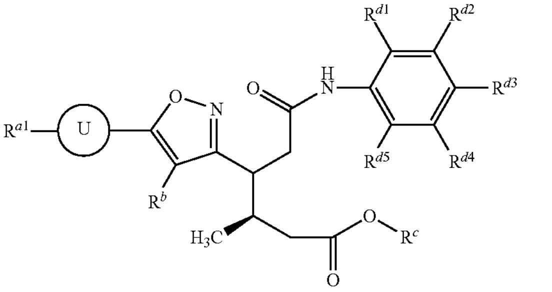

-continued
[IV-B21-C2]
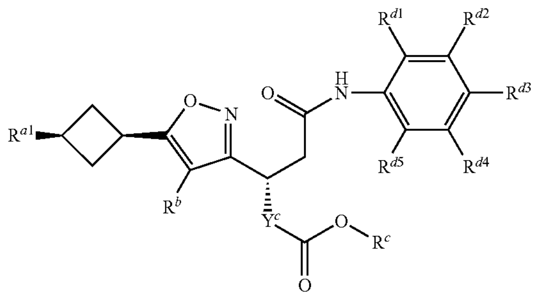
[IV-B21-C1]
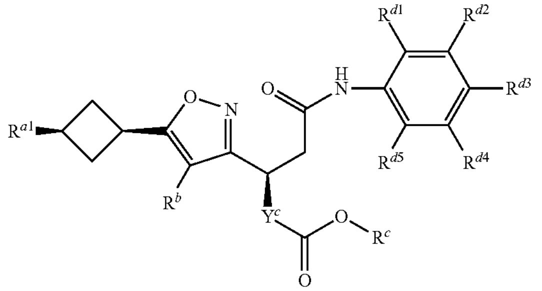
[IV-B22-C1]
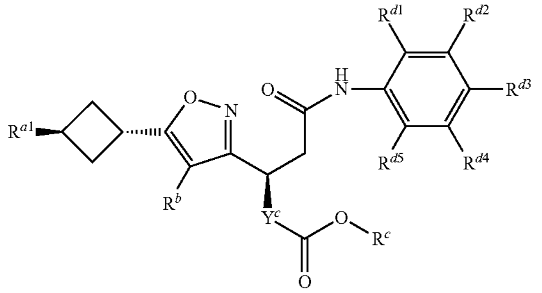
[IV-B22-C2]
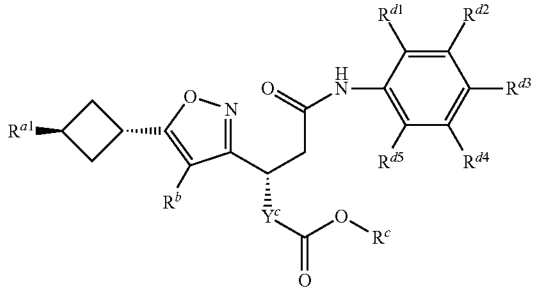
[V]
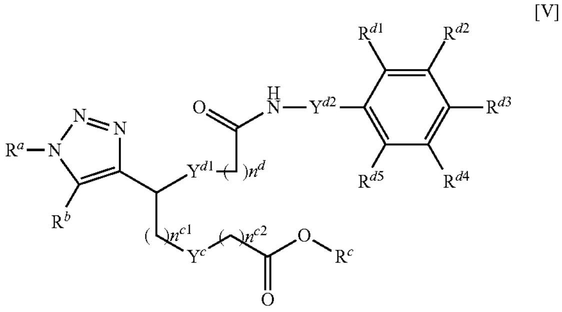
-continued
[V-A]
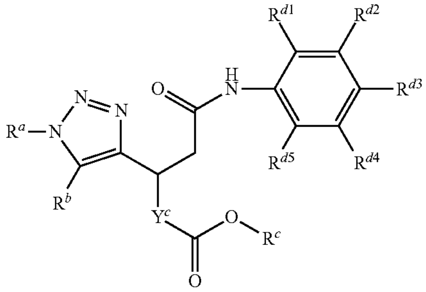
[V-B]
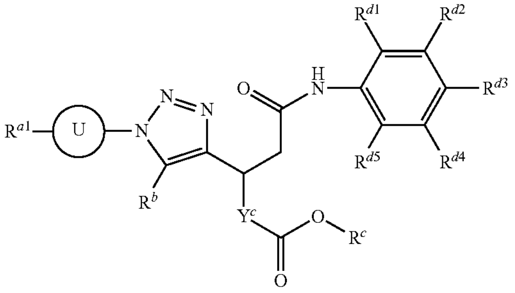
[V-C1]
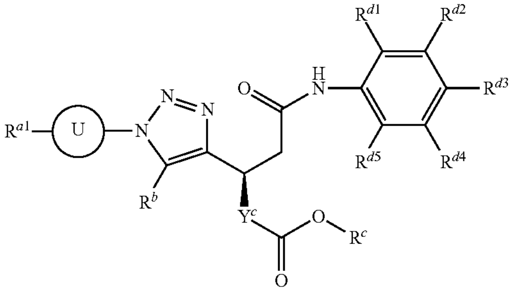
[V-C2]
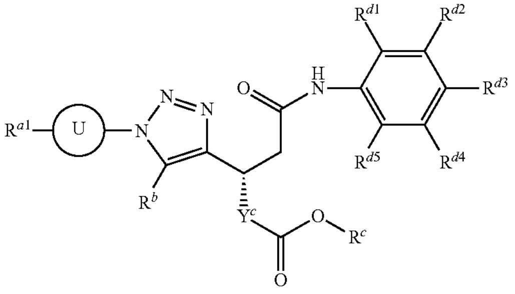
[V-B21-C2]
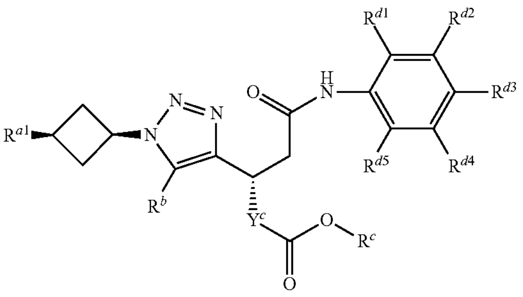

-continued

[V-B21-C1]

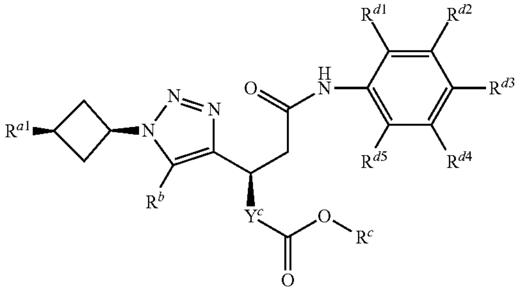

[V-B22-C1]

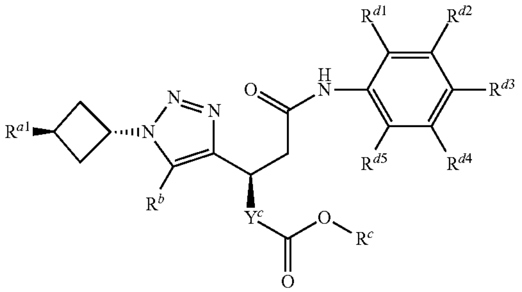

[V-B22-C2]

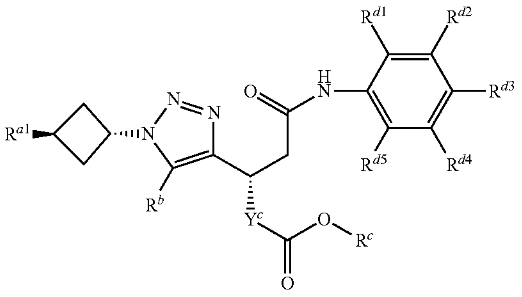

wherein $R^{a1}$ is $C_{1-6}$ alkyl group,

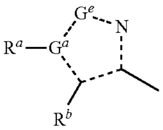 is 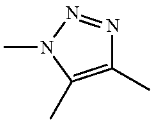 or 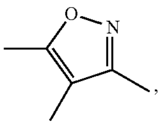, and the other symbols are as defined in [01].

The preferred aspect of compounds of formula [I-W] or [I] includes compounds of the following formulae:

[I-C2-W]

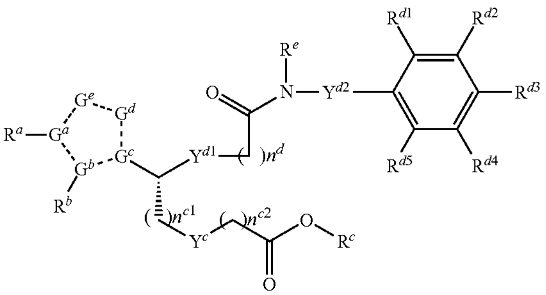

-continued

[IV-B21-C2]

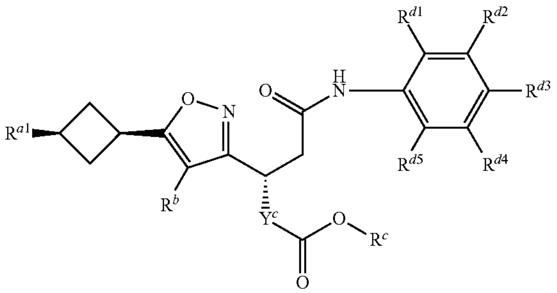

The preferred aspect of compounds of formula [I-W] or [I] includes compounds of the following formulae:

[IV-B21-C2-R01]

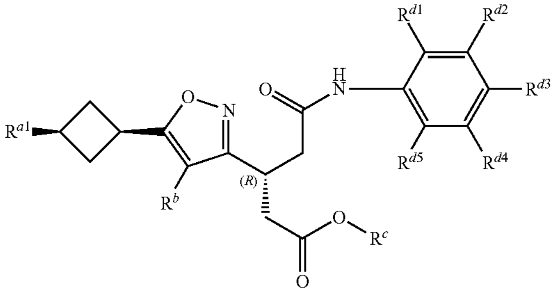

[IV-B21-C2-S02]

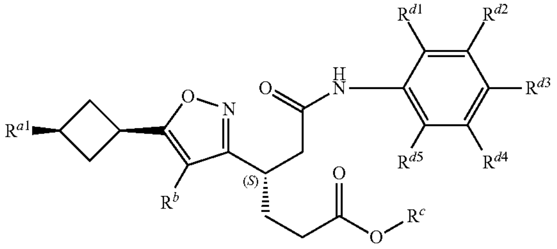

The preferred compound of formula [I-W] or [I] includes compounds of the following formulae:

TABLE 1

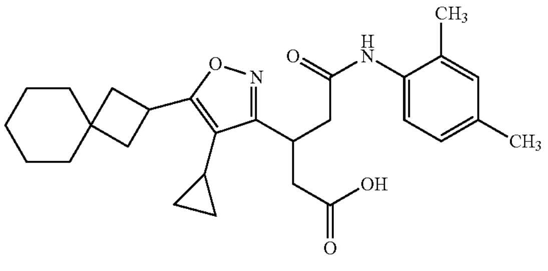 [SMILES: Cc1ccc(NC(=O)CC(CC(=O)O)c2noc(C3CC4(CCCCC4)C3)c2C2CC2)c(C)c1]

TABLE 1-continued
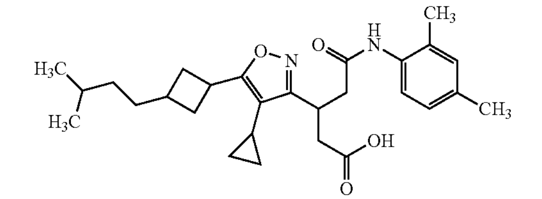 [SMILES: Cc1ccc(NC(=O)CC(CC(=O)O)c2noc(C3CC(CCC(C)C)C3)c2C2CC2)c(C)c1]
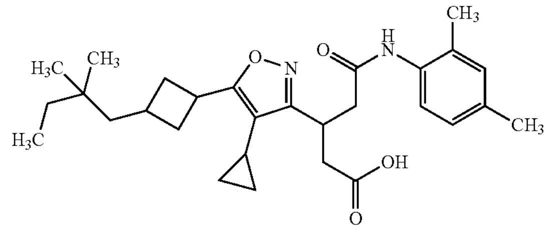 [SMILES: CCC(C)(C)CC1CC(c2onc(C(CC(=O)O)CC(=O)Nc3ccc(C)cc3C)c2C2CC2)C1]
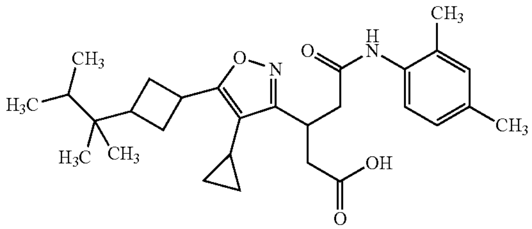 [SMILES: Cc1ccc(NC(=O)CC(CC(=O)O)c2noc(C3CC(C(C)(C)C(C)C)C3)c2C2CC2)c(C)c1]
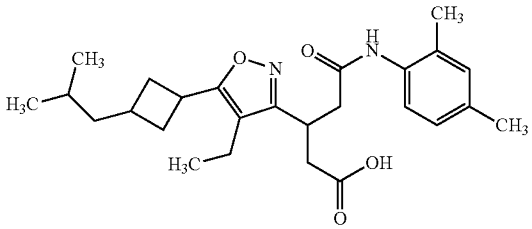 [SMILES: CCc1c(C(CC(=O)O)CC(=O)Nc2ccc(C)cc2C)noc1C1CC(CC(C)C)C1]
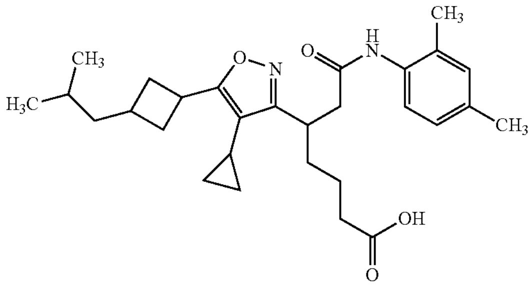 [SMILES: Cc1ccc(NC(=O)CC(CCCC(=O)O)c2noc(C3CC(CC(C)C)C3)c2C2CC2)c(C)c1]
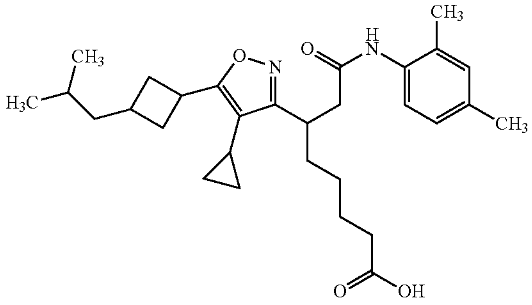 [SMILES: Cc1ccc(NC(=O)CC(CCCCC(=O)O)c2noc(C3CC(CC(C)C)C3)c2C2CC2)c(C)c1]
TABLE 1-continued
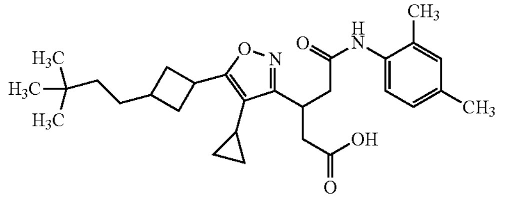 [SMILES: Cc1ccc(NC(=O)CC(CC(=O)O)c2noc(C3CC(CCC(C)(C)C)C3)c2C2CC2)c(C)c1]
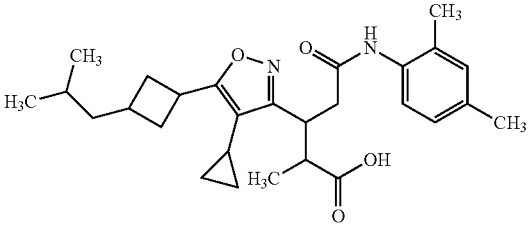 [SMILES: Cc1ccc(NC(=O)CC(c2noc(C3CC(CC(C)C)C3)c2C2CC2)C(C)C(=O)O)c(C)c1]
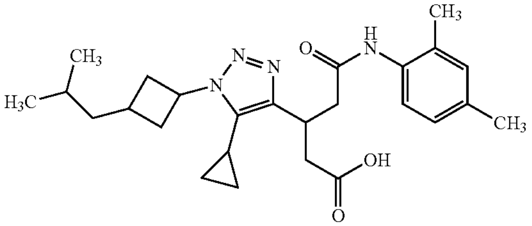 [SMILES: Cc1ccc(NC(=O)CC(CC(=O)O)c2nnn(C3CC(CC(C)C)C3)c2C2CC2)c(C)c1]
TABLE 2
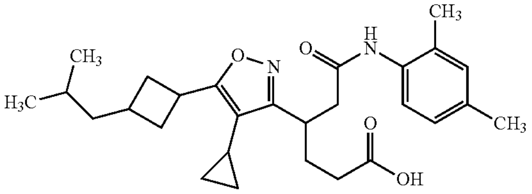
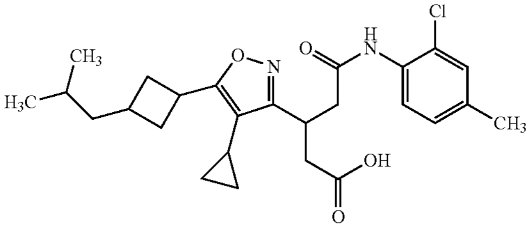 [SMILES: Cc1ccc(NC(=O)CC(CC(=O)O)c2noc(C3CC(CC(C)C)C3)c2C2CC2)c(Cl)c1]
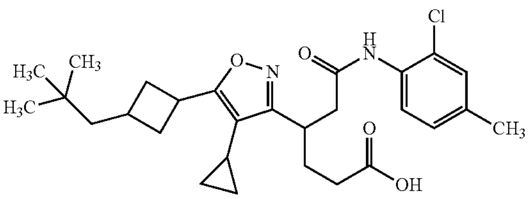 [SMILES: Cc1ccc(NC(=O)CC(CCC(=O)O)c2noc(C3CC(CC(C)(C)C)C3)c2C2CC2)c(Cl)c1]
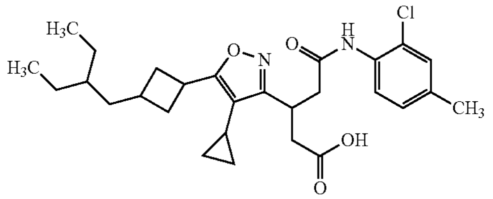 [SMILES: CCC(CC)CC1CC(c2onc(C(CC(=O)O)CC(=O)Nc3ccc(C)cc3Cl)c2C2CC2)C1]

TABLE 2-continued
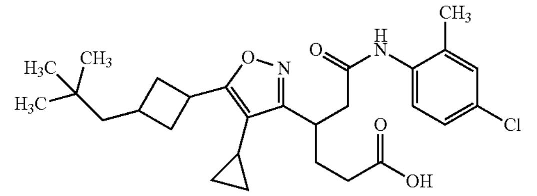 [SMILES: Cc1cc(Cl)ccc1NC(=O)CC(CCC(=O)O)c1noc(C2CC(CC(C)(C)C)C2)c1C1CC1]
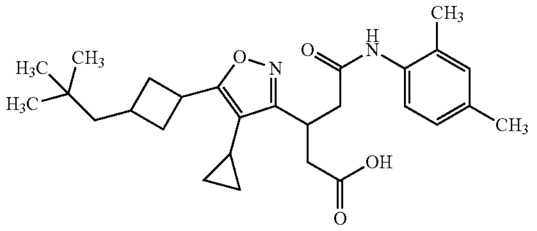 [SMILES: Cc1ccc(NC(=O)CC(CC(=O)O)c2noc(C3CC(CC(C)(C)C)C3)c2C2CC2)c(C)c1]
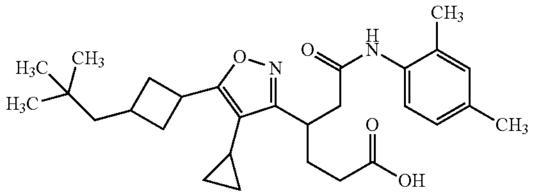
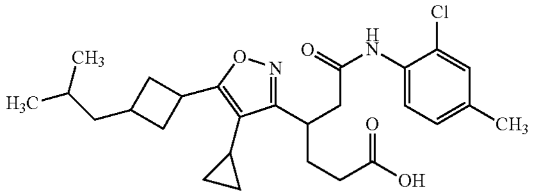 [SMILES: Cc1ccc(NC(=O)CC(CCC(=O)O)c2noc(C3CC(CC(C)C)C3)c2C2CC2)c(Cl)c1]
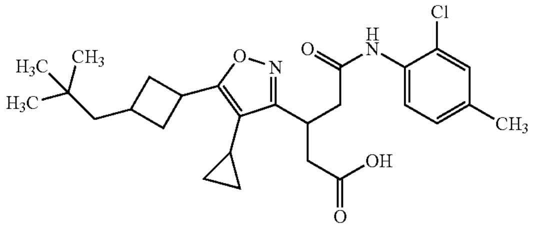 [SMILES: Cc1ccc(NC(=O)CC(CC(=O)O)c2noc(C3CC(CC(C)(C)C)C3)c2C2CC2)c(Cl)c1]
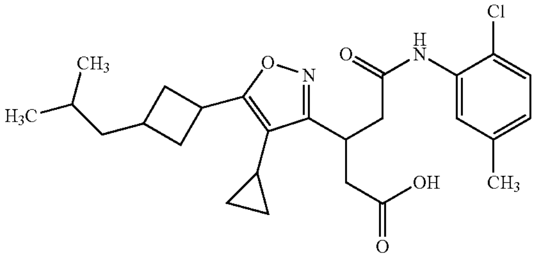 [SMILES: Cc1ccc(Cl)c(NC(=O)CC(CC(=O)O)c2noc(C3CC(CC(C)C)C3)c2C2CC2)c1]
TABLE 3
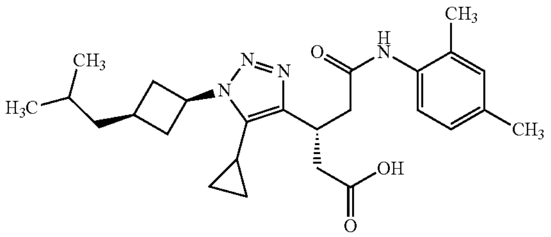 [SMILES: Cc1ccc(NC(=O)C[C@H](CC(=O)O)c2nnn([C@H]3C[C@@H](CC(C)C)C3)c2C2CC2)c(C)c1]
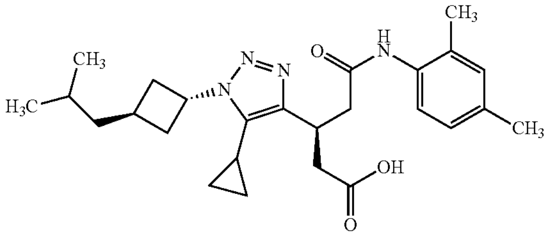 [SMILES: Cc1ccc(NC(=O)C[C@@H](CC(=O)O)c2nnn([C@H]3C[C@H](CC(C)C)C3)c2C2CC2)c(C)c1]
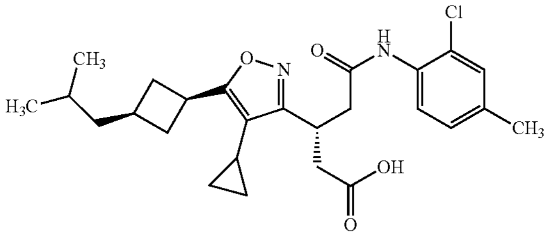 [SMILES: Cc1ccc(NC(=O)C[C@H](CC(=O)O)c2noc([C@H]3C[C@@H](CC(C)C)C3)c2C2CC2)c(Cl)c1]
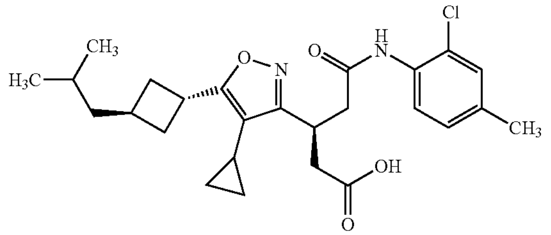 [SMILES: Cc1ccc(NC(=O)C[C@@H](CC(=O)O)c2noc([C@H]3C[C@H](CC(C)C)C3)c2C2CC2)c(Cl)c1]
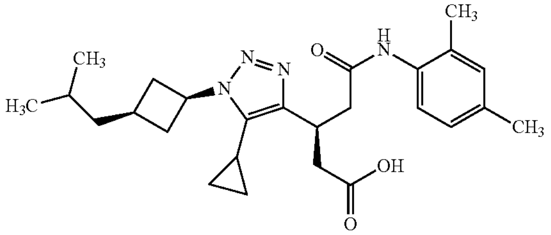 [SMILES: Cc1ccc(NC(=O)C[C@@H](CC(=O)O)c2nnn([C@H]3C[C@@H](CC(C)C)C3)c2C2CC2)c(C)c1]
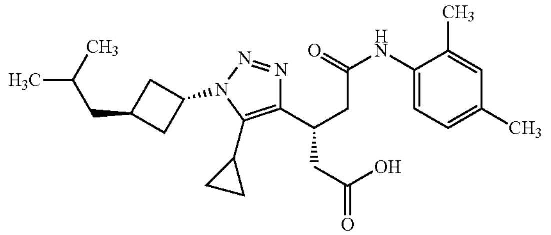 [SMILES: Cc1ccc(NC(=O)C[C@H](CC(=O)O)c2nnn([C@H]3C[C@H](CC(C)C)C3)c2C2CC2)c(C)c1]

TABLE 3-continued
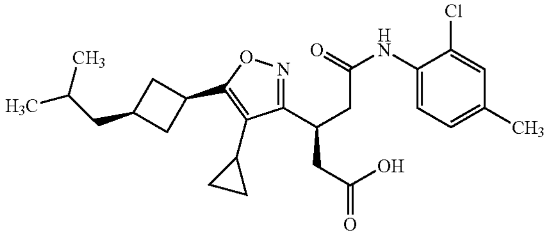 [SMILES: Cc1ccc(NC(=O)C[C@@H](CC(=O)O)c2noc([C@H]3C[C@@H](CC(C)C)C3)c2C2CC2)c(Cl)c1]
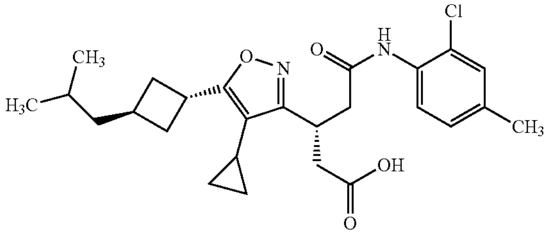 [SMILES: Cc1ccc(NC(=O)C[C@H](CC(=O)O)c2noc([C@H]3C[C@H](CC(C)C)C3)c2C2CC2)c(Cl)c1]
TABLE 4
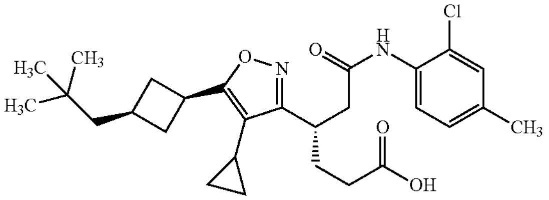 [SMILES: Cc1ccc(NC(=O)C[C@H](CCC(=O)O)c2noc([C@H]3C[C@@H](CC(C)(C)C)C3)c2C2CC2)c(Cl)c1]
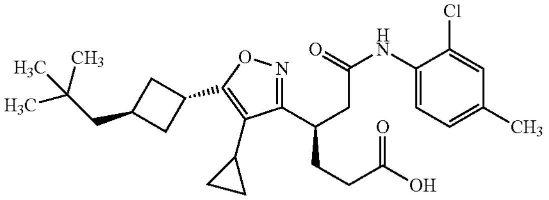 [SMILES: Cc1ccc(NC(=O)C[C@@H](CCC(=O)O)c2noc([C@H]3C[C@H](CC(C)(C)C)C3)c2C2CC2)c(Cl)c1]
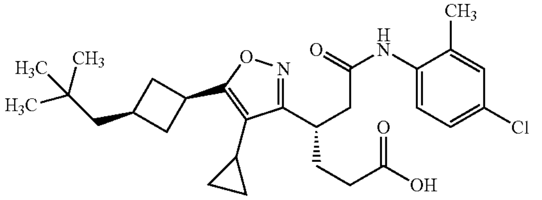 [SMILES: Cc1cc(Cl)ccc1NC(=O)C[C@H](CCC(=O)O)c1noc([C@H]2C[C@@H](CC(C)(C)C)C2)c1C1CC1]
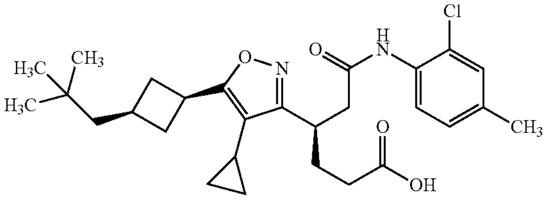 [SMILES: Cc1ccc(NC(=O)C[C@@H](CCC(=O)O)c2noc([C@H]3C[C@@H](CC(C)(C)C)C3)c2C2CC2)c(Cl)c1]
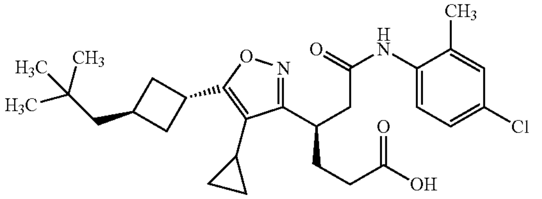 [SMILES: Cc1cc(Cl)ccc1NC(=O)C[C@@H](CCC(=O)O)c1noc([C@H]2C[C@H](CC(C)(C)C)C2)c1C1CC1]
TABLE 4-continued
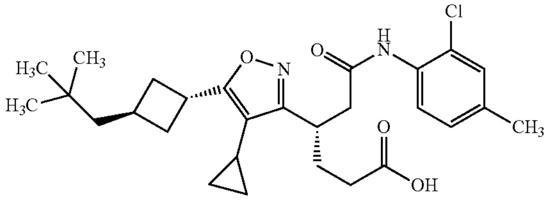 [SMILES: Cc1ccc(NC(=O)C[C@H](CCC(=O)O)c2noc([C@H]3C[C@H](CC(C)(C)C)C3)c2C2CC2)c(Cl)c1]
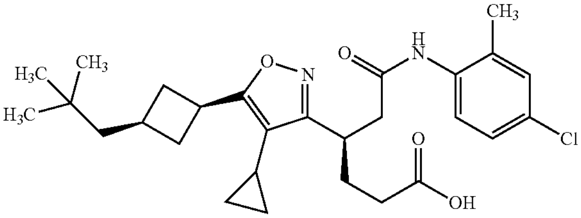 [SMILES: Cc1cc(Cl)ccc1NC(=O)C[C@@H](CCC(=O)O)c1noc([C@H]2C[C@@H](CC(C)(C)C)C2)c1C1CC1]
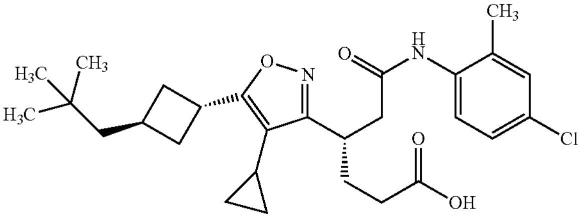 [SMILES: Cc1cc(Cl)ccc1NC(=O)C[C@H](CCC(=O)O)c1noc([C@H]2C[C@H](CC(C)(C)C)C2)c1C1CC1]
TABLE 5
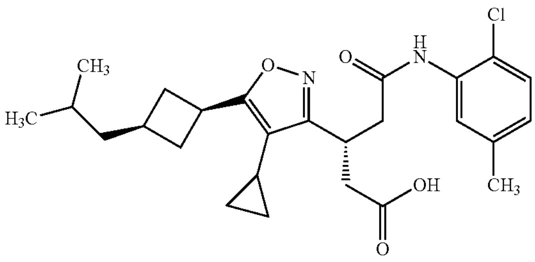 [SMILES: Cc1ccc(Cl)c(NC(=O)C[C@H](CC(=O)O)c2noc([C@H]3C[C@@H](CC(C)C)C3)c2C2CC2)c1]
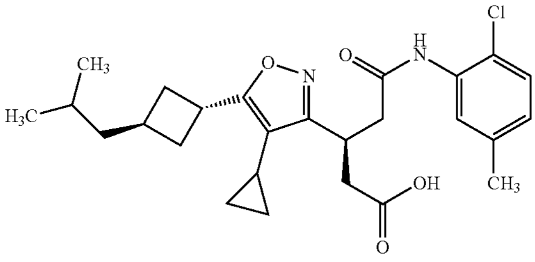 [SMILES: Cc1ccc(Cl)c(NC(=O)C[C@@H](CC(=O)O)c2noc([C@H]3C[C@H](CC(C)C)C3)c2C2CC2)c1]
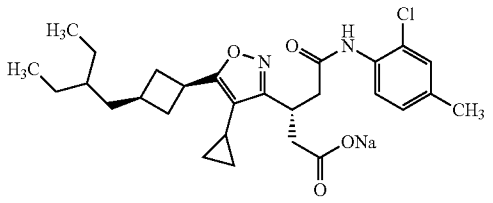

TABLE 5-continued
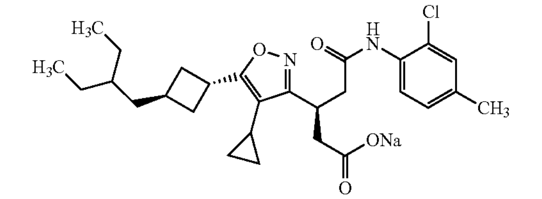
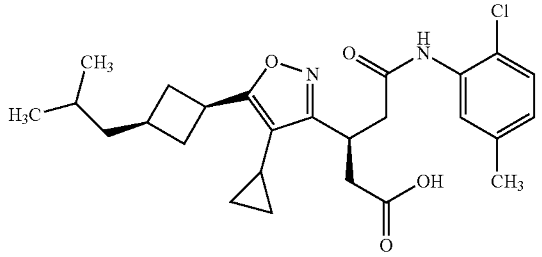 [SMILES: Cc1ccc(Cl)c(NC(=O)C[C@@H](CC(=O)O)c2noc([C@H]3C[C@@H](CC(C)C)C3)c2C2CC2)c1]
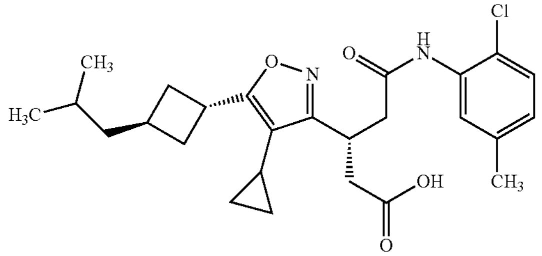 [SMILES: Cc1ccc(Cl)c(NC(=O)C[C@H](CC(=O)O)c2noc([C@H]3C[C@H](CC(C)C)C3)c2C2CC2)c1]
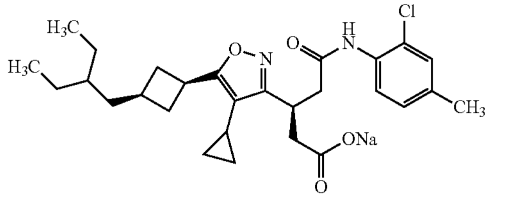
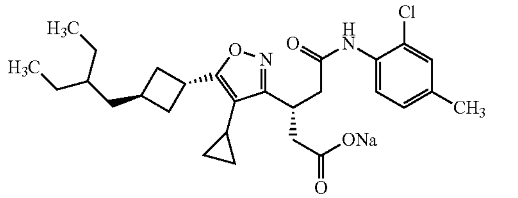
TABLE 6
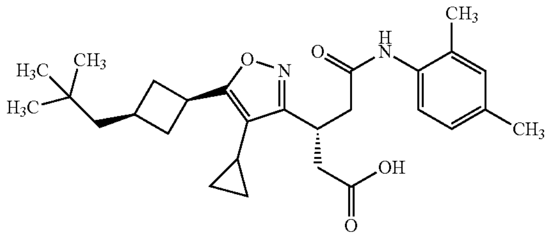 [SMILES: Cc1ccc(NC(=O)C[C@H](CC(=O)O)c2noc([C@H]3C[C@@H](CC(C)(C)C)C3)c2C2CC2)c(C)c1]
TABLE 6-continued
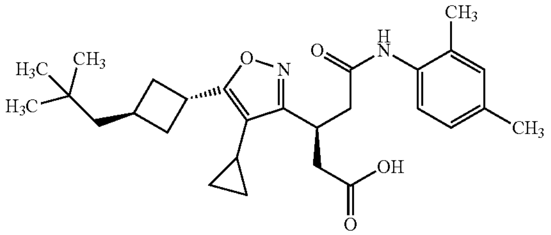 [SMILES: Cc1ccc(NC(=O)C[C@@H](CC(=O)O)c2noc([C@H]3C[C@H](CC(C)(C)C)C3)c2C2CC2)c(C)c1]
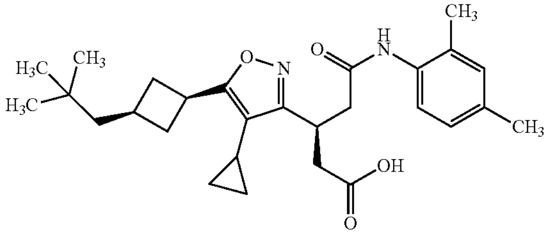 [SMILES: Cc1ccc(NC(=O)C[C@@H](CC(=O)O)c2noc([C@H]3C[C@@H](CC(C)(C)C)C3)c2C2CC2)c(C)c1]
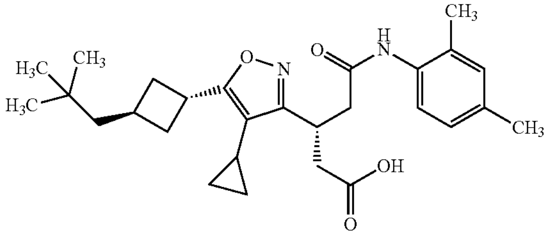 [SMILES: Cc1ccc(NC(=O)C[C@H](CC(=O)O)c2noc([C@H]3C[C@H](CC(C)(C)C)C3)c2C2CC2)c(C)c1]
TABLE 7
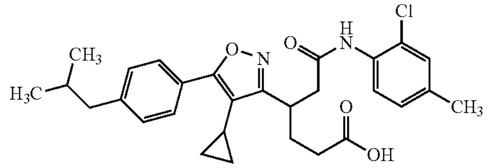 [SMILES: Cc1ccc(NC(=O)CC(CCC(=O)O)c2noc(-c3ccc(CC(C)C)cc3)c2C2CC2)c(Cl)c1]
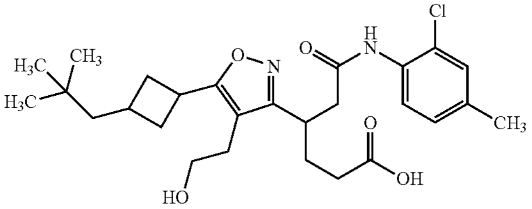 [SMILES: Cc1ccc(NC(=O)CC(CCC(=O)O)c2noc(C3CC(CC(C)(C)C)C3)c2CCO)c(Cl)c1]
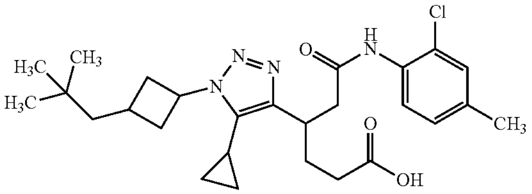 [SMILES: Cc1ccc(NC(=O)CC(CCC(=O)O)c2nnn(C3CC(CC(C)(C)C)C3)c2C2CC2)c(Cl)c1]
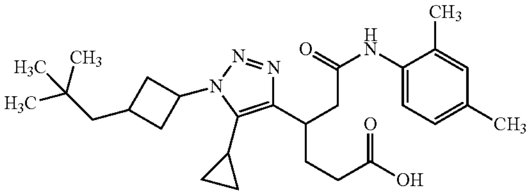

TABLE 7-continued
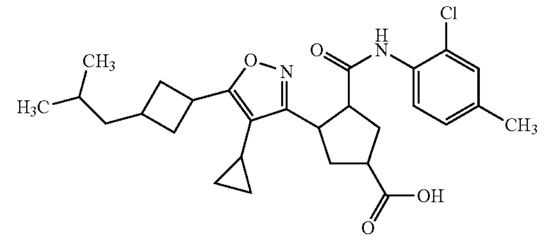 [SMILES: Cc1ccc(NC(=O)C2CC(C(=O)O)CC2c2noc(C3CC(CC(C)C)C3)c2C2CC2)c(Cl)c1]
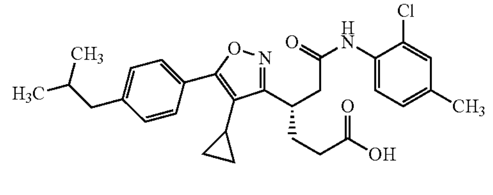
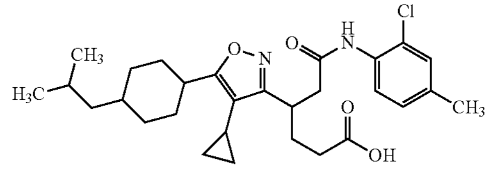 [SMILES: Cc1ccc(NC(=O)CC(CCC(=O)O)c2noc(C3CCC(CC(C)C)CC3)c2C2CC2)c(Cl)c1]
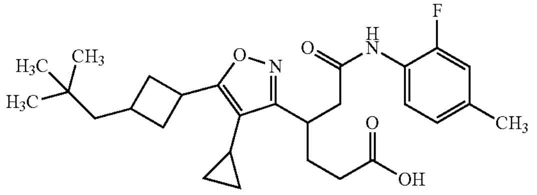
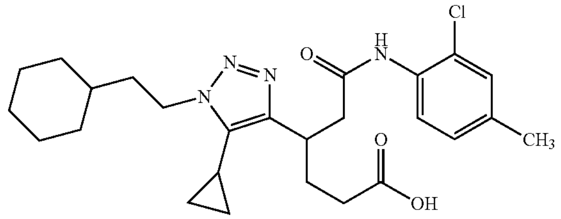 [SMILES: Cc1ccc(NC(=O)CC(CCC(=O)O)c2nnn(CCC3CCCCC3)c2C2CC2)c(Cl)c1]
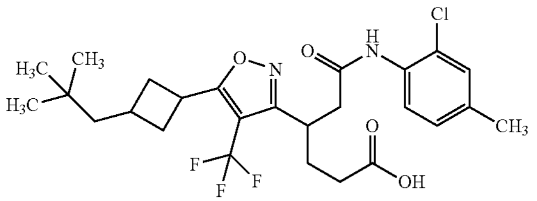 [SMILES: Cc1ccc(NC(=O)CC(CCC(=O)O)c2noc(C3CC(CC(C)(C)C)C3)c2C(F)(F)F)c(Cl)c1]
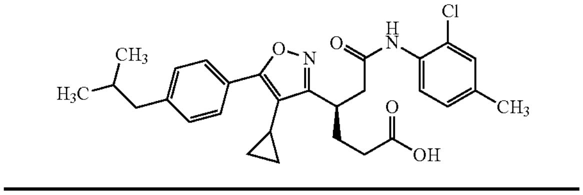
TABLE 8
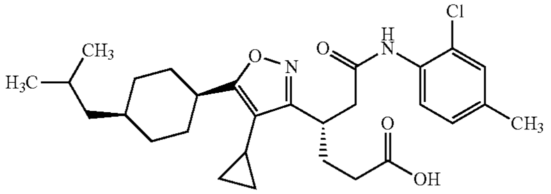 [SMILES: Cc1ccc(NC(=O)C[C@H](CCC(=O)O)c2noc([C@H]3CC[C@@H](CC(C)C)CC3)c2C2CC2)c(Cl)c1]
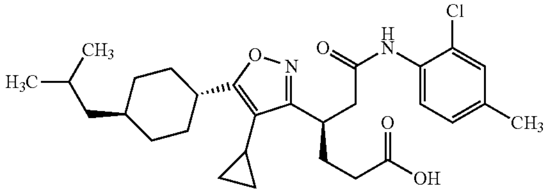 [SMILES: Cc1ccc(NC(=O)C[C@@H](CCC(=O)O)c2noc([C@H]3CC[C@H](CC(C)C)CC3)c2C2CC2)c(Cl)c1]
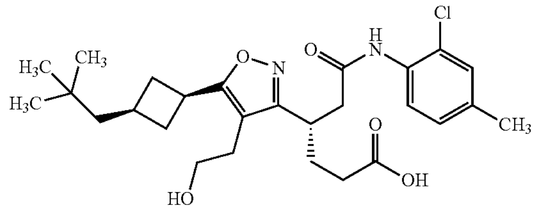 [SMILES: Cc1ccc(NC(=O)C[C@H](CCC(=O)O)c2noc([C@H]3C[C@@H](CC(C)(C)C)C3)c2CCO)c(Cl)c1]
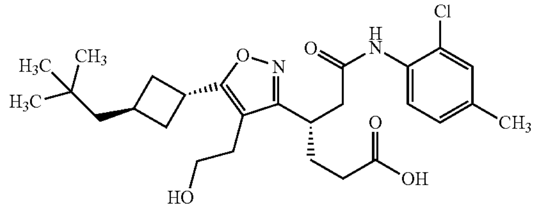 [SMILES: Cc1ccc(NC(=O)C[C@H](CCC(=O)O)c2noc([C@H]3C[C@H](CC(C)(C)C)C3)c2CCO)c(Cl)c1]
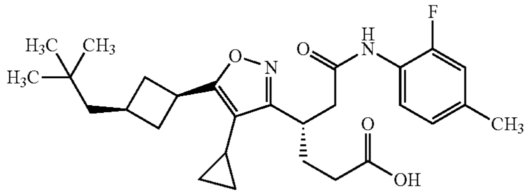 [SMILES: Cc1ccc(NC(=O)C[C@H](CCC(=O)O)c2noc([C@H]3C[C@@H](CC(C)(C)C)C3)c2C2CC2)c(F)c1]
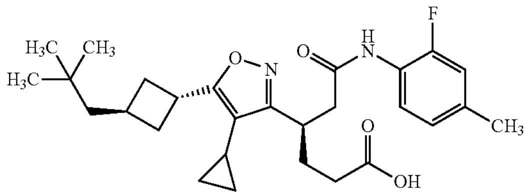 [SMILES: Cc1ccc(NC(=O)C[C@@H](CCC(=O)O)c2noc([C@H]3C[C@H](CC(C)(C)C)C3)c2C2CC2)c(F)c1]
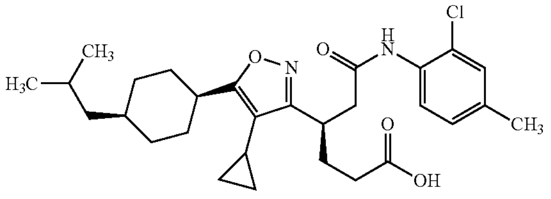 [SMILES: Cc1ccc(NC(=O)C[C@@H](CCC(=O)O)c2noc([C@H]3CC[C@@H](CC(C)C)CC3)c2C2CC2)c(Cl)c1]

TABLE 8-continued
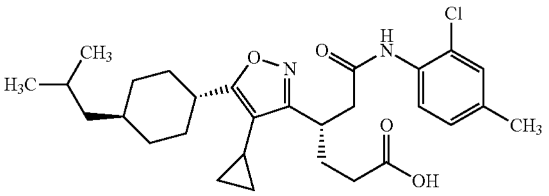 [SMILES: Cc1ccc(NC(=O)C[C@H](CCC(=O)O)c2noc([C@H]3CC[C@H](CC(C)C)CC3)c2C2CC2)c(Cl)c1]
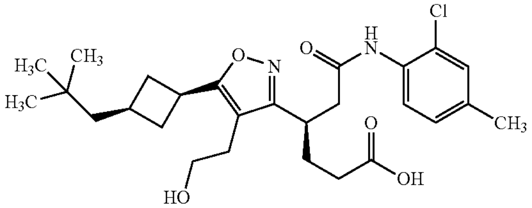 [SMILES: Cc1ccc(NC(=O)C[C@@H](CCC(=O)O)c2noc([C@H]3C[C@@H](CC(C)(C)C)C3)c2CCO)c(Cl)c1]
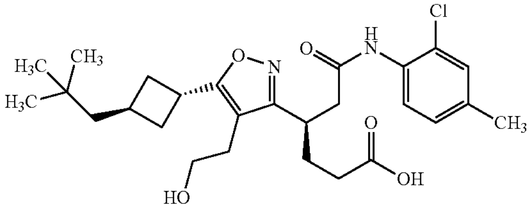 [SMILES: Cc1ccc(NC(=O)C[C@@H](CCC(=O)O)c2noc([C@H]3C[C@H](CC(C)(C)C)C3)c2CCO)c(Cl)c1]
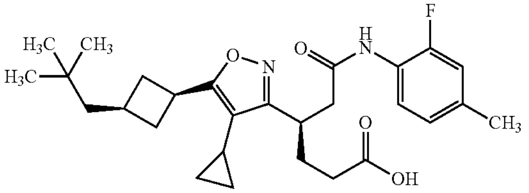 [SMILES: Cc1ccc(NC(=O)C[C@@H](CCC(=O)O)c2noc([C@H]3C[C@@H](CC(C)(C)C)C3)c2C2CC2)c(F)c1]
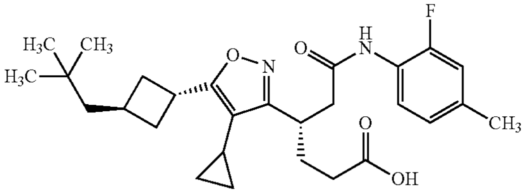 [SMILES: Cc1ccc(NC(=O)C[C@H](CCC(=O)O)c2noc([C@H]3C[C@H](CC(C)(C)C)C3)c2C2CC2)c(F)c1]
TABLE 9
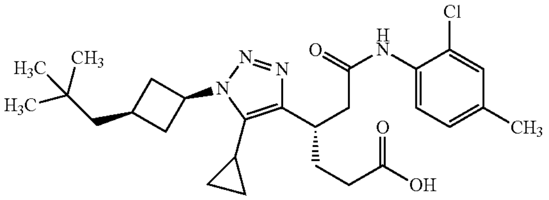 [SMILES: Cc1ccc(NC(=O)C[C@H](CCC(=O)O)c2nnn([C@H]3C[C@@H](CC(C)(C)C)C3)c2C2CC2)c(Cl)c1]
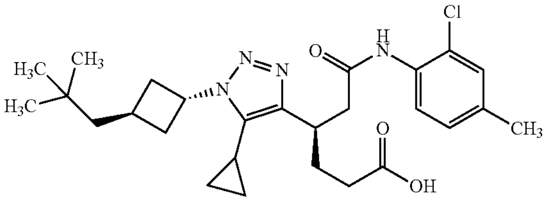 [SMILES: Cc1ccc(NC(=O)C[C@@H](CCC(=O)O)c2nnn([C@H]3C[C@H](CC(C)(C)C)C3)c2C2CC2)c(Cl)c1]
TABLE 9-continued
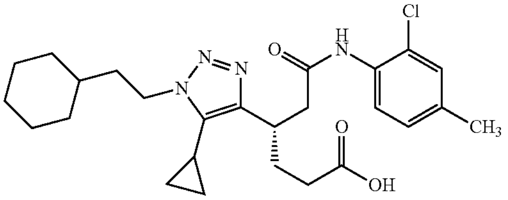 [SMILES: Cc1ccc(NC(=O)C[C@H](CCC(=O)O)c2nnn(CCC3CCCCC3)c2C2CC2)c(Cl)c1]
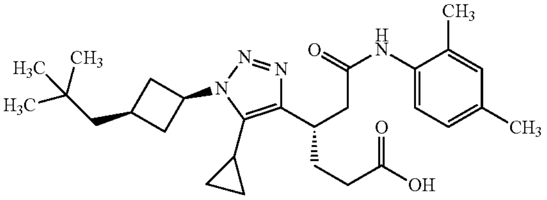 [SMILES: Cc1ccc(NC(=O)C[C@H](CCC(=O)O)c2nnn([C@H]3C[C@@H](CC(C)(C)C)C3)c2C2CC2)c(C)c1]
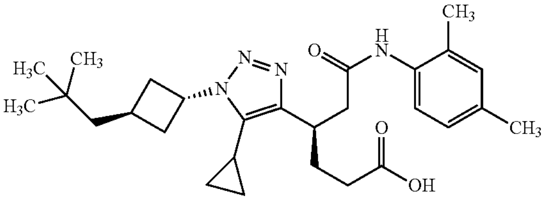 [SMILES: Cc1ccc(NC(=O)C[C@@H](CCC(=O)O)c2nnn([C@H]3C[C@H](CC(C)(C)C)C3)c2C2CC2)c(C)c1]
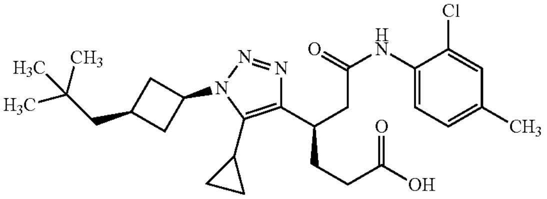 [SMILES: Cc1ccc(NC(=O)C[C@@H](CCC(=O)O)c2nnn([C@H]3C[C@@H](CC(C)(C)C)C3)c2C2CC2)c(Cl)c1]
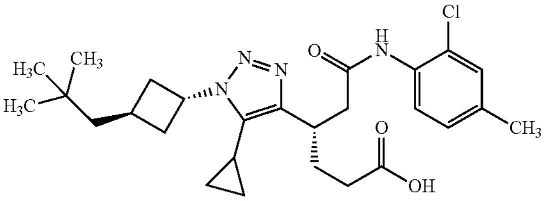 [SMILES: Cc1ccc(NC(=O)C[C@H](CCC(=O)O)c2nnn([C@H]3C[C@H](CC(C)(C)C)C3)c2C2CC2)c(Cl)c1]
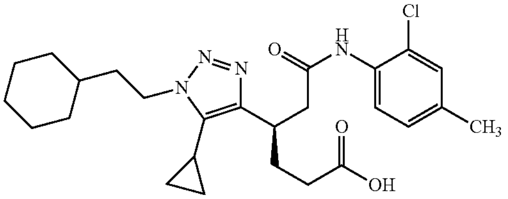 [SMILES: Cc1ccc(NC(=O)C[C@@H](CCC(=O)O)c2nnn(CCC3CCCCC3)c2C2CC2)c(Cl)c1]
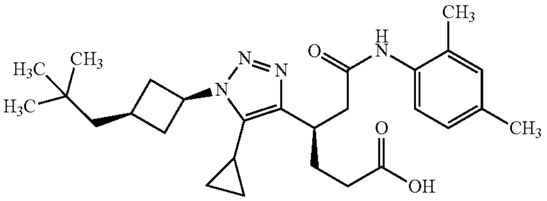 [SMILES: Cc1ccc(NC(=O)C[C@@H](CCC(=O)O)c2nnn([C@H]3C[C@@H](CC(C)(C)C)C3)c2C2CC2)c(C)c1]

TABLE 9-continued
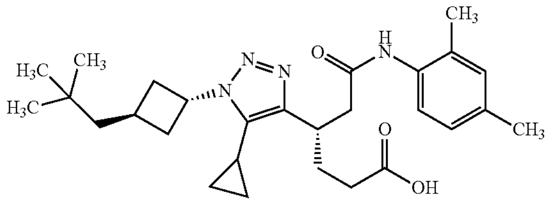
TABLE 10
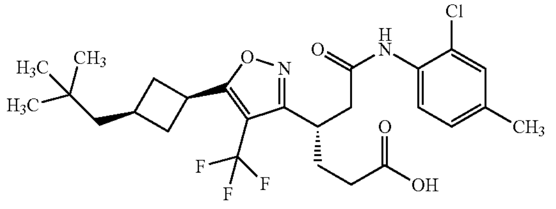 [SMILES: Cc1ccc(NC(=O)C[C@H](CCC(=O)O)c2noc([C@H]3C[C@@H](CC(C)(C)C)C3)c2C(F)(F)F)c(Cl)c1]
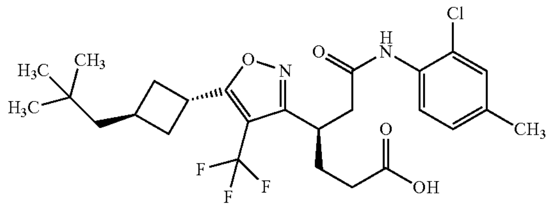 [SMILES: Cc1ccc(NC(=O)C[C@@H](CCC(=O)O)c2noc([C@H]3C[C@H](CC(C)(C)C)C3)c2C(F)(F)F)c(Cl)c1]
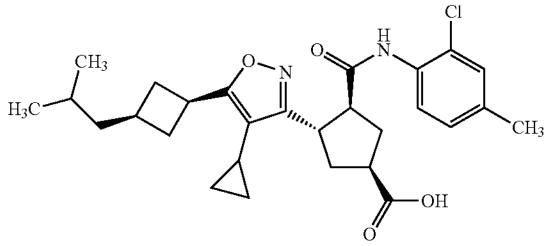 [SMILES: Cc1ccc(NC(=O)[C@H]2C[C@@H](C(=O)O)C[C@@H]2c2noc([C@H]3C[C@@H](CC(C)C)C3)c2C2CC2)c(Cl)c1]
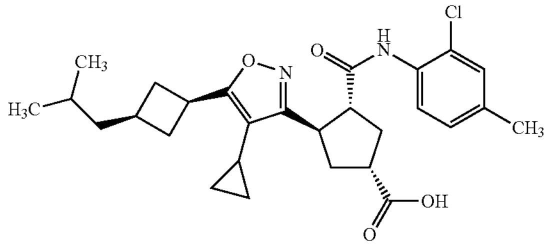 [SMILES: Cc1ccc(NC(=O)[C@@H]2C[C@H](C(=O)O)C[C@H]2c2noc([C@H]3C[C@@H](CC(C)C)C3)c2C2CC2)c(Cl)c1]
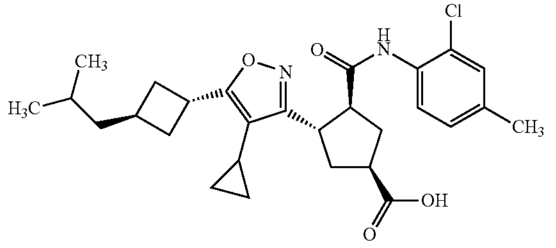 [SMILES: Cc1ccc(NC(=O)[C@H]2C[C@@H](C(=O)O)C[C@@H]2c2noc([C@H]3C[C@H](CC(C)C)C3)c2C2CC2)c(Cl)c1]
TABLE 10-continued
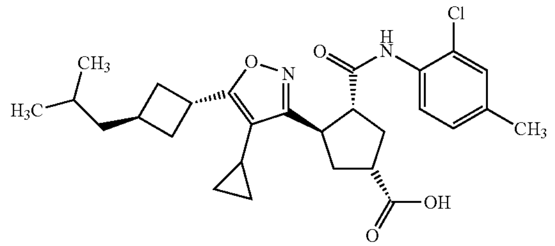
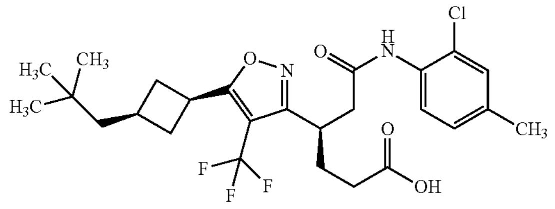 [SMILES: Cc1ccc(NC(=O)C[C@@H](CCC(=O)O)c2noc([C@H]3C[C@@H](CC(C)(C)C)C3)c2C(F)(F)F)c(Cl)c1]
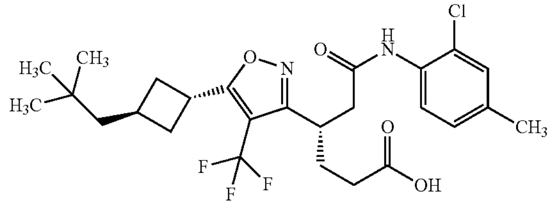 [SMILES: Cc1ccc(NC(=O)C[C@H](CCC(=O)O)c2noc([C@H]3C[C@H](CC(C)(C)C)C3)c2C(F)(F)F)c(Cl)c1]
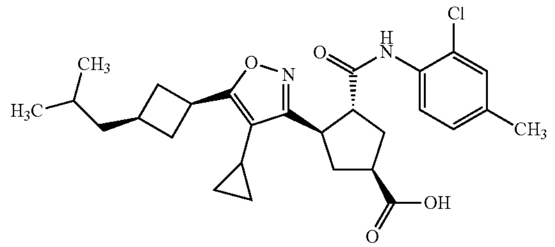 [SMILES: Cc1ccc(NC(=O)[C@@H]2C[C@@H](C(=O)O)C[C@H]2c2noc([C@H]3C[C@@H](CC(C)C)C3)c2C2CC2)c(Cl)c1]
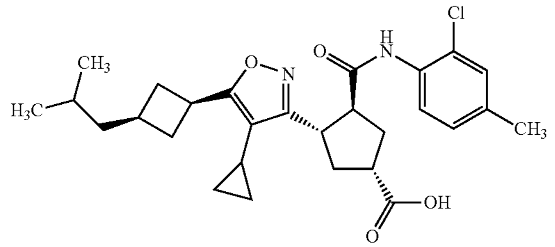 [SMILES: Cc1ccc(NC(=O)[C@H]2C[C@H](C(=O)O)C[C@@H]2c2noc([C@H]3C[C@@H](CC(C)C)C3)c2C2CC2)c(Cl)c1]
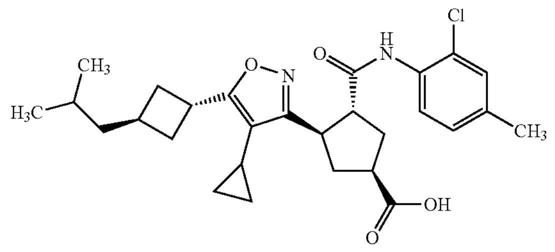 [SMILES: Cc1ccc(NC(=O)[C@@H]2C[C@@H](C(=O)O)C[C@H]2c2noc([C@H]3C[C@H](CC(C)C)C3)c2C2CC2)c(Cl)c1]

TABLE 10-continued
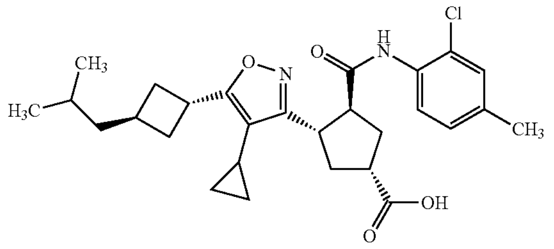 [SMILES: Cc1ccc(NC(=O)[C@H]2C[C@H](C(=O)O)C[C@@H]2c2noc([C@H]3C[C@H](CC(C)C)C3)c2C2CC2)c(Cl)c1]
TABLE 11
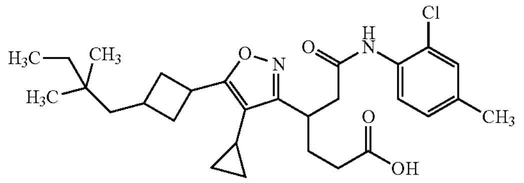
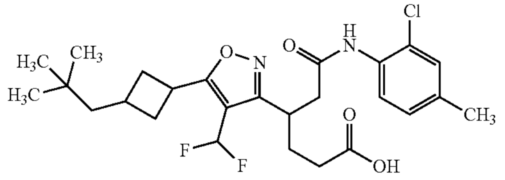 [SMILES: Cc1ccc(NC(=O)CC(CCC(=O)O)c2noc(C3CC(CC(C)(C)C)C3)c2C(F)F)c(Cl)c1]
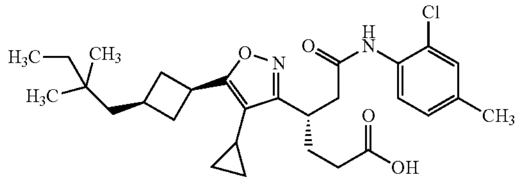 [SMILES: CCC(C)(C)C[C@H]1C[C@@H](c2onc([C@@H](CCC(=O)O)CC(=O)Nc3ccc(C)cc3Cl)c2C2CC2)C1]
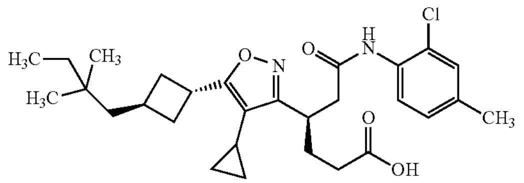 [SMILES: CCC(C)(C)C[C@H]1C[C@H](c2onc([C@H](CCC(=O)O)CC(=O)Nc3ccc(C)cc3Cl)c2C2CC2)C1]
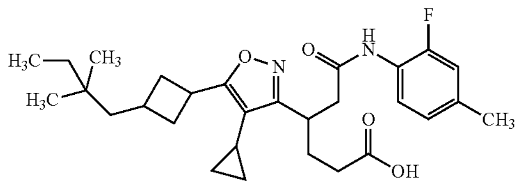 [SMILES: CCC(C)(C)CC1CC(c2onc(C(CCC(=O)O)CC(=O)Nc3ccc(C)cc3F)c2C2CC2)C1]
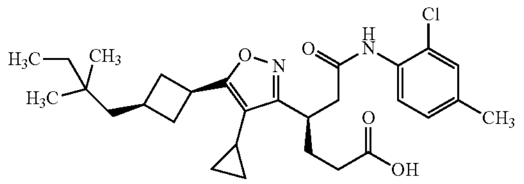 [SMILES: CCC(C)(C)C[C@H]1C[C@@H](c2onc([C@H](CCC(=O)O)CC(=O)Nc3ccc(C)cc3Cl)c2C2CC2)C1]
TABLE 11-continued
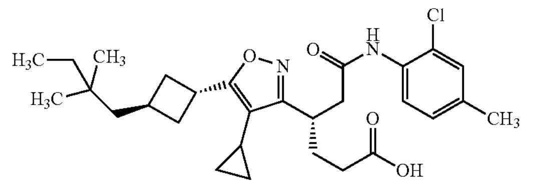 [SMILES: CCC(C)(C)C[C@H]1C[C@H](c2onc([C@@H](CCC(=O)O)CC(=O)Nc3ccc(C)cc3Cl)c2C2CC2)C1]
TABLE 12
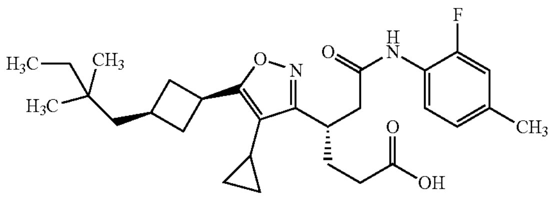 [SMILES: CCC(C)(C)C[C@H]1C[C@@H](c2onc([C@@H](CCC(=O)O)CC(=O)Nc3ccc(C)cc3F)c2C2CC2)C1]
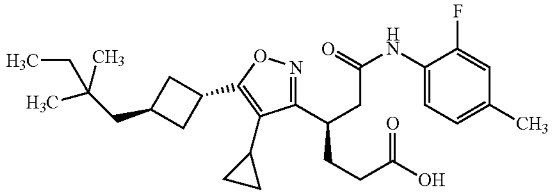 [SMILES: CCC(C)(C)C[C@H]1C[C@H](c2onc([C@H](CCC(=O)O)CC(=O)Nc3ccc(C)cc3F)c2C2CC2)C1]
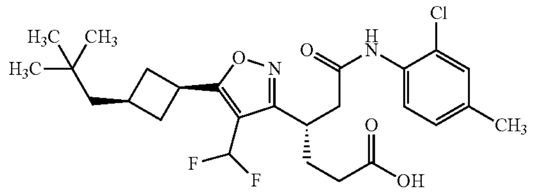 [SMILES: Cc1ccc(NC(=O)C[C@H](CCC(=O)O)c2noc([C@H]3C[C@@H](CC(C)(C)C)C3)c2C(F)F)c(Cl)c1]
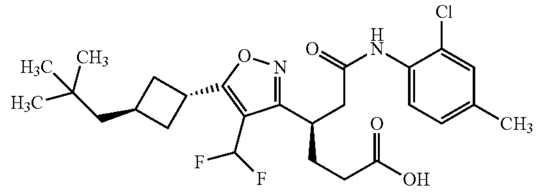 [SMILES: Cc1ccc(NC(=O)C[C@@H](CCC(=O)O)c2noc([C@H]3C[C@H](CC(C)(C)C)C3)c2C(F)F)c(Cl)c1]
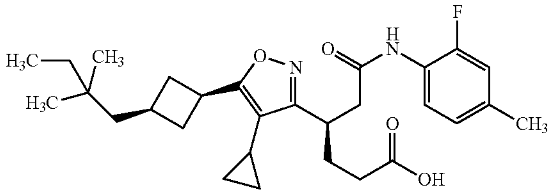 [SMILES: CCC(C)(C)C[C@H]1C[C@@H](c2onc([C@H](CCC(=O)O)CC(=O)Nc3ccc(C)cc3F)c2C2CC2)C1]
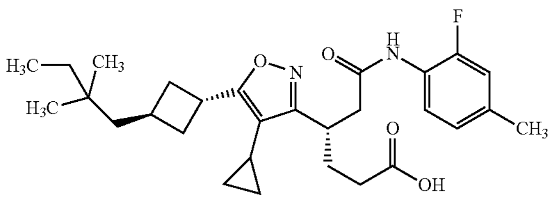 [SMILES: CCC(C)(C)C[C@H]1C[C@H](c2onc([C@@H](CCC(=O)O)CC(=O)Nc3ccc(C)cc3F)c2C2CC2)C1]

TABLE 12-continued

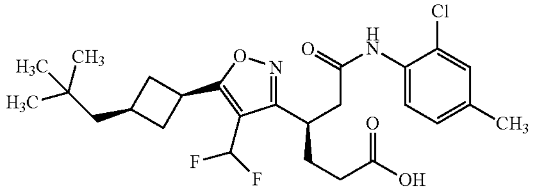 [SMILES: Cc1ccc(NC(=O)C[C@@H](CCC(=O)O)c2noc([C@H]3C[C@@H](CC(C)(C)C)C3)c2C(F)F)c(Cl)c1]

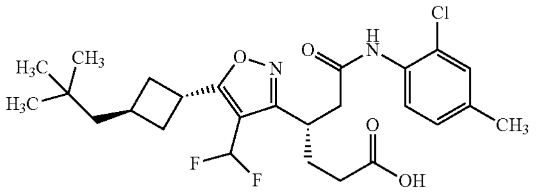 [SMILES: Cc1ccc(NC(=O)C[C@H](CCC(=O)O)c2noc([C@H]3C[C@H](CC(C)(C)C)C3)c2C(F)F)c(Cl)c1]

"Pharmaceutically acceptable salts" may be any nontoxic salt of the present invention compound, for example, include salts formed with inorganic acid, organic acid, inorganic base, organic base, amino acid and the like.

The inorganic acid salts include for example, salts formed with hydrochloric acid, nitric acid, sulfuric acid, phosphoric acid, hydrobromic acid and the like.

The organic acid salts include for example, salts formed with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

The salts formed with inorganic base include for example, sodium salt, potassium salt, calcium salt, magnesium salt, ammonium salt and the like.

The salts formed with organic base include for example salts formed with methylamine, ethylamine, diethylamine, trimethylamine, triethylamine, ethanolamine, diethanolamine, triethanolamine, ethylenediamine, tris(hydroxymethyl)methylamine, cyclohexylamine, dicyclohexylamine, N,N'-dibenzyl ethylenediamine, guanidine, pyridine, picoline, choline, cinchonine, meglumine and the like.

The salts formed with amino acid include for example, salts formed with lysine, arginine, aspartic acid, glutamic acid and the like.

Such salts can be formed by reacting compounds of formula [I-W] or [I] with inorganic base, organic base, inorganic acid, organic acid, or amino acid according to conventional methods.

The term "solvate" refers to the compounds of formula [I-W] or [I] or pharmaceutically acceptable salts thereof which coordinate to the solvent molecules, and also includes hydrates. Such solvates are preferably pharmaceutically acceptable solvates. Such solvate includes for example hydrate, ethanol solvate, dimethylsulfoxide solvate and the like of compounds of formula [I-W] or [I] or pharmaceutically acceptable salts thereof. The specific example includes hemihydrate, monohydrate, dihydrate or mono(ethanol)solvate of compounds of formula [I-W] or [I] or monohydrate of sodium salt of compounds of formula [I-W] or [I], 2/3 (ethanol)solvate of dihydrochloride of the same and the like. Such solvates can be produced according to conventional methods.

In addition, the compounds of formula [I-W] or [I] may have a variety of "isomer". For example, the compounds of formula [I-W] or [I] can exist in E or Z forms or cis or trans isomers as geometric isomers. Moreover, the compounds of formula [I-W] or [I] which have asymmetric carbon atoms include enantiomers and diastereomers as stereoisomers according to said asymmetric carbon atoms. Besides, the compounds of formula [I-W] or [I] which have axial chirality include stereoisomers according to said axial chirality. In some cases, tautomer may be included. Therefore, the present invention includes all of these isomers and mixtures thereof.

[I-W]

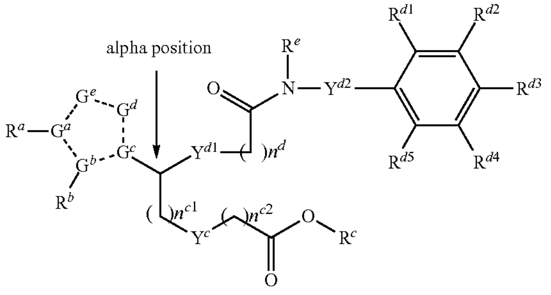

When a specific configuration, especially, of geometric isomer or of the asymmetric carbon atom of the alpha position from the 5-membered ring (-$G^a$-$G^b$-$G^c$-$G^d$-$G^e$-) not indicated in the structural formula such as formula [I-W] or [I], the compounds of the structural formula includes all of isomers such as geometric isomers (cis or trans isomers) and stereoisomers (E or Z forms), and mixtures thereof.

When the structure of compounds is predictable based on the starting material such as an optically-active compound, the intermediate or the synthesis process, such structural formula mean the predictable structure.

In addition, the compound of formula [I-W] or [I] may be labeled with one or more isotopes such as $^3H$, $^{14}C$, $^{35}S$ and the like. Besides, the compound of formula [I-W] or [I] also includes an isotopic compound thereof wherein one or more $^1H$ are replaced with $^2H$(D).

The compounds of formula [I-W] or [I] or pharmaceutically acceptable salts thereof are preferably purified to be substantively pure, more preferably 80% or purer.

According to the present invention, prodrugs of compounds of formula [I-W] or [I] may also be a useful medicine. The "prodrug" as used herein refers to derivatives the present invention compound having a chemically or metabolically decomposable group, which show the inherent pharmaceutical activity upon hydrolysis, solvolysis, or other decompositions under physiological conditions in vivo, and may also be a complex connected with bonds other than covalent bonds or a salt. Prodrugs can be used for example, for improving absorption of oral administration or targeting the object site. A modified site includes highly reactive functional groups in the present invention compounds, such as hydroxyl group, carboxyl group, amino group, thiol group and the like.

The group that modifies the hydroxyl group includes specifically acetyl group, propionyl group, isobutyryl group, pivaloyl group, palmitoyl group, benzoyl group, 4-methylbenzoyl group, dimethylcarbamoyl group, dimethylaminomethylcarbonyl group, sulfo group, alanyl group, fumary group and the like. In addition, 3-(sodium carboxylate)benzoyl group, 2-(sodium carboxylate)ethylcarbonyl group and the like are also included.

The group that modifies the carboxyl group includes specifically methyl group, ethyl group, propyl group, isopropyl group, butyl group, isobutyl group, tert-butyl group, pivaloyloxymethyl group, carboxymethyl group, dimethylaminomethyl group, 1-(acetyloxy)ethyl group, 1-(ethoxycarbonyloxy)ethyl group, 1-(isopropyloxycarbonyloxy)ethyl group, 1-(cyclohexyloxycarbonyloxy)ethyl group, (5-methyl-2-oxo-1,3-dioxol-4-yl)methyl group, benzyl group, phenyl group, o-tolyl group, morpholinoethyl group, N,N-diethylcarbamoylmethyl group, phthalidyl group and the like.

The group that modifies the amino group includes specifically tert-butyl group, docosanoyl group, pivaloylmethyloxy group, alanyl group, hexylcarbamoyl group, pentylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group, (5-methyl-2-oxo-1,3-dioxol-4-yl)methoxycarbonyl group, tetrahydrofuranyl group, pyrrolidylmethyl group and the like.

The term "pharmaceutical composition" includes a mixture comprising one or more active ingredients and one or more pharmaceutically acceptable carriers, for example, oral preparations such as tablet, capsule, granule, powder, troche, syrup, emulsion suspension and the like or parenteral preparations such as external preparation, suppository, injection, eye drop, a preparation for transnasal administration and a preparation for lung administration and the like.

Pharmaceutical compositions of the present invention can be prepared by mixing suitably the compounds of formula [I-W] or [I] or pharmaceutically acceptable salts thereof with at least one pharmaceutically acceptable carrier and the like according to conventional methods in the art of medicinal preparations. Content rate of the compounds of formula [I-W] or [I] or pharmaceutically acceptable salts thereof in the pharmaceutical composition includes for example, 0.1 to 100%, preferably 0.1 to 70% by weight in the composition while it varies depending on dosage forms, dosage amounts and the like.

The term "pharmaceutically acceptable carriers" includes all sorts of organic or inorganic carriers which are commonly-used as a material for drug formulations, such as excipient, disintegrant, binder, fluidizer, lubricant and the like for solid preparations and solvent, solubilizing agent, suspending agent, tonicity agent, buffering agent, soothing agent and the like for liquid preparations. Such preparations may employ further additives such as preservative, antioxidant, colorant, sweetening agent and the like as necessary.

The term "excipient" includes for example, lactose, white soft sugar, D-mannitol, D-sorbitol, cornstarch, dextrin, microcrystalline cellulose, crystalline cellulose, carmellose, carmellose calcium, sodium carboxymethylstarch, low substituted hydroxypropylcellulose, gum arabic and the like.

The term "disintegrant" includes for example, carmellose, carmellose calcium, carmellose sodium, sodium carboxymethylstarch, croscarmellose sodium, crospovidone, low substituted hydroxypropylcellulose, hydroxypropylmethylcellulose, crystalline cellulose and the like.

The term "binder" includes for example, hydroxypropylcellulose, hydroxypropylmethylcellulose, povidone, crystalline cellulose, white soft sugar, dextrin, starch, gelatin, carmellose sodium, gum arabic and the like.

The term "fluidizer" includes for example, light anhydrous silicic acid, magnesium stearate and the like.

The term "lubricant" includes for example, magnesium stearate, calcium stearate, talc and the like.

The term "solvent" includes for example, purified water, ethanol, propyleneglycol, macrogol, sesame oil, corn oil, olive oil and the like.

The term "solubilizing agent" includes for example, propyleneglycol, D-mannitol, benzyl benzoate, ethanol, triethanolamine, sodium carbonate, sodium citrate and the like.

The term "suspending agent" includes for example, benzalkonium chloride, carmellose, hydroxypropylcellulose, propyleneglycol, povidone, methylcellulose, glyceryl monostearate and the like.

The term "tonicity agent" includes for example, glucose, D-sorbitol, sodium chloride, D-mannitol and the like.

The term "buffering agent" includes for example, disodium hydrogen phosphate, sodium acetate, sodium carbonate, sodium citrate and the like.

The term "soothing agent" includes for example, benzyl alcohol and the like.

The term "preservative" includes for example, methyl parahydroxybenzoate, ethyl parahydroxybenzoate, propyl parahydroxybenzoate, chlorobutanol, benzyl alcohol, sodium dehydroacetate, sorbic acid and the like.

The term "antioxidant" includes for example, sodium sulfite, ascorbic acid and the like.

The term "colorant" includes for example, food dye such as Food Red No. 2 and No. 3, Food Yellow No. 4 and No. 5 and the like, β-carotene and the like.

The term "sweetening agent" includes for example saccharin sodium, dipotassium glycyrrhizate, aspartame and the like.

The pharmaceutical compositions of the present invention can be administered to human as well as mammals other than human such as mice, rat, hamster, guinea pig, rabbit, cat, dog, pig, cattle, horse, sheep, monkey and the like orally or parenterally such as locally, rectally and intravenously. While the dosage amount may vary depending on subject, disease, symptom, dosage form, route of administration and the like, for example when it is administered orally to an adult patient with autoimmune disease such as rheumatoid arthritis, psoriasis, inflammatory bowel disease, multiple sclerosis and systemic lupus erythematosus and the like, or allergic disease (body weight: about 60 kg) the dosage amount of the present invention compound of an active ingredient ranges generally from about 1 mg to about 1 g per day, which can be administered once to several times.

The compounds of formula [I-W] or [I] or pharmaceutically acceptable salts thereof can inhibit RORγ, thereby they can be used as an active ingredient for treating or preventing a disease such as autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease such as asthma; dry eye; fibrosis; and metabolic disease such as diabetes.

"Inhibit RORγ" means that a function of RORγ is inhibited to make the activity thereof disappear or reduced. It includes, for example, the function of RORγ is inhibited according to Biological assay 1 described hereafter.

The preferred aspect of "Inhibit RORγ" includes "Inhibit human RORγ".

The compounds of formula [I-W] or [I] or pharmaceutically acceptable salts thereof can be used in combination with other one or more medicament (hereinafter called additional medicament(s)) according to methods commonly used in the art of medicine, which is hereinafter called combination use.

The timing of administration of the compounds of formula [I-W] or [I] or pharmaceutically acceptable salts thereof and additional medicament(s) is not limited and they may be administered to a subject in a form of combination drug or may be administered simultaneously or at regular intervals. In addition, the compounds of formula [I-W] or [I] or pharmaceutically acceptable salts thereof may be used as a kit comprising the pharmaceutical composition of the present invention and additional medicament(s).

The dosage amount of the additional medicament(s) may follow one employed in clinical practice, and may be determined appropriately depending on subject, disease, symptom, dosage form, route of administration, timing of administration, combination and the like. The mode of additional medicament(s) is not limited as long as the present invention compounds or salts thereof and the additional medicament(s) are combined.

The additional medicament(s) include for example, (1) a medicament for treating or preventing autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes;

(2) a medicament for treating or preventing allergic disease such as asthma;

(3) a medicament for treating or preventing metabolic disease such as diabetes;

(4) a medicament for treating or preventing dry eye; and (5) a medicament for treating or preventing fibrosis.

One to three medicament selected from the above (1) to (5) may be employed in combination with the compounds of formula [I-W] or [I] or pharmaceutically acceptable salts thereof.

The medicament for treating or preventing autoimmune disease includes, for example, methotrexate to treat or prevent rheumatoid arthritis, and ciclosporin A and methotrexate to treat or prevent psoriasis.

Next, some examples of processes for preparing the compound of the present invention are shown as follows. However, the processes for preparing the present invention compound should not be limited thereto.

It is possible to modify the processes to carry out the preparation more effectively, for example, introducing a protecting group into a functional group followed by deprotecting it in a subsequent step; using a precursor having a functional group in a step followed by converting it to the desired functional group in a subsequent step; exchanging the order of preparation methods or steps thereof, even though not mentioned in these examples.

The workup after the reaction in each step can be carried out by a commonly-used method, wherein the isolation and purification may be carried out by a conventional method selected from crystallization, recrystallization, distillation, separating, silicagel chromatography, preparative HPLC and the like, or a combination thereof, as appropriate.

A racemic form of the compound can be obtained by using an achiral compound as a material, ligand, or reagent, or by mixing of enantiomers.

The following abbreviations are used in the preparation methods and Examples herein:

p-toluenesulfonyl group (pTs), methanesulfonyl group (Ms), tert-butyldimethylsilyl group (TBDMS)

tert-butyldiphenylsilyl group (TBDPS)

trimethylsilyl group (TMS)

triethylsilyl group (TES)

trifluoromethanesulfonyloxy group (OTf)

tert-butoxycarbonyl group (Boc)

benzyl group (Bn)

phenyl group (Ph)

acetyl group (Ac)

n-butyl group (nBu)

tert-butyl group (tBu)

isopropyl group (iPr)

ethyl group (Et)

methyl group (Me)

lithium diisopropylamide (LDA)

diisobutylaluminum hydride (DIBAL)

1-ethyl-3-(3-dimethylaminopropyl)carbodiimide hydrochloride (WSC.HCl)

1-hydroxy-1H-benzotriazole monohydrate ($HOBt.H_2O$)

tetrabutylammonium fluoride (TBAF)

1,8-diazabicyclo[5.4.0]undec-7-ene (DBU)

trifluoroacetic acid (TFA)

trifluoroacetic anhydride (TFAA)

1,1,3,3-tetramethyldisiloxane (TMDS)

Dess-Martin reagent (DMP)

lithium hexamethyldisilazide (LHMDS)

4-dimethylaminopyridine (DMAP)

2,2,6,6-tetramethyl-1-piperidinyloxy radical (TEMPO)

dimethylsulfoxide (DMSO)

N,N-dimethylformamide (DMF)

tetrahydrofuran (THF)

N,N-dimethylacetamide (DMA)

hexamethylphosphoric triamide (HMPA)

In the following schemes,

"X" is a leaving group such as halogen, and trifluoromethanesulfonyloxy, preferably bromo, and iodine;

"$P^{N1}$" is a protecting group for amine, and includes for example, tert-butoxycarbonyl group, and benzyloxycarbonyl group, preferably tert-butoxycarbonyl group.

"$P^{O}$" and "$P^{O1}$" is a protecting group for hydroxyl group, and includes for example, tert-butyldimethylsilyl group, tert-butyldiphenylsilyl group, acetyl group, benzyl group and the like, preferably tert-butyldiphenylsilyl group, and benzyl group.

"$P^{C}$" is a protecting group for carboxyl group, and includes for example, methyl group, ethyl group, tert-butyl group, benzyl group and the like, preferably methyl group, tert-butyl group, and benzyl group.

"AUX-H" is a chiral auxiliary reagent, and includes for example (R)-4-benzyl-2-oxazolidinone, (S)-4-benzyl-2-oxazolidinone, (R)-4-isopropyl-2-oxazolidinone, (S)-4-isopropyl-2-oxazolidinone, (4S,5R)-4-methyl-5-phenyl-2-oxazolidinone, (4R,5S)-4-methyl-5-phenyl-2-oxazolidinone and the like, preferably (R)-4-benzyl-2-oxazolidinone, (S)-4-benzyl-2-oxazolidinone.

"AUX" is a chiral auxiliary group.

"Q" is a group comprising boron, zinc, tin or the like, and includes for example, boronic acid, dialkoxyboron, halogeno zinc, and trialkyltin.

Each symbol is as defined in the above [01].

Preparation Method 1

Preparation method 1

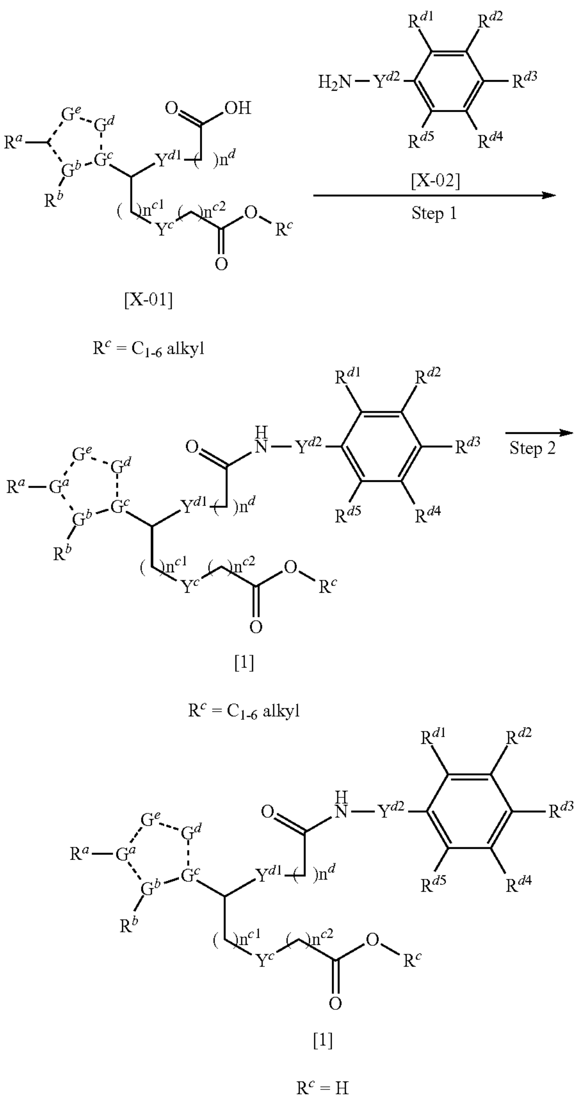

Each of the steps in the above Preparation method 1 is as follows.

Step 1

Compound [I] ($R^c$=$C_{1-6}$ alkyl group) can be obtained by reacting Compound [X-01] with Reactant [X-02] in the presence of a condensing agent in a solvent under the condition of a common amide bond formation reaction.

The solvent for the reaction includes for example, hydrocarbon solvent such as benzene, toluene, xylene, and hexane; halogenated solvent such as dichloromethane, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), carbonyldiimidazole (CDI), and O-(7-azabenzotriazole-1-yl)-N,N,N',N',-tetramethyluronium hexafluorophosphate (HATU). As appropriate, 1-hydroxy-1H-benzotriazole monohydrate ($HOBt.H_2O$), 4-dimethylaminopyridine (DMAP), N,N-diisopropylethylamine and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate ($HOBt.H_2O$) and mixture of O-(7-azabenzotriazole-1-yl)-N,N,N',N',-tetramethyluronium hexafluorophosphate (HATU) and N,N-diisopropylethylamine.

The reaction temperature generally ranges room temperature to about 120° C., preferably room temperature to about 100° C.

The reaction time generally ranges about 30 minutes to 3 days, preferably about 1 hr to 1 day.

Alternatively, in the above amidation reaction, compound [I] ($R^c$=$C_{1-6}$ alkyl group) can be prepared by the reaction of an acid halide or mixed acid anhydride of compound [X-01] with compound [X-02].

The acid halide of compound [X-01] can be derived by the reaction of an carboxylic acid of compound [X-01] with thionyl chloride, oxalyl chloride etc. wherein a catalytic amount of N,N-dimethylformamide may be added.

The mixed acid anhydride of compound [X-01] can be derived by the reaction of a carboxylic acid of compound [X-01] with ethyl chlorocarbonate etc.

Step 2

Compound [I] ($R^c$=hydrogen) can be obtained from Compound [I] ($R^c$=$C_{1-6}$ alkyl group) in a solvent under the condition of a common ester hydrolysis reaction. The ester hydrolysis reaction may be carried out under the alkaline or acidic condition.

The base for the alkaline condition includes for example, an aqueous solution of alkali metal hydroxide such as lithium hydroxide, sodium hydroxide, and potassium hydroxide. The preferred base for the reaction includes aqueous sodium hydroxide, and aqueous lithium hydroxide.

The acid for the acidic condition includes for example, hydrochloric acid, hydrobromic acid, sulfuric acid, and trifluoroacetic acid. The preferred acid for the reaction includes hydrochloric acid, hydrobromic acid, and trifluoroacetic acid.

The solvent for the reaction includes for example, hydrocarbon solvent such as benzene, toluene, xylene, and hexane; alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; acetic acid, and water. The preferred solvent for the reaction includes methanol, ethanol, methylene chloride, chloroform, tetrahydrofuran, toluene, acetic acid, and water.

The reaction temperature generally ranges about 0° C. to 120° C., preferably room temperature to about 100° C.

The reaction time generally ranges about 30 minutes to 3 days, preferably about 1 hr to 1 day.

Preparation Method 2

The case of that the 5-membered ring is isoxazole:

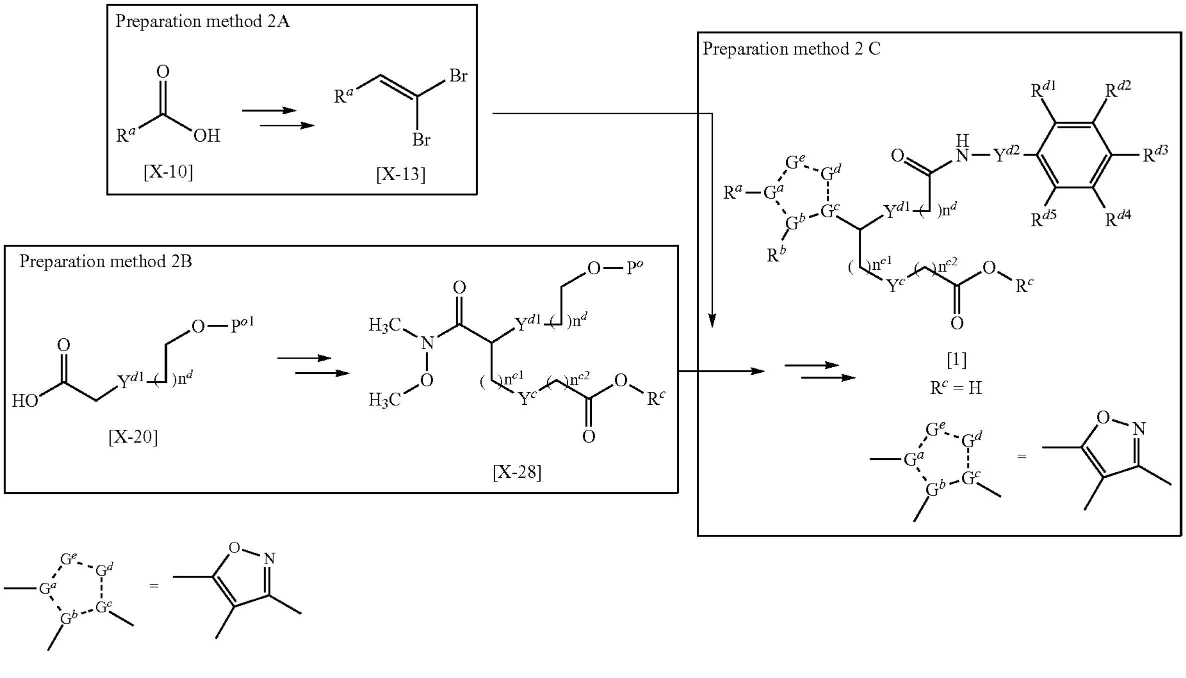

Preparation Method 2A

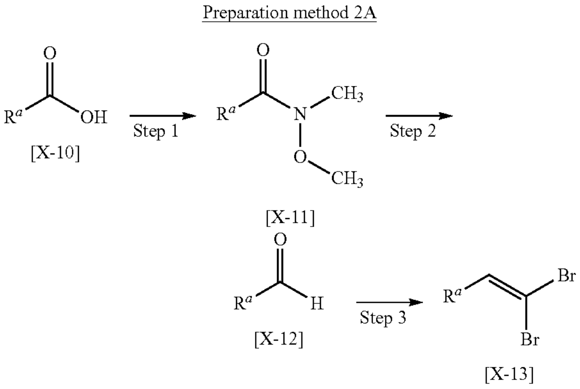

Step 1

Compound [X-11] can be obtained by the reaction of Compound [X-10] with N,O-dimethylhydroxylamine or hydrochloride thereof in the presence of a condensing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). As appropriate, 1-hydroxy-1H-benzotriazole monohydrate ($HOBt.H_2O$), 4-dimethylaminopyridine (DMAP) and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate ($HOBt.H_2O$) and a mixture of water-soluble carbodiimide (WSC.HCl: 1-ethyl-3-(3-dimethylaminopropyl)carbodiimide hydrochloride) and 4-dimethylaminopyridine (DMAP).

The reaction temperature generally ranges room temperature to about 120° C., preferably room temperature to about 100° C.

The reaction time generally ranges about 30 minutes to 3 days, preferably about 1 hr to 1 day.

Step 2

Compound [X-12] can be obtained by reacting Compound [X-11] in the presence of a reducing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; and ethers solvent such as diethyl ether, tetrahydrofuran, dioxane, 1,2-dimethoxyethane, and diglyme, which may be used alone or as a mixture of two or more. The preferred solvent for the reaction includes toluene, methylene chloride, chloroform, hexane, and tetrahydrofuran.

The reducing agent for the reaction includes for example, diisobutylaluminum hydride, and lithium aluminium hydride. The preferred reducing agent for the reaction includes diisobutylaluminum hydride.

The reaction temperature generally ranges about −78° C. to room temperature, preferably about −78° C. to 0° C.

The reaction time generally ranges about 30 minutes to 3 days, preferably about 1 hr to 1 day.

Step 3

Compound [X-13] can be obtained by reacting Compound [X-12] with carbon tetrabromide in the presence of triphenylphosphine in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; and ethers solvent such as diethyl ether, tetrahydrofuran, dioxane, 1,2-dimethoxyethane, and diglyme, which may be used alone or as a mixture of two or more. The preferred solvent for the reaction includes toluene, methylene chloride, and hexane.

The reaction temperature generally ranges about −30° C. to 100° C., preferably about 0° C. to room temperature.

The reaction time generally ranges about 30 minutes to 3 days, preferably about 30 minutes to 1 day.

Preparation Method 2B

Preparation method 2B

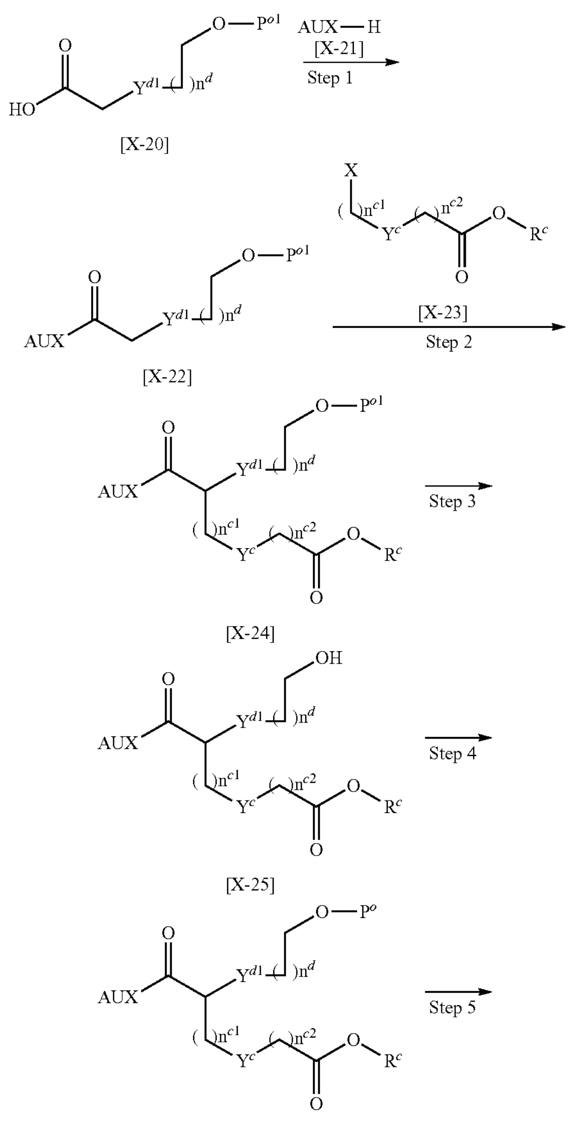

[X-20] [X-22] [X-24] [X-25] [X-26]

-continued

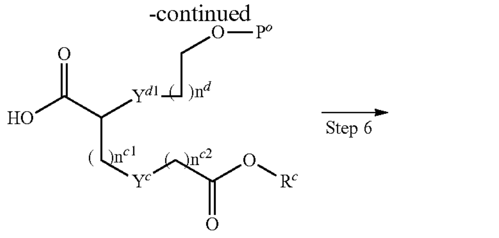

[X-27]

One example of AUX-H:

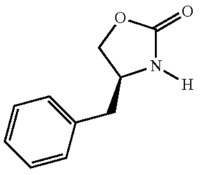

[X-21]

Step 1

Compound [X-22] can be obtained by the reaction of Compound [X-20] with Reactant [X-21] in the presence of a condensing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N-dicyclohexylcarbodiimide (DCC), diphenylphosphoryl azide (DPPA), and carbonyldiimidazole (CDI). As appropriate, 1-hydroxy-1H-benzotriazole monohydrate ($HOBt.H_2O$), 4-dimethylaminopyridine (DMAP) and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate ($HOBt.H_2O$) and a mixture of water-soluble carbodiimide (WSC.HCl: 1-ethyl-3-(3-dimethylaminopropyl)carbodiimide hydrochloride) and 4-dimethylaminopyridine (DMAP).

The reaction temperature generally ranges room temperature to about 120° C., preferably room temperature to about 100° C.

The reaction time generally ranges about 30 minutes to 3 days, preferably about 1 hr to 1 day.

Step 2

Compound [X-24] can be obtained by the reaction of Compound [X-22] with Reactant [X-23] in the presence of a base in a solvent.

The solvent for the reaction includes for example, hydrocarbon solvent such as benzene, toluene, xylene, and hexane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone, which may be used alone or as a mixture of two or more. The preferred solvent for the reaction includes tetrahydrofuran.

The base for the reaction includes for example, sodium hexamethyldisilazide, lithium hexamethyldisilazide, and lithium diisopropylamide (LDA). The preferred base for the reaction includes sodium hexamethyldisilazide and lithium hexamethyldisilazide.

The reaction temperature generally ranges about −78° C. to 50° C., preferably about −78° C. to room temperature.

The reaction time generally ranges about 30 minutes to 3 days, preferably about 30 minutes to 1 day.

Step 3

Compound [X-25] can be obtained by removal of the protecting group $P^{O1}$ from Compound [X-24] in a solvent. When the protecting group $P^{O1}$ is a benzyl group, the protecting group may be removed by the catalytic hydrogenation reaction under normal pressure or medium pressure (for example, 3 atm).

The catalyst for the catalytic hydrogenation reaction includes for example, palladium on activated carbon, palladium hydroxide, and Raney nickel. The preferred catalyst for the reaction includes palladium on activated carbon, and palladium hydroxide.

The solvent for the catalytic hydrogenation reaction includes for example, alcohols solvent such as methanol, ethanol, isopropyl alcohol, and tert-butanol; esters solvent such as ethyl acetate, methyl acetate, and butyl acetate; ethers solvent such as diethyl ether, tetrahydrofuran, dioxane, 1,2-dimethoxyethane, and diglyme; acetic acid, and water, which may be used alone or as a mixture of two or more. The preferred solvent for the reaction includes methanol, ethanol, ethyl acetate, and tetrahydrofuran.

The reaction temperature generally ranges room temperature to about 100° C., preferably room temperature to about 80° C.

The reaction time generally ranges about 30 minutes to 7 days, preferably about 1 hr to 5 days.

Step 4

Compound [X-26] can be obtained by introducing the protecting group $P^{O}$ into Compound [X-25] in a solvent.

When the protecting group $P^{O}$ is a silyl group, Compound [X-26] can be obtained by using silylation agent in the presence of a base.

The solvent for the reaction includes for example, esters solvent such as ethyl acetate, methyl acetate, and butyl acetate; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes N,N-dimethylformamide.

The base for the reaction includes for example, triethylamine, pyridine, and imidazole. The preferred base for the reaction includes imidazole.

The silylation agent for the reaction includes for example, tert-butylchlorodiphenylsilane, tert-butylchlorodimethylsilane, and tert-butyldimethylsilyl trifluoromethanesulfonate. The preferred silylation agent for the reaction includes tert-butylchlorodiphenylsilane.

The reaction temperature generally ranges room temperature to about 100° C., preferably room temperature to about 80° C.

The reaction time generally ranges about 30 minutes to 3 days, preferably about 1 hr to 1 day.

Step 5

Compound [X-27] can be obtained by hydrolysis reaction of Compound [X-26] in a solvent under the commonly-used condition. The hydrolysis reaction may be performed under the alkaline or acidic condition.

The base for the alkaline condition includes for example, an aqueous solution of alkali metal hydroxide such as lithium hydroxide, sodium hydroxide, and potassium hydroxide; and inorganic peroxide such as lithium peroxide, potassium peroxide, and sodium peroxide. The preferred base for the reaction includes lithium peroxide.

The acid for the acidic condition includes for example, hydrochloric acid, acetic acid, hydrobromic acid, sulfuric acid, trifluoroacetic acid, and p-toluenesulfonic acid monohydrate. The preferred acid for the reaction includes hydrochloric acid, acetic acid, and p-toluenesulfonic acid monohydrate.

The solvent for the reaction includes for example, hydrocarbon solvent such as benzene, toluene, xylene, and hexane; alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; acetic acid, and water, which may be used alone or as a mixture of two or more. The preferred solvent for the reaction includes tetrahydrofuran, and water.

The reaction temperature generally ranges about −30° C. to 80° C., preferably about 0° C. to room temperature.

The reaction time generally ranges about 30 minutes to 3 days, preferably about 30 minutes to 1 day.

Step 6

Compound [X-28] can be obtained by the reaction of Compound [X-27] with N,O-dimethylhydroxylamine or hydrochloride thereof in the presence of a condensing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). As appropriate, 1-hydroxy-1H-benzotriazole monohydrate ($HOBt.H_2O$), 4-dimethylaminopyridine (DMAP) and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate ($HOBt.H_2O$) and a mixture of water-soluble carbodiimide (WSC.HCl: 1-ethyl-3-(3-dimethylaminopropyl)carbodiimide hydrochloride) and 4-dimethylaminopyridine (DMAP).

The reaction temperature generally ranges room temperature to about 120° C., preferably room temperature to about 100° C.

The reaction time generally ranges about 30 minutes to 3 days, preferably about 1 hr to 1 day.

Preparation Method 2C

Preparation method 2C

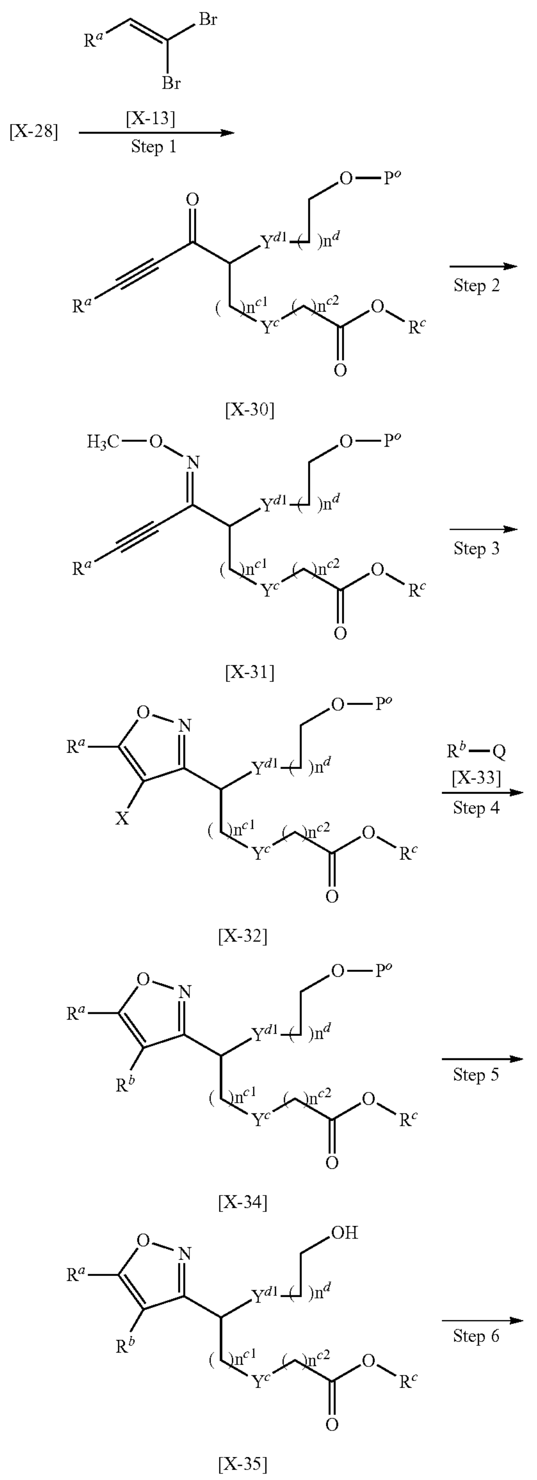

-continued

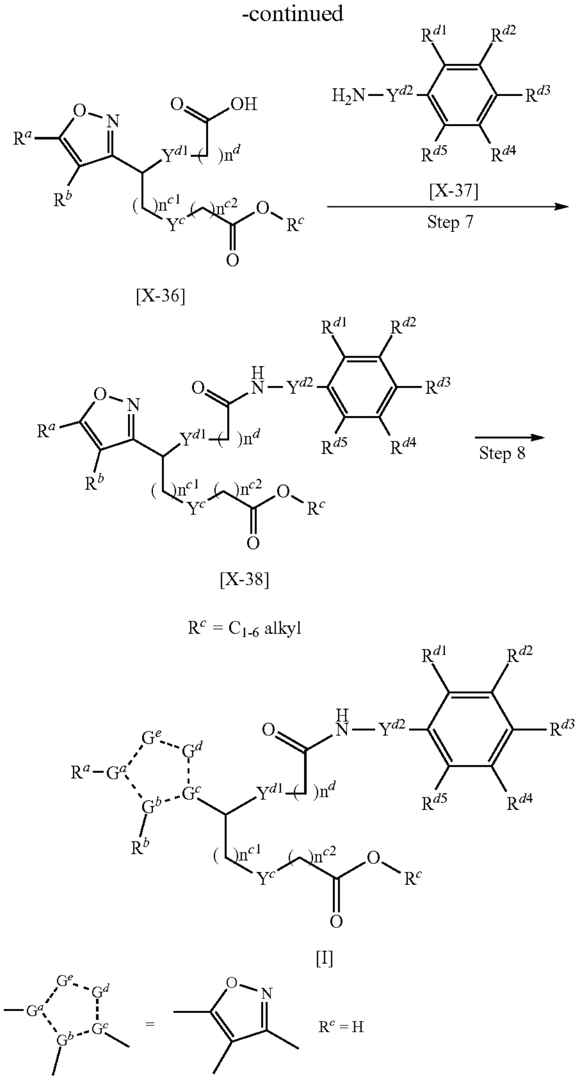

Step 1

Compound [X-30] can be obtained by the reaction of Compound [X-28] with Compound [X-13] in the presence of base in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; and ethers solvent such as diethyl ether, tetrahydrofuran, dioxane, 1,2-dimethoxyethane, and diglyme, which may be used alone or as a mixture of two or more. The preferred solvent for the reaction includes tetrahydrofuran, toluene, methylene chloride, and hexane.

The base for the reaction includes for example, butyllithium, methyllithium, ethylmagnesium bromide, lithium diisopropylamide (LDA) and the like. The preferred base for the reaction includes butyllithium, and lithium diisopropylamide (LDA).

The reaction temperature generally ranges about −78° C. to 50° C., preferably about −78° C. to room temperature.

The reaction time generally ranges about 30 minutes to 3 days, preferably about 1 hr to 1 day.

Step 2

Compound [X-31] can be obtained by the reaction of Compound [X-30] with O-methylhydroxylamine or hydrochloride thereof in a solvent.

The solvent for the reaction includes for example, alcohols solvent such as methanol, ethanol, and isopropyl alcohol; hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone; water, and pyridine, which may be used alone or as a mixture of two or more. The preferred solvent for the reaction includes methanol, ethanol, pyridine, tetrahydrofuran, toluene, methylene chloride, and hexane.

The reaction temperature generally ranges about −10° C. to 50° C., preferably about 0° C. to room temperature.

The reaction time generally ranges about 30 minutes to 3 days, preferably about 1 hr to 1 day.

Step 3

Compound [X-32] can be obtained by the cyclization reaction of Compound [X-31] in the presence of halogen or organohalide in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone, which may be used alone or as a mixture of two or more. The preferred solvent for the reaction includes acetonitrile, and methylene chloride. The halogen or organohalide for the reaction includes for example, bromine, iodine, N-bromosuccinimide, N-iodosuccinimide, and iodine monochloride. The preferred halogen or organohalide for the reaction includes iodine, and iodine monochloride.

The reaction temperature generally ranges about −10° C. to 50° C., preferably about 0° C. to room temperature.

The reaction time generally ranges about 30 minutes to 3 days, preferably about 30 minutes to 1 day.

Step 4

Compound [X-34] can be obtained by the reaction of Compound [X-32] with Compound [X-33] in the presence of a metal catalyst in a solvent.

When Compound [X-33] is alkylboronic acid or arylboronic acid, the "boronic acid" moiety thereof is boronic acid itself or an ester thereof, and preferably an ester thereof. As Compound [X-33], an alkylzinc or arylzinc reagent, an alkylmagnesium or arylmagnesium reagent or the like may be used.

The solvent for the reaction includes for example, hydrocarbon solvent such as benzene, toluene, xylene, and hexane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; and water, which may be used alone or as a mixture of two or more. The preferred solvent for the reaction includes N,N-dimethylformamide.

The metal catalyst for the reaction includes for example, a palladium catalyst such as bis(triphenylphosphine)palladium (II)dichloride, and 1,1'-bis(diphenylphosphino)ferrocene-palladium(II)dichloride, preferably bis(triphenylphosphine) palladium(II)dichloride.

The metal catalyst for the reaction also includes a nickel catalyst such as [1,2-bis(diphenylphosphino)ethane]nickel (II)dichloride, and nickel(II)acetylacetonate, and an iron catalyst such as iron(III)chloride.

As appropriate, a base or an inorganic salt may be added.

The base or inorganic salt for the reaction includes for example, alkali metal phosphate such as tripotassium phosphate; alkali metal carbonate such as sodium carbonate, and potassium carbonate; alkali metal acetate such as sodium acetate; and fluoride salt such as cesium fluoride and the like, preferably tripotassium phosphate.

The reaction temperature generally ranges about −10° C. to 150° C., preferably about 0° C. to 100° C.

The reaction time generally ranges about 30 minutes to 3 days, preferably about 1 hr to 1 day.

Step 5

Compound [X-35] can be obtained by removal of the protecting group $P^O$ from Compound [X-34] in the presence of tetrabutylammonium fluoride (TBAF) in a solvent.

The solvent for the reaction includes for example, alcohols solvent such as methanol, ethanol, isopropyl alcohol, and tert-butanol; esters solvent such as ethyl acetate, methyl acetate, and butyl acetate; hydrocarbon solvent such as benzene, toluene, xylene, and hexane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; acetic acid, and water, which may be used alone or as a mixture of two or more.

The preferred solvent for the reaction includes methanol, ethanol, ethyl acetate, tetrahydrofuran, acetic acid, and water.

The reaction temperature generally ranges about −10° C. to 150° C., preferably about 0° C. to 80° C.

The reaction time generally ranges about 30 minutes to 5 days, preferably about 1 hr to 3 days.

Step 6

Compound [X-36] can be obtained by the reaction of Compound [X-35] in the presence of an oxidant in a solvent.

The oxidant for the reaction includes for example, 2,2,6,6-tetramethyl-1-piperidinyloxy radical (TEMPO), potassium permanganate, aqueous hydrogen peroxide, pyridinium dichromate, and chromium oxide. The preferred oxidant for the reaction includes 2,2,6,6-tetramethyl-1-piperidinyloxy radical (TEMPO).

Alternatively, Compound [X-36] can be prepared by obtaining an aldehyde derived from Compound [X-35], and the oxidant for the reaction includes for example, pyridinium dichromate (PDC), pyridinium chlorochromate (PCC), and dimethyl sulfoxide (DMSO) activated by oxalyl chloride, Dess-Martin reagent, and sodium chlorite.

The solvent for the reaction includes for example, halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; and water, which may be used alone or as a mixture of two or more. The preferred solvent for the reaction includes methylene chloride, chloroform, tetrahydrofuran, acetonitrile, and water.

The reaction temperature generally ranges about −10° C. to 150° C., preferably about 0° C. to 80° C.

The reaction time generally ranges about 30 minutes to 5 days, preferably about 1 hr to 3 days.

Step 7

Compound [X-38] ($R^c$=$C_{1-6}$ alkyl group) can be obtained by the reaction of Compound [X-36] with Reactant [X-37] in the presence of a condensing agent in a solvent under the condition of a common amide bond formation reaction.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), carbonyldiimidazole (CDI), and O-(7-azabenzotriazole-1-yl)-N,N,N',N',-tetramethyluronium hexafluorophosphate (HATU). As appropriate, 1-hydroxy-1H-benzotriazole monohydrate ($HOBt.H_2O$), 4-dimethylaminopyridine (DMAP), N,N-diisopropylethylamine and the like may be added.

The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate ($HOBt.H_2O$) and a mixture of O-(7-azabenzotriazole-1-yl)-N,N,N',N',-tetramethyluronium hexafluorophosphate (HATU) and N,N-diisopropylethylamine.

The reaction temperature generally ranges room temperature to about 120° C., preferably room temperature to about 100° C.

The reaction time generally ranges about 30 minutes to 3 days, preferably about 1 hr to 1 day.

Step 8

Compound [I] ($R^c$=hydrogen) can be obtained from Compound [X-38] ($R^c$=$C_{1-6}$ alkyl group) in a solvent under the condition of a common ester hydrolysis reaction. The ester hydrolysis reaction may be performed under the alkaline or acidic condition.

The base for the alkaline condition includes for example, an aqueous solution of alkali metal hydroxide such as lithium hydroxide, sodium hydroxide, and potassium hydroxide. The preferred base for the reaction includes aqueous sodium hydroxide, and aqueous lithium hydroxide.

The acid for the acidic condition includes for example, hydrochloric acid, hydrobromic acid, sulfuric acid, and trifluoroacetic acid. The preferred acid for the reaction includes hydrochloric acid, hydrobromic acid, and trifluoroacetic acid.

The solvent for the reaction includes for example, hydrocarbon solvent such as benzene, toluene, xylene, and hexane; alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; and polar solvent such as acetic acid and water. The preferred solvent for the reaction includes methanol, ethanol, methylene chloride, chloroform, tetrahydrofuran, toluene, acetic acid, and water.

The reaction temperature generally ranges about 0° C. to 120° C., preferably room temperature to about 100° C.

The reaction time generally ranges about 30 minutes to 3 days, preferably about 1 hr to 1 day.

In Step 1 of Preparation method 2B, a racemic form of [X-21] may be used to give Compound [I] ($R^c$=hydrogen) which is in racemic form as a final product.

Preparation Method 3

The case of that the 5-membered ring is isoxazole:

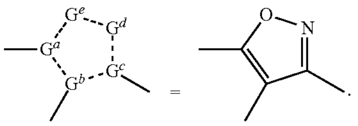

The case of that $Y^c$ is single bond or alkylene.

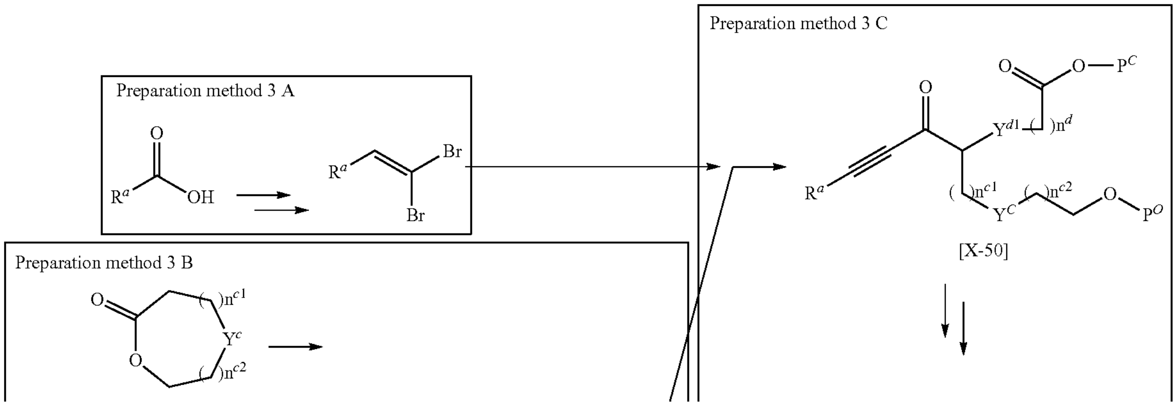

[X-50]

-continued

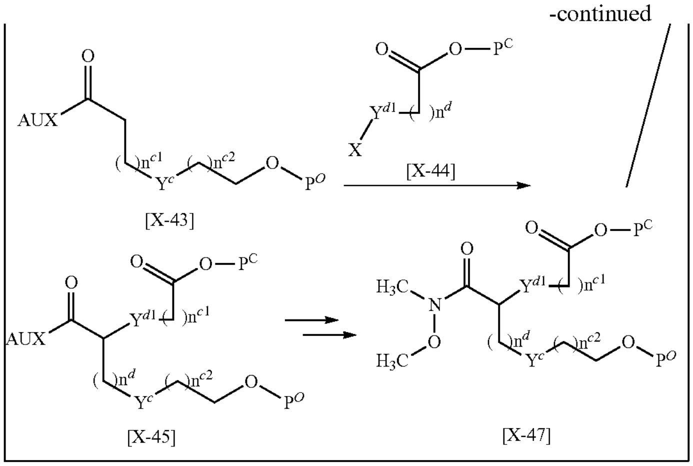

[X-43] [X-45] [X-47]

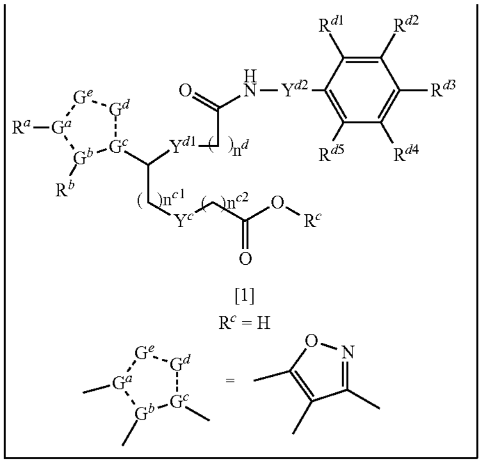

[1]

$R^c$ = H

Preparation Method 3A

Preparation method 3A

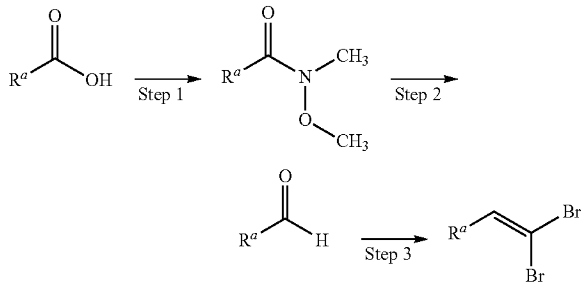

The preparation method 3A may be performed in a similar manner to that described in Preparation method 2A.

Preparation Method 3B

Preparation method 3B

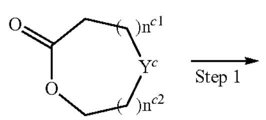

[X-40]

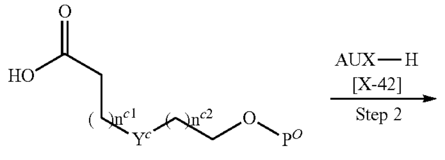

[X-41]

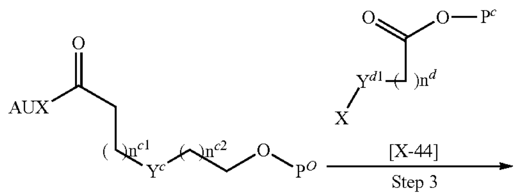

[X-43]

-continued

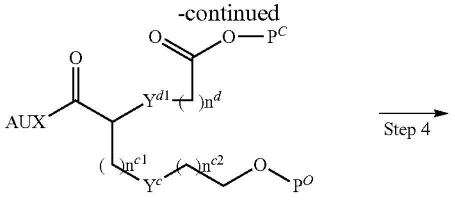

[X-45]

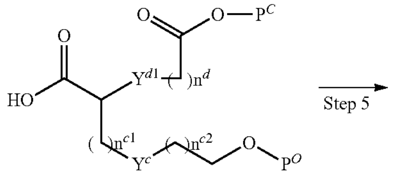

[X-46]

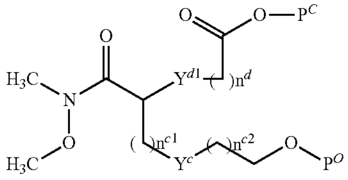

[X-47]

Step 1

Compound [X-41] can be obtained by the reaction of Compound [X-40] with a benzyl halide in the presence of base in a solvent.

The solvent for the reaction includes for example, hydrocarbon solvent such as benzene, toluene, xylene, and hexane; and ethers solvent such as diethyl ether, tetrahydrofuran, dioxane, 1,2-dimethoxyethane, and diglyme, which may be used alone or as a mixture of two or more. The preferred solvent for the reaction includes toluene.

The base for the reaction includes for example, an aqueous solution of alkali metal hydroxide such as lithium hydroxide, sodium hydroxide, and potassium hydroxide. The preferred base for the reaction includes potassium hydroxide.

The reaction temperature generally ranges room temperature to about 180° C., preferably room temperature to about 150° C.

The reaction time generally ranges about 30 minutes to 3 days, preferably about 1 hr to 1 day.

Step 2

Compound [X-43] can be obtained by the reaction of Compound [X-41] with Reactant [X-42] in the presence of a condensing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). As appropriate, 1-hydroxy-1H-benzotriazole monohydrate (HOBt.$H_2O$), 4-dimethylaminopyridine (DMAP) and the like may be added.

The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate (HOBt.$H_2O$) and a mixture of water-soluble carbodiimide (WSC.HCl: 1-ethyl-3-(3-dimethylaminopropyl)carbodiimide hydrochloride) and 4-dimethylaminopyridine (DMAP).

The reaction temperature generally ranges room temperature to about 120° C., preferably room temperature to about 100° C.

The reaction time generally ranges about 30 minutes to 3 days, preferably about 1 hr to 1 day.

Step 3

Compound [X-45] can be obtained by the reaction of Compound [X-43] with Reactant [X-44] in the presence of a base in a solvent.

The solvent for the reaction includes for example, hydrocarbon solvent such as benzene, toluene, xylene, and hexane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes tetrahydrofuran.

The base for the reaction includes for example, sodium hexamethyldisilazide, lithium hexamethyldisilazide, and lithium diisopropylamide (LDA). The preferred base for the reaction includes sodium hexamethyldisilazide and lithium hexamethyldisilazide.

The reaction temperature generally ranges about −78° C. to 50° C., preferably about −78° C. to room temperature.

The reaction time generally ranges about 30 minutes to 3 days, preferably about 30 minutes to 1 day.

Step 4

Compound [X-46] can be obtained by hydrolysis reaction of Compound [X-45] in a solvent under the commonly-used condition. The hydrolysis reaction may be performed under the alkaline or acidic condition.

The base for the alkaline condition includes for example, an aqueous solution of alkali metal hydroxide such as lithium hydroxide, sodium hydroxide, and potassium hydroxide; inorganic peroxide such as lithium peroxide, potassium peroxide, and sodium peroxide. The preferred base for the reaction includes lithium peroxide.

The acid for the acidic condition includes for example, hydrochloric acid, acetic acid, hydrobromic acid, sulfuric acid, trifluoroacetic acid, and p-toluenesulfonic acid monohydrate. The preferred acid for the reaction includes hydrochloric acid, acetic acid, and p-toluenesulfonic acid monohydrate.

The solvent for the reaction includes for example, hydrocarbon solvent such as benzene, toluene, xylene, and hexane; alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; acetic acid, and water, which may be used alone or as a mixture of two or more. The preferred solvent for the reaction includes tetrahydrofuran, and water.

The reaction temperature generally ranges about −30° C. to 80° C., preferably about 0° C. to room temperature.

The reaction time generally ranges about 30 minutes to 3 days, preferably about 30 minutes to 1 day.

Step 5

Compound [X-47] can be obtained by the reaction of Compound [X-46] and N,O-dimethylhydroxylamine or hydrochloride thereof in the presence of a condensing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). As appropriate, 1-hydroxy-1H-benzotriazole monohydrate (HOBt.$H_2O$), 4-dimethylaminopyridine (DMAP) and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate (HOBt.$H_2O$) and a mixture of water-soluble carbodiimide (WSC.HCl: 1-ethyl-3-(3-dimethylaminopropyl)carbodiimide hydrochloride) and 4-dimethylaminopyridine (DMAP).

The reaction temperature generally ranges room temperature to about 120° C., preferably room temperature to about 100° C.

The reaction time generally ranges about 30 minutes to 3 days, preferably about 1 hr to 1 day.

Preparation Method 3C

Preparation method 3C

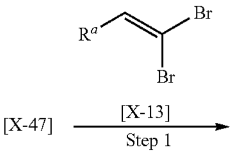

-continued

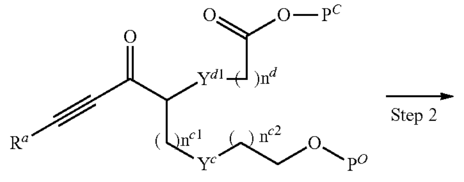

[X-50]

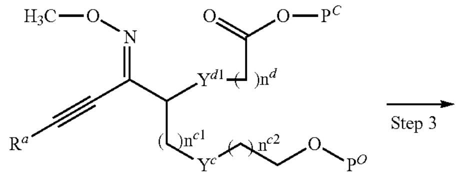

[X-51]

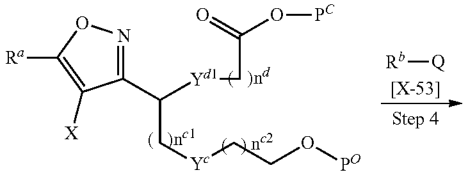

[X-52]

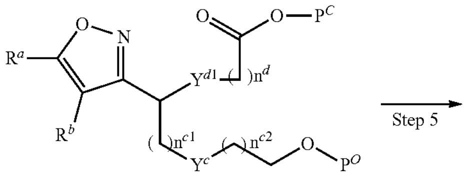

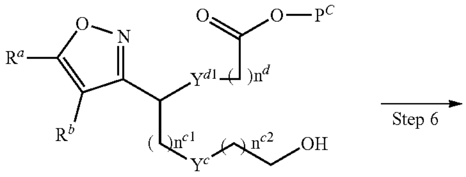

[X-55]

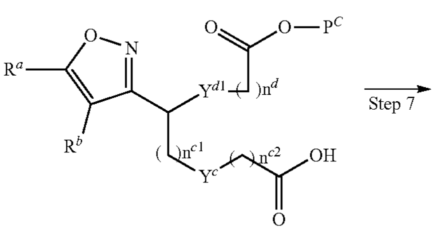

[X-56]

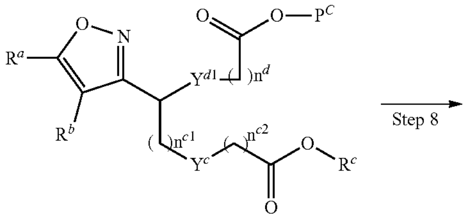

[X-57]

-continued

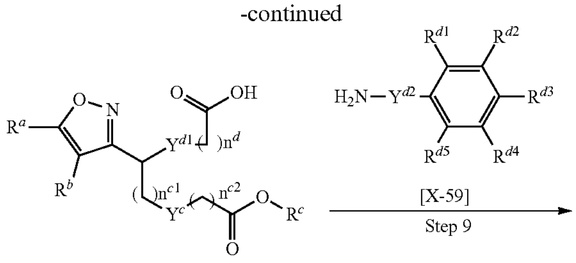

[X-58]

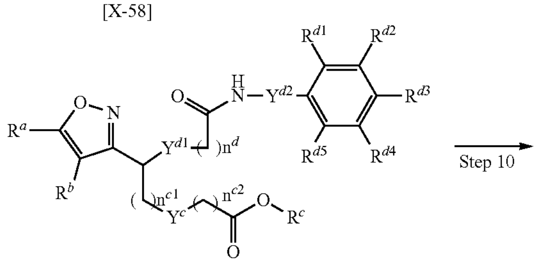

[X-60]

$R^c = C_{1-6}$ alkyl

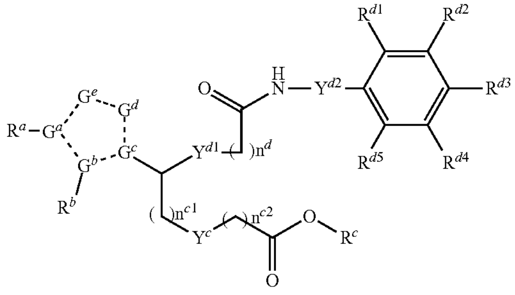

[I]

$R^c$ = H

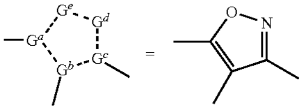

Step 1

Compound [X-50] can be obtained by the reaction of Compound [X-47] with Compound [X-13] in the presence of base in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; and ethers solvent such as diethyl ether, tetrahydrofuran, dioxane, 1,2-dimethoxyethane, and diglyme, which may be used alone or as a mixture of two or more. The preferred solvent for the reaction includes tetrahydrofuran, toluene, methylene chloride, and hexane. The base for the reaction includes for example, butyllithium, methyllithium, ethylmagnesium bromide, lithium diisopropylamide (LDA) and the like. The preferred base for the reaction includes butyllithium, and lithium diisopropylamide (LDA).

The reaction temperature generally ranges about −78° C. to 50° C., preferably about −78° C. to room temperature.

The reaction time generally ranges about 30 minutes to 3 days, preferably about 1 hr to 1 day.

Step 2

Compound [X-51] can be obtained by the reaction of Compound [X-50] with O-methylhydroxylamine or hydrochloride thereof in a solvent.

The solvent for the reaction includes for example, alcohols solvent such as methanol, ethanol, and isopropyl alcohol; hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; water, and pyridine, which may be used alone or as a mixture of two or more. The preferred solvent for the reaction includes methanol, ethanol, pyridine, tetrahydrofuran, toluene, methylene chloride, and hexane.

The reaction temperature generally ranges about −10° C. to 50° C., preferably about 0° C. to room temperature.

The reaction time generally ranges about 30 minutes to 3 days, preferably about 1 hr to 1 day.

Step 3

Compound [X-52] can be obtained by the cyclization reaction of Compound [X-51] in the presence of halogen or organohalide in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes acetonitrile, and methylene chloride.

The halogen or organohalide for the reaction includes for example, bromine, iodine, N-bromosuccinimide, N-iodosuccinimide, and iodine monochloride. The preferred halogen or halide for the reaction includes iodine, and iodine monochloride.

The reaction temperature generally ranges about −10° C. to 50° C., preferably about 0° C. to room temperature.

The reaction time generally ranges about 30 minutes to 3 days, preferably about 30 minutes to 1 day.

Step 4

Compound [X-54] can be obtained by the reaction of Compound [X-52] with Compound [X-53] in the presence of a metal catalyst in a solvent.

When Compound [X-53] is alkylboronic or arylboronic acid, these may be alkylboronic or arylboronic acid itself or an ester thereof, and the ester thereof is preferred. As the Compound [X-53], an alkylzinc or arylzinc reagent, an alkylmagnesium or arylmagnesium reagent or the like may be used.

The solvent for the reaction includes for example, hydrocarbon solvent such as benzene, toluene, xylene, and hexane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; and water, which may be used alone or as a mixture of two or more. The preferred solvent for the reaction includes N,N-dimethylformamide.

The metal catalyst for the reaction includes for example, a palladium catalyst such as bis(triphenylphosphine)palladium (II)dichloride, and 1,1'-bis(diphenylphosphino)ferrocene-palladium(II)dichloride, preferably bis(triphenylphosphine) palladium(II)dichloride.

The metal catalyst for the reaction also includes a nickel catalyst such as [1,2-bis(diphenylphosphino)ethane]nickel (II)dichloride, and nickel(II)acetylacetonate, and an iron catalyst such as iron(III)chloride.

As appropriate, a base or an inorganic salt may be added.

The base or inorganic salt for the reaction includes for example, alkali metal phosphate such as tripotassium phosphate; alkali metal carbonate such as sodium carbonate, and potassium carbonate; alkali metal acetate such as sodium acetate; and fluoride salt such as cesium fluoride and the like, preferably cesium fluoride and tripotassium phosphate.

The reaction temperature generally ranges about −10° C. to 150° C., preferably about 0° C. to 100° C.

The reaction time generally ranges about 30 minutes to 3 days, preferably about 1 hr to 1 day.

Step 5

Compound [X-55] can be obtained by removal of the protecting group $P^O$ from Compound [X-54] in a solvent.

When the protecting group $P^O$ is a benzyl group, the protecting group may be removed by the catalytic hydrogenation reaction under normal pressure or medium pressure (for example, 3 atm).

The catalyst for the reaction includes for example, palladium on activated carbon, palladium hydroxide, and Raney nickel. The preferred catalyst for the reaction includes palladium on activated carbon and palladium hydroxide.

The solvent for the reaction includes for example, alcohols solvent such as methanol, ethanol, isopropyl alcohol, and tert-butanol; esters solvent such as ethyl acetate, methyl acetate, and butyl acetate; ethers solvent such as diethyl ether, tetrahydrofuran, dioxane, 1,2-dimethoxyethane, and diglyme; acetic acid, and water, which may be used alone or as a mixture of two or more. The preferred solvent for the reaction includes methanol, ethanol, ethyl acetate, and tetrahydrofuran.

The reaction temperature generally ranges room temperature to about 100° C., preferably room temperature to about 80° C.

The reaction time generally ranges about 30 minutes to 7 days, preferably about 1 hr to 5 days.

Step 6

Compound [X-56] can be obtained by the reaction of Compound [X-55] in the presence of an oxidant in a solvent.

The oxidant for the reaction includes for example, 2,2,6,6-tetramethyl-1-piperidinyloxy radical (TEMPO), potassium permanganate, aqueous hydrogen peroxide, pyridinium dichromate, and chromium oxide. The preferred oxidant for the reaction includes 2,2,6,6-tetramethyl-1-piperidinyloxy radical (TEMPO). Alternatively, Compound [X-56] can be prepared by obtaining an aldehyde derived from Compound [X-55], and the oxidant for the reaction includes for example, pyridinium dichromate (PDC), pyridinium chlorochromate (PCC), and dimethyl sulfoxide (DMSO) activated by oxalyl chloride, Dess-Martin reagent, and sodium chlorite.

The solvent for the reaction includes for example, halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and water, which may be used alone or as a mixture of two or more. The preferred solvent for the reaction includes methylene chloride, chloroform, tetrahydrofuran, and water.

The reaction temperature generally ranges about −10° C. to 150° C., preferably about 0° C. to 80° C.

The reaction time generally ranges about 30 minutes to 5 days, preferably about 1 hr to 3 days.

Step 7

Compound [X-57] can be obtained by alkylation reaction of Compound [X-56] in the presence of base in a solvent.

The solvent for the reaction includes for example, ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes N,N-dimethylformamide, and acetonitrile.

The base for the reaction includes for example, potassium carbonate, sodium carbonate, sodium hydrogen carbonate and the like. The preferred base for the reaction includes potassium carbonate, and sodium carbonate.

The alkylating agent for the reaction includes for example, methyl iodide, ethyl iodide and the like. The preferred alkylating agent for the reaction includes methyl iodide.

The reaction temperature generally ranges room temperature to about 120° C., preferably room temperature to about 100° C.

The reaction time generally ranges about 30 minutes to 3 days, preferably about 1 hr to 1 day.

Alternatively, Compound [X-57] can be obtained by reacting Compound [X-56] with an alcohol in the presence of a condensing agent, or by reacting Compound [X-56] with trimethylsilyldiazomethane.

Step 8

Compound [X-58] can be obtained from Compound [X-57] in a solvent under the acidic condition of ester hydrolysis reaction.

The acid for the reaction includes for example, hydrochloric acid, hydrobromic acid, sulfuric acid, and trifluoroacetic acid. The preferred acid for the reaction includes hydrochloric acid, hydrobromic acid, and trifluoroacetic acid.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; and polar solvent such as acetic acid and water. The preferred solvent for the reaction includes methylene chloride, chloroform, tetrahydrofuran, toluene, acetic acid, and water.

The reaction temperature generally ranges about 0° C. to 120° C., preferably room temperature to about 100° C.

The reaction time generally ranges about 10 minutes to 3 days, preferably about 30 min. to 1 day.

Step 9

Compound [X-60] ($R^c$=$C_{1-6}$ alkyl group) can be obtained by the reaction of Compound [X-58] with Reactant [X-59] in the presence of a condensing agent in a solvent under the condition of a common amide bond formation reaction.

The solvent for the reaction includes for example, for example, hydrocarbon solvent such as benzene, toluene, xylene, and hexane; halogenated solvent such as dichloromethane, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), carbonyldiimidazole (CDI), and O-(7-azabenzotriazole-1-yl)-N,N,N',N',-tetramethyluronium hexafluorophosphate (HATU). As appropriate, 1-hydroxy-1H-benzotriazole monohydrate (HOBt.$H_2O$), 4-dimethylaminopyridine (DMAP), N,N-diisopropylethylamine and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate (HOBt.$H_2O$) and a mixture of O-(7-azabenzotriazole-1-yl)-N,N,N',N',-tetramethyluronium hexafluorophosphate (HATU) and N,N-diisopropylethylamine.

The reaction temperature generally ranges room temperature to about 120° C., preferably room temperature to about 100° C.

The reaction time generally ranges about 30 minutes to 3 days, preferably about 1 hr to 1 day.

Step 10

Compound [I] ($R^c$=hydrogen) can be obtained from Compound [X-60] ($R^c$=$C_{1-6}$ alkyl group) in a solvent under the condition of a common ester hydrolysis reaction. The ester hydrolysis reaction may be performed under the alkaline or acidic condition.

The base for the alkaline condition includes for example, an aqueous solution of alkali metal hydroxide such as lithium hydroxide, sodium hydroxide, and potassium hydroxide. The preferred base for the reaction includes aqueous sodium hydroxide and aqueous lithium hydroxide.

The acid for the acidic condition includes for example, hydrochloric acid, hydrobromic acid, sulfuric acid, and trifluoroacetic acid. The preferred acid for the reaction includes hydrochloric acid, hydrobromic acid, and trifluoroacetic acid.

The solvent for the reaction includes for example, hydrocarbon solvent such as benzene, toluene, xylene, and hexane; alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; and polar solvent such as acetic acid, water and the like. The preferred solvent for the reaction includes methanol, ethanol, methylene chloride, chloroform, tetrahydrofuran, toluene, acetic acid, and water.

The reaction temperature generally ranges about 0° C. to 120° C., preferably room temperature to about 100° C.

The reaction time generally ranges about 30 minutes to 3 days, preferably about 1 hr to 1 day.

In Step 2 of Preparation method 3B, an racemic form of [X-42] may be used to give Compound [I] ($R^c$=hydrogen) which is in racemic form as a final product.

Preparation Method 4

The case of that the 5-membered ring is triazole:

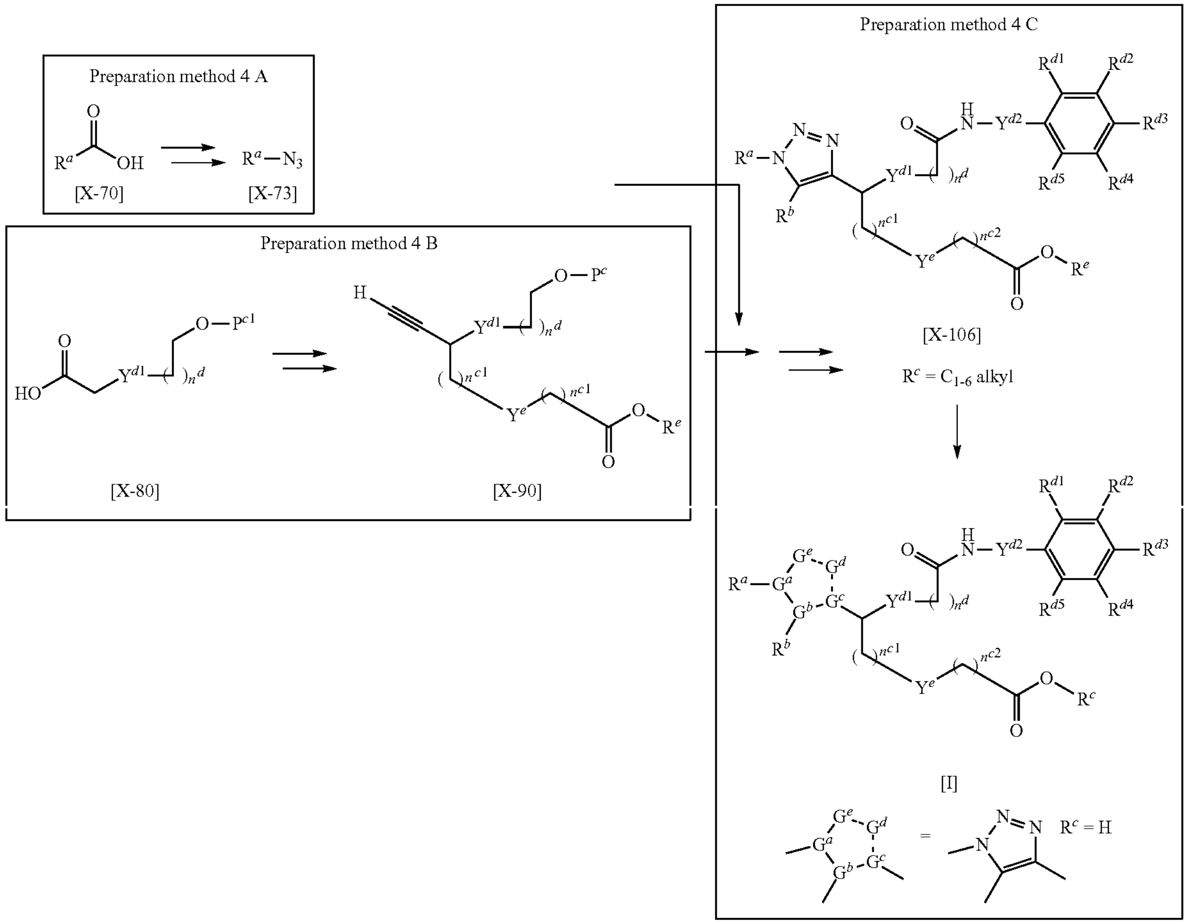

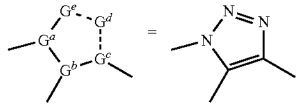

Preparation Method 4A

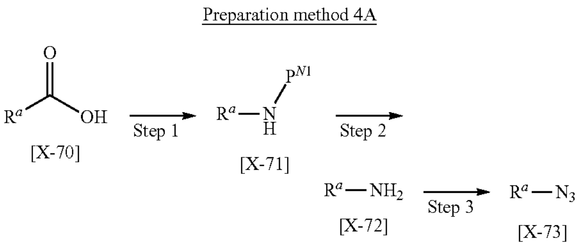

The example of Preparation method 4A includes the following scheme:

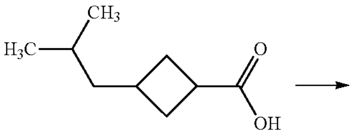

-continued

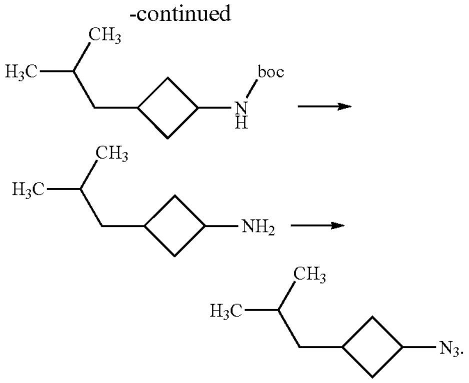

Step 1

Compound [X-71] can be obtained by the reaction of Compound [X-70] with diphenylphosphoryl azide (DPPA) and an alcohol in the presence of a base in a solvent.

The solvent for the reaction includes for example, alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; and polar solvent such as N,N-dimethylformamide, and acetonitrile. The preferred solvent for the reaction includes tert-butanol, toluene, and tetrahydrofuran.

The base for the reaction includes for example, an organic base such as triethylamine, N,N-diisopropylethylamine, pyridine and the like. The preferred base for the reaction includes triethylamine.

The alcohol for the reaction includes for example, methanol, ethanol, isopropyl alcohol, tert-butanol, benzyl alcohol and the like. The preferred alcohol for the reaction includes tert-butanol.

The reaction temperature generally ranges about 0° C. to 150° C., preferably room temperature to about 100° C.

The reaction time generally ranges about 30 minutes to 3 days, preferably about 1 hr to 1 day.

Step 2

Compound [X-72] can be obtained by removal of the protecting group $P^{N1}$ from Compound [X-71] in the presence of an acid in a solvent.

The solvent for the reaction includes for example, alcohols solvent such as methanol, ethanol, and isopropyl alcohol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; polar solvent such as N,N-dimethylformamide, and acetonitrile; acetic acid, and water. The preferred solvent for the reaction includes ethyl acetate, and dioxane.

The acid for the reaction includes for example, hydrochloric acid, hydrobromic acid, sulfuric acid, and trifluoroacetic acid. The preferred acid for the reaction includes hydrochloric acid, and trifluoroacetic acid.

The reaction temperature generally ranges about 0° C. to 150° C., preferably room temperature to about 100° C.

The reaction time generally ranges about 30 minutes to 3 days, preferably about 1 hr to 1 day.

Step 3

Compound [X-73] can be obtained by the reaction of Compound [X-72] with imidazole-1-sulfonyl azide hydrochloride in the presence of a base in a solvent.

The solvent for the reaction includes for example, alcohols solvent such as methanol, ethanol, and isopropyl alcohol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; and polar solvent such as N,N-dimethylformamide, and acetonitrile. The preferred solvent for the reaction includes methanol.

The base for the reaction includes for example, potassium carbonate, sodium carbonate and the like. The preferred base for the reaction includes potassium carbonate.

The reaction temperature generally ranges about 0° C. to 150° C., preferably room temperature to about 100° C.

The reaction time generally ranges about 30 minutes to 3 days, preferably about 1 hr to 1 day.

Preparation Method 4B

Preparation method 4 B

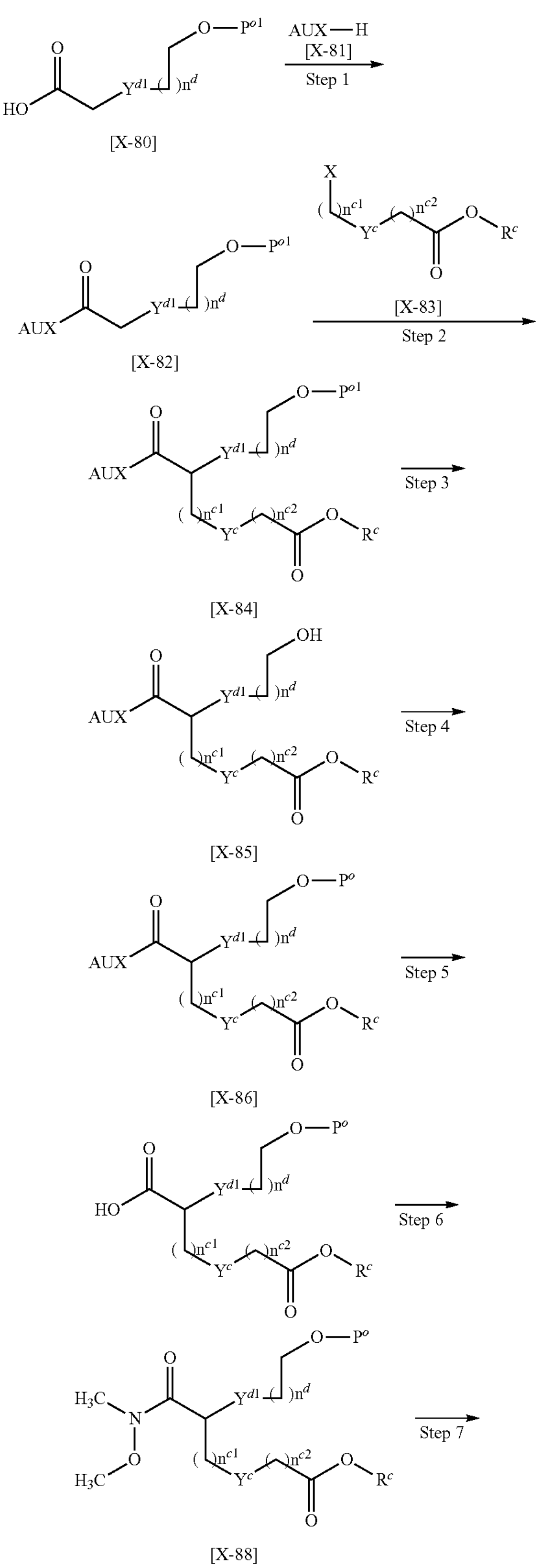

-continued

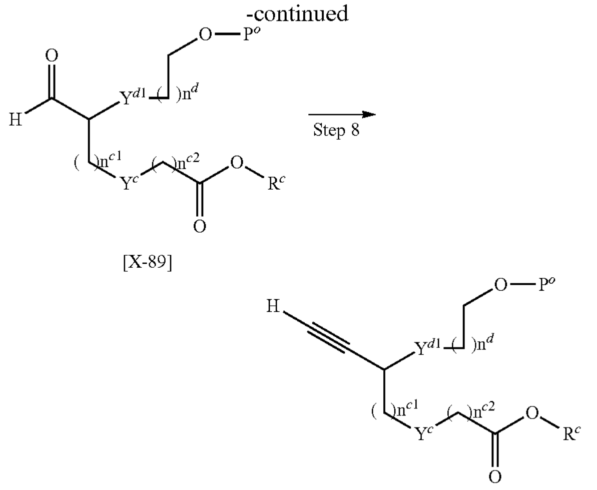

[X-89]

[X-90]

The example of Step 7 and Step 8 of Preparation method 4B includes the following scheme:

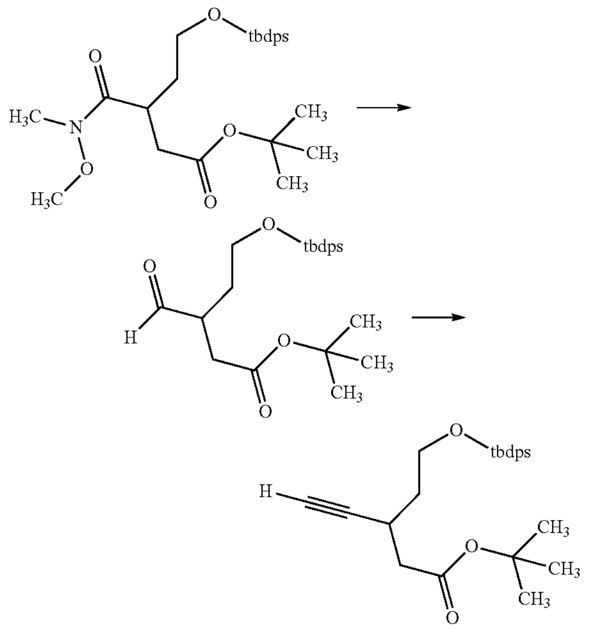

Step 1

Compound [X-82] can be obtained by the reaction of Compound [X-80] with Reactant [X-81] in the presence of a condensing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). As appropriate, 1-hydroxy-1H-benzotriazole monohydrate ($HOBt.H_2O$), 4-dimethylaminopyridine (DMAP) and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate ($HOBt.H_2O$) and a mixture of water-soluble carbodiimide (WSC.HCl: 1-ethyl-3-(3-dimethylaminopropyl)carbodiimide hydrochloride) and 4-dimethylaminopyridine (DMAP).

The reaction temperature generally ranges room temperature to about 120° C., preferably room temperature to about 100° C.

The reaction time generally ranges about 30 minutes to 3 days, preferably about 1 hr to 1 day.

Step 2

Compound [X-84] can be obtained by the reaction of Compound [X-82] with Reactant [X-83] in the presence of a base in a solvent.

The solvent for the reaction includes for example, hydrocarbon solvent such as benzene, toluene, xylene, and hexane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes tetrahydrofuran.

The base for the reaction includes for example, sodium hexamethyldisilazide, lithium hexamethyldisilazide, and lithium diisopropylamide (LDA). The preferred base for the reaction includes sodium hexamethyldisilazide and lithium hexamethyldisilazide.

The reaction temperature generally ranges about −78° C. to 50° C., preferably about −78° C. to room temperature.

The reaction time generally ranges about 30 minutes to 3 days, preferably about 30 minutes to 1 day.

Step 3

Compound [X-85] can be obtained by removal of the protecting group $P^{O1}$ from Compound [X-84] in a solvent.

When the protecting group $P^{O1}$ is a benzyl group, the protecting group may be removed by the catalytic hydrogenation reaction under normal pressure or medium pressure (for example, 3 atm).

The catalyst for the catalytic hydrogenation reaction includes for example, palladium on activated carbon, palladium hydroxide, and Raney nickel. The preferred catalyst for the reaction includes palladium on activated carbon and palladium hydroxide.

The solvent for the catalytic hydrogenation reaction includes for example, alcohols solvent such as methanol, ethanol, isopropyl alcohol, and tert-butanol; esters solvent such as ethyl acetate, methyl acetate, and butyl acetate; ethers solvent such as diethyl ether, tetrahydrofuran, dioxane, 1,2-dimethoxyethane, and diglyme; acetic acid, and water, which may be used alone or as a mixture of two or more. The preferred solvent for the reaction includes methanol, ethanol, ethyl acetate, and tetrahydrofuran.

The reaction temperature generally ranges room temperature to about 100° C., preferably room temperature to about 80° C.

The reaction time generally ranges about 30 minutes to 7 days, preferably about 1 hr to 5 days.

Step 4

Compound [X-86] can be obtained by introducing the protecting group $P^O$ into Compound [X-85] in a solvent.

When the protecting group $P^O$ is a silyl group, Compound [X-86] can be obtained by using silylation agent in the presence of a base.

The solvent for the reaction includes for example, esters solvent such as ethyl acetate, methyl acetate, and butyl acetate; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes N,N-dimethylformamide.

The base for the reaction includes for example, triethylamine, pyridine, and imidazole. The preferred base for the reaction includes imidazole.

The silylation agent for the reaction includes for example, tert-butylchlorodiphenylsilane, tert-butylchlorodimethylsilane, and tert-butyldimethylsilyl trifluoromethanesulfonate. The preferred silylation agent for the reaction includes tert-butylchlorodiphenylsilane.

The reaction temperature generally ranges room temperature to about 100° C., preferably room temperature to about 80° C.

The reaction time generally ranges about 30 minutes to 3 days, preferably about 1 hr to 1 day.

Step 5

Compound [X-87] can be obtained by hydrolysis reaction of Compound [X-86] in a solvent under the commonly-used condition. The hydrolysis reaction may be performed under the alkaline or acidic condition.

The base for the alkaline condition includes for example, an aqueous solution of alkali metal hydroxide such as lithium hydroxide, sodium hydroxide, and potassium hydroxide; inorganic peroxide such as lithium peroxide, potassium peroxide, and sodium peroxide. The preferred base for the reaction includes lithium peroxide.

The acid for the acidic condition includes for example, hydrochloric acid, acetic acid, hydrobromic acid, sulfuric acid, trifluoroacetic acid, and p-toluenesulfonic acid monohydrate. The preferred acid for the reaction includes hydrochloric acid, acetic acid, and p-toluenesulfonic acid monohydrate.

The solvent for the reaction includes for example, hydrocarbon solvent such as benzene, toluene, xylene, and hexane; alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; acetic acid, and water, which may be used alone or as a mixture of two or more. The preferred solvent for the reaction includes tetrahydrofuran and water.

The reaction temperature generally ranges about −30° C. to 80° C., preferably about 0° C. to room temperature.

The reaction time generally ranges about 30 minutes to 3 days, preferably about 30 minutes to 1 day.

Step 6

Compound [X-88] can be obtained by the reaction of Compound [X-87] with N,O-dimethylhydroxylamine or hydrochloride thereof in the presence of a condensing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). As appropriate, 1-hydroxy-1H-benzotriazole monohydrate ($HOBt.H_2O$), 4-dimethylaminopyridine (DMAP) and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate ($HOBt.H_2O$) and a mixture of water-soluble carbodiimide (WSC.HCl: 1-ethyl-3-(3-dimethylaminopropyl)carbodiimide hydrochloride) and 4-dimethylaminopyridine (DMAP).

The reaction temperature generally ranges room temperature to about 120° C., preferably room temperature to about 100° C.

The reaction time generally ranges about 30 minutes to 3 days, preferably about 1 hr to 1 day.

Step 7

Compound [X-89] can be obtained by the reaction of Compound [X-88] in the presence of a reducing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme, which may be used alone or as a mixture of two or more. The preferred solvent for the reaction includes toluene, methylene chloride, chloroform, hexane, and tetrahydrofuran.

The reducing agent for the reaction includes for example, diisobutylaluminum hydride, and lithium aluminium hydride. The preferred reducing agent for the reaction includes diisobutylaluminum hydride.

The reaction temperature generally ranges about −78° C. to room temperature, preferably about −78° C. to 0° C.

The reaction time generally ranges about 30 minutes to 3 days, preferably about 1 hr to 1 day.

Step 8

Compound [X-90] can be obtained by the reaction of Compound [X-89] with dimethyl (1-diazo-2-oxopropyl)phosphonate in a solvent.

The solvent for the reaction includes for example, alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; and polar solvent such as N,N-dimethylformamide, and acetonitrile. The preferred solvent for the reaction includes methanol.

The reaction temperature generally ranges about 0° C. to 150° C., preferably room temperature to about 100° C.

The reaction time generally ranges about 30 minutes to 3 days, preferably about 1 hr to 1 day.

Preparation Method 4C
Preparation method 4 C
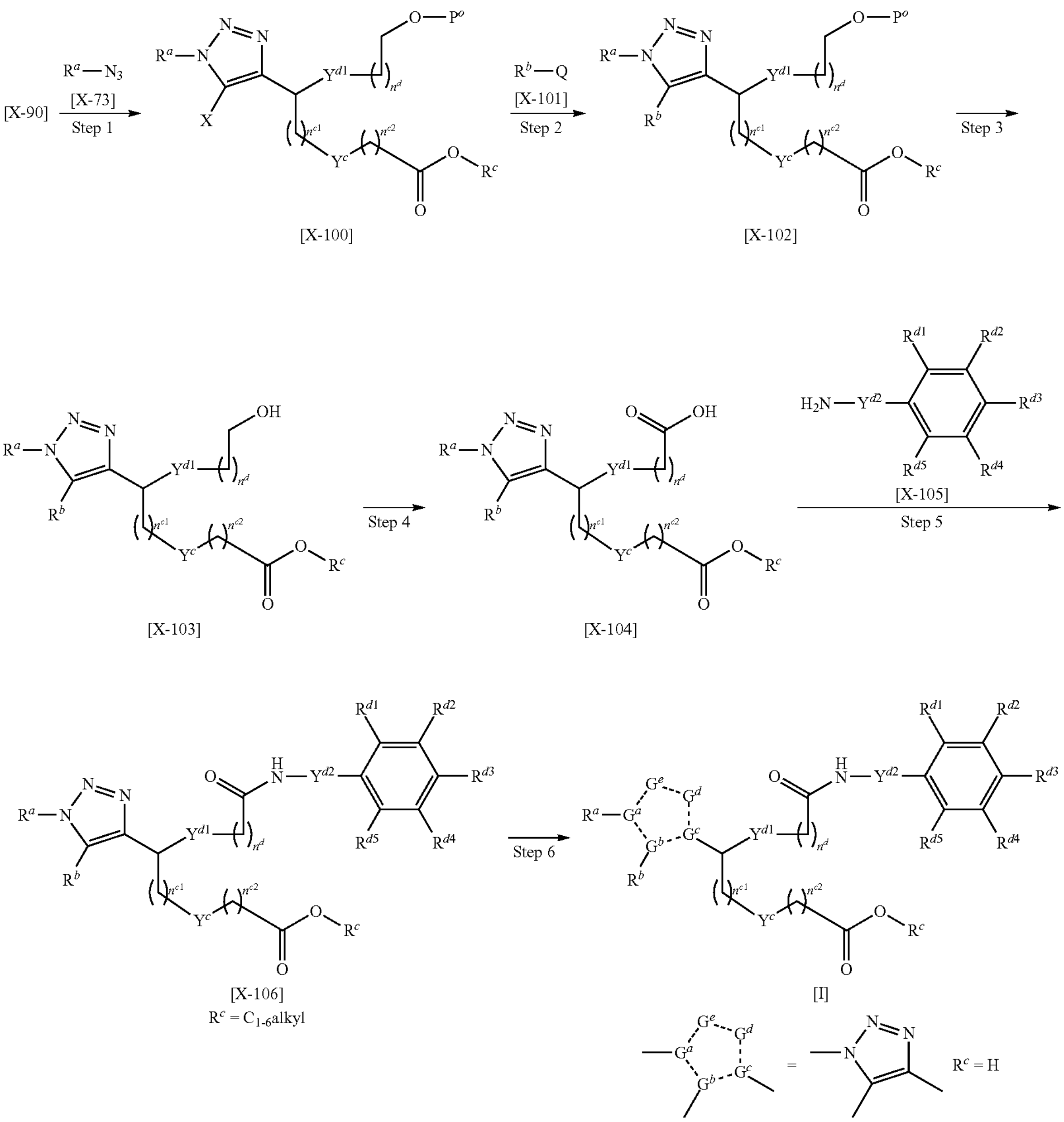
The example of Preparation method 4A includes the following scheme:
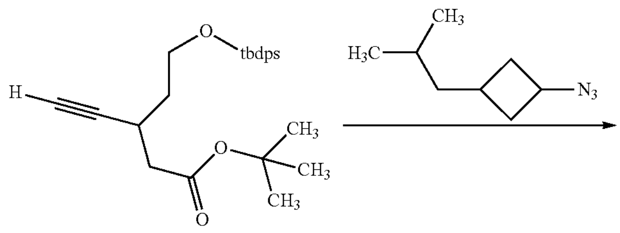

-continued

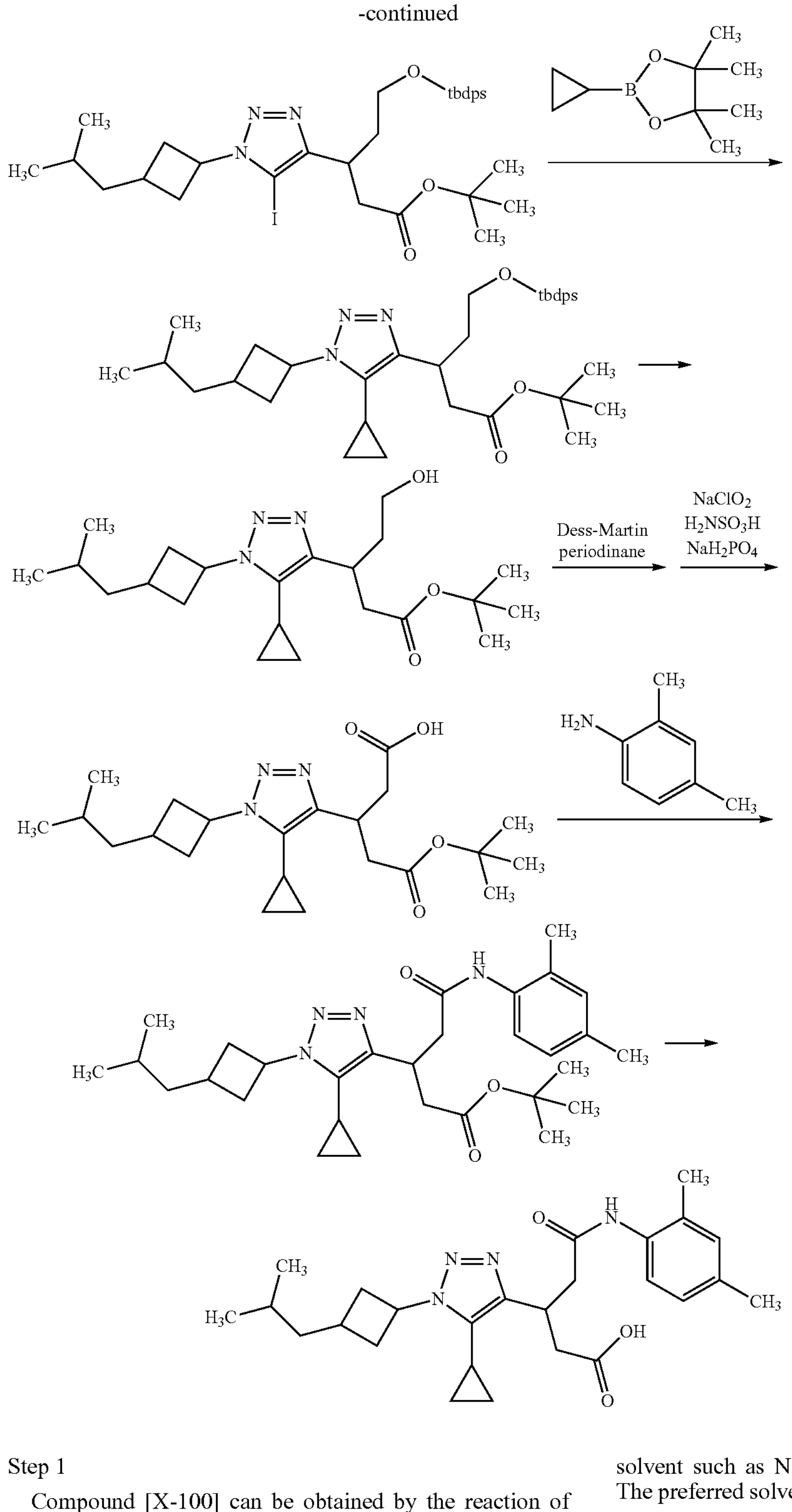

Step 1

Compound [X-100] can be obtained by the reaction of Compound [X-90] with Compound [X-73] in a solvent.

The solvent for the reaction includes for example, alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; and polar solvent such as N,N-dimethylformamide, and acetonitrile. The preferred solvent for the reaction includes tetrahydrofuran.

The reaction temperature generally ranges about 0° C. to 150° C., preferably room temperature to about 100° C.

The reaction time generally ranges about 30 minutes to 3 days, preferably about 1 hr to 1 day.

Step 2

Compound [X-102] can be obtained by the reaction of Compound [X-100] with Compound [X-101] in the presence of a metal catalyst in a solvent.

When Compound [X-101] is alkylboronic or arylboronic acid, these may be alkylboronic or arylboronic acid itself or an ester thereof, and the ester thereof is preferred. As the Compound [X-101], an alkylzinc or arylzinc reagent, an alkylmagnesium or arylmagnesium reagent or the like may be used.

The solvent for the reaction includes for example, hydrocarbon solvent such as benzene, toluene, xylene, and hexane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; and water, which may be used alone or as a mixture of two or more. The preferred solvent for the reaction includes N,N-dimethylformamide.

The metal catalyst for the reaction includes for example, a palladium catalyst such as bis(triphenylphosphine)palladium (II)dichloride, and 1,1'-bis(diphenylphosphino)ferrocene-palladium(II)dichloride, preferably bis(triphenylphosphine) palladium(II)dichloride.

The metal catalyst for the reaction also includes a nickel catalyst such as [1,2-bis(diphenylphosphino)ethane]nickel (II)dichloride, and nickel(II)acetylacetonate, and an iron catalyst such as iron(III)chloride.

As appropriate a base or an inorganic salt may be added.

The base or inorganic salt for the reaction includes for example, alkali metal phosphate such as tripotassium phosphate; alkali metal carbonate such as sodium carbonate, and potassium carbonate; alkali metal acetate such as sodium acetate; and fluoride salt such as cesium fluoride and the like, preferably tripotassium phosphate.

The reaction temperature generally ranges about −10° C. to 150° C., preferably about 0° C. to 100° C.

The reaction time generally ranges about 30 minutes to 3 days, preferably about 1 hr to 1 day.

Step 3

Compound [X-103] can be obtained by removal the protecting group of from Compound [X-102] in the presence of tetrabutylammonium fluoride (TBAF) in a solvent.

The solvent for the reaction includes for example, alcohols solvent such as methanol, ethanol, isopropyl alcohol, and tert-butanol; esters solvent such as ethyl acetate, methyl acetate, and butyl acetate; hydrocarbon solvent such as benzene, toluene, xylene, and hexane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes tetrahydrofuran.

The reaction temperature generally ranges about −10° C. to 150° C., preferably about 0° C. to 80° C.

The reaction time generally ranges about 30 minutes to 5 days, preferably about 1 hr to 3 days.

Step 4

Compound [X-104] can be obtained by the reaction of Compound [X-103] in the presence of an oxidant in a solvent.

The oxidant for the reaction includes for example, 2,2,6,6-tetramethyl-1-piperidinyloxy radical (TEMPO), potassium permanganate, aqueous hydrogen peroxide, pyridinium dichromate, and chromium oxide. The preferred oxidant for the reaction includes 2,2,6,6-tetramethyl-1-piperidinyloxy radical (TEMPO).

Alternatively, Compound [X-104] can be prepared by obtaining an aldehyde derived from Compound [X-103], and the oxidant for the reaction includes for example, pyridinium dichromate (PDC), pyridinium chlorochromate (PCC), and dimethyl sulfoxide (DMSO) activated by oxalyl chloride, Dess-Martin reagent, and sodium chlorite.

The solvent for the reaction includes for example, halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; polar solvents such as N,N-dimethylformamide, dimethyl sulfoxide, acetonitrile, and acetone; and water, which may be used alone or as a mixture of two or more.

The preferred solvent for the reaction includes methylene chloride, chloroform, tetrahydrofuran, acetonitrile, and water.

The reaction temperature generally ranges about −10° C. to 150° C., preferably about 0° C. to 80° C.

The reaction time generally ranges about 30 minutes to 5 days, preferably about 1 hr to 3 days.

Step 5

Compound [X-106] ($R^c$=$C_{1-6}$ alkyl group) can be obtained by the reaction of Compound [X-104] with Reactant [X-105] in the presence of a condensing agent in a solvent under the condition of a common amide bond formation reaction.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), carbonyldiimidazole (CDI), and O-(7-azabenzotriazole-1-yl)-N,N,N',N',-tetramethyluronium hexafluorophosphate (HATU). As appropriate, 1-hydroxy-1H-benzotriazole monohydrate ($HOBt.H_2O$), 4-dimethylaminopyridine (DMAP), N,N-diisopropylethylamine and the like may be added. The preferred condensing agent for the reaction includes a mixture of water-soluble carbodiimide (WSC.HCl: 1-ethyl-3-(3-dimethylaminopropyl)carbodiimide hydrochloride) and 1-hydroxy-1H-benzotriazole monohydrate ($HOBt.H_2O$), and a mixture of O-(7-azabenzotriazole-1-yl)-N,N,N',N',-tetramethyluronium hexafluorophosphate (HATU) and N,N-diisopropylethylamine.

The reaction temperature generally ranges room temperature to about 120° C., preferably room temperature to about 100° C.

The reaction time generally ranges about 30 minutes to 3 days, preferably about 1 hr to 1 day.

Step 6

Compound [I] ($R^c$=hydrogen) can be obtained from Compound [X-106] ($R^c$=$C_{1-6}$ alkyl group) in a solvent under the condition of a common ester hydrolysis reaction. The ester hydrolysis reaction may be performed under the alkaline or acidic condition.

The base for the alkaline condition includes for example, an aqueous solution of alkali metal hydroxide such as lithium hydroxide, sodium hydroxide, and potassium hydroxide. The preferred base for the reaction includes aqueous sodium hydroxide and aqueous lithium hydroxide.

The acid for the acidic condition includes for example, hydrochloric acid, hydrobromic acid, sulfuric acid, and trifluoroacetic acid. The preferred acid for the reaction includes hydrochloric acid, hydrobromic acid, and trifluoroacetic acid.

The solvent for the reaction includes for example, hydrocarbon solvent such as benzene, toluene, xylene, and hexane; alcohols solvent such as methanol, ethanol, isopropyl alcohol, and tert-butanol; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; esters solvent such as ethyl acetate, methyl acetate, and butyl acetate; and polar solvent such as acetic acid and water. The preferred solvent for the reaction includes methanol, ethanol, methylene chloride, chloroform, tetrahydrofuran, toluene, acetic acid, and water.

The reaction temperature generally ranges about 0° C. to 120° C., preferably room temperature to about 100° C.

The reaction time generally ranges about 30 minutes to 3 days, preferably about 1 hr to 1 day.

In Step 1 of Preparation method 4B, an racemic form of [X-81] may be used to give Compound [I] ($R^c$=hydrogen) which is in racemic form as a final product.

Preparation Method 5

The case of that $R^a$ has the following structure wherein the cyclic moiety U is cyclobutane ring:

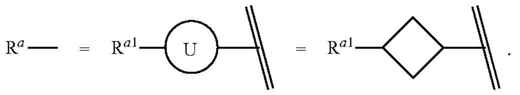

Step 1

Compound [X-191] can be obtained by amidation reaction of Compound [X-190] with piperidine in the presence of a condensing agent in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more. The preferred solvent for the reaction includes methylene chloride, chloroform, and N,N-dimethylformamide.

The condensing agent for the reaction includes for example, water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). As appropriate, 1-hydroxy-1H-benzotriazole monohydrate ($HOBt.H_2O$), 4-dimethylaminopyridine (DMAP) and the like may be added. The preferred condensing agent for the reaction Preparation method 5

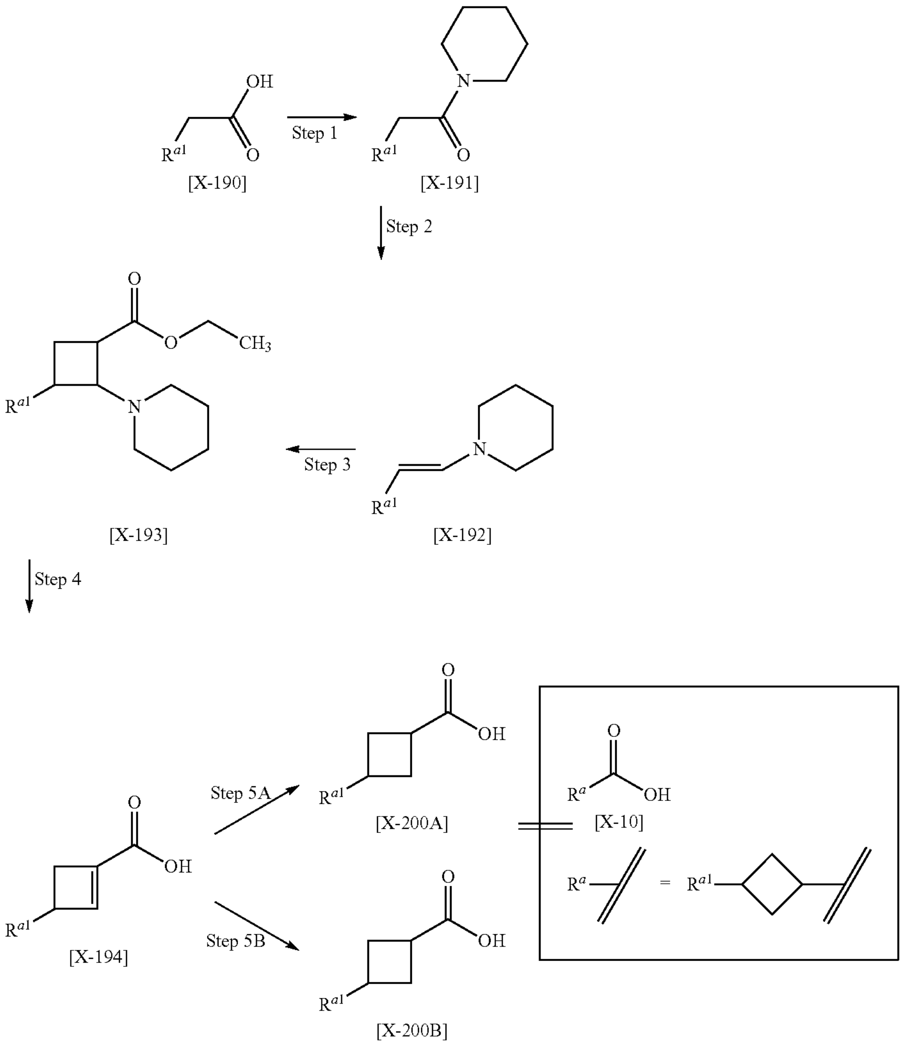

includes a mixture of water-soluble carbodiimide (WSC.HCl: 1-ethyl-3-(3-dimethylaminopropyl)carbodiimide hydrochloride) and 1-hydroxy-1H-benzotriazole monohydrate (HOBt.$H_2O$) and a mixture of water-soluble carbodiimide (WSC.HCl: 1-ethyl-3-(3-dimethylaminopropyl)carbodiimide hydrochloride) and 4-dimethylaminopyridine (DMAP).

The reaction temperature generally ranges room temperature to about 120° C., preferably room temperature to about 100° C.

The reaction time generally ranges about 30 minutes to 3 days, preferably about 1 hr to 1 day.

Step 2

Compound [X-192] can be obtained by the reaction of Compound [X-191] with 1,1,3,3-tetramethyldisiloxane in the presence of ($Ph_3P$)IrCl(CO) in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvent such as acetonitrile, which may be used alone or as a mixture of two or more. The preferred solvent for the reaction includes toluene.

The reaction temperature generally ranges about 0° C. to 120° C., preferably room temperature to about 100° C.

The reaction time generally ranges about 30 minutes to 2 days, preferably about 30 min. to 1 day.

Step 3

Compound [X-193] can be obtained by the reaction of Compound [X-192] with ethyl acrylate in a solvent.

The solvent for the reaction includes for example, hydrocarbon solvent such as benzene, toluene, xylene, and hexane; halogenated solvent such as methylene chloride, chloroform, carbon tetrachloride, and 1,2-dichloroethane; ethers solvent such as diethyl ether, tetrahydrofuran, dioxane, 1,2-dimethoxyethane, and diglyme; and polar solvents such as N,N-dimethylformamide, dimethyl sulfoxide, acetonitrile, and acetone, which may be used alone or as a mixture of two or more.

The preferred solvent for the reaction includes acetonitrile. The reaction temperature generally ranges room temperature to about 150° C., preferably room temperature to about 120° C.

The reaction time generally ranges about 30 minutes to 2 days, preferably about 1 hr to 1 day.

Step 4

Compound [X-194] can be obtained by quaternizing the amino group of Compound [X-193] with p-toluenesulfonate and the like followed by reacting the quaternized Compound [X-193] with a base.

The base for the reaction includes for example, an aqueous solution of alkali metal hydroxide such as lithium hydroxide, sodium hydroxide, and potassium hydroxide. The preferred base for the reaction includes an aqueous solution of potassium hydroxide.

The reaction temperature generally ranges room temperature to about 150° C., preferably room temperature to about 120° C.

The reaction time generally ranges about 30 minutes to 2 days, preferably about 1 hr to 1 day.

Step 5A 3-substituted cyclobutanecarboxylic acid [X-200A] can be obtained by the catalytic hydrogenation reaction of Compound [X-194] in a solvent under normal pressure or medium pressure (for example, 3 atm).

The catalyst for the catalytic hydrogenation reaction includes for example, palladium on activated carbon, rhodium on activated carbon, palladium hydroxide, and Raney nickel. The preferred catalyst for the reaction includes palladium on activated carbon, and rhodium on activated carbon.

The solvent for the catalytic hydrogenation reaction includes for example, alcohols solvent such as methanol, ethanol, isopropyl alcohol, and tert-butanol; esters solvent such as ethyl acetate, methyl acetate, and butyl acetate; ethers solvent such as diethyl ether, tetrahydrofuran, dioxane, 1,2-dimethoxyethane, and diglyme; acetic acid, and water, which may be used alone or as a mixture of two or more. The preferred solvent for the reaction includes methanol, and tetrahydrofuran.

The reaction temperature generally ranges room temperature to about 100° C., preferably room temperature to about 80° C.

The reaction time generally ranges about 30 minutes to 7 days, preferably about 1 hr to 5 days.

Step 5B

3-Substituted cyclobutanecarboxylic acid [X-200B] can be obtained by reduction reaction of Compound [X-194] using zinc in the presence of hydrochloric acid in a solvent.

The compound [X-200B] is a stereoisomer (cis-trans isomer) of the compound [X-200A].

The solvent for the reaction includes for example, ethers solvent such as diethyl ether, tetrahydrofuran, dioxane, 1,2-dimethoxyethane, and diglyme; acetic acid, and water, which may be used alone or as a mixture of two or more. The preferred solvent for the reaction includes tetrahydrofuran, and water.

The reaction temperature generally ranges room temperature to about 150° C., preferably room temperature to about 120° C.

The reaction time generally ranges about 30 minutes to 3 days, preferably about 1 hr to 1 day.

In Preparation methods 2, 3, and 4, Compound [I] wherein "$R^a$" has the following structure can be prepared by using the compounds [X-200A] or [X-200B] obtained in preparation method 5 as the carboxylic acid compound [X-10] and the like.

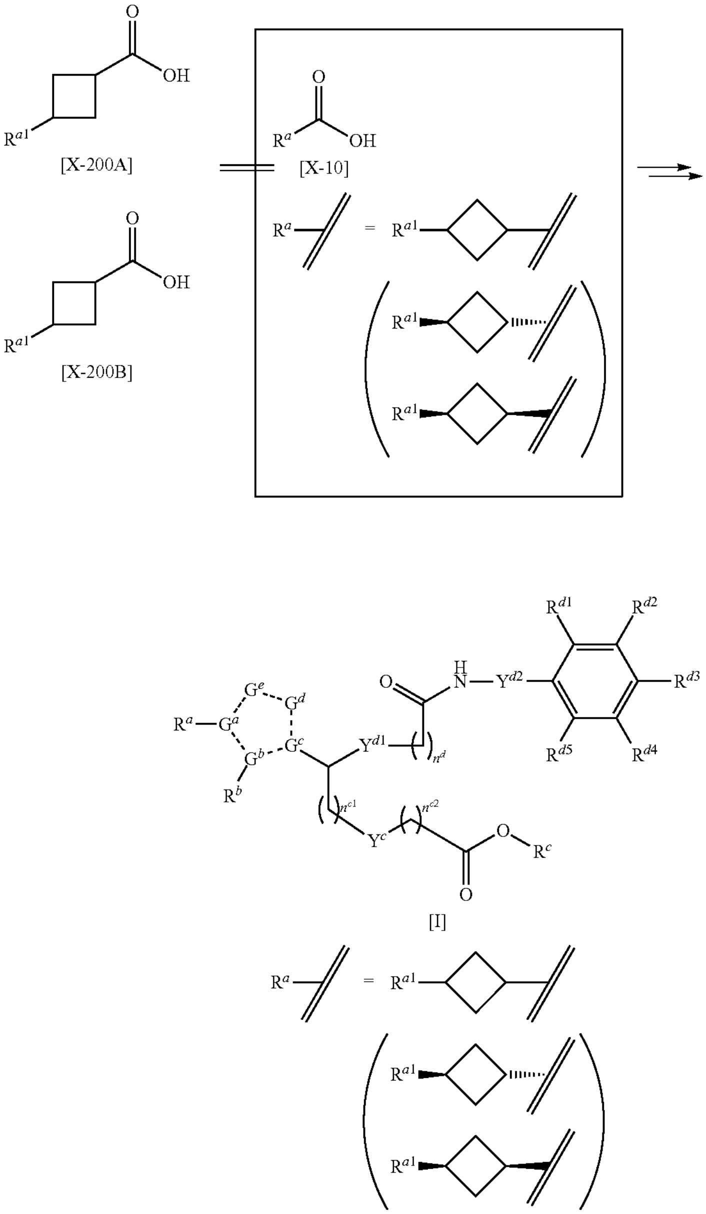
[X-200A]
[X-200B]
[X-10]
[I]
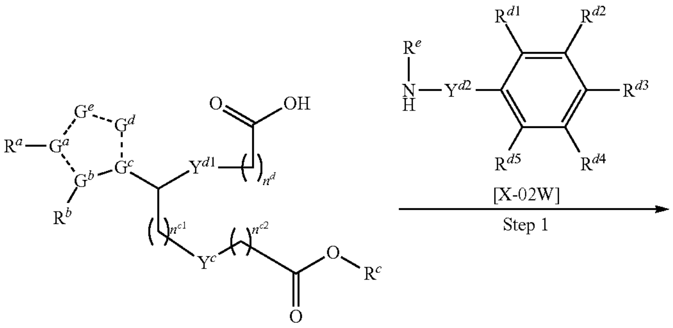
[X-02W]
[X-101]
$R^c = C_{1-6}alkyl$ -continued

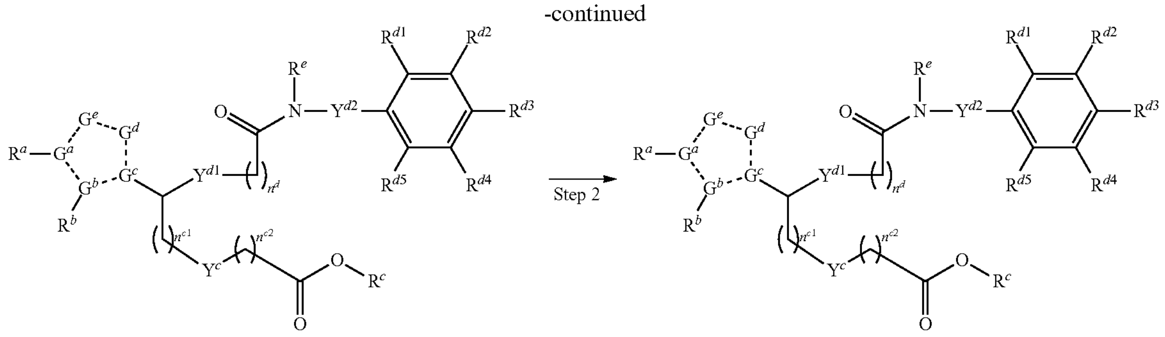

[I-W]
$R^c = C_{1-6}$alkyl

[I-W]
$R^c$ = H

The followings explain the each step in Preparation method 6.

Step 1

Compound [I-W] ($R^c$=$C_{1-6}$ alkyl group) can be obtained by the reaction of compound [X-01] with compound [X-02W] in the presence of a condensing agent in a solvent under the condition of a common amide bond formation reaction.

The solvent for the reaction, the reaction temperature, the reaction time are similar to those of Step 1 of Preparation method 1.

Alternatively, in the above amidation reaction, compound [I-W] ($R^c$=$C_{1-6}$ alkyl group) can be prepared by the reaction of an acid halide or mixed acid anhydride of compound [X-01] with compound [X-02W].

The acid halide of compound [X-01] can be derived by the reaction of a carboxylic acid of compound [X-01] with thionyl chloride, oxalyl chloride etc. wherein a catalytic amount of N,N-dimethylformamide may be added.

The mixed acid anhydride of compound [X-01] can be derived by the reaction of a carboxylic acid of compound [X-01] with ethyl chlorocarbonate etc.

Step 2

Compound [I-W] ($R^c$=hydrogen) can be obtained from compound [I-W] ($R^c$=$C_{1-6}$ alkyl group) in a solvent under the condition of ester hydrolysis reaction.

The solvent for the reaction, the reaction temperature, the reaction time are similar to those of Step 2 of Preparation method 1.

EXAMPLE

According to the above preparation methods, the compounds listed in FIGS. 1-41 were prepared.

The following working Examples serve to illustrate the present invention more specifically, which does not intend to limit the present invention.

The specific optical rotation was measured using the following instrument.

Instrument: AUTOPOL V (RUDOLPH RESEARCH ANALYTICAL)

Example A-82

4-(2-Chloro-5-methylphenylcarbamoyl)-3-[4-cyclopropyl-5-(3-isobutylcyclobutyl)isoxazol-3-yl]butanoic acid

(A-82-1) 4-Methyl-1-piperidin-1-ylpentan-1-one

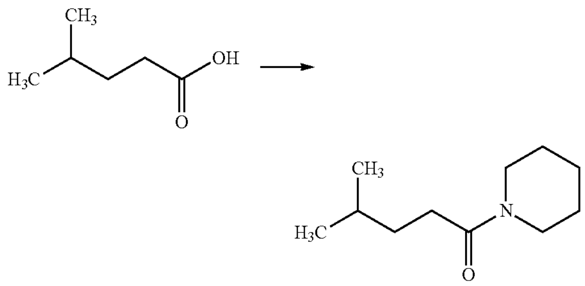

4-Methylvaleric acid (238 g) and DMF (833 mL) were mixed. After an addition of piperidine (233 mL), $HOBt.H_2O$ (361 g) and WSC.HCl (452 g) to the mixture at ice temperature, the resulting mixture was stirred at RT overnight. To the reaction was added water (1000 mL) at ice temperature and the resulting mixture was extracted with toluene (500 mL×2). The organic layer was washed with aqueous 10 w/v % sodium carbonate (500 mL+300 mL) and water (500 mL×2). The organic layer was concentrated in vacuo to give the title compound (414.29 g) as a crude product.

(A-82-2) 1-(4-Methyl-1-pentenyl)piperidine

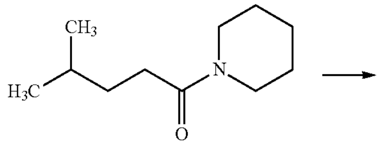

-continued

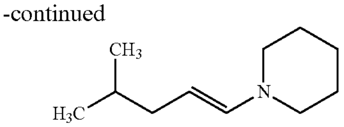

4-Methyl-1-piperidin-1-ylpentan-1-one (372.4 g) and toluene (1000 mL) were mixed. To the mixture was added $(Ph_3P)IrCl(CO)$ (633 mg). In a water-bath, 1,1,3,3-tetramethyldisiloxane (627 mL) was added dropwise to the mixture. The resulting mixture was stirred at RT for 2 hr. The reaction mixture was concentrated in vacuo to give the title compound (844 g) as a crude product.

(A-82-3) Ethyl 3-isobutyl-2-piperidin-1-ylcyclobutanecarboxylate

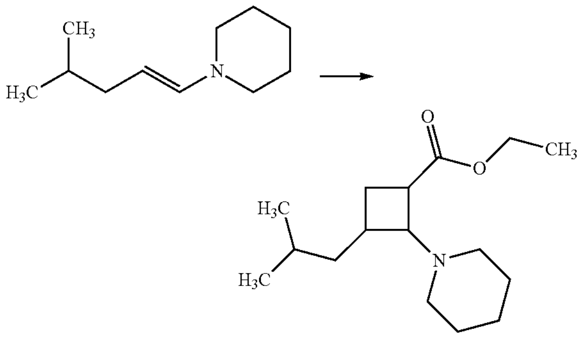

1-(4-Methyl-1-pentenyl)piperidine (844 g) and acetonitrile (70 mL) were mixed. The ethyl acrylate (443 mL) and hydroquinone (447 mg) were added to the mixture. The resulting mixture was stirred at 95° C. overnight. The reaction mixture was concentrated in vacuo to give the title compound (994.08 g) as a crude product.

(A-82-4) 3-Isobutyl-1-cyclobutenecarboxylic acid

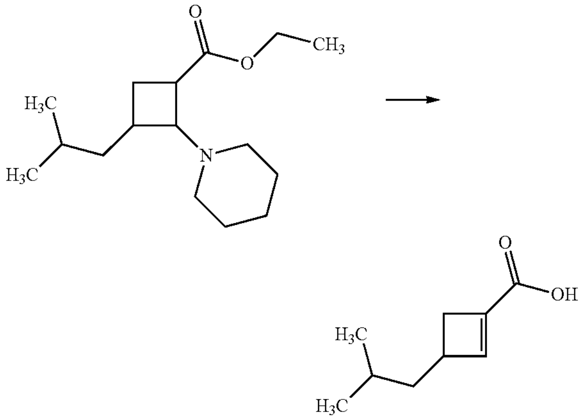

Ethyl 3-isobutyl-2-piperidin-1-ylcyclobutanecarboxylate (994 g) and methyl p-toluenesulfonate (337 mL) were mixed. The mixture was stirred at 110° C. for 2 hr and water (1100 mL) was added to the mixture. The resulting mixture was washed with tert-butyl methyl ether/hexane=1/1 (600 mL) and hexane (600 mL). To the aqueous layer was added potassium hydroxide (503 g) at ice temperature. The resulting mixture was stirred at 95° C. for 4 hr. The reaction mixture was washed with diethyl ether (500 mL) and diethyl ether/hexane=1/1 (500 mL). To the aqueous layer was added concentrated hydrochloric acid (672 mL) at ice temperature. The mixture was extracted with ethyl acetate (1 L×2). The combined organic layer was washed with water (500 mL×2) and brine (500 mL), then dried over sodium sulfate. The sodium sulfate was filtered off and the filtrate was concentrated in vacuo to give the title compound (240 g) as a crude product.

(A-82-5) 3-Isobutylcyclobutanecarboxylic acid

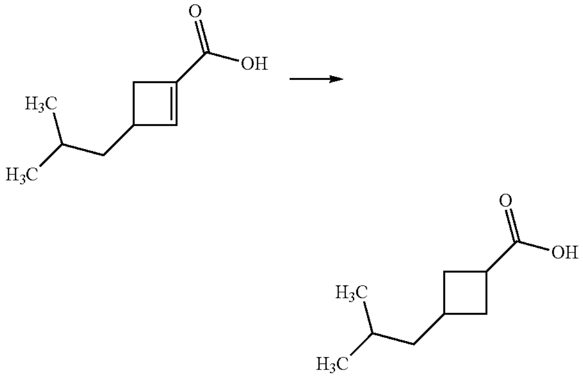

3-Isobutyl-1-cyclobutenecarboxylic acid (188 g) and tetrahydrofuran (2000 mL) were mixed. To the mixture was added 5 w/w % rhodium on activated carbon (5.64 g). The resulting mixture was stirred at RT for 7 hr under hydrogen atmosphere (1 atm). The 5 w/w % rhodium on activated carbon was filtered off and the filtrate was concentrated in vacuo to give the title compound (134.06 g) as a crude product.

(A-82-6) N-Methoxy-N-methyl-3-isobutylcyclobutanecarboxamide

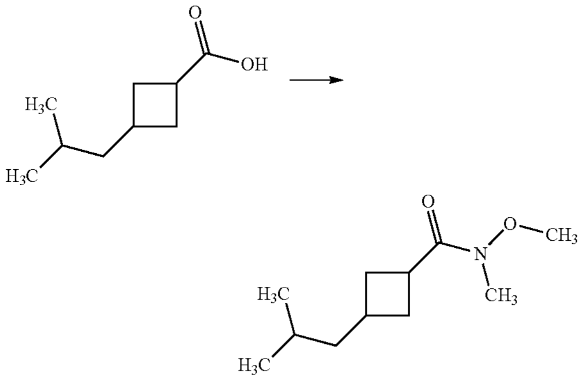

3-Isobutylcyclobutanecarboxylic acid (62.7 g) and DMF (500 mL) were mixed. To the mixture were added N,O-dimethylhydroxylamine hydrochloride (46.9 g), triethylamine (83.9 mL), $HOBt.H_2O$ (73.8 g) and WSC.HCl (92.3 g). The resulting mixture was stirred at RT overnight. To the reaction mixture was added water (500 mL). The mixture was extracted with ethyl acetate/hexane=1/1 (250 mL×2). The combined organic layer was washed with water (250 mL), aqueous 10 w/v % sodium carbonate (250 mL), water (250 mL), 1 N hydrochloric acid (500 mL), water, saturated aqueous sodium bicarbonate (250 mL) and then brine (250 mL). The organic layer was dried over magnesium sulfate. The magnesium sulfate was filtered off and the filtrate was concentrated in vacuo to give the title compound (87.5 g) as a crude product.

(A-82-7) 3-Isobutylcyclobutanecarbaldehyde

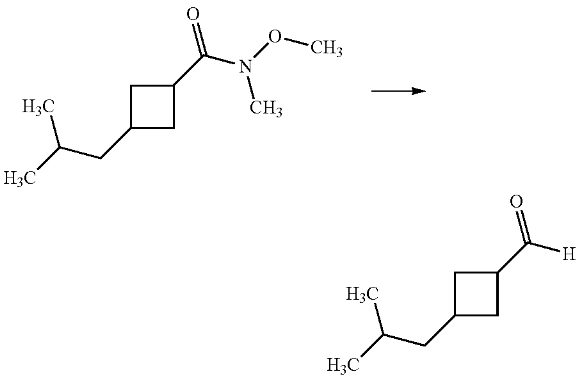

To a solution of N-methoxy-N-methyl-3-isobutylcyclobutanecarboxamide (77 g) in methylene chloride (235 mL) was added dropwise diisobutylaluminum hydride (1.0 M in methylene chloride) (473.2 mL) at −78° C. The mixture was stirred at −78° C. for 2 hr. After an addition of 1.5 M sulfuric acid (630 mL) at ice temperature, the mixture was extracted with methylene chloride. The combined organic layer was washed with 1.5 M sulfuric acid, water and brine, then dried over magnesium sulfate. The magnesium sulfate was filtered off and the filtrate comprising the title compound was used in the next step.

(A-82-8) 1-(2,2-Dibromovinyl)-3-isobutylcyclobutane

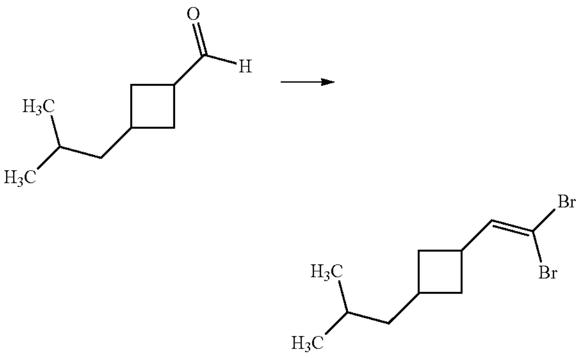

To a solution of carbon tetrabromide (168 g) in methylene chloride (252 mL) was added dropwise a solution of triphenylphosphine (266 g) in methylene chloride (350 mL) at ice temperature. The mixture was stirred at ice temperature for 20 min. To the mixture was then added dropwise a solution of 3-isobutylcyclobutanecarbaldehyde in methylene chloride at ice temperature. The mixture was stirred at ice temperature for 20 min. After an addition of aqueous 10 w/v % sodium carbonate (1 L) dropwise to the mixture, the mixture was extracted with methylene chloride (200 mL×2). The combined organic layer was washed with water and brine, then dried over magnesium sulfate. The magnesium sulfate was filtered off and the filtrate was concentrated in vacuo. To the resultant residue were added hexane/chloroform=1/1 (750 mL), silica gel (750 mL) and hexane (900 mL). The mixture was filtered and the filtrate was concentrated in vacuo. To the resultant residue was added hexane (500 mL). The mixture was filtered and the filtrate was concentrated in vacuo. The resultant residue was purified by silica gel column chromatography (Eluent: hexane) to give the title compound (76.21 g).

(A-82-9) (S)-4-Benzyl-3-(4-benzyloxybutyryl)oxazolidin-2-one

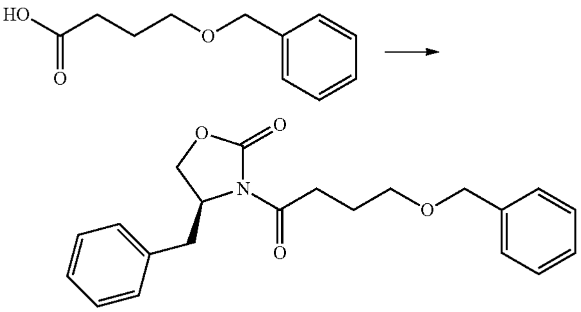

4-Benzyloxybutyric acid (238 g), (S)-4-benzyl-2-oxazolidinone (217 g) and chloroform (1300 mL) were mixed. After an addition of 4-dimethylaminopyridine (45 g) and WSC.HCl (282 g) to the mixture at ice temperature, the resulting mixture was stirred at RT overnight. The reaction mixture was concentrated in vacuo and toluene (2 L) was poured into the residue. The mixture was washed with 1 N hydrochloric acid (1.5 L), saturated aqueous sodium bicarbonate (2 L) and brine (1.5 L), then dried over sodium sulfate. The sodium sulfate was filtered off and the filtrate was concentrated in vacuo to give the title compound (424.8 g) as a crude product.

(A-82-10) tert-Butyl 3-((S)-4-benzyl-2-oxooxazolidine-3-carbonyl)-5-benzyloxyvalerate

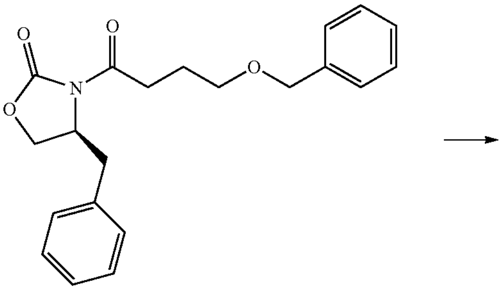

-continued

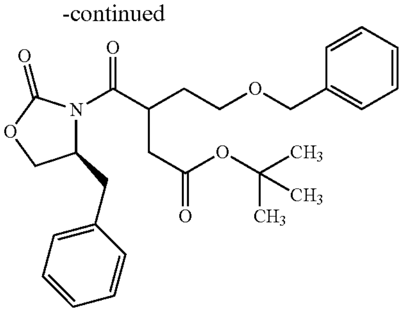

(S)-4-Benzyl-3-(4-benzyloxybutyryl)oxazolidin-2-one (410 g) and tetrahydrofuran (1.6 L) were mixed. To the mixture was added dropwise sodium hexamethyldisilazane (38% (approximately 1.9 mol/L) in tetrahydrofuran) (702 mL) at −78° C. The reaction temperature was rose to −50° C. and stirred at the same temperature. After cooling to −78° C., tert-butyl bromoacetate (275 mL) was added dropwise to the mixture. The reaction temperature was gradually rose to −15° C. and N,N,N'-triethylethylenediamine (120 mL) was added dropwise to the mixture. After stirring at the same temperature, ice water (1.6 L) was poured into the reaction and the mixture was extracted with toluene (2.4 L). The organic layer was washed with aqueous 20 w/v % citric acid (2.4 L), water (1.6 L), saturated aqueous sodium bicarbonate (2 L) and brine (1.6 L), then dried over sodium sulfate. The sodium sulfate was filtered off and the filtrate was concentrated in vacuo to give a residue (648.8 g). 565 g of the residue was mixed with methanol (2260 mL) and activated carbon (85 g). The resulting mixture was stirred at 75° C. for 2 hr. The activated carbon was filtered off and the filtrate was concentrated in vacuo to give the title compound (569.9 g) as a crude product.

(A-82-11) tert-Butyl 3-((S)-4-benzyl-2-oxooxazolidine-3-carbonyl)-5-hydroxyvalerate

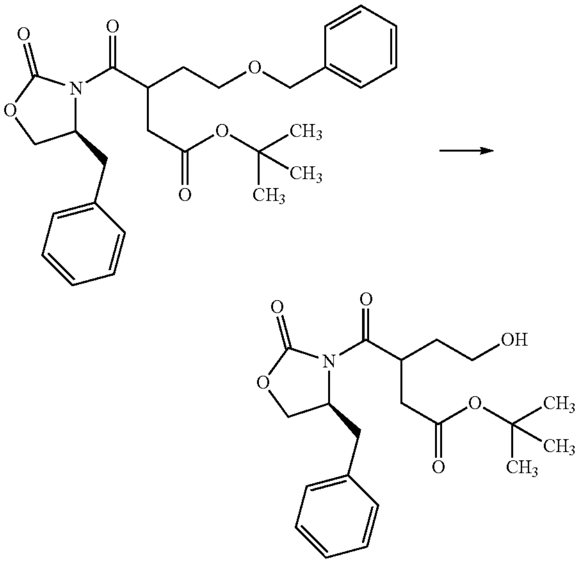

tert-Butyl 3-((S)-4-benzyl-2-oxooxazolidine-3-carbonyl)-5-benzyloxyvalerate (500 g), ethyl acetate (750 mL) and tetrahydrofuran (1510 mL) were mixed. To the mixture was added 20 w/w % palladium hydroxide (50 g). The mixture was stirred for 4.5 hr under hydrogen atmosphere (1 atm). The palladium hydroxide was filtered off and the filtrate was concentrated in vacuo to give the title compound (455.76 g) as a crude product.

(A-82-12) tert-Butyl 3-((S)-4-benzyl-2-oxooxazolidine-3-carbonyl)-5-(tert-butyldiphenylsilanyloxy) valerate

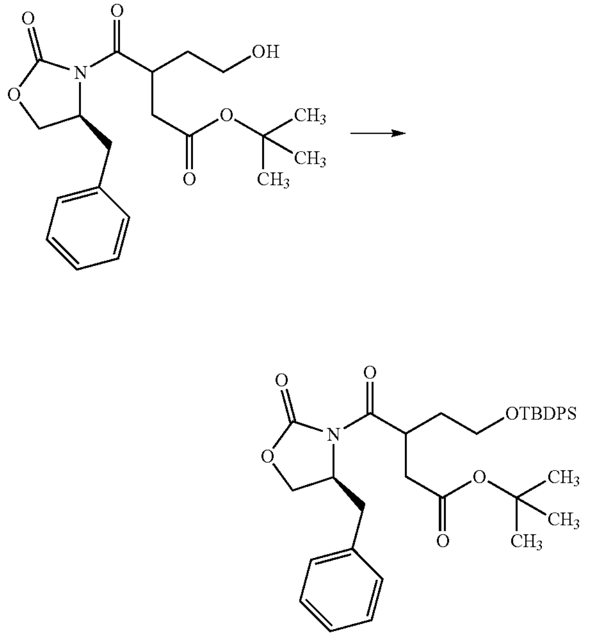

tert-Butyl 3-((S)-4-benzyl-2-oxooxazolidine-3-carbonyl)-5-hydroxyvalerate (401 g) and DMF (2000 mL) were mixed. To the mixture were added imidazole (160 g) and tert-butylchlorodiphenylsilane (287 mL) at ice temperature. The mixture was stirred at RT for 1 hr. After pouring water (1.2 L) into the reaction, the mixture was extracted with toluene (2.3 L). The organic layer was washed with aqueous 20 w/v % citric acid (1.6 L), water (2 L) and 10 w/v % brine (1.6 L), then dried over sodium sulfate. The sodium sulfate was filtered off and the filtrate was concentrated in vacuo to give the title compound (744.2 g) as a crude product.

(A-82-13) 4-tert-Butyl 2-[2-(tert-butyldiphenylsilanyloxy)ethyl]succinate

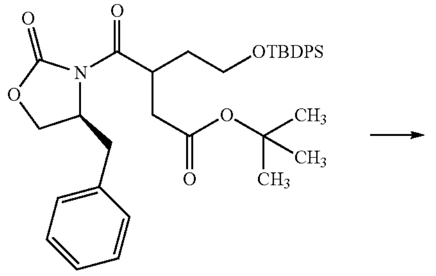

-continued

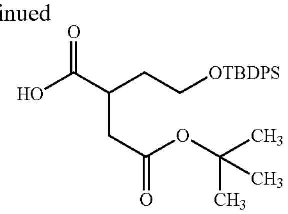

Lithium hydroxide monohydrate (58 g), tetrahydrofuran (1300 mL) and water (600 mL) were mixed. To the mixture was added dropwise aqueous 30 w/w % hydrogen peroxide (256 mL) at ice temperature. The mixture was stirred at the same temperature for 1 hr and a solution of tert-butyl 3-((S)-4-benzyl-2-oxooxazolidine-3-carbonyl)-5-(tert-butyldiphenylsilanyloxy)valerate (744 g) in tetrahydrofuran (1200 mL) was added dropwise to this mixture at ice temperature. After stirring at RT for 2 hr, aqueous sodium hydrogen sulfite (332 g) (1.3 L) was added dropwise to the reaction mixture at ice temperature. The mixture was extracted with ethyl acetate (3.6 L). The organic layer was washed with water (2 L) and 10 w/v % saline solution (2 L), then concentrated in vacuo to give a residue (706.7 g). After combining the oil, hexane (3.5 L) and aqueous 1 M sodium carbonate (2.8 L), the aqueous layer was extracted and washed with hexane (1.5 L). To the resulting aqueous layer was added dropwise 6 N hydrochloric acid (865 mL) at ice temperature and the mixture was extracted with ethyl acetate (2.2 L). The organic layer was washed with water (2.2 L) and 10 w/v % saline solution (1.5 L), then dried over sodium sulfate. The sodium sulfate was filtered off and the filtrate was concentrated in vacuo. After an addition of diisopropyl ether (1.1 L) and hexane (1.6 L) to the residue, the mixture was stirred at RT. The resultant precipitate was collected by filtration to give the title compound (437.4 g).

(A-82-14) tert-Butyl 5-(tert-butyldiphenylsilanyloxy)-3-methoxymethylcarbamoylvalerate

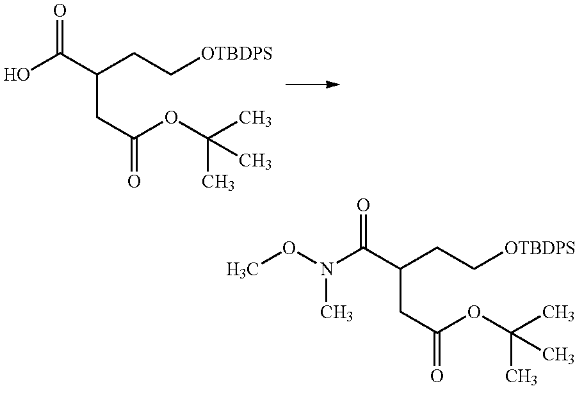

4-tert-Butyl 2-[2-(tert-butyldiphenylsilanyloxy)ethyl]succinate (437.4 g), triethylamine (171 mL) and DMF (2000 mL) were mixed. To the mixture were added N,O-dimethylhydroxylamine hydrochloride (111 g), HOBt.$H_2O$ (161 g) and WSC.HCl (201 g) at ice temperature. After stirring at RT overnight, water (800 mL) was poured into the reaction mixture and the mixture was extracted with hexane (2.4 L). The organic layer was washed with water (1.2 L) and 10 w/v % saline solution (1.2 L). The aqueous layer was extracted with hexane (2.4 L) once again and the combined organic layer was dried over sodium sulfate. The sodium sulfate was filtered off and the filtrate was concentrated in vacuo to give the title compound (425.1 g) as a crude product.

(A-82-15) tert-Butyl 3-[2-(tert-butyldiphenylsilanyloxy)ethyl]-6-(3-isobutylcyclobutyl)-4-oxo-5-hexynoate

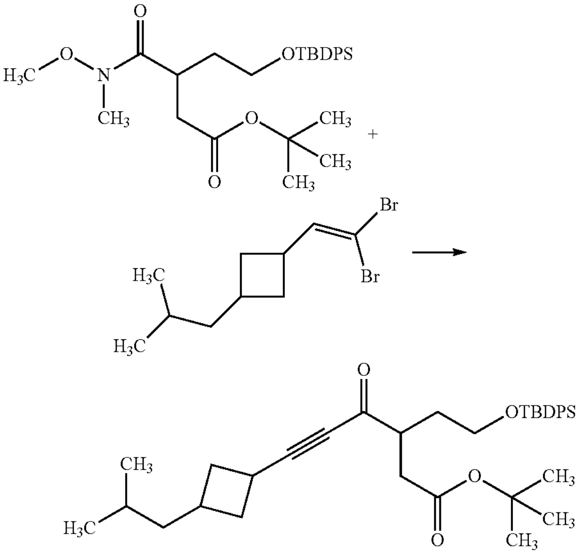

1-(2,2-Dibromovinyl)-3-isobutylcyclobutane (40 g) and tetrahydrofuran (280 mL) were mixed. To the mixture was added n-butyllithium (2.66 M in hexane) (104 mL) dropwise at −78° C. The mixture was stirred at ice temperature and a solution of tert-butyl 5-(tert-butyldiphenylsilanyloxy)-3-methoxymethylcarbamoylvalerate (54 g) in tetrahydrofuran (100 mL) was added dropwise to the mixture. After stirring at ice temperature for 1 hr, saturated aqueous ammonium chloride (180 mL) and water (100 mL) were added to the reaction mixture. The mixture was extracted with ethyl acetate (600 mL), washed with saturated aqueous ammonium chloride (180 mL and 400 mL) and dried over sodium sulfate. The sodium sulfate was filtered off and the filtrate was concentrated in vacuo. After an addition of silica gel (90 g) and ethyl acetate/hexane=1/20 (600 mL) into the resultant residue, the mixture was stirred at RT for 1 hr. The silica gel was filtered off and the filtrate was concentrated in vacuo to give the title compound (60.09 g) as a crude product.

(A-82-16) tert-Butyl 3-[2-(tert-butyldiphenylsilanyloxy)ethyl]-6-(3-isobutylcyclobutyl)-4-methoxyimino-5-hexynoate

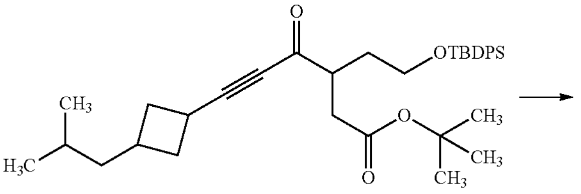

-continued

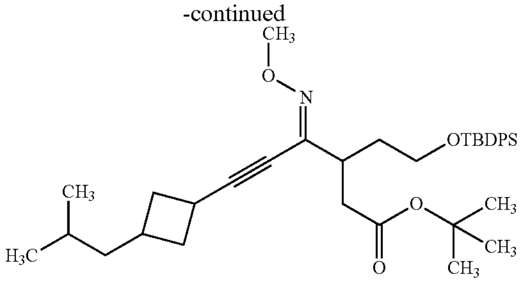

tert-Butyl 3-[2-(tert-butyldiphenylsilanyloxy)ethyl]-6-(3-isobutylcyclobutyl)-4-oxo-5-hexynoate (58.1 g) and methanol (300 mL) were mixed. To the mixture were added sodium sulfate (21.55 g), pyridine (30 mL) and O-methylhydroxylammonium chloride (12.67 g) at ice temperature. The mixture was stirred at RT overnight and the resultant precipitate was removed by filtration. After concentration of the filtrate in vacuo, toluene (350 mL) was poured into the residue. The mixture was washed with 1 N hydrochloric acid (300 mL), water (300 mL) and brine (150 mL), then dried over sodium sulfate. The sodium sulfate was filtered off and the filtrate was concentrated in vacuo. After an addition of silica gel (80 g) and ethyl acetate/hexane=1/20 (600 mL) to the residue, the mixture was stirred at RT for 1 hr. The silica gel was filtered off and the filtrate was concentrated in vacuo to give the title compound (55.54 g) as a crude product.

(A-82-17) tert-Butyl 5-(tert-butyldiphenylsilanyloxy)-3-[4-iodo-5-(3-isobutylcyclobutyl)isoxazol-3-yl]valerate

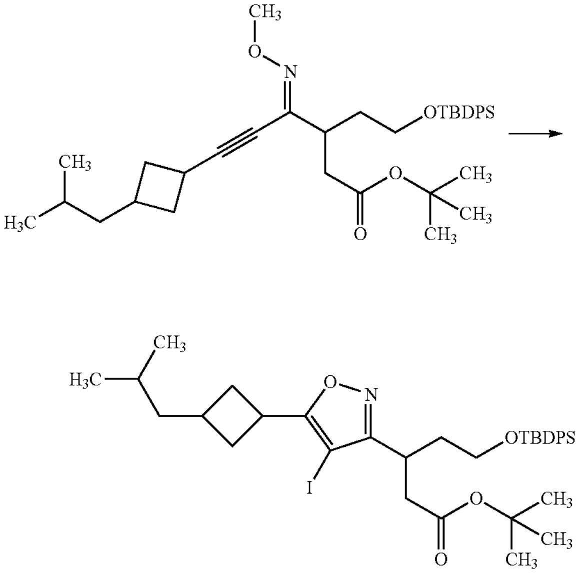

tert-Butyl 3-[2-(tert-butyldiphenylsilanyloxy)ethyl]-6-(3-isobutylcyclobutyl)-4-methoxyimino-5-hexynoate (53.6 g) and acetonitrile (320 mL) were mixed. To the mixture was added iodine (49.6 g) at ice temperature and the reaction mixture was stirred for 3 hr. After pouring the mixture into the solution of aqueous 20 w/v % sodium thiosulfate (380 mL) at ice temperature, the mixture was extracted with chloroform (1 L) and dried over magnesium sulfate. The magnesium sulfate was filtered off and the filtrate was concentrated in vacuo. After an addition of silica gel (80 g) and ethyl acetate/hexane=1/20 (600 mL) to the residue, the mixture was stirred at RT for 1 hr. The silica gel was filtered off and the filtrate was concentrated in vacuo. The residue was purified twice by silica gel column chromatography (Eluent: ethyl acetate/hexane=1/60→1/50→1/45) to give the title compound (38.2 g).

(A-82-18) tert-Butyl 5-(tert-butyldiphenylsilanyloxy)-3-[4-cyclopropyl-5-(3-isobutylcyclobutyl)isoxazol-3-yl]valerate

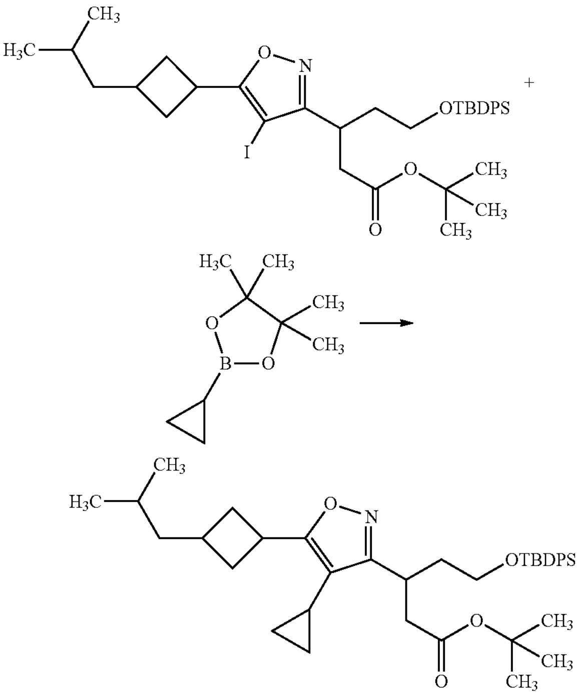

tert-Butyl 5-(tert-butyldiphenylsilanyloxy)-3-[4-iodo-5-(3-isobutylcyclobutyl)isoxazol-3-yl]valerate (37.44 g), 2-cyclopropyl-4,4,5,5-tetramethyl-[1,3,2]dioxaborolane (17.58 g) and DMF (262 mL) were mixed. After the resulting solution was degassed by bubbling argon, tripotassium phosphate (33.32 g) and $PdCl_2(PPh_3)_2$ (3.67 g) were added to the mixture. The mixture was stirred at 80° C. overnight. After water (200 mL) was poured into the reaction, the resultant precipitate was removed by filtration and the filtrate was extracted with toluene (600 mL). The organic layer was washed with water (200 mL×2, 320 mL) and brine (160 mL), then dried over sodium sulfate. The sodium sulfate was filtered off and the filtrate was concentrated in vacuo. After an addition of silica gel (45 g) and ethyl acetate/hexane=1/20 (400 mL) to the residue, the mixture was stirred at RT. The silica gel was filtered off and the filtrate was concentrated in vacuo. The residue was purified by silica gel column chromatography (Eluent: ethyl acetate/hexane=1/80→1/60→1/50) to give the title compound (20.2 g).

(A-82-19) tert-Butyl 3-[4-cyclopropyl-5-(3-isobutylcyclobutyl)isoxazol-3-yl]-5-hydroxyvalerate

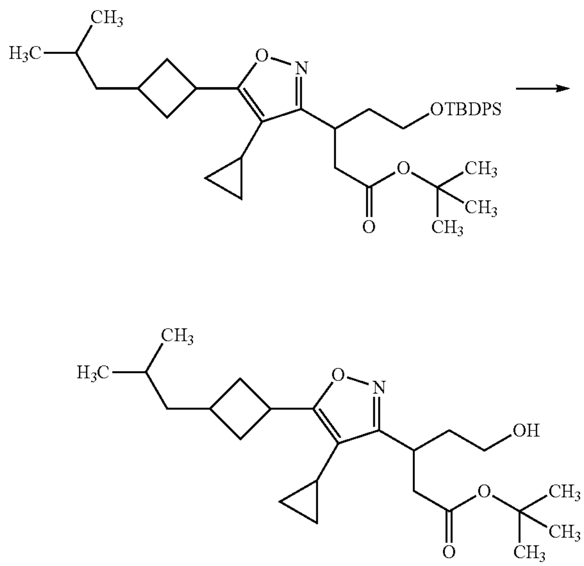

tert-Butyl 5-(tert-butyldiphenylsilanyloxy)-3-[4-cyclopropyl-5-(3-isobutylcyclobutyl)isoxazol-3-yl]valerate (17.62 g) and tetrahydrofuran (106 mL) were mixed. After an addition of acetic acid/water=4/1 (2.45 mL) and tetrabutylammonium fluoride (1 M in tetrahydrofuran) (39.2 mL) to the solution at ice temperature, the mixture was stirred at RT overnight. The reaction mixture was concentrated in vacuo and purified by silica gel column chromatography (Eluent: ethyl acetate/hexane=1/6→1/2) to give the title compound (11.82 g).

(A-82-20) Mono-tert-butyl 3-[4-cyclopropyl-5-(3-isobutylcyclobutyl)isoxazol-3-yl]glutarate

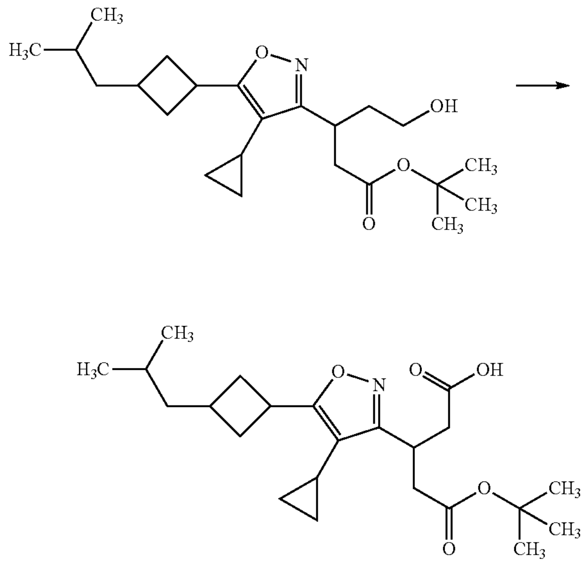

tert-Butyl 3-[4-cyclopropyl-5-(3-isobutylcyclobutyl)isoxazol-3-yl]-5-hydroxyvalerate (11 g), acetonitrile (110 mL) and 1 M phosphate buffer (27.5 mL) were mixed. To the mixture were added 2,2,6,6-tetramethyl-1-piperidinyloxy radical (TEMPO)(438 mg) and sodium chlorite (5.08 g) at RT. After an addition of aqueous sodium hypochlorite (55 mL) dropwise to the mixture at ice temperature, the mixture was stirred at RT for 15 min. Aqueous 20 w/v % sodium thiosulfate (200 mL) was added to the reaction at ice temperature, the mixture was extracted with ethyl acetate (400 mL). The organic layer was washed with aqueous 5 w/v % potassium hydrogen sulfate (200 mL), water (200 mL) and brine (100 mL), then dried over magnesium sulfate. The magnesium sulfate was filtered off and the filtrate was concentrated in vacuo to give the title compound (12.2 g) as a crude product.

(A-82-21) tert-Butyl 4-(2-chloro-5-methylphenylcarbamoyl)-3-[4-cyclopropyl-5-(3-isobutylcyclobutyl)isoxazol-3-yl]butanoate

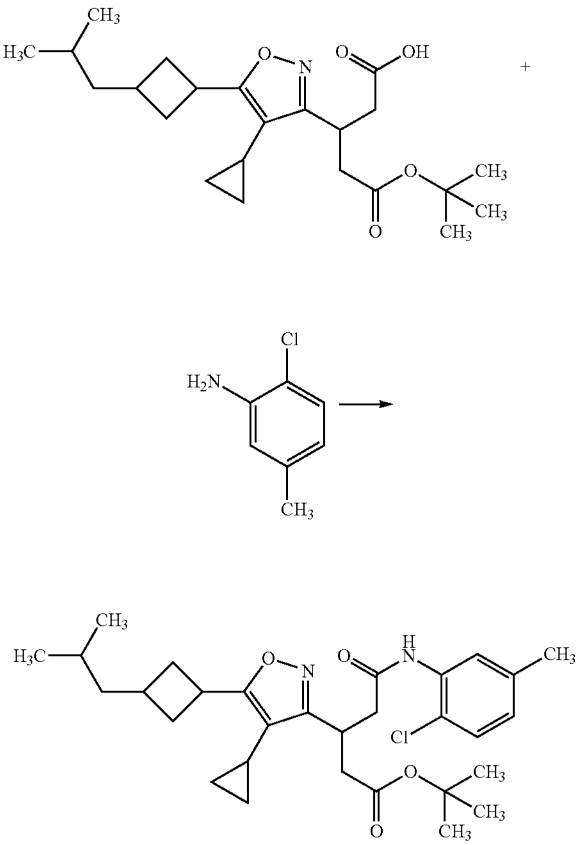

Mono-tert-butyl 3-[4-cyclopropyl-5-(3-isobutylcyclobutyl)isoxazol-3-yl]glutarate (2.83 g) and DMF (28 mL) were mixed. After an addition of 2-chloro-5-methylphenylamine (1.184 g), HOBt.$H_2O$ (1.28 g) and WSC.HCl (1.60 g) to the resultant solution, the mixture was stirred at RT for 2 days. To the reaction mixture was added saturated aqueous sodium bicarbonate, and the mixture was extracted with ethyl acetate. The organic layer was washed with saturated aqueous sodium bicarbonate, water and brine, then dried over sodium sulfate. The sodium sulfate was filtered off and the filtrate was concentrated in vacuo. The resultant residue was purified by silica gel column chromatography (Eluent: ethyl acetate/hexane=1/15→1/10→1/8) to give the title compound (1.241 g).

(A-82-22) 4-(2-Chloro-5-methylphenylcarbamoyl)-3-[4-cyclopropyl-5-(3-isobutylcyclobutyl)isoxazol-3-yl]butanoic acid

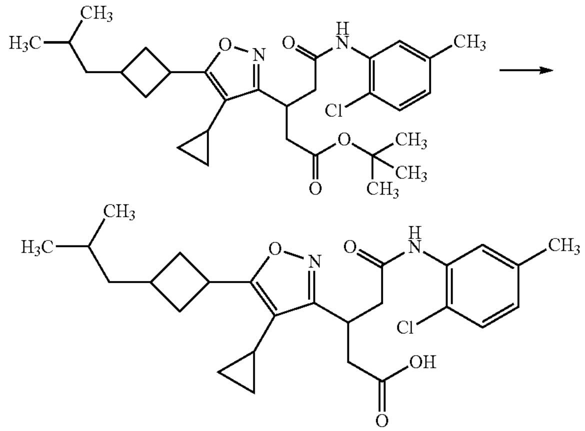

tert-Butyl 4-(2-Chloro-5-methylphenylcarbamoyl)-3-[4-cyclopropyl-5-(3-isobutylcyclobutyl)isoxazol-3-yl]butanoate (1.09 g) and toluene (3.2 mL) were mixed. To the mixture was added trifluoroacetic acid (3.2 mL) at ice temperature and the mixture was stirred at RT for 30 min. After water (5 mL) was poured into the reaction mixture dropwise at ice temperature, aqueous 4 N sodium hydroxide was added to the mixture dropwise and the mixture was extracted with ethyl acetate. The organic layer was washed with brine and dried over sodium sulfate. The sodium sulfate was filtered off and the filtrate was concentrated in vacuo. The resultant residue was purified by silica gel column chromatography (Eluent: ethyl acetate/hexane=1/5→1/3→1/2→2/1→methanol/chloroform=1/8) to give the title compound (905 mg). The title compound was analyzed using a chiral column. The retention time of the title compound was 6.6 min., and the optical purity thereof was 94.8% ee.

The condition for the analysis using the chiral column was as follows:

Instrument: HPLC System Shimadzu High performance liquid chromatography Prominence Column: DAICEL CHIRALPAK AD-3R 0.46 cm ϕ×15 cm Column temperature: 40° C.

Mobile phase: (A solution) 10 mM phosphate buffer (pH=2.6), (B solution) acetonitrile Composition of Mobile phase: A solution:B solution=30:70

Flow rate: 0.5 mL/min

Detection: UV (220 nm)

Example A-16

4-(2-Chloro-4-methylphenylcarbamoyl)-3-[4-cyclopropyl-5-(3-isobutylcyclobutyl)isoxazol-3-yl]butanoic acid (A-16-1) tert-Butyl 4-(2-chloro-4-methylphenylcarbamoyl)-3-[4-cyclopropyl-5-(3-isobutylcyclobutyl)isoxazol-3-yl]butanoate

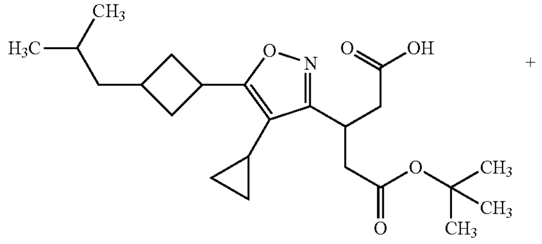

-continued

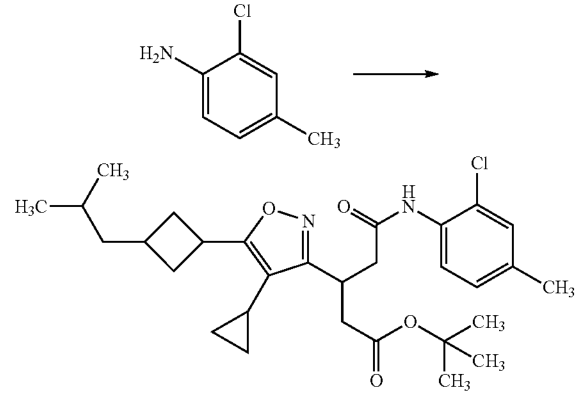

Mono-tert-butyl 3-[4-cyclopropyl-5-(3-isobutylcyclobutyl)isoxazol-3-yl]glutarate (245 mg) and DMF (2 mL) were mixed. After an addition of 2-chloro-4-methylphenylamine (67 mg), HOBt.$H_2O$ (87 mg) and WSC.HCl (108 mg) to the mixture, the reaction mixture was stirred at RT. Water was added to the reaction mixture and the mixture was extracted with ethyl acetate. The organic layer was washed with saturated aqueous sodium bicarbonate, water and brine, then dried over sodium sulfate. The sodium sulfate was filtered off and the filtrate was concentrated in vacuo. The resultant residue was purified by preparative chromatography (Eluent: ethyl acetate/hexane=1/4) to give the title compound (131 mg).

(A-16-2) 4-(2-Chloro-4-methylphenylcarbamoyl)-3-[4-cyclopropyl-5-(3-isobutylcyclobutyl)isoxazol-3-yl]butanoic acid

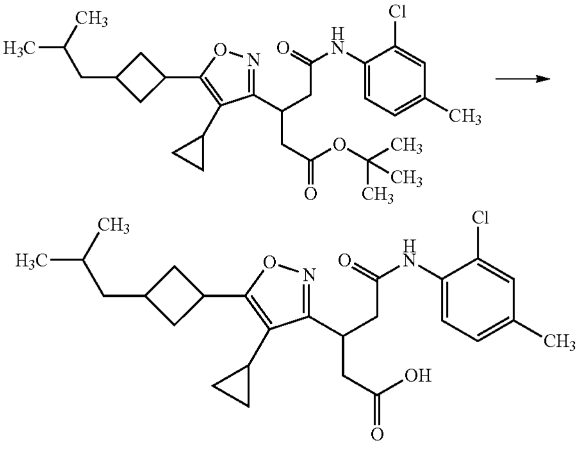

tert-Butyl 4-(2-chloro-4-methylphenylcarbamoyl)-3-[4-cyclopropyl-5-(3-isobutylcyclobutyl)isoxazol-3-yl]butanoate (131 mg) and water (0.8 mL) were mixed. After an addition of 25 w/w % hydrogen bromide in acetic acid (1.64 mL) to the reaction mixture, the mixture was stirred at RT for 1.5 hr. Sodium acetate and water were added to the reaction mixture and the mixture was extracted with ethyl acetate. The organic layer was washed with water and brine, then dried over sodium sulfate. The sodium sulfate was filtered off and the filtrate was concentrated in vacuo. The resultant residue was purified by preparative chromatography (Eluent: methanol/chloroform=1/9) to give the title compound (97.3 mg). The specific optical rotation value of the title compound was $[\alpha]_D^{25}$=+32.7° (c=1.00, methanol). The title compound was analyzed using a chiral column. The retention time of the title compound was 6.8 min., and the optical purity thereof was 95.1% ee. The condition for the analysis using the chiral column was as follows:

Instrument: HPLC System Shimadzu High performance liquid chromatography Prominence Column: DAICEL CHIRALPAK AD-3R 0.46 cm ϕ×15 cm Column temperature: 40° C.

Mobile phase: (A solution) 10 mM phosphate buffer (pH=2.6), (B solution) acetonitrile Composition of Mobile phase: A solution:B solution=30:70

Flow rate: 0.5 mL/min

Detection: UV (220 nm)

Example of Crystallization

Potassium Salt of Example A-16

Example A-16 (0.5 g) was dissolved in ethanol (5.0 mL), and aqueous 1 mol/L KOH (1.06 mL) was added into the mixture at ice temperature.

The mixture was stirred at RT for 10 minutes, then the solvent was removed under reduced pressure to give potassium salt of Example A-16 as a solid (0.539 g). The solid (0.050 g) was dissolved in isobutyl acetate (0.2 mL), and the mixture was stirred at RT for 2 days. The precipitated solid was collected on a filter and dried under reduced pressure at RT to give a crystal (0.010 g).

Example A-53

4-{4-Cyclopropyl-5-[3-(2,2-dimethylpropyl)cyclobutyl]isoxazol-3-yl}-5-(2,2-dimethylphenylcarbamoyl) valeric acid

(A-53-1) 4,4-Dimethyl-2-pentenoic acid

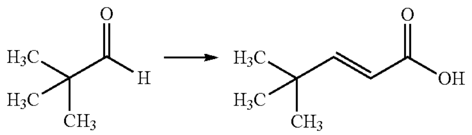

To 20% sodium ethoxide in ethanol (1.02 L) was added ethyl diethylphosphonoacetate (516 mL) dropwise at ice temperature. After the mixture was stirred at ice temperature for 1.5 hr, a solution of 2,2-dimethylpropionaldehyde (260 mL) in tetrahydrofuran (510 mL) was added to the mixture at ice temperature. The mixture was stirred at RT for 3.5 hr and aqueous 4 N sodium hydroxide (885 mL) was added to the mixture at ice temperature. After the mixture was stirred overnight at RT, 6 N hydrochloric acid (802 mL) was added to the reaction mixture at ice temperature. The mixture was extracted with ethyl acetate (1 L), washed with water (1 L×5) and brine (500 mL), then dried over magnesium sulfate. The magnesium sulfate was filtered off and the filtrate was concentrated in vacuo to give the title compound (289 g) as a crude product.

In addition, the title compound (54 g) was also prepared as a crude product using 2,2-dimethylpropionaldehyde (50 mL) in the same way as described above.

(A-53-2) 4,4-Dimethylvaleric acid

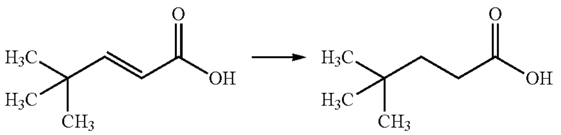

4,4-Dimethyl-2-pentenoic acid (343 g), methanol/tetrahydrofuran=3/1 (150 mL) and ethanol (1240 mL) were mixed. After an addition of 10 w/w % palladium on activated carbon (31 g) to the mixture, the mixture was stirred at RT for 10.5 hr under hydrogen atmosphere (1 atm). The 10 w/w % palladium on activated carbon was filtered off and the filtrate was concentrated in vacuo to give the title compound (354 g) as a crude product.

(A-53-3) 4,4-Dimethyl-1-piperidin-1-ylpentan-1-one

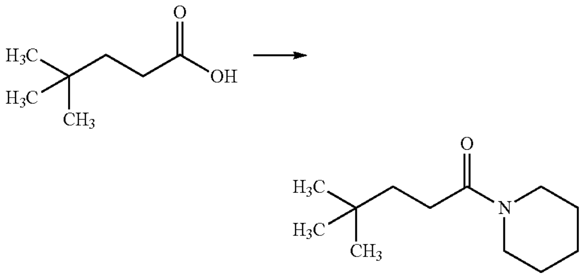

4,4-Dimethylvaleric acid (348 g), piperidine (291 mL) and DMF (1.7 L) were mixed. To the mixture were added $HOBt.H_2O$ (450 g) and WSC.HCl (563 g) at ice temperature. After the mixture was stirred at RT overnight, water (1.7 L) was added to the reaction mixture at ice temperature and the mixture was extracted with toluene (500 mL, and 400 mL×2). The organic layer was washed with aqueous 10 w/v % sodium carbonate (1 L) and water (1 L), then concentrated in vacuo to give the title compound (508 g) as a crude product.

(A-53-4) 1-(4,4-Dimethyl-1-pentenyl)piperidine

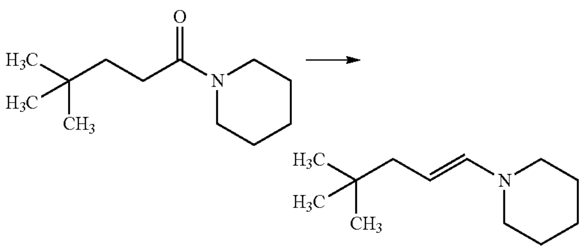

4,4-Dimethyl-1-piperidin-1-ylpentan-1-one (508 g) and toluene (1220 mL) were mixed. After an addition of $(Ph_3P)IrCl(CO)$ (802 mg) to the mixture, 1,1,3,3-tetramethyldisiloxane (795 mL) was added dropwise to the reaction under water-cooling. The mixture was stirred at RT for 3 hr, then concentrated in vacuo to give the title compound (1171 g) as a crude product.

(A-53-5) Ethyl 3-(2,2-dimethylpropyl)-2-piperidin-1-ylcyclobutanecarboxylate

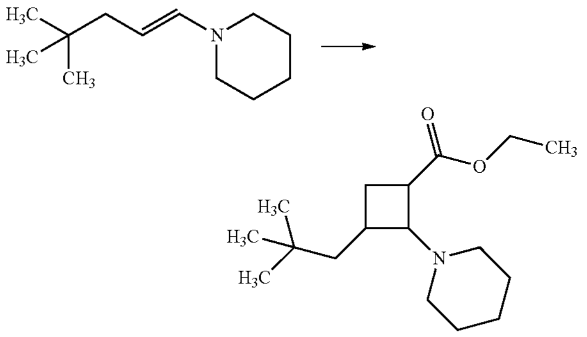

1-(4,4-Dimethyl-1-pentenyl)piperidine (1146 g) and acetonitrile (910 mL) were mixed. After an addition of ethyl acrylate (549 mL) and hydroquinone (553 mg) to the mixture, the mixture was stirred at 90° C. overnight. The reaction mixture was concentrated in vacuo to give the title compound (1470 g) as a crude product.

(A-53-6) 3-(2,2-Dimethylpropyl)-1-cyclobutenecarboxylic acid

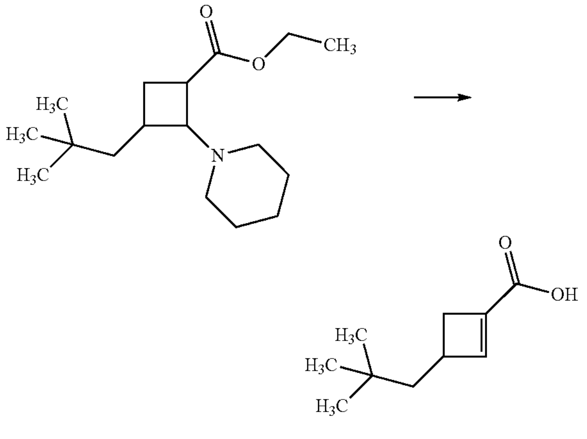

Ethyl 3-(2,2-dimethylpropyl)-2-piperidin-1-ylcyclobutanecarboxylate (1470 g) and methyl p-toluenesulfonate (417 mL) were mixed. After the mixture was stirred at 105° C. for 2 hr, water (2100 mL) was poured into the reaction mixture and the aqueous layer was extracted. The aqueous layer was washed with tert-butyl methyl ether/hexane=1/1 (800 mL) and hexane (600 mL). To the aqueous layer was added potassium hydroxide (663 g) at ice temperature and the mixture was stirred at 100° C. for 2 hr. After the reaction mixture was washed with tert-butyl methyl ether/hexane=1/1 (600 mL×2), concentrated hydrochloric acid (500 mL) and 6 N hydrochloric acid (606 mL) were added to the aqueous layer at ice temperature. The mixture was extracted with ethyl acetate (600 mL×2). The combined organic layer was washed with water (1 L×2) and brine (500 mL), then dried over magnesium sulfate. The magnesium sulfate was filtered off and the filtrate was concentrated in vacuo to give the title compound (278 g) as a crude product.

(A-53-7) 3-(2,2-Dimethylpropyl)cyclobutanecarboxylic acid

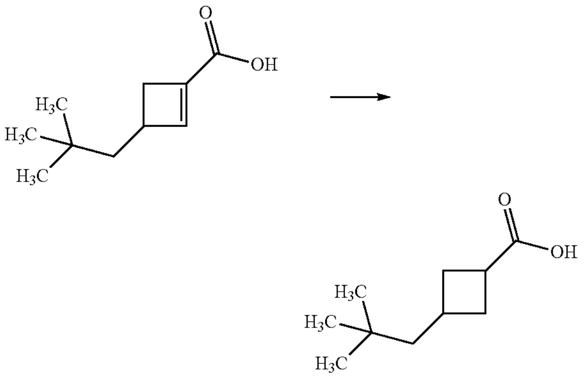

3-(2,2-Dimethylpropyl)-1-cyclobutenecarboxylic acid (163 g) and tetrahydrofuran (1300 mL) were mixed. After an addition of 5 w/w % rhodium on activated carbon (8.2 g) to the mixture, the mixture was stirred at RT for 35 hr under hydrogen atmosphere (1 atm). The 5 w/w % rhodium on activated carbon was filtered off and the filtrate was concentrated in vacuo to give the title compound (175.56 g) as a crude product.

$^1$H-NMR (400 MHz, DMSO-d6) 0.83 (s, 9H), 1.26 (d, J=5.95 Hz, 2H), 1.68-1.78 (m, 2H), 2.19-2.29 (m, 3H), 2.81-2.93 (m, 1H), 11.95 (s, 1H)

(A-53-8) N-Methoxy-N-methyl-3-(2,2-dimethylpropyl)cyclobutanecarboxamide

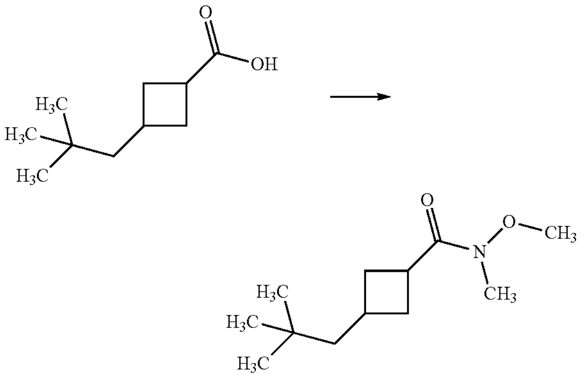

3-(2,2-Dimethylpropyl)cyclobutanecarboxylic acid (75.2 g) and DMF (600 mL) were mixed. After an addition of N,O-dimethylhydroxylamine hydrochloride (51.7 g), triethylamine (92.4 mL), HOBt.$H_2O$ (81.2 g) and WSC.HCl (101.6 g) to the mixture, the mixture was stirred at RT overnight. Water was poured into the reaction and the mixture was extracted with ethyl acetate/hexane=1/1. The organic layer was washed with 1 N hydrochloric acid, water, aqueous 10 w/v % sodium carbonate and water, then dried over sodium sulfate. The sodium sulfate was filtered off and the filtrate was concentrated in vacuo to give the title compound (95.2 g) as a crude product.

(A-53-9) 3-(2,2-Dimethylpropyl)cyclobutanecarbaldehyde

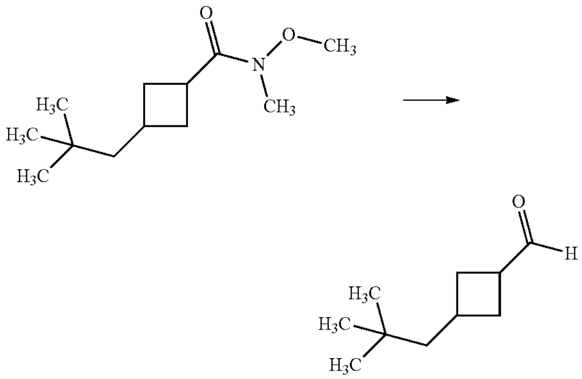

To a solution of N-methoxy-N-methyl-3-(2,2-dimethylpropyl)cyclobutanecarboxamide (95.2 g) in toluene (330 mL) was added diisobutylaluminum hydride (1.0M in toluene) (486 mL) dropwise at −78° C. After the mixture was stirred at −78° C. for 3 hr, 1.5 M sulfuric acid (648 mL) was added dropwise to the mixture at ice temperature. The mixture was extracted with toluene and the combined organic layer was washed with 1 M sulfuric acid, water and brine, then dried over sodium sulfate. The sodium sulfate was filtered off and the filtrate comprising the title compound was used in the next step.

(A-53-10) 1-(2,2-Dibromovinyl)-3-(2,2-dimethylpropyl)cyclobutane

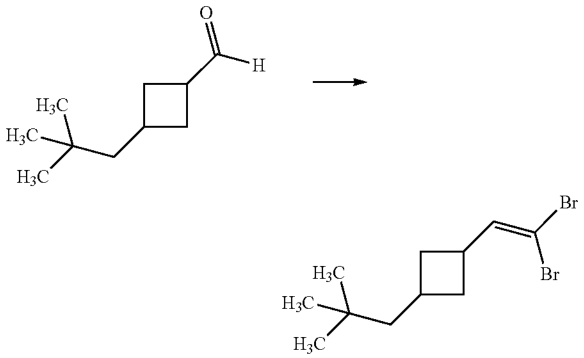

To a solution of carbon tetrabromide (205 g) in methylene chloride (600 mL) was added a solution of triphenylphosphine (325 g) in methylene chloride (350 mL) dropwise at ice temperature. After the mixture was stirred at ice temperature for 45 min, a solution of 3-(2,2-dimethylpropyl)cyclobutanecarbaldehyde in toluene was added to the reaction at ice temperature. The mixture was stirred at ice temperature for 1 hr and aqueous 10 w/v % sodium carbonate (660 mL) was added to the mixture dropwise at the same temperature. The resultant precipitate was filtered off and the filtrate was extracted with chloroform. The organic layer was washed with water and brine, then dried over sodium sulfate. After an addition of silica gel to the mixture, the mixture was stirred at RT. The sodium sulfate and silica gel were filtered off and the filtrate was concentrated in vacuo. The resultant residue was purified by silica gel column chromatography (Eluent: hexane) to give the title compound (120.33 g).

(A-53-11) 5-Benzyloxyvaleric acid

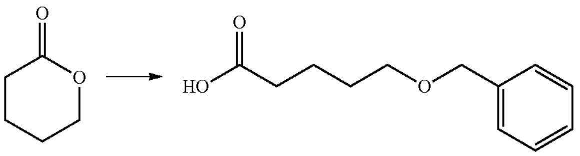 [SMILES: O=C1CCCCO1 ; O=C(O)CCCCOCc1ccccc1]

δ-Valerolactone (50 g) and toluene (500 mL) were mixed. To the mixture were added potassium hydroxide (158 g) and benzyl bromide (178 mL). The mixture was stirred at 125° C. overnight. To the reaction mixture was added water (350 mL) at ice temperature. The organic layer was removed, and the aqueous layer was washed with tert-butyl methyl ether (150 mL×3). To the resulting aqueous layer were added concentrated hydrochloric acid (75 mL) and 6 N hydrochloric acid (40 mL) at ice temperature. The mixture was extracted with ethyl acetate (250 mL, 100 mL). The combined organic layer was washed with brine (100 mL), then dried over magnesium sulfate. The magnesium sulfate was filtered off and the filtrate was concentrated in vacuo to give the title compound (79.2 g) as a crude product.

In addition, the title compound (8.77 g) was also prepared as a crude product using δ-valerolactone (5 g) in the same way as described above.

(A-53-12) (R)-4-Benzyl-3-(5-benzyloxypentanoyl)oxazolidin-2-one

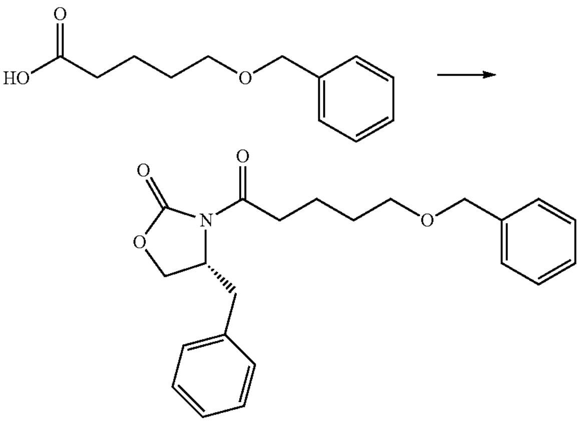

5-Benzyloxyvaleric acid (87.97 g), (R)-4-benzyl-2-oxazolidinone (74.8 g) and chloroform (880 mL) were mixed. To the mixture were added 4-dimethylaminopyridine (51.5 g) and WSC.HCl (85 g). The mixture was stirred at RT for 2.5 hr. The reaction mixture was concentrated in vacuo. To the resultant residue was added ethyl acetate (360 mL). To the mixture were added 2 N hydrochloric acid (211 mL) and water (100 mL), and the mixture was extracted with ethyl acetate (180 mL). The organic layer was washed with 2 N hydrochloric acid (105 mL), water (90 mL), saturated aqueous sodium bicarbonate (90 mL×2) and brine (90 mL), then dried over magnesium sulfate. The magnesium sulfate was filtered off and the filtrate was concentrated in vacuo to give the title compound (148 g) as a crude product.

(A-53-13) tert-Butyl 3-((R)-4-benzyl-2-oxooxazolidin-3-carbonyl)-6-benzyloxyhexanoate

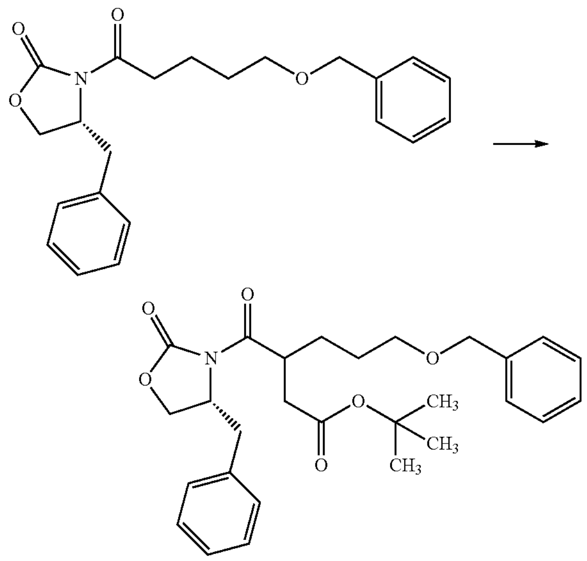

A solution of (R)-4-benzyl-3-(5-benzyloxypentanoyl)oxazolidin-2-one (132 g) in tetrahydrofuran (660 mL) was added dropwise to a mixture of sodium hexamethyldisilazane (1.9 M in tetrahydrofuran) (702 mL) and tetrahydrofuran (660 mL) at −78° C. The reaction temperature was rose to −40° C. To the mixture was added dropwise tert-butyl bromoacetate (85 mL) at −78° C. The reaction temperature was rose to −36° C. To the mixture was added dropwise N,N,N'-triethylethylenediamine (33 mL) at ice temperature. And then, to the mixture were added water (530 mL) and hexane (660 mL). The aqueous layer was removed, and the organic layer was washed with aqueous 20 w/v % citric acid (660 mL×3), water (660 mL), saturated aqueous sodium bicarbonate (660 mL) and brine (660 mL), then dried over magnesium sulfate. The magnesium sulfate was filtered off and the filtrate was concentrated in vacuo to give the title compound (196 g) as a crude product.

(A-53-14) 4-tert-Butyl 2-(3-benzyloxypropyl)succinate

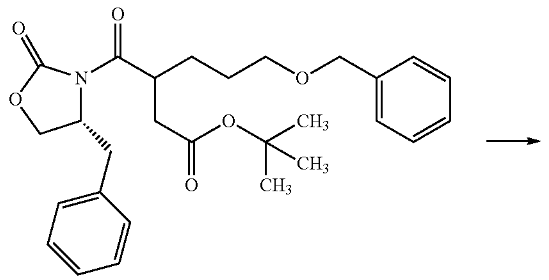

-continued

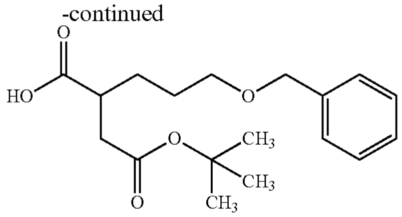

Lithium hydroxide monohydrate (25.8 g) tetrahydrofuran (694 mL) and water (522 mL) were mixed. To the mixture was added dropwise aqueous 30 w/w % hydrogen peroxide (139 mL) at ice temperature. The mixture was stirred for 30 min. and a solution of tert-butyl 3-((R)-4-benzyl-2-oxooxazolidine-3-carbonyl)-6-benzyloxyhexanoate (172.73 g) in tetrahydrofuran (347 mL) was added dropwise to the mixture at ice temperature. The mixture was stirred for 3 hr. To the reaction mixture was then added dropwise a solution of sodium hydrogen sulfite (206 g) in water (794 mL) at ice temperature. To the mixture was added hexane. The organic layer was removed, and the aqueous layer was washed with tert-butyl methyl ether (500 mL×2). To the aqueous layer were added aqueous 25 w/v % potassium hydrogen sulfate (200 mL), ethyl acetate (500 mL) and aqueous 25 w/v % potassium hydrogen sulfate (470 mL). The organic layer was removed, and the aqueous layer was extracted with ethyl acetate (170 mL). The combined organic layer was washed with brine, then dried over magnesium sulfate. The magnesium sulfate was filtered off and the filtrate was concentrated in vacuo to give the title compound (80 g) as a crude product. The title compound was analyzed using a chiral column. The retention time of the title compound was 13.4 min., and the optical purity thereof was 94.1% ee.

The condition for the analysis using the chiral column was as follows:

Instrument: HPLC System Shimadzu High performance liquid chromatography Prominence Column: DAICEL CHIRALPAK AD-3R 0.46 cm ϕ×15 cm Column temperature: 40° C.

Mobile phase: (A solution) 10 mM phosphate buffer (pH=2.6), (B solution) acetonitrile Composition of Mobile phase: A solution:B solution=55:45

Flow rate: 0.5 mL/min

Detection: UV (220 nm)

(A-53-15) tert-Butyl 6-benzyloxy-3-(methoxymethylcarbamoyl)hexanoate

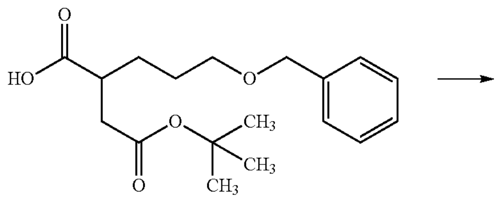

-continued

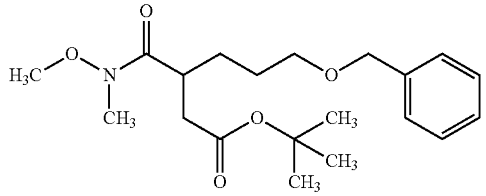

4-tert-Butyl 2-(3-benzyloxypropyl)succinate (80 g), triethylamine (48.4 mL) and DMF (400 mL) were mixed. To the mixture were added N,O-dimethylhydroxylamine hydrochloride (31.5 g), $HOBt.H_2O$ (45.6 g) and WSC.HCl (57.1 g) at ice temperature. The mixture was stirred at RT overnight. To the reaction mixture was added water (400 mL), and the mixture was extracted with hexane (480 mL, 480 mL, 240 mL). The combined organic layer was washed with aqueous 10 w/v % sodium carbonate (240 mL×3), aqueous 10 w/v % potassium hydrogen sulfate (240 mL), water (240 mL) and brine (240 mL), then dried over magnesium sulfate. The magnesium sulfate was filtered off and the filtrate was concentrated in vacuo to give the title compound (84.1 g) as a crude product.

(A-53-16) tert-Butyl 3-(3-benzyloxypropyl)-6-[3-(2,2-dimethylpropyl)cyclobutyl]-4-oxo-5-hexynoate

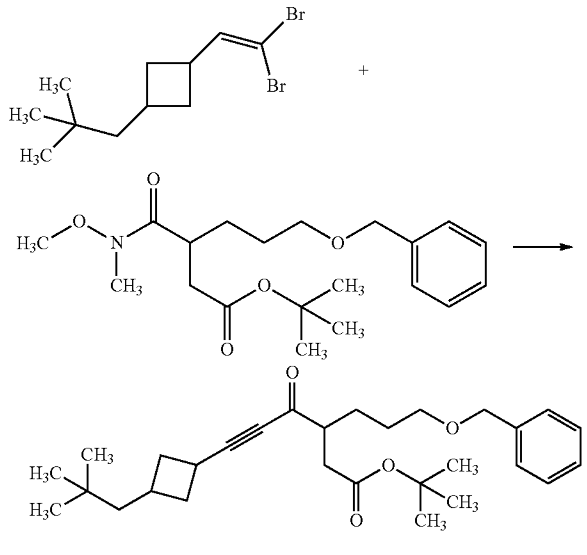

1-(2,2-dibromovinyl)-3-(2,2-dimethylpropyl)cyclobutane (5 g) and tetrahydrofuran (50 mL) were mixed. To the mixture was added n-butyllithium (1.65 M in hexane) (20.5 mL) dropwise at −78° C. The mixture was stirred at ice temperature for 30 min. and a solution of tert-butyl 6-benzyloxy-3-(methoxymethylcarbamoyl)hexanoate (4.13 g) in tetrahydrofuran (25 mL) was added dropwise to the mixture. After stirring at ice temperature for 20 min., saturated aqueous ammonium chloride was added to the reaction mixture. The mixture was extracted with ethyl acetate. The organic layer was washed with brine, then dried over magnesium sulfate. The magnesium sulfate was filtered off and the filtrate was concentrated in vacuo. The resultant residue was purified by silica gel column chromatography (Eluent: ethyl acetate/hexane=1/20) to give the title compound (3.45 g).

(A-53-17) tert-Butyl 3-(3-benzyloxypropyl)-6-[3-(2,2-dimethylpropyl)cyclobutyl]-4-methoxyimino-5-hexynoate

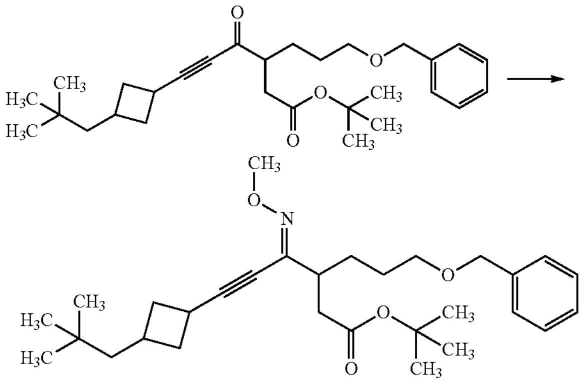

tert-Butyl 3-(3-benzyloxypropyl)-6-[3-(2,2-dimethylpropyl)cyclobutyl]-4-oxo-5-hexynoate (3.44 g) and methanol (35 mL) were mixed. To the mixture were added sodium sulfate (2.15 g), pyridine (3.5 mL) and O-methylhydroxylammonium chloride (1.26 g). The mixture was stirred at RT overnight. The mixture was then filtered, and the filtrate was concentrated in vacuo. To the resultant residue was added water, and the mixture was extracted with ethyl acetate. The organic layer was washed with water and brine, then dried over magnesium sulfate. The magnesium sulfate was filtered off and the filtrate was concentrated in vacuo. To the resultant residue was added silica gel (5 g), and the mixture was stirred at RT for 10 min. The silica gel was filtered off and the filtrate was concentrated in vacuo to give the title compound (3.38 g) as a crude product.

(A-53-18) tert-Butyl 6-benzyloxy-3-{5-[3-(2,2-dimethylpropyl)cyclobutyl]-4-iodoisoxazole-3-yl}hexanoate

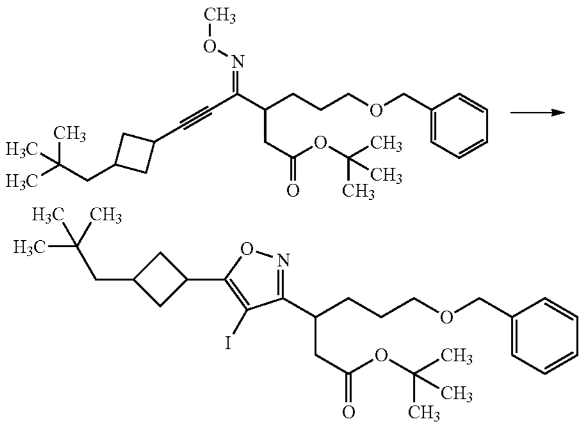

tert-Butyl 3-(3-benzyloxypropyl)-6-[3-(2,2-dimethylpropyl)cyclobutyl]-4-methoxyimino-5-hexynoate (3.37 g) and methylene chloride (70 mL) were mixed. To the mixture was added iodine monochloride (1 M in methylene chloride) (7.66 mL) at ice temperature. The mixture was stirred at ice temperature for 1 hr, and then to the mixture was added aqueous solution of sodium sulfite. The mixture was extracted with chloroform. The organic layer was washed with water and brine, then dried over magnesium sulfate. The magnesium sulfate was filtered off and the filtrate was concentrated in vacuo to give the title compound (4.21 g) as a crude product.

(A-53-19) tert-Butyl 6-benzyloxy-3-{4-cyclopropyl-5-[3-(2,2-dimethylpropyl)cyclobutyl]isoxazol-3-yl]hexanoate

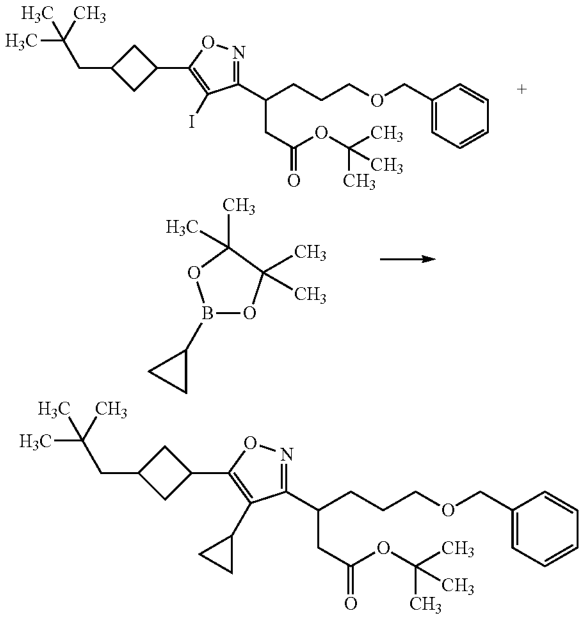

tert-Butyl 6-benzyloxy-3-{5-[3-(2,2-dimethylpropyl)cyclobutyl]-4-iodoisoxazole-3-yl}hexanoate (4.20 g), 2-cyclopropyl-4,4,5,5-tetramethyl-[1,3,2]dioxaborolane (2.34 g), tripotassium phosphate (5.92 g), DMF (90 mL) and water (10 mL) were mixed. The mixture was degassed by bubbling argon gas. To the mixture was added $PdCl_2(PPh_3)_2$ (734 mg). The mixture was stirred at 80° C. for 1 hr. To the reaction mixture was added ethyl acetate, and then the mixture was filtered. The aqueous layer was removed, and the organic layer was washed with water and brine, then dried over magnesium sulfate. The magnesium sulfate was filtered off and the filtrate was concentrated in vacuo. The resultant residue was purified by silica gel column chromatography (Eluent: ethyl acetate/hexane=1/25) to give the title compound (980 mg). A mixture of the title compound and impurities thereof (1.24 g) was also obtained.

(A-53-20) tert-Butyl 3-{4-cyclopropyl-5-[3-(2,2-dimethylpropyl)cyclobutyl]isoxazol-3-yl]-6-hydroxyhexanoate

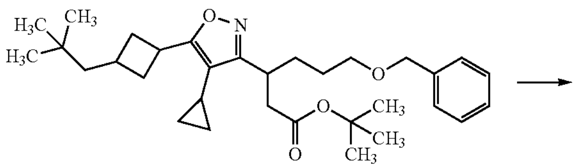

-continued

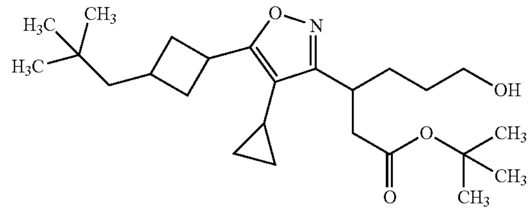

tert-Butyl 6-benzyloxy-3-{4-cyclopropyl-5-[3-(2,2-dimethylpropyl)cyclobutyl]isoxazol-3-yl]hexanoate (980 mg), methanol (10 mL) and tetrahydrofuran (3 mL) were mixed. To the mixture was added 7.5 w/w % palladium on activated carbon (200 mg). The mixture was stirred at RT under hydrogen atmosphere (1 atm) for 5 hr. The catalyst was freshened up, and the mixture was stirred at RT under hydrogen atmosphere (1 atm) overnight. The 7.5 w/w % palladium on activated carbon was filtered off and the filtrate was concentrated in vacuo.

The resultant residue was purified by silica gel column chromatography (Eluent: ethyl acetate/hexane=1/10→1/4) to give the title compound (700 mg). tert-Butyl 6-benzyloxy-3-{4-cyclopropyl-5-[3-(2,2-dimethylpropyl)cyclobutyl]isoxazol-3-yl]hexanoate with impurities thereof (1.24 g) which is obtained in the foregoing step was also reacted in a similar way to the above, and purified by silica gel column chromatography to give the title compound (759 mg).

(A-53-21) 1-tert-Butyl 3-{4-cyclopropyl-5-[3-(2,2-dimethylpropyl)cyclobutyl]isoxazol-3-yl}adipate

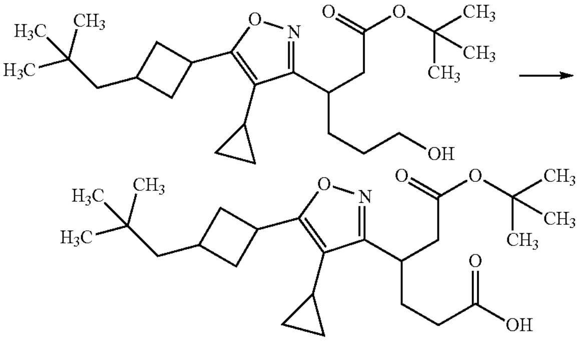

tert-Butyl 3-{4-Cyclopropyl-5-[3-(2,2-dimethylpropyl)cyclobutyl]isoxazol-3-yl]-6-hydroxyhexanoate (1.42 g), acetonitrile (28 mL), and 0.1 M phosphate buffer (14 mL) were mixed. To the mixture were added 2,2,6,6-tetramethyl-1-piperidinyloxy radical (TEMPO) (159 mg) and sodium chlorite (1.15 g) at RT. To the mixture was added dropwise aqueous sodium hypochlorite (28 mL) at ice temperature. The mixture was stirred for 2 hr, and then to the mixture were added disodium hydrogenphosphate(12-hydrate) (716 mg) and sodium dihydrogenphosphate(2-hydrate) (312 mg). The mixture was stirred at RT for 50 min. To the mixture was added aqueous 20 w/v % sodium thiosulfate (20 mL) at ice temperature. The mixture was extracted with ethyl acetate. The organic layer was washed with aqueous 5 w/v % citric acid and brine, then dried over magnesium sulfate. The magnesium sulfate was filtered off and the filtrate was concentrated in vacuo to give the title compound (1.45 g) as a crude product.

(A-53-22) 1-tert-Butyl, 6-methyl 3-{4-cyclopropyl-5-[3-(2,2-dimethylpropyl)cyclobutyl]isoxazol-3-yl}adipate

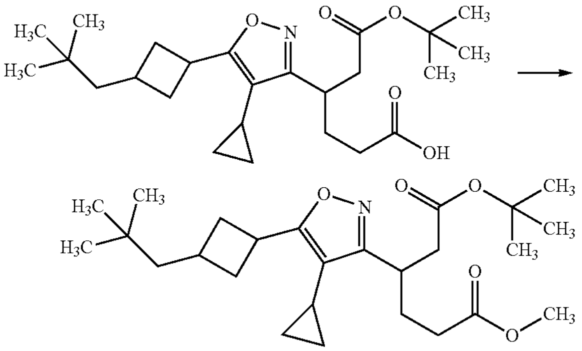

1-tert-Butyl 3-[4-cyclopropyl-5-[3-(2,2-dimethylpropyl)cyclobutyl]isoxazol-3-yl]adipate (100 mg) and DMF (1 mL) were mixed. To the mixture were added methyl iodide (0.0287 mL) and potassium carbonate (41.5 mg) at ice temperature. The mixture was stirred at RT for 1 hr, and then to the mixture was added aqueous 5 w/v % potassium hydrogen sulfate at ice temperature. The mixture was extracted with ethyl acetate. The organic layer was washed with water and brine, then dried over magnesium sulfate. The magnesium sulfate was filtered off and the filtrate was concentrated in vacuo to give the title compound (110 mg) as a crude product.

1-tert-Butyl 3-{4-cyclopropyl-5-[3-(2,2-dimethylpropyl)cyclobutyl]isoxazol-3-yl}adipate (1.35 g) and DMF (11 mL) were mixed. To the mixture were added methyl iodide (0.388 mL) and potassium carbonate (559 mg) at ice temperature. The mixture was stirred at RT for 1 hr, and then to the mixture was added water at ice temperature. The mixture was mixed with the crude product of 1-tert-butyl, 6-methyl 3-{4-cyclopropyl-5-[3-(2,2-dimethylpropyl)cyclobutyl]isoxazol-3-yl}adipate (110 mg) obtained previously. The resulting mixture was extracted with toluene. The organic layer was washed with water and brine, then dried over magnesium sulfate. The magnesium sulfate was filtered off and the filtrate was concentrated in vacuo to give the title compound (1.53 g) as a crude product.

(A-53-23) 6-Methyl 3-{4-cyclopropyl-5-[3-(2,2-dimethylpropyl)cyclobutyl]isoxazol-3-yl}adipate

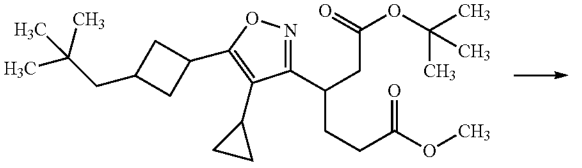

-continued

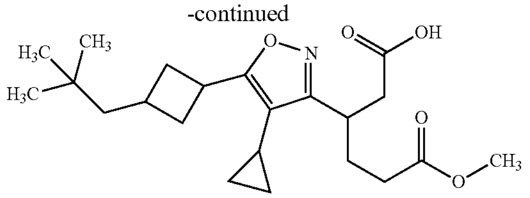

1-tert-Butyl, 6-methyl 3-{4-cyclopropyl-5-[3-(2,2-dimethylpropyl)cyclobutyl]isoxazol-3-yl}adipate (1.50 g) and chloroform (15 mL) were mixed. To the mixture was added trifluoroacetic acid (3 mL) at ice temperature. The mixture was stirred at RT overnight. The reaction mixture was concentrated in vacuo, and then azeotroped twice with toluene to give the title compound (1.43 g) as a crude product.

(A-53-24) Methyl 4-{4-cyclopropyl-5-[3-(2,2-dimethylpropyl)cyclobutyl]isoxazol-3-yl}-5-(2,4-dimethylphenylcarbamoyl)valerate

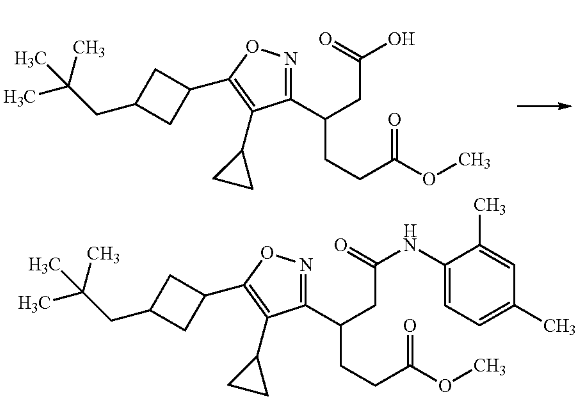

6-Methyl 3-{4-cyclopropyl-5-[3-(2,2-dimethylpropyl)cyclobutyl]isoxazol-3-yl}adipate (100 mg), 2,4-dimethylphenylamine (0.0379 mL) and DMF (1 mL) were mixed. To the mixture were added triethylamine (0.0354 mL), HOBt.$H_2O$ (47 mg) and WSC.HCl (58.8 mg) at ice temperature. The mixture was stirred at RT overnight. To the reaction mixture was added saturated aqueous sodium bicarbonate at ice temperature. The mixture was extracted with ethyl acetate. The organic layer was washed with water and brine, then dried over magnesium sulfate. The magnesium sulfate was filtered off and the filtrate was concentrated in vacuo. The resultant residue was purified by preparative chromatography (Eluent: ethyl acetate/hexane=1/4) to give the title compound (115 mg).

(A-53-25) 4-{4-Cyclopropyl-5-[3-(2,2-dimethylpropyl)cyclobutyl]isoxazol-3-yl}-5-(2,4-dimethylphenylcarbamoyl)valeric acid

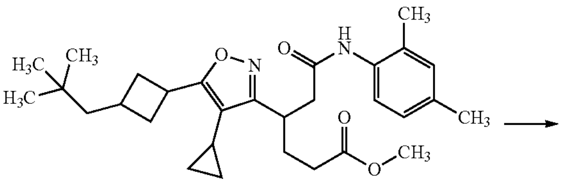

-continued

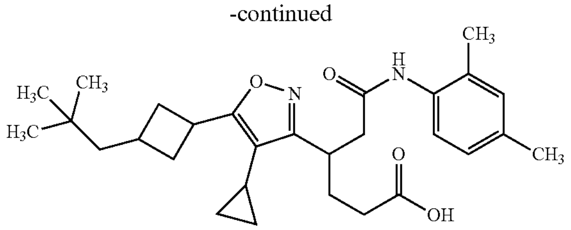

Methyl 4-{4-cyclopropyl-5-[3-(2,2-dimethylpropyl)cyclobutyl]isoxazol-3-yl}-5-(2,4-dimethylphenylcarbamoyl) valerate (115 mg) and acetic acid (1.2 mL) were mixed. To the mixture was added 47% hydrobromic acid (0.6 mL) at 10° C. The mixture was stirred at RT and further stirred at 60° C. To the reaction mixture was added sodium acetate (492 mg) at ice temperature. The mixture was extracted with ethyl acetate. The organic layer was washed with water and brine, then dried over magnesium sulfate. The magnesium sulfate was filtered off and the filtrate was concentrated in vacuo. The resultant residue was purified by preparative chromatography (Eluent: methanol/chloroform/acetic acid=1/20/0.05) to give the title compound (109 mg). The resulting title compound was analyzed using a chiral column. The retention time of the title compound was 24.7 min., and the optical purity thereof was 94.9% ee.

The condition for the analysis using the chiral column was as follows:

Instrument: HPLC System Shimadzu High performance liquid chromatography Prominence Column: DAICEL CHIRALPAK AD-3R 0.46 cm ϕ×15 cm Column temperature: 40° C.

Mobile phase:

(A solution) 10 mM phosphate buffer (pH=2.6), (B solution) acetonitrile

Gradient: The mobile phase was constantly changed from A solution:B solution=60:40 to A solution:B solution=30:70 over 20 min., and then the mobile phase of A solution:B solution=30:70 was hold for 5 min. The mobile phase was then changed from A solution:B solution=30:70 to A solution:B solution=60:40 over 1 min., and then the mobile phase of A solution:B solution=60:40 was hold for 4 min.

Flow rate: 0.5 mL/min

Detection: UV (220 nm)

Example A-79

5-(4-Chloro-2-methylphenylcarbamoyl)-4-{4-cyclopropyl-5-[3-(2,2-dimethylpropyl)cyclobutyl]isoxazol-3-yl}valeric acid

(A-79-1) Methyl 5-(4-chloro-2-methylphenylcarbamoyl)-4-{4-cyclopropyl-5-[3-(2,2-dimethylpropyl)cyclobutyl]isoxazol-3-yl}valerate

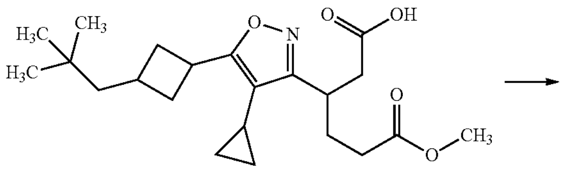

-continued

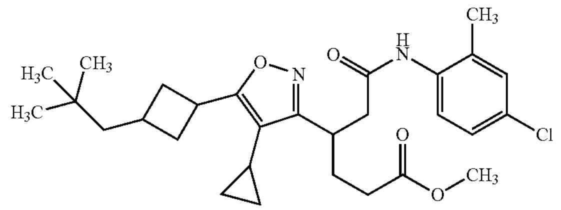

6-Methyl 3-{4-cyclopropyl-5-[3-(2,2-dimethylpropyl)cyclobutyl]isoxazol-3-yl}adipate (100 mg), 4-chloro-2-methylphenylamine (43.5 mg) and DMF (1 mL) were mixed. To the mixture were added HOBt.$H_2O$ (47 mg) and WSC.HCl (58.8 mg) at ice temperature. The mixture was stirred at RT, and further stirred at 70° C. To the reaction mixture was added saturated aqueous sodium bicarbonate at ice temperature. The mixture was extracted with ethyl acetate. The organic layer was washed with water and brine, then dried over magnesium sulfate. The magnesium sulfate was filtered off and the filtrate was concentrated in vacuo. The resultant residue was purified by preparative chromatography (Eluent: ethyl acetate/hexane=1/4) to give the title compound (72.8 mg).

(A-79-2) 5-(4-Chloro-2-methylphenylcarbamoyl)-4-{4-cyclopropyl-5-[3-(2,2-dimethylpropyl)cyclobutyl] isoxazol-3-yl}valeric acid

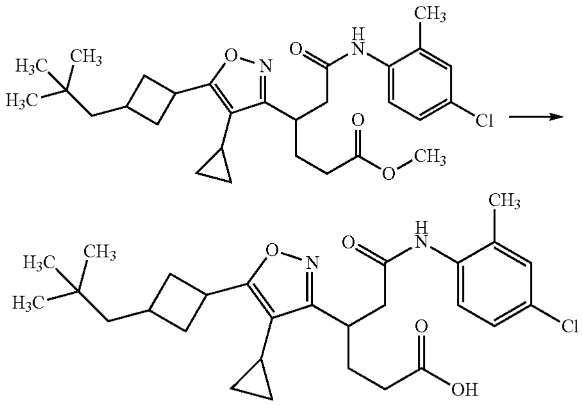

Methyl 5-(4-chloro-2-methylphenylcarbamoyl)-4-{4-cyclopropyl-5-[3-(2,2-dimethylpropyl)cyclobutyl]isoxazol-3-yl}valerate (72.5 mg) and acetic acid (0.725 mL) were mixed. To the mixture was added 48 w/v % hydrobromic acid (0.363 mL) at RT. The mixture was stirred at 60° C., and then to the reaction mixture was added sodium acetate (287 mg) at ice temperature. The mixture was extracted with ethyl acetate. The organic layer was washed with water and brine, then dried over magnesium sulfate. The magnesium sulfate was filtered off and the filtrate was concentrated in vacuo. The resultant residue was purified by preparative chromatography (Eluent: methanol/chloroform/acetic acid=1/20/0.05) to give the title compound (49.1 mg). The specific optical rotation value of the title compound was $[\alpha]_D^{25}$=+32.0° (c=1.00, methanol). The title compound was analyzed using a chiral column. The retention time of the title compound was 26.8 min., and the optical purity thereof was 94.8% ee.

The condition for the analysis using the chiral column was as follows:

Instrument: HPLC System Shimadzu High performance liquid chromatography Prominence Column: DAICEL CHIRALPAK AD-3R 0.46 cm ϕ×15 cm Column temperature: 40° C.

Mobile phase: (A solution) 10 mM phosphate buffer (pH=2.6), (B solution) acetonitrile Gradient: The mobile phase was constantly changed from A solution:B solution=60:40 to A solution:B solution=30:70 over 20 min., and then the mobile phase of A solution:B solution=30:70 was hold for 5 min. The mobile phase was then changed from A solution:B solution=30:70 to A solution:B solution=60:40 over 1 min. and then the mobile phase of A solution:B solution=60:40 was hold for 4 min.

Flow rate: 0.5 mL/min

Detection: UV (220 nm)

Example of Crystallization

Example A-79

Example A-79 (0.1 g) was dissolved in acetonitrile (0.5 mL). The solvent was evaporated in the air at RT to give a crystal.

Example A-58

5-(2-Chloro-4-methylphenylcarbamoyl)-4-{4-cyclopropyl-5-[3-(2,2-dimethylpropyl)cyclobutyl]isoxazol-3-yl}valeric acid (A-58-1) Methyl 5-(2-chloro-4-methylphenylcarbamoyl)-4-{4-cyclopropyl-5-[3-(2,2-dimethylpropyl)cyclobutyl]isoxazol-3-yl}valerate

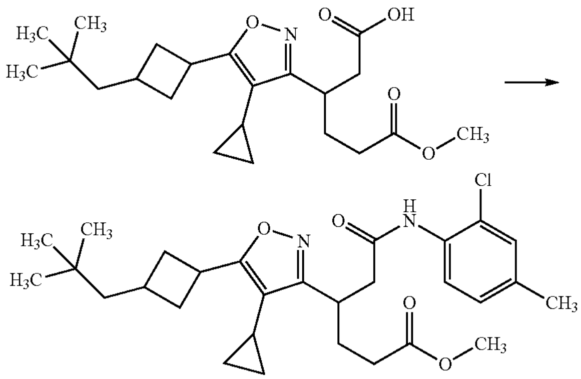

6-Methyl 3-[4-Cyclopropyl-5-[3-(2,2-dimethylpropyl)cyclobutyl]isoxazol-3-yl]adipate (100 mg), 2-chloro-4-methylphenylamine (0.0377 mL) and DMF (1 mL) were mixed. To the mixture were added triethylamine (0.0354 mL), $HOBt.H_2O$ (47 mg) and WSC.HCl (58.8 mg) at ice temperature. The mixture was stirred at RT overnight. To the reaction mixture was added saturated aqueous sodium bicarbonate at ice temperature. The mixture was extracted with ethyl acetate. The organic layer was washed with water, 1 N hydrochloric acid and brine, then dried over magnesium sulfate. The magnesium sulfate was filtered off and the filtrate was concentrated in vacuo. The resultant residue was purified by preparative chromatography (Eluent: ethyl acetate/hexane=1/8) to give the title compound (63.3 mg).

(A-58-2) 5-(2-Chloro-4-methylphenylcarbamoyl)-4-{4-cyclopropyl-5-[3-(2,2-dimethylpropyl)cyclobutyl]isoxazol-3-yl}valeric acid

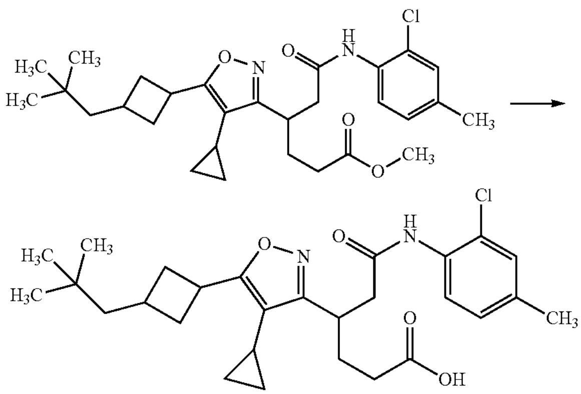

Methyl 5-(2-chloro-4-methylphenylcarbamoyl)-4-{4-cyclopropyl-5-[3-(2,2-dimethylpropyl)cyclobutyl]isoxazol-3-yl}valerate (63.3 mg) and acetic acid (0.6 mL) were mixed. To the mixture was added 48 w/v % hydrobromic acid (0.3 mL) at 10° C. The mixture was stirred at RT, and further stirred at 50° C. To the reaction mixture were added sodium acetate (250 mg) and water at ice temperature. The mixture was extracted twice with ethyl acetate. The organic layer was washed with water and brine, then dried over magnesium sulfate. The magnesium sulfate was filtered off and the filtrate was concentrated in vacuo. The resultant residue was purified by preparative chromatography (Eluent: methanol/chloroform/acetic acid=1/20/0.1) to give the title compound (56.7 mg).

The specific optical rotation value of the title compound was $[\alpha]_D^{25}$=+20.6° (c=1.00, methanol). The title compound was analyzed using a chiral column. The retention time of the title compound was 26.4 min., and the optical purity thereof was 95.9% ee.

The condition for the analysis using the chiral column was as follows:

Instrument: HPLC System Shimadzu High performance liquid chromatography Prominence Column: DAICEL CHIRALPAK AD-3R 0.46 cm ϕ×15 cm Column temperature: 40° C.

Mobile phase: (A solution) 10 mM phosphate buffer (pH=2.6), (B solution) acetonitrile Gradient: The mobile phase was constantly changed from A solution:B solution=60:40 to A solution:B solution=30:70 over 20 min., and then the mobile phase of A solution:B solution=30:70 was hold for 5 min. The mobile phase was then changed from A solution:B solution=30:70 to A solution:B solution=60:40 over 1 min., and then the mobile phase of A solution:B solution=60:40 was hold for 4 min.

Flow rate: 0.5 mL/min

Detection: UV (220 nm)

Example of Crystallization

Example A-58

Example compound A-58 (0.1 g) was dissolved in isobutyl acetate (0.3 mL) at 60° C., then heptane (0.9 mL) was added to the mixture. The mixture was stirred at 40° C. for 1.5 hr, and stirred at RT overnight. The precipitated solid was collected on a filter at RT and dried under reduced pressure to give a crystal (0.063 g).

Example A-75

4-(2-Chloro-4-methylphenylcarbamoyl)-3-{4-cyclopropyl-5-[3-(2-ethylbutyl)cyclobutyl]isoxazol-3-yl}butanoic acid (A-75-1) Ethyl 4-ethyl-2-hexanoate

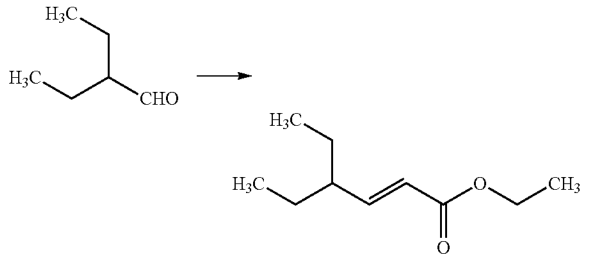

Potassium tert-butoxide (35.5 g) was suspended in tetrahydrofuran (400 mL). To the suspension was added dropwise a solution of ethyl diethylphosphonoacetate (62.8 mL) in tetrahydrofuran (300 mL) at ice temperature. The mixture was stirred at RT for 30 min., and then to the mixture was added dropwise a solution of 2-ethylbutyraldehyde (37 mL) in tetrahydrofuran (50 mL) at ice temperature. The mixture was stirred at RT for 90 min., and then to the mixture was added water (100 mL). The mixture was extracted with ethyl acetate. The organic layer was washed with water/brine=1/1 (200 mL) and brine (100 mL), then dried over sodium sulfate. The sodium sulfate was filtered off and the filtrate was concentrated in vacuo to give the title compound (55.3 g) as a crude product.

(A-75-2) 4-Ethylhexanoic Acid

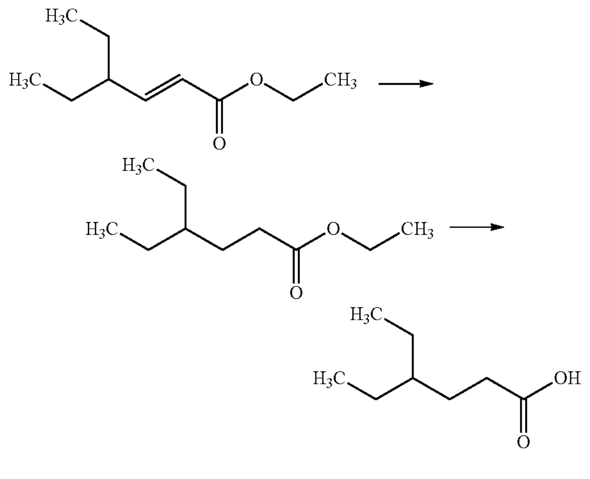

Eethyl 4-ethyl-2-hexenoate (55.3 g) was dissolved in a mixture of tetrahydrofuran (150 mL) and ethanol (150 mL). To the solution was added 5 w/w % palladium on activated carbon (5.5 g). The mixture was stirred at RT for 3.5 hr under hydrogen atmosphere (1 atm). The 5 w/w % palladium on activated carbon was filtered off using Celite. To the filtrate was added aqueous 4 N sodium hydroxide (111 mL). The mixture was stirred at RT overnight. The reaction mixture was washed with hexane. To the aqueous layer was added 4 N hydrochloric acid (113 mL). The mixture was extracted with ethyl acetate. The organic layer was washed with water/brine=1/1 (300 mL) and brine (150 mL), then dried over sodium sulfate. The sodium sulfate was filtered off and the filtrate was concentrated in vacuo to give the title compound (47.0 g) as a crude product.

(A-75-3) 4-Ethyl-1-piperidin-1-ylhexan-1-one

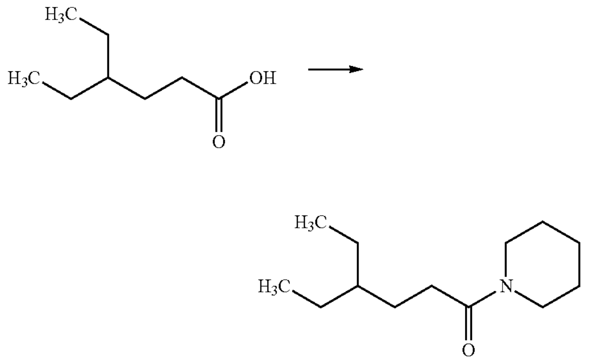

4-Ethylhexanoic acid (47.0 g) was dissolved in DMF (190 mL). To the solution were added piperidine (34.0 mL), $HOBt.H_2O$ (52.7 g) and WSC.HCl (66.1 g). The mixture was stirred at RT overnight. To the reaction mixture were added ethyl acetate (300 mL) and 1 N hydrochloric acid (100 mL) at ice temperature. The aqueous layer was removed and the organic layer was washed with saturated aqueous sodium bicarbonate (150 mL×2) and brine (100 mL×2), then dried over sodium sulfate. The sodium sulfate was filtered off and the filtrate was concentrated in vacuo to give the title compound (59.8 g) as a crude product.

(A-75-4) 1-(4-Ethyl-1-hexenyl)piperidine

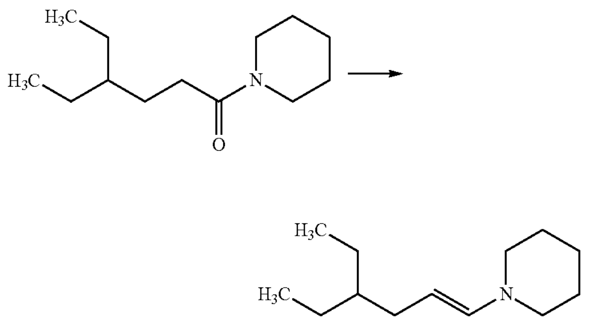

4-Ethyl-1-piperidin-1-ylhexan-1-one (59.8 g) was dissolved in toluene (500 mL). To the solution was added $(Ph_3P)IrCl(CO)$ (95.9 mg). To the mixture was added 1,1,3,3-tetramethyldisiloxane (82.3 mL) in a water-bath. The mixture was stirred in a water-bath for 3 hr. The reaction mixture was concentrated in vacuo to give the title compound (98.1 g) as a crude product.

(A-75-5) Ethyl 3-(2-ethylbutyl)-2-piperidin-1-ylcyclobutanecarboxylate

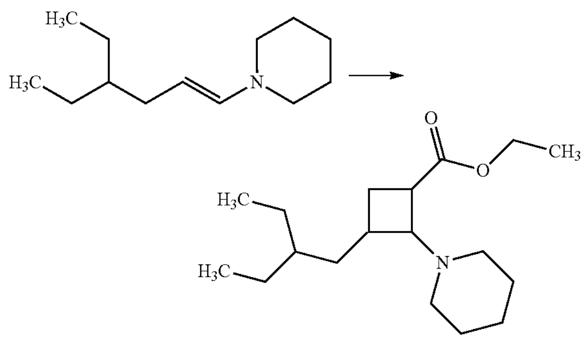

1-(4-Ethyl-1-hexenyl)piperidine (98.1 g) and acetonitrile (70 mL) were mixed. To the mixture were added ethyl acrylate (53.0 mL) and hydroquinone (271 mg). The mixture was stirred at 100° C. overnight. The reaction mixture was concentrated in vacuo to give the title compound (132 g) as a crude product.

(A-75-6) 3-(2-Ethylbutyl)-1-cyclobutenecarboxylic acid

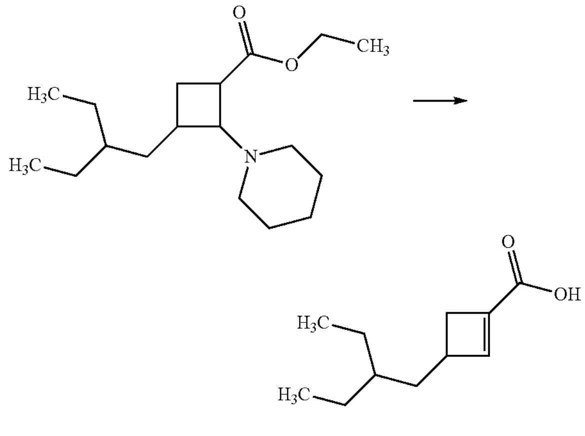

Ethyl 3-(2-ethylbutyl)-2-piperidin-1-ylcyclobutanecarboxylate (132 g) and methyl p-toluenesulfonate (41.0 mL) were mixed. The mixture was stirred at 100° C. for 3.5 hr. After an addition of water (70 mL), the mixture was washed with tert-butyl methyl ether/heptane=1/1 (120 mL). To the aqueous layer was added aqueous 8 N potassium hydroxide (140 mL). The mixture was stirred at 105° C. for 3 hr. The reaction mixture was washed with tert-butyl methyl ether (150 mL). The organic layer was extracted with water (50 mL). To the combined aqueous layer was added concentrated hydrochloric acid (105 mL) at ice temperature. The aqueous layer was extracted with ethyl acetate (250 mL×2). The combined organic layer was washed with water (100 mL) and brine (100 mL), then dried over sodium sulfate. The sodium sulfate was filtered off and the filtrate was concentrated in vacuo to give the title compound (39.0 g) as a crude product.

(A-75-7) 3-(2-Ethylbutyl)cyclobutanecarboxylic acid

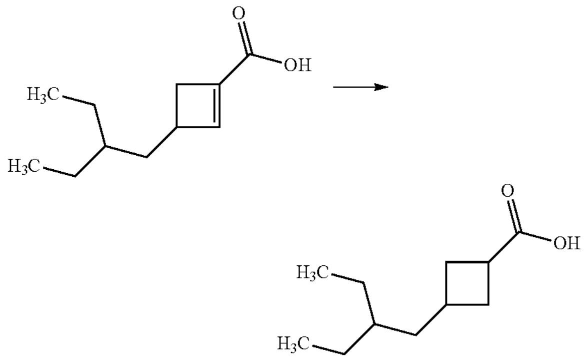

3-(2-Ethylbutyl)-1-cyclobutenecarboxylic acid (39.0 g) was dissolved in tetrahydrofuran (200 mL). To the solution was added 5 w/w % palladium on activated carbon (5.5 g). The mixture was stirred at RT overnight under hydrogen atmosphere (1 atm). The 5 w/w % palladium on activated carbon was filtered off using Celite and the filtrate was concentrated in vacuo. The residue was purified by silica gel column chromatography (Eluent: ethyl acetate/hexane=1/4→1/2) to give the title compound (25.2 g).

(A-75-8) N-Methoxy-N-methyl-3-(2-ethylbutyl)cyclobutanecarboxamide

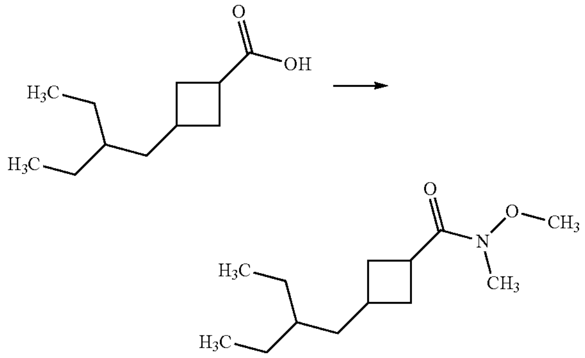

3-(2-Ethylbutyl)cyclobutanecarboxylic acid (10.0 g) and chloroform (100 mL) were mixed. To the mixture were added N,O-dimethylhydroxylamine hydrochloride (6.36 g), N,N-diisopropylethylamine (11.3 mL), WSC.HCl (12.5 g) and 4-dimethylaminopyridine (7.96 g) at ice temperature. The mixture was stirred at RT overnight. After an addition of 6 N hydrochloric acid (40 mL) at ice temperature, the aqueous layer was removed. The organic layer was washed with 1 N hydrochloric acid (50 mL), water (50 mL), saturated aqueous sodium bicarbonate (50 mL) and brine (50 mL), then dried over sodium sulfate. The sodium sulfate was filtered off and the filtrate was concentrated in vacuo to give the title compound (13.2 g) as a crude product.

(A-75-9) 3-(2-Ethylbutyl)cyclobutanecarbaldehyde

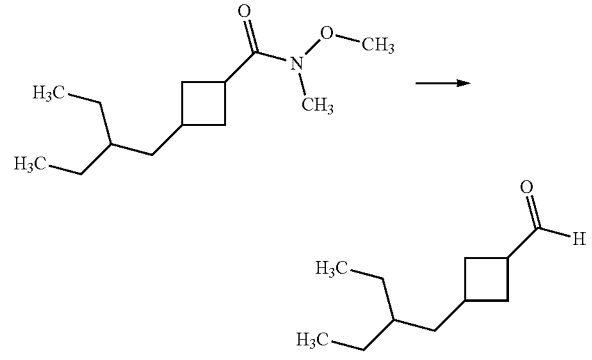

To a solution of N-methoxy-N-methyl-3-(2-ethylbutyl)cyclobutanecarboxamide (13.2 g) in methylene chloride (35 mL) was added dropwise diisobutylaluminum hydride (1.0 M in methylene chloride)(76.0 mL) at −78° C. After stirring at −78° C. for 2.5 hr, 1 M sulfuric acid was added dropwise to the mixture. The mixture was stirred at ice temperature for 20 min. The organic layer was removed, and the aqueous layer was extracted with methylene chloride (15 mL×2). The combined organic layer was washed with 0.5 N sulfuric acid (50 mL×2), water (50 mL) and brine, then dried over sodium sulfate. The sodium sulfate was filtered off and the filtrate comprising the title compound was used in the next step.

(A-75-10) 1-(2,2-Dibromovinyl)-3-(2-ethylbutyl)cyclobutane

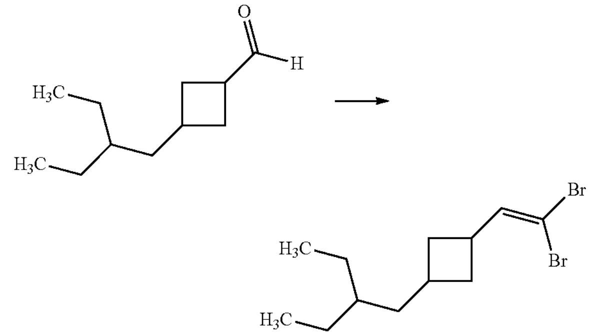

To a solution of carbon tetrabromide (27.0 g) in methylene chloride (27 mL) was added dropwise a solution of triphenylphosphine (42.8 g) in methylene chloride (85 mL) at ice temperature. The mixture was stirred at ice temperature for 20 min., and then to the mixture was added dropwise a solution of 3-(2-ethylbutyl)cyclobutanecarbaldehyde in methylene chloride at ice temperature. After stirring at ice temperature for 40 min., saturated aqueous sodium bicarbonate (250 mL) was added dropwise to the mixture. The aqueous layer was removed, and the organic layer was washed with water (50 mL) and brine (50 mL), then dried over sodium sulfate. The sodium sulfate was filtered off and the filtrate was concentrated in vacuo. To the residue were added hexane/chloroform=1/1 (100 mL), silica gel (50 g) and hexane (300 mL). The mixture was filtered and the filtrate was concentrated in vacuo. To the residue was added hexane (300 mL), and the mixture was filtered. The filtrate was concentrated in vacuo. The resultant residue was purified by silica gel column chromatography (Eluent: hexane) to give the title compound (9.78 g).

(A-75-11) tert-Butyl 3-[2-(tert-butyldiphenylsilanyloxy)ethyl]-6-[3-(2-ethylbutyl)cyclobutyl]-4-oxo-5-hexynoate

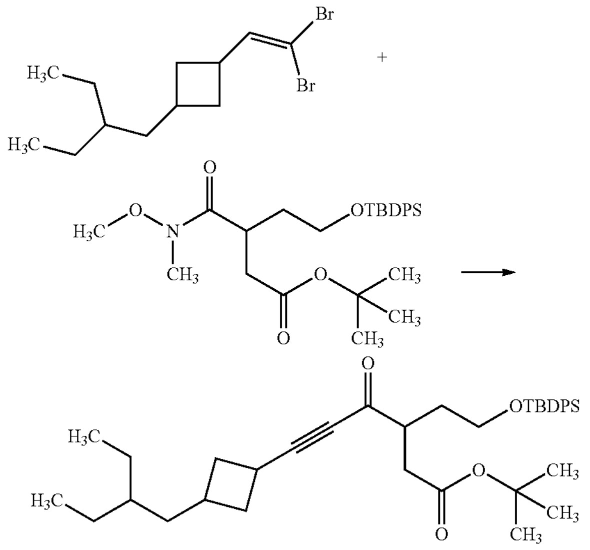

1-(2,2-Dibromovinyl)-3-(2-ethylbutyl)cyclobutane (9.78 g) and tetrahydrofuran (100 mL) were mixed. To the mixture was added dropwise n-butyllithium (1.65 M in hexane) (39 mL) at −78° C. The mixture was stirred under ambient temperature. To the mixture was added dropwise a solution of tert-butyl 5-(tert-butyldiphenylsilanyloxy)-3-methoxymethylcarbamoylvalerate (10.6 g) in tetrahydrofuran (30 mL) at ice temperature. After stirring at ice temperature for 2 hr., saturated aqueous ammonium chloride (150 mL) was added to the reaction mixture. The mixture was extracted with ethyl acetate (150 mL, 100 mL). The combined organic layer was washed with water (75 mL) and brine (75 mL, 50 mL), then dried over sodium sulfate. The sodium sulfate was filtered off and the filtrate was concentrated in vacuo. The resultant residue was purified by silica gel column chromatography (Eluent: ethyl acetate/hexane=1/40→1/30→1/20) to give the title compound (9.70 g).

(A-75-12) tert-Butyl 3-[2-(tert-butyldiphenylsilanyloxy)ethyl]-6-[3-(2-ethylbutyl)cyclobutyl]-4-methoxyimino-5-hexynoate

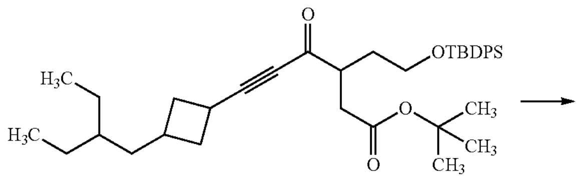

-continued

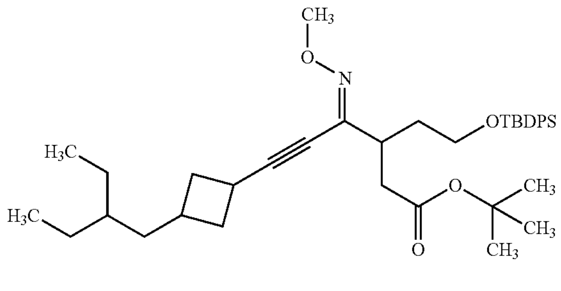

tert-Butyl 3-[2-(tert-butyldiphenylsilanyloxy)ethyl]-6-[3-(2-ethylbutyl)cyclobutyl]-4-oxo-5-hexynoate (9.70 g) and methanol (70 mL) were mixed. To the mixture were added sodium sulfate (4.57 g), pyridine (7.0 mL) and O-methylhydroxylammonium chloride (2.69 g). The mixture was stirred at RT overnight and filtered. The filtrate was concentrated in vacuo. The resultant residue was purified by silica gel column chromatography (Eluent: ethyl acetate/hexane=1/30→1/20) to give the title compound (7.85 g).

(A-75-13) tert-Butyl 5-(tert-butyldiphenylsilanyloxy)-3-{5-[3-(2-ethylbutyl)cyclobutyl]-4-iodoisoxazol-3-yl}valerate

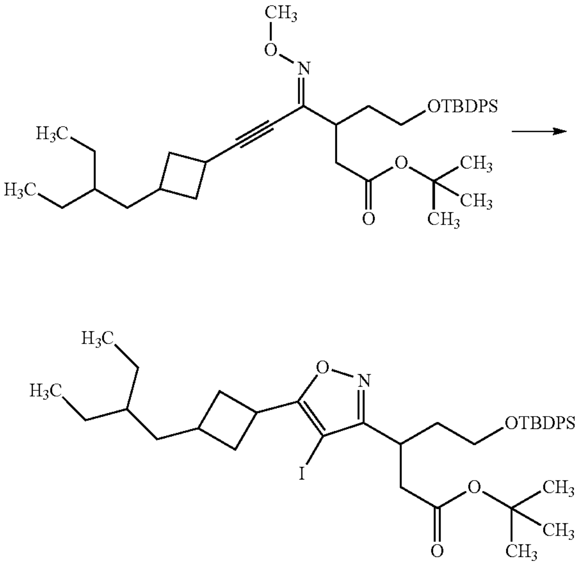

tert-Butyl 3-[2-(tert-butyldiphenylsilanyloxy)ethyl]-6-[3-(2-ethylbutyl)cyclobutyl]-4-methoxyimino-5-hexynoate (7.50 g) and acetonitrile (60 mL) were mixed. To the mixture was added iodine (7.54 g) was added at ice temperature. The mixture was stirred for 4.5 hr, and then to the mixture were added aqueous 5 w/v % sodium thiosulfate (50 mL), ethyl acetate (200 mL) and aqueous 5 w/v % sodium thiosulfate (75 mL, 150 mL) at ice temperature. The aqueous layer was removed, and the organic layer was washed with saturated aqueous sodium bicarbonate/brine=1/1 (100 mL) and brine (50 mL), then dried over sodium sulfate. The sodium sulfate was filtered off and the filtrate was concentrated in vacuo. The resultant residue was purified twice by silica gel column chromatography (Eluent: ethyl acetate/hexane=1/50→1/40→1/20) to give the title compound (7.1 g).

(A-75-14) tert-Butyl 5-(tert-butyldiphenylsilanyloxy)-3-{4-cyclopropyl-5-[3-(2-ethylbutyl)cyclobutyl]isoxazol-3-yl}valerate

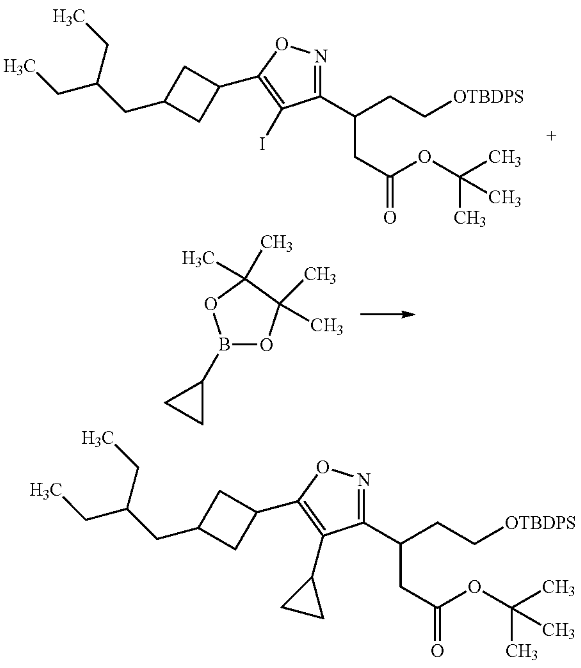

tert-Butyl 5-(tert-butyldiphenylsilanyloxy)-3-{5-[3-(2-ethylbutyl)cyclobutyl]-4-iodoisoxazol-3-yl}valerate (4.96 g), 2-cyclopropyl-4,4,5,5-tetramethyl-[1,3,2]dioxaborolane (1.68 g), tripotassium phosphate (5.66 g), $PdCl_2(PPh_3)_2$ (468 mg) and N,N-dimethylacetamide (50 mL) were mixed. The mixture was stirred at 80° C. for 5 hr. To the reaction mixture were added ethyl acetate (50 mL) and Celite at RT, and the mixture was filtered. The collected solid was washed with ethyl acetate (50 mL×2). The filtrate was washed with water/brine=1/1 (100 mL×2) and brine (50 mL), then dried over sodium sulfate. The sodium sulfate was filtered off and the filtrate was concentrated in vacuo. The resultant residue was purified by silica gel column chromatography (Eluent: ethyl acetate/hexane=1/50→1/40→1/30→1/20) to give the title compound (2.86 g).

(A-75-15) tert-Butyl 3-[4-cyclopropyl-5-[3-(2-ethylbutyl)cyclobutyl]isoxazol-3-yl]-5-hydroxyvalerate

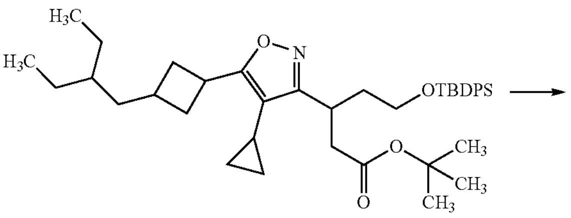

-continued

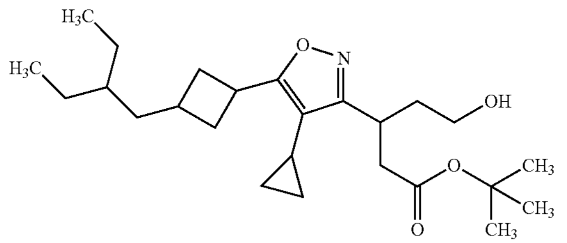

To tetrabutylammonium fluoride (1 M in tetrahydrofuran) (6.26 mL) were added water (0.0725 mL), acetic acid (0.29 mL) and a solution of tert-butyl 5-(tert-butyldiphenylsilanyloxy)-3-{4-cyclopropyl-5-[3-(2-ethylbutyl)cyclobutyl]isoxazol-3-yl}valerate (2.76 g) in tetrahydrofuran (20 mL) at ice temperature. The mixture was stirred at RT overnight. The reaction mixture was concentrated in vacuo. The residue was purified by silica gel column chromatography (Eluent: ethyl acetate/hexane=1/6→1/4→1/2) to give the title compound (1.72 g).

(A-75-16) Mono-tert-butyl 3-{4-Cyclopropyl-5-[3-(2-ethylbutyl)cyclobutyl]isoxazol-3-yl}glutarate

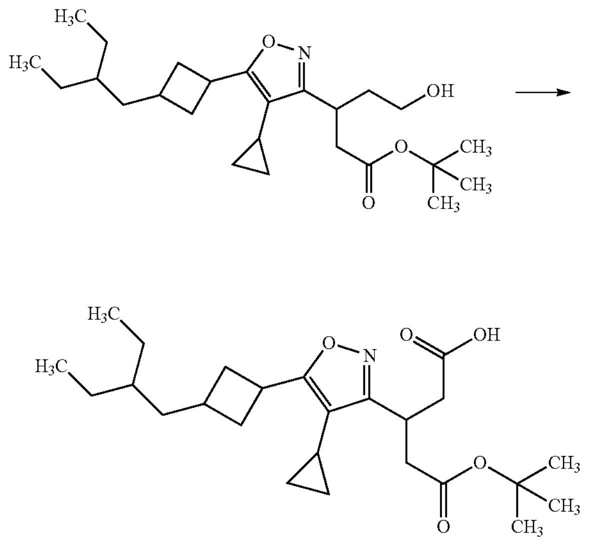

tert-Butyl 3-{4-cyclopropyl-5-[3-(2-ethylbutyl)cyclobutyl]isoxazol-3-yl}-5-hydroxyvalerate (1.72 g), acetonitrile (35 mL) and 0.5 M phosphate buffer (17 mL) were mixed. To the mixture were added 2,2,6,6-tetramethyl-1-piperidinyloxy radical (TEMPO) (60.4 mg), sodium chlorite (1.31 g) and aqueous sodium hypochlorite (8.6 mL) at RT. The mixture was stirred for 1 hr, and then to the mixture were added aqueous 5 w/v % sodium thiosulfate (80 mL) and aqueous 10 w/v % citric acid (50 mL) at ice temperature. The mixture was extracted with ethyl acetate (100 mL). The organic layer was washed with brine (30 mL), then dried over sodium sulfate. The sodium sulfate was filtered off and the filtrate was concentrated in vacuo to give the title compound (1.78 g) as a crude product.

(A-75-17) tert-Butyl 4-(2-chloro-4-methylphenylcarbamoyl)-3-{4-cyclopropyl-5-[3-(2-ethylbutyl)cyclobutyl]isoxazol-3-yl}butanoate

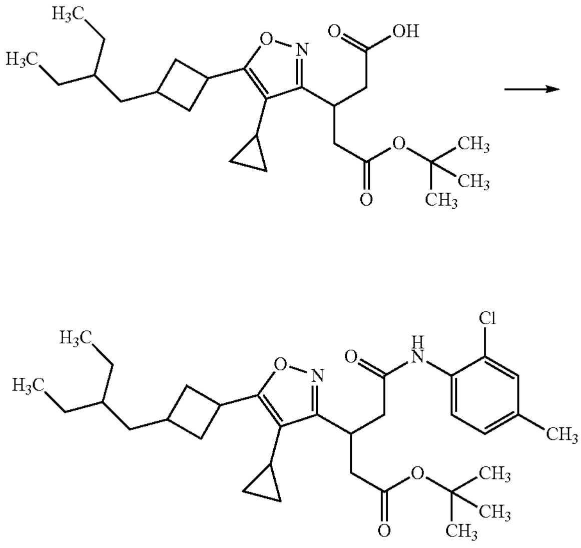

Mono-tert-butyl 3-{4-cyclopropyl-5-[3-(2-ethylbutyl)cyclobutyl]isoxazol-3-yl}glutarate (150 mg) and DMF (1.5 mL) were mixed. To the mixture were added HOBt.$H_2O$ (63.5 mg), WSC.HCl (79.6 mg) and 2-chloro-4-methylphenylamine (0.0512 mL). The mixture was stirred at RT overnight. To the reaction mixture was added ethyl acetate. The mixture was washed with aqueous 10 w/v % citric acid, water, saturated aqueous sodium bicarbonate and brine, then dried over sodium sulfate. The sodium sulfate was filtered off and the filtrate was concentrated in vacuo. The resultant residue was purified by preparative chromatography (Eluent: ethyl acetate/hexane=1/6) to give the title compound (122 mg).

(A-75-18) 4-(2-chloro-4-methylphenylcarbamoyl)-3-{4-cyclopropyl-5-[3-(2-ethylbutyl)cyclobutyl]isoxazol-3-yl}butanoic acid

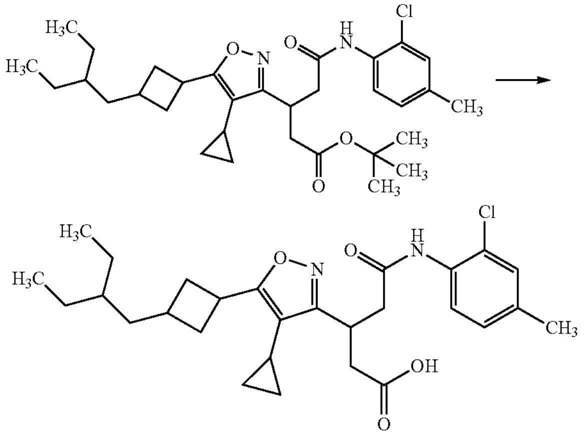

tert-Butyl 4-(2-chloro-4-methylphenylcarbamoyl)-3-{4-cyclopropyl-5-[3-(2-ethylbutyl)cyclobutyl]isoxazol-3-yl}butanoate (122 mg) and water (0.7 mL) were mixed. To the mixture was added a solution of 25 w/w % hydrogen bromide in acetic acid (1.4 mL) at ice temperature. After stirring at RT for 2 hr, aqueous 4 N sodium hydroxide (1.65 mL) was added to the reaction mixture at ice temperature. The mixture was extracted with ethyl acetate. The organic layer was washed with water and brine, then dried over magnesium sulfate. The magnesium sulfate was filtered off and the filtrate was concentrated in vacuo. The resultant residue was purified by preparative chromatography (Eluent: methanol/chloroform/acetic acid=1/20/0.1) to give the title compound (56.7 mg). The title compound was analyzed using a chiral column. The retention time of the title compound was 8.2 min., and the optical purity thereof was 90.5% ee.

The condition for the analysis using the chiral column was as follows:

Instrument: HPLC System Shimadzu High performance liquid chromatography Prominence Column: DAICEL CHIRALPAK AD-3R 0.46 cm ϕ×15 cm Column temperature: 40° C.

Mobile phase: (A solution) 10 mM phosphate buffer (pH=2.6), (B solution) acetonitrile Composition of Mobile phase: A solution:B solution=30:70

Flow rate: 0.5 mL/min

Detection: UV (220 nm)

Example A-27

3-[5-Cyclopropyl-1-(3-isobutylcyclobutyl)-1H-[1,2,3]triazol-4-yl]-4-(2,4-dimethylphenylcarbamoyl)butyric acid (A-27-1) tert-Butyl (3-isobutylcyclobutyl)carbamate

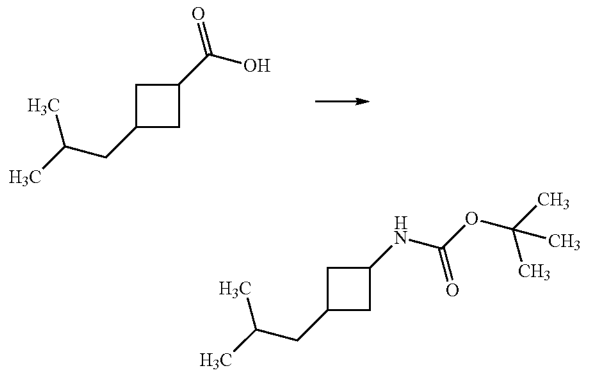

3-Isobutylcyclobutanecarboxylic acid (3.00 g) and tert-butanol (30 mL) were mixed. To the mixture were added triethylamine (4.28 mL) and diphenylphosphoryl azide (5.38 mL) at ice temperature. After stirring at 95° C. overnight, the reaction mixture was concentrated in vacuo. To the resultant residue was added ethyl acetate. The mixture was washed with water and brine, then dried over magnesium sulfate. The magnesium sulfate was filtered off and the filtrate was concentrated in vacuo. The resultant residue was purified by silica gel column chromatography (Eluent: ethyl acetate/hexane=1/40) to give the title compound (2.91 g).

(A-27-2) 3-Isobutylcyclobutylamine hydrochloride

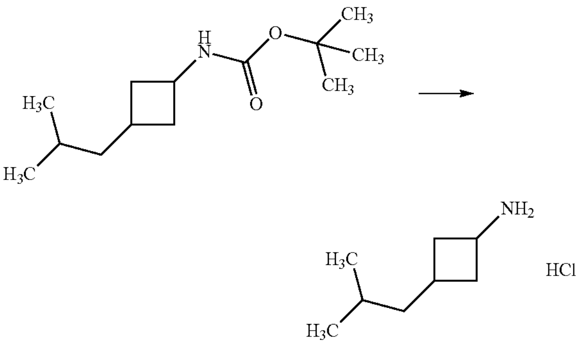

tert-Butyl (3-isobutylcyclobutyl)carbamate (2.90 g) and dioxane (15 mL) were mixed. To the mixture was added a solution of 4 N hydrochloric acid in dioxane (15 mL) at 10° C. The mixture was stirred at RT overnight. The reaction mixture was concentrated in vacuo to give the title compound (1.97 g) as a crude product.

(A-27-3) Imidazole-1-sulfonyl azide hydrochloride

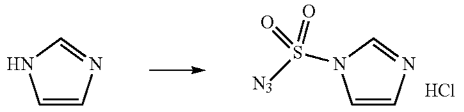 [SMILES: c1c[nH]cn1 ; [N-]=[N+]=NS(=O)(=O)n1ccnc1 ; Cl]

Sodium azide (13.0 g) and acetonitrile (200 mL) were mixed. To the mixture was added dropwise sulfuryl chloride (16.1 mL) at ice temperature. The mixture was stirred at RT overnight, and then to the mixture was added imidazole (25.9 g) at ice temperature. The mixture was stirred at RT for 4 hr, and then to the mixture was added ethyl acetate. The mixture was washed with water (400 mL×2) and saturated aqueous sodium bicarbonate (400 mL×2), then dried over magnesium sulfate. The magnesium sulfate was filtered off. To the filtrate was added a solution of hydrochloric acid in ethyl acetate at ice temperature. The precipitated solid was collected on a filter to give the title compound (27.7 g).

(A-27-4) 1-Azide-3-isobutylcyclobutane

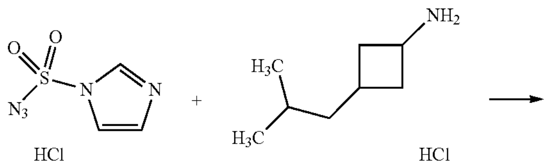

-continued

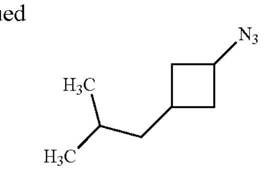

3-Isobutylcyclobutylamine hydrochloride (655 mg), copper(II)sulfate pentahydrate (10 mg) and methanol (6.5 mL) were mixed. To the mixture were added potassium carbonate (1.49 g) and imidazole-1-sulfonyl azide hydrochloride (1.01 g) at ice temperature. The mixture was stirred at RT overnight, and then to the mixture were added 1 N hydrochloric acid, water, and brine at ice temperature. The mixture was extracted with tetrahydrofuran. The organic layer was washed with 1 N hydrochloric acid and brine, then dried over magnesium sulfate. The magnesium sulfate was filtered off and the filtrate comprising the title compound was used in the next step.

(A-27-5) tert-Butyl 5-(tert-butyldiphenylsilanyloxy)-3-formylvalerate

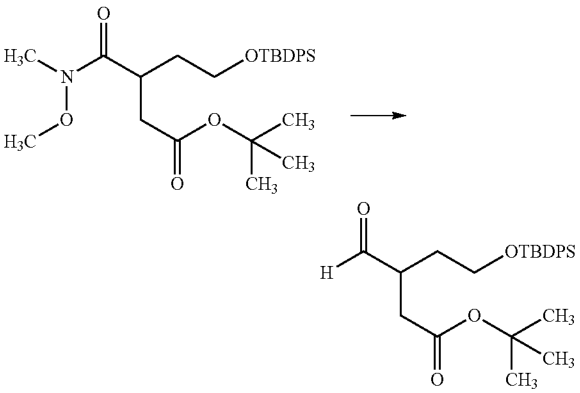

tert-Butyl 5-(tert-butyldiphenylsilanyloxy)-3-methoxymethylcarbamoylvalerate (4.61 g) and tetrahydrofuran (60 mL) were mixed. To the mixture was added dropwise diisobutylaluminum hydride (1.0 M in toluene) (13.1 mL) at −78° C. The mixture was stirred at −78° C. for 1.5 hr. To the mixture was added dropwise acetic acid (0.515 mL). After an addition of aqueous Rochelle salt at −20° C., the mixture was extracted with ethyl acetate. The organic layer washed with water, then dried over magnesium sulfate. The magnesium sulfate was filtered off and the filtrate was concentrated in vacuo. The resultant residue was purified by silica gel column chromatography (Eluent: ethyl acetate/hexane=1/25) to give the title compound (2.60 g).

(A-27-6) tert-Butyl 3-ethynylhexanoate

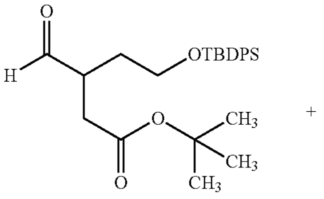

-continued

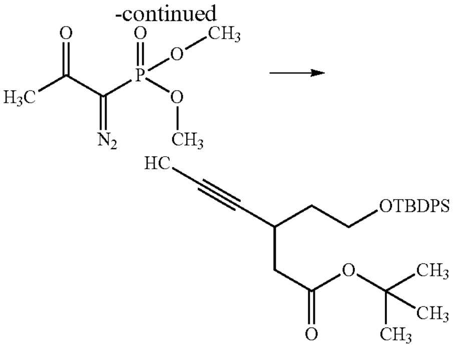

tert-Butyl 5-(tert-butyldiphenylsilanyloxy)-3-formylvalerate (2.20 g), dimethyl (1-diazo-2-oxopropyl)phosphonate (0.899 mL) and methanol (22 mL) were mixed. To the mixture was added potassium carbonate (1.31 g) at ice temperature. After stirring at RT for 2 hr, saturated aqueous sodium bicarbonate was added to the reaction mixture at ice temperature. The mixture was extracted with ethyl acetate. The organic layer was washed with water and brine, then dried over magnesium sulfate. The magnesium sulfate was filtered off and the filtrate was concentrated in vacuo. The resultant residue was purified by silica gel column chromatography (Eluent: ethyl acetate/hexane=1/70→1/50) to give the title compound (1.12 g).

(A-27-7) tert-Butyl 5-(tert-butyldiphenylsilanyloxy)-3-[5-iodo-1-(3-isobutylcyclobutyl)-1H-[1,2,3]triazol-4-yl]valerate

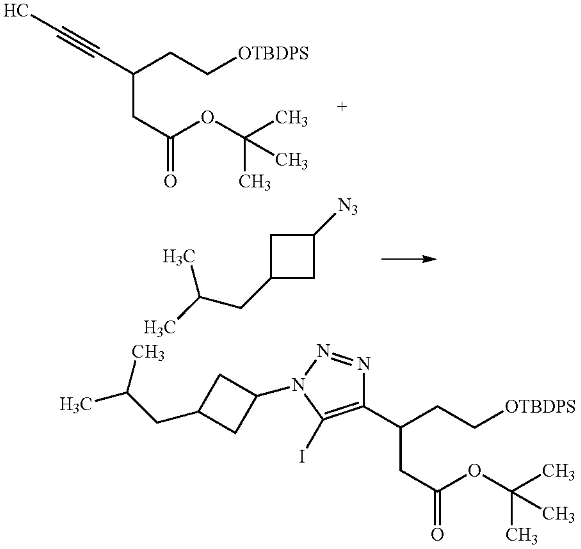

tert-Butyl 3-ethynylhexanoate (1.10 g), the solution of 1-azide-3-isobutylcyclobutane in tetrahydrofuran which was prepared in the step (A-27-4) as described above, and tetrahydrofuran (20 mL) were mixed. To the mixture was added N,N-diisopropylethylamine (0.878 mL), N-bromosuccinimide (493 mg) and copper(I)iodide (528 mg) at ice temperature. The mixture was stirred at RT overnight. The reaction mixture was filtered, and the filtrate was concentrated in vacuo. After an addition of aqueous 10 w/w % ammonia to the resultant residue at ice temperature, the mixture was extracted with ethyl acetate. The organic layer was washed with water and brine, then dried over magnesium sulfate. The magnesium sulfate was filtered off and the filtrate was concentrated in vacuo. The resultant residue was purified by silica gel column chromatography (Eluent: ethyl acetate/hexane=1/40→1/12) to give the title compound (353 mg).

(A-27-8) tert-Butyl 5-(tert-butyldiphenylsilanyloxy)-3-[5-cyclopropyl-1-(3-isobutylcyclobutyl)-1H-[1,2,3]triazol-4-yl]valerate

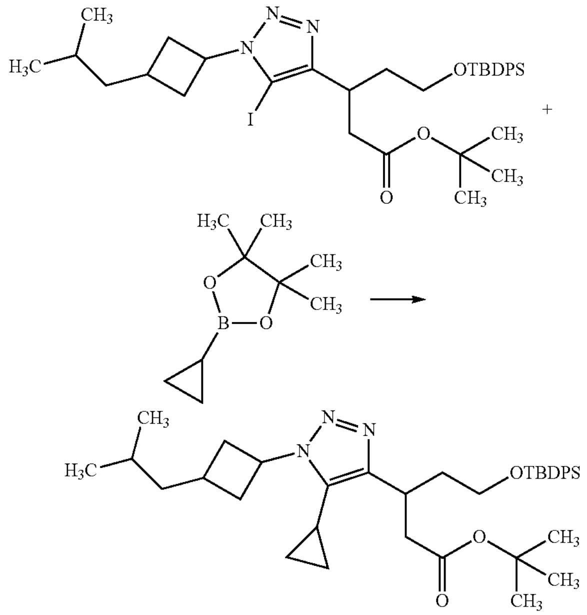

tert-Butyl 5-(tert-butyldiphenylsilanyloxy)-3-[5-iodo-1-(3-isobutylcyclobutyl)-1H-[1,2,3]triazol-4-yl]valerate (340 mg), 2-cyclopropyl-4,4,5,5-tetramethyl-[1,3,2]dioxaborolane (0.16 mL), tripotassium phosphate (403 mg), N,N-dimethylacetamide (3.4 mL) and water (0.85 mL) were mixed. The mixture was degassed by bubbling argon gas. To the mixture was added $PdCl_2(PPh_3)_2$ (50 mg). The mixture was stirred at 80° C. for 1 hr. To the reaction mixture was added ethyl acetate at ice temperature, and then the mixture was filtered. The filtrate was washed with water and brine, then dried over magnesium sulfate. The magnesium sulfate was filtered off and the filtrate was concentrated in vacuo. The resultant residue was purified by silica gel column chromatography (Eluent: ethyl acetate/hexane=1/20) to give the title compound (238 mg).

(A-27-9) tert-Butyl 3-[5-cyclopropyl-1-(3-isobutylcyclobutyl)-1H-[1,2,3]triazol-4-yl]-5-hydroxyvalerate

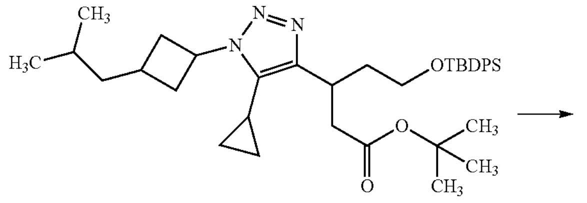

-continued

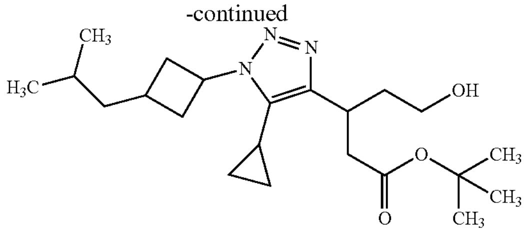

tert-Butyl 5-(tert-butyldiphenylsilanyloxy)-3-[5-cyclopropyl-1-(3-isobutylcyclobutyl)-1H-[1,2,3]triazol-4-yl]valerate (233 mg) and tetrahydrofuran (3.0 mL) were mixed. To the mixture were added tetrabutylammonium fluoride (1 M in tetrahydrofuran) (0.444 mL) and 80 v/v % aqueous acetic acid (0.045 mL) at ice temperature. The mixture was stirred at RT overnight. After an addition of brine at ice temperature, the mixture was extracted with ethyl acetate. The organic layer was washed with brine, then dried over magnesium sulfate. The magnesium sulfate was filtered off and the filtrate was concentrated in vacuo. The resultant residue was purified by silica gel column chromatography (Eluent: ethyl acetate/hexane=1/2) to give the title compound (107 mg).

(A-27-10) tert-Butyl 3-[5-cyclopropyl-1-(3-isobutylcyclobutyl)-1H-[1,2,3]triazol-4-yl]-5-oxovalerate

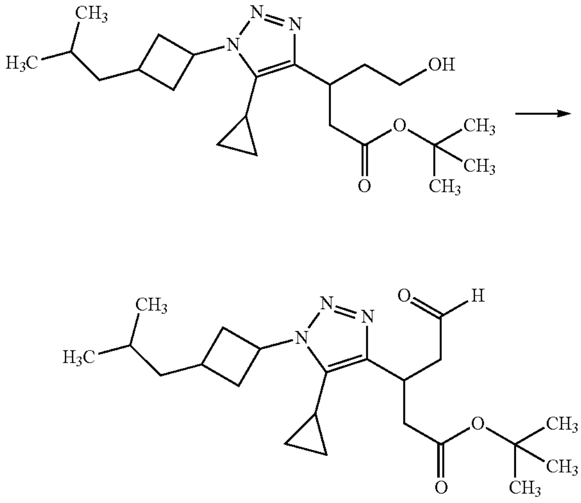

tert-Butyl 3-[5-cyclopropyl-1-(3-isobutylcyclobutyl)-1H-[1,2,3]triazol-4-yl]-5-hydroxyvalerate (106 mg) and chloroform (1 mL) were mixed. To the mixture was added Dess-Martin reagent (130 mg) at ice temperature. After stirring at RT for 1 hr, saturated aqueous sodium bicarbonate and ethyl acetate were added to the mixture at ice temperature. The mixture was extracted with ethyl acetate. The organic layer was washed with saturated aqueous sodium bicarbonate, water and brine, then dried over magnesium sulfate. The magnesium sulfate was filtered off and the filtrate was concentrated in vacuo to give the title compound (106 mg) as a crude product.

(A-27-11) Mono-tert-butyl 3-[5-cyclopropyl-1-(3-isobutylcyclobutyl)-1H-[1,2,3]triazol-4-yl]glutarate

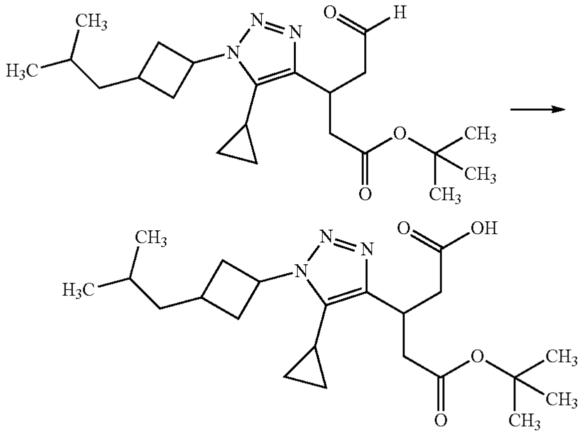

tert-Butyl 3-[5-cyclopropyl-1-(3-isobutylcyclobutyl)-1H-[1,2,3]triazol-4-yl]-5-oxovalerate (106 mg), tetrahydrofuran (1 mL) and water (0.2 mL) were mixed. To the mixture were added sodium dihydrogenphosphate (48.8 mg) and amidosulfuric acid (36.8 mg) at ice temperature. The mixture was stirred at RT for 5 min., and then to the mixture was added dropwise a solution of sodium chlorite (39.8 mg) in water (0.2 mL) at ice temperature. After stirring at RT for 1 hr., aqueous sodium thiosulfate and brine were added to the mixture at ice temperature. The mixture was extracted with ethyl acetate. The organic layer was washed with brine, then dried over magnesium sulfate. The magnesium sulfate was filtered off and the filtrate was concentrated in vacuo the title compound (111 mg) to give as a crude product.

(A-27-12) tert-Butyl 3-[5-cyclopropyl-1-(3-isobutylcyclobutyl)-1H-[1,2,3]triazol-4-yl]-4-(2,4-dimethylphenylcarbamoyl)butyrate

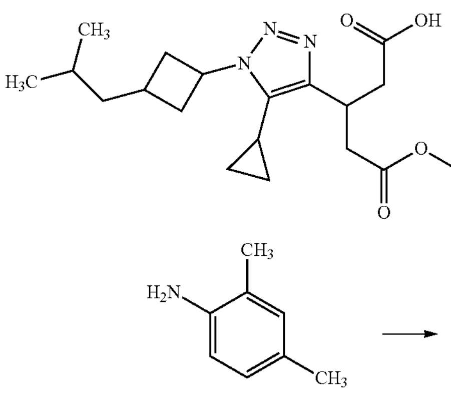

-continued

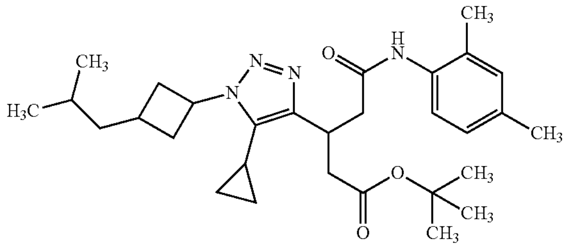

Mono-tert-butyl 3-[5-cyclopropyl-1-(3-isobutylcyclobutyl)-1H-[1,2,3]triazol-4-yl]glutarate (106 mg), 2,4-dimethylphenylamine (0.0356 mL) and DMF (1 mL) were mixed. To the mixture were added HOBt.$H_2O$ (48.2 mg) and WSC.HCl (60.3 mg) at ice temperature. After stirring at RT overnight, saturated aqueous sodium bicarbonate was added to the reaction mixture at ice temperature. The mixture was extracted with ethyl acetate. The organic layer was washed with water and brine, then dried over sodium sulfate. The sodium sulfate was filtered off and the filtrate was concentrated in vacuo. The resultant residue was purified by preparative chromatography (Eluent: ethyl acetate/hexane=1/2) to give the title compound (105 mg).

(A-27-13) 3-[5-Cyclopropyl-1-(3-isobutylcyclobutyl)-1H-[1,2,3]triazol-4-yl]-4-(2,4-dimethylphenylcarbamoyl)butyric acid

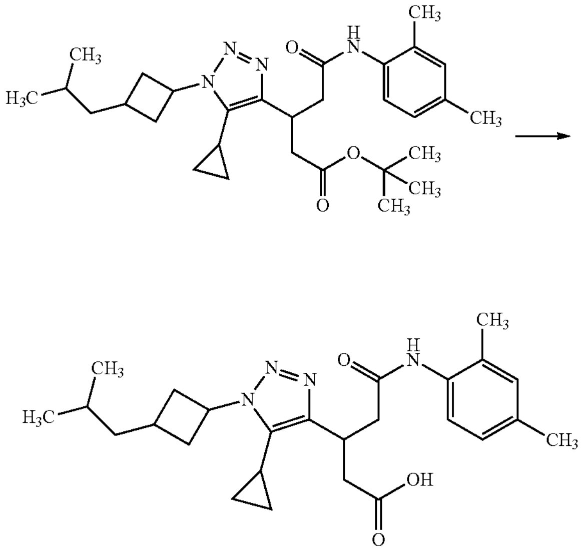

tert-Butyl 3-[5-cyclopropyl-1-(3-isobutylcyclobutyl)-1H-[1,2,3]triazol-4-yl]-4-(2,4-dimethylphenylcarbamoyl)butyrate (100 mg) and chloroform (0.8 mL) were mixed. To the mixture was added trifluoroacetic acid (0.2 mL) at ice temperature. After stirring at RT for 6 hr, the reaction mixture was concentrated in vacuo. The resultant residue was purified by preparative chromatography (Eluent: chloroform/methanol/acetic acid=20/1/0.1) to give the title compound (79.5 mg).

Example B-1

5-(2-Chloro-4-methylphenylcarbamoyl)-4-{4-cyclopropyl-5-[3-(2,2-dimethylpropyl)cyclobutyl]isoxazol-3-yl}valeric acid (B-1-1) 3-(2,2-Dimethylpropyl)cyclobutanecarboxylic acid

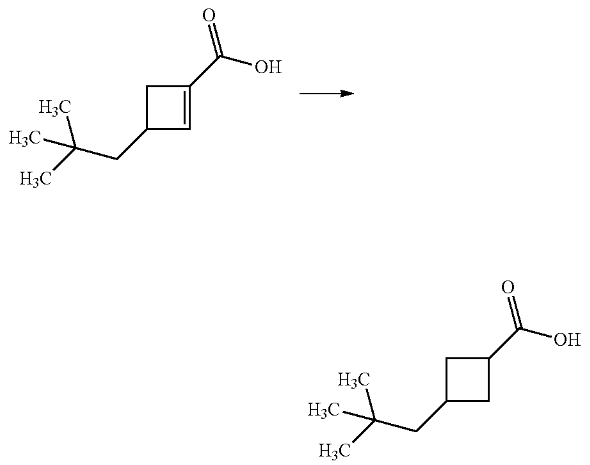

3-(2,2-dimethylpropyl)-1-cyclobutenecarboxylic acid (10 g), tetrahydrofuran (100 mL) and 6 N hydrochloric acid (100 mL) were mixed. To the mixture was added zinc (30 g) at ice temperature. The mixture was stirred at 70° C. overnight. After an addition of 6 N hydrochloric acid and water the mixture was filtered. The filtrate was extracted with ethyl acetate (150 mL, 100 mL). The organic layer was washed with brine (100 mL), then dried over sodium sulfate. The sodium sulfate was filtered off and the filtrate was concentrated in vacuo to give the title compound (11.6 g) as a crude product.

$^1$H-NMR (400 MHz, DMSO-d6) 0.82 (s, 9H), 1.34 (d, J=7.25 Hz, 2H), 1.81-1.90 (m, 2H), 2.19-2.29 (m, 2H), 2.40-2.49 (m, 1H), 2.87-2.96 (m, 1H), 12.02 (brs, 1H)

(B-1-2) 5-(2-chloro-4-methylphenylcarbamoyl)-4-{4-cyclopropyl-5-[3-(2,2-dimethylpropyl)cyclobutyl]isoxazol-3-yl}valeric acid The title compound (318 mg) was prepared by using 3-(2,2-dimethylpropyl)cyclobutanecarboxylic acid prepared in the step (B-1-1) described above according to the step described in Example A-53 (A-53-8) and the subsequent steps.

Example A-85

4-(2-Chloro-4-methylphenylcarbamoyl)-3-{4-cyclopropyl-5-[3-(2-ethylbutyl)cyclobutyl]isoxazol-3-yl}butanoate sodium

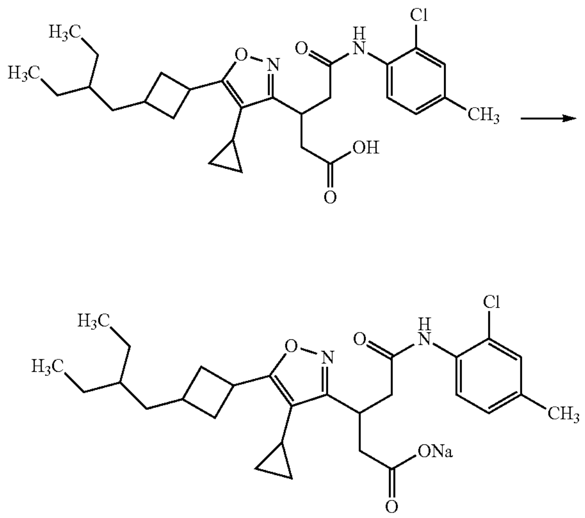

4-(2-Chloro-4-methylphenylcarbamoyl)-3-{4-cyclopropyl-5-[3-(2-ethylbutyl)cyclobutyl]isoxazol-3-yl}butanoic acid (28.9 mg) and ethanol (1 mL) were mixed. To the mixture was added aqueous 1 N sodium hydroxide (0.0577 mL) at ice temperature. The mixture was stirred at ice temperature 20 min., and then the solvent was evaporated to give the title compound (30.4 mg) as a crude product.

Example A-78

The compound is a typical example of compounds wherein $Y^c$ is $C_{3-10}$ cycloalkylene group which may be substituted with the same or different 1 to 5 substituents selected from Group A, for example, cyclobutane ring.

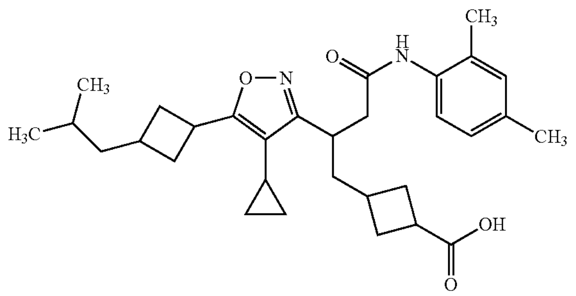

-continued
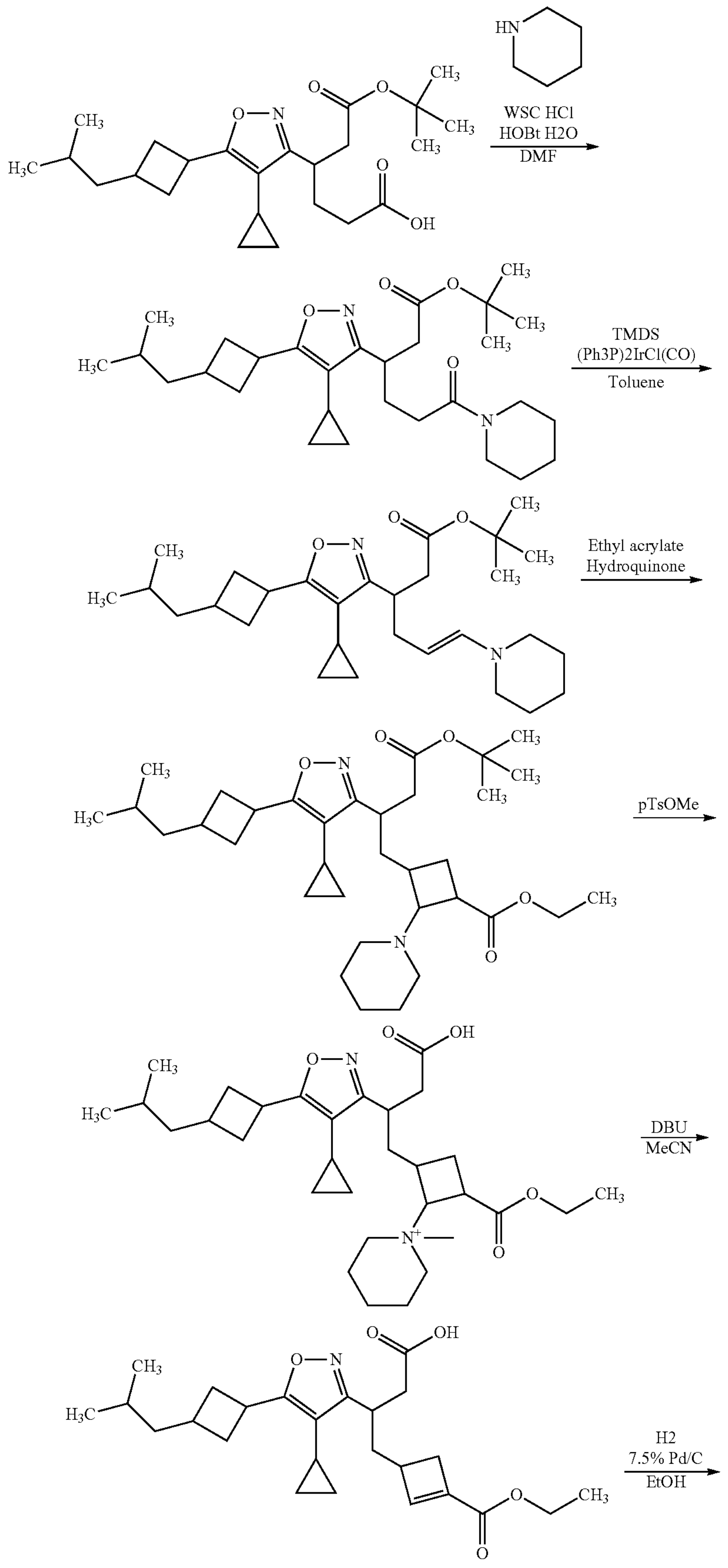

-continued

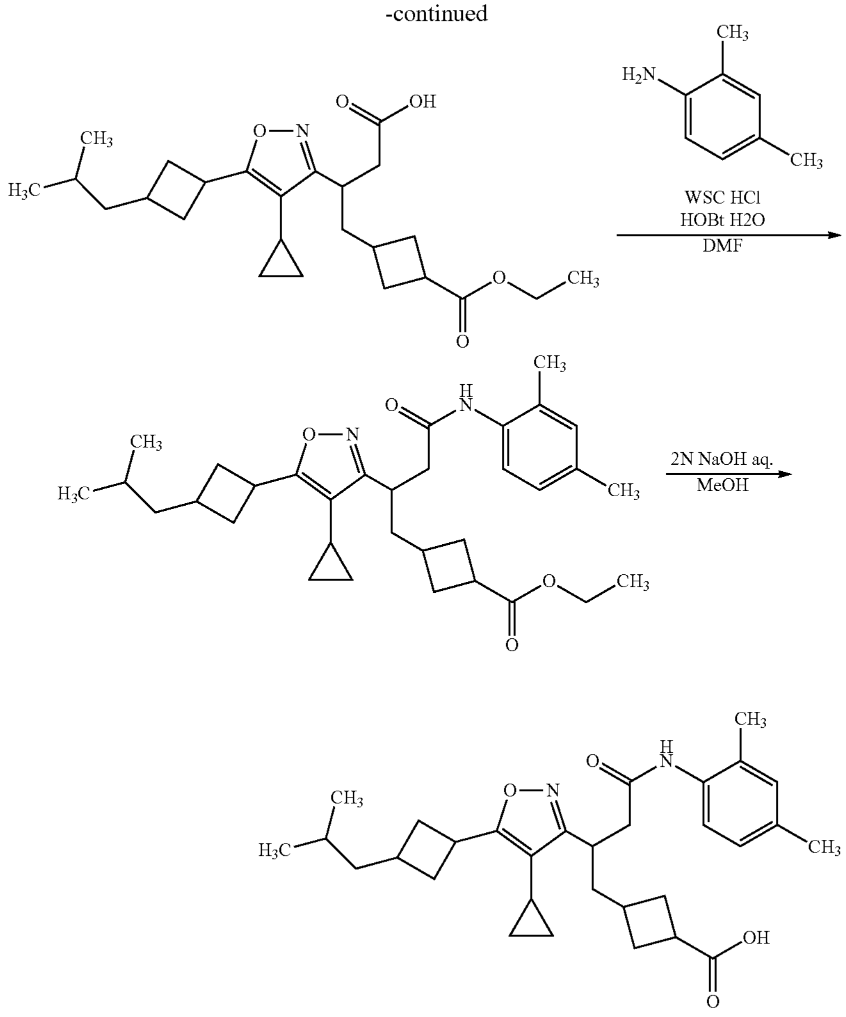

Example A-65

The compound is a typical example of compounds wherein $Y^c$ is monocyclic heteroaromatic group which may be substituted with the same or different 1 to 5 substituents selected from Group A wherein the monocyclic heteroaromatic ring consists of carbon atoms and the same or different 1 to 4 hetero atoms selected from nitrogen atom, oxygen atom and sulfur atom, and is 3 to 7-membered, for example, thiazole.

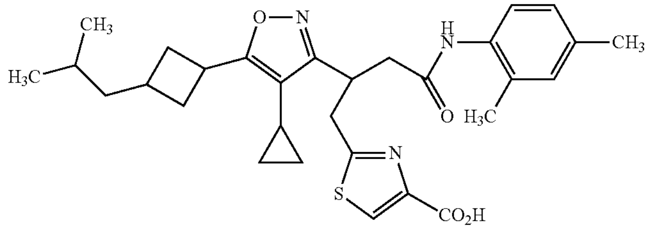

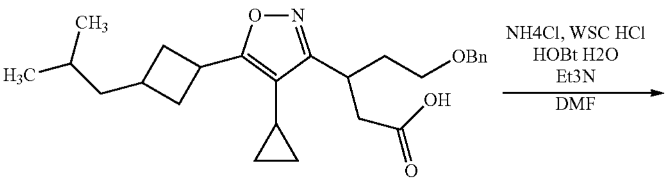

-continued
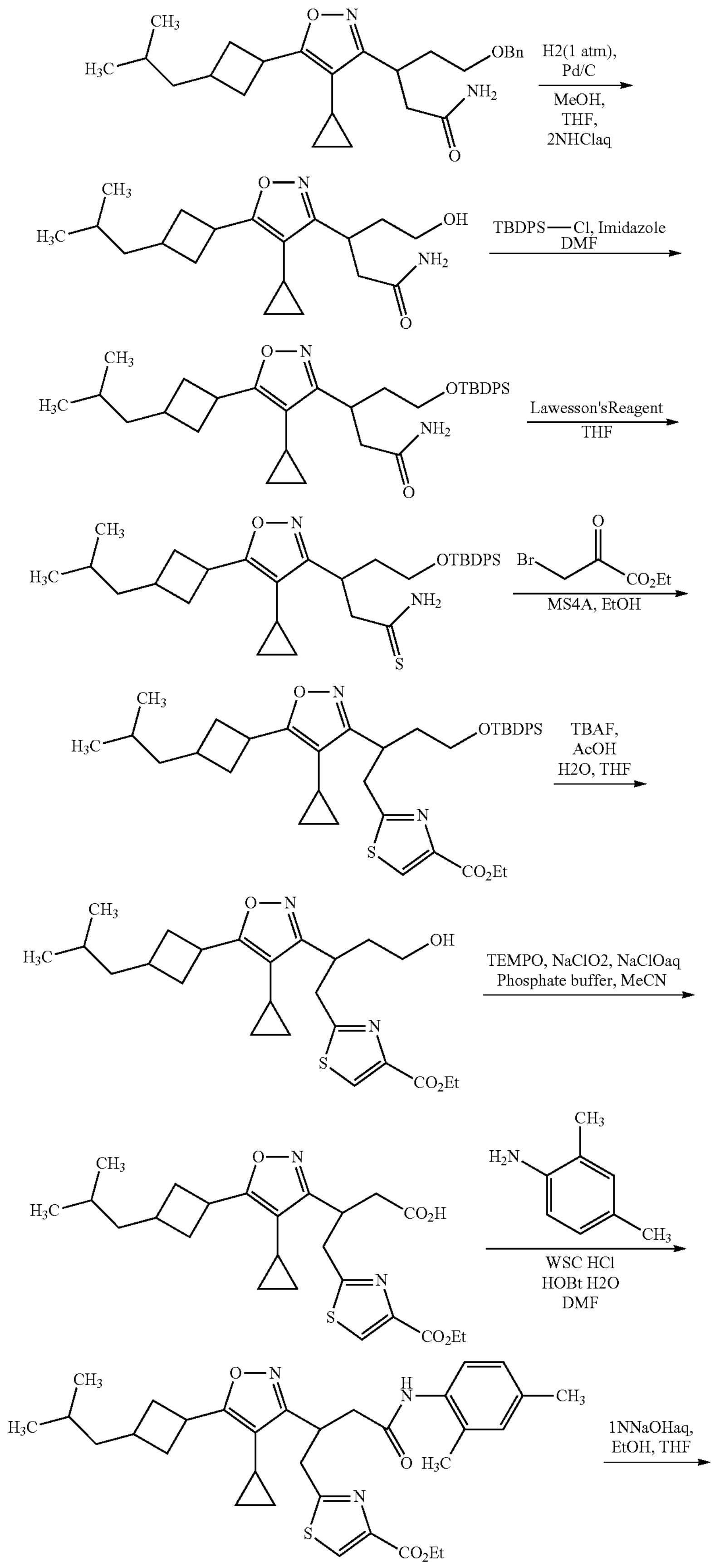

-continued
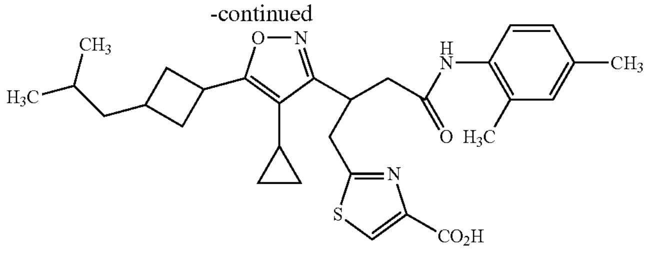
Example A-8
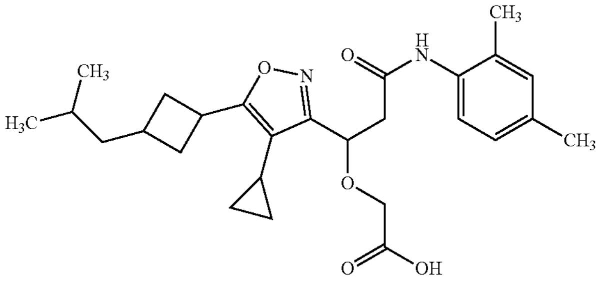
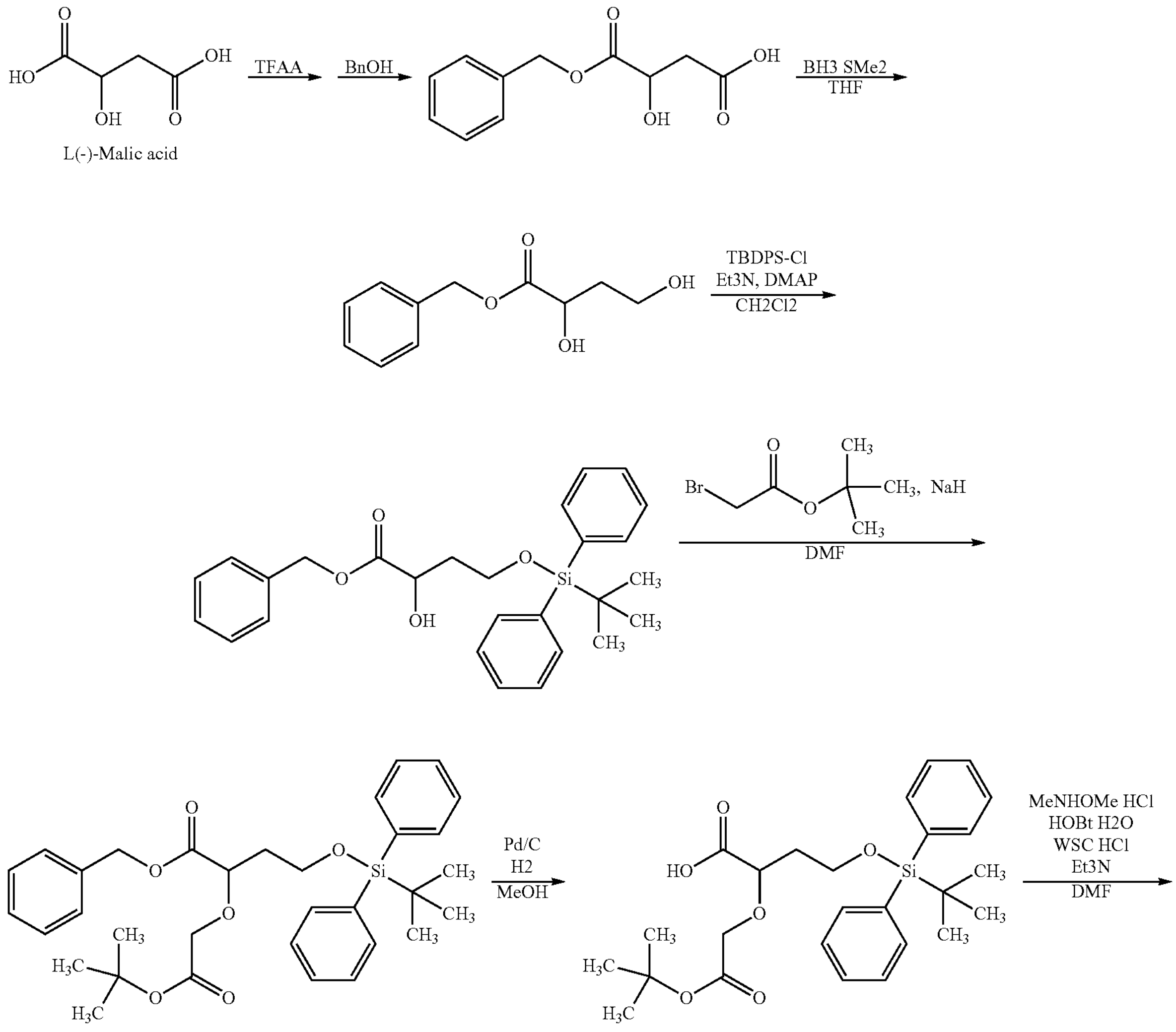

-continued
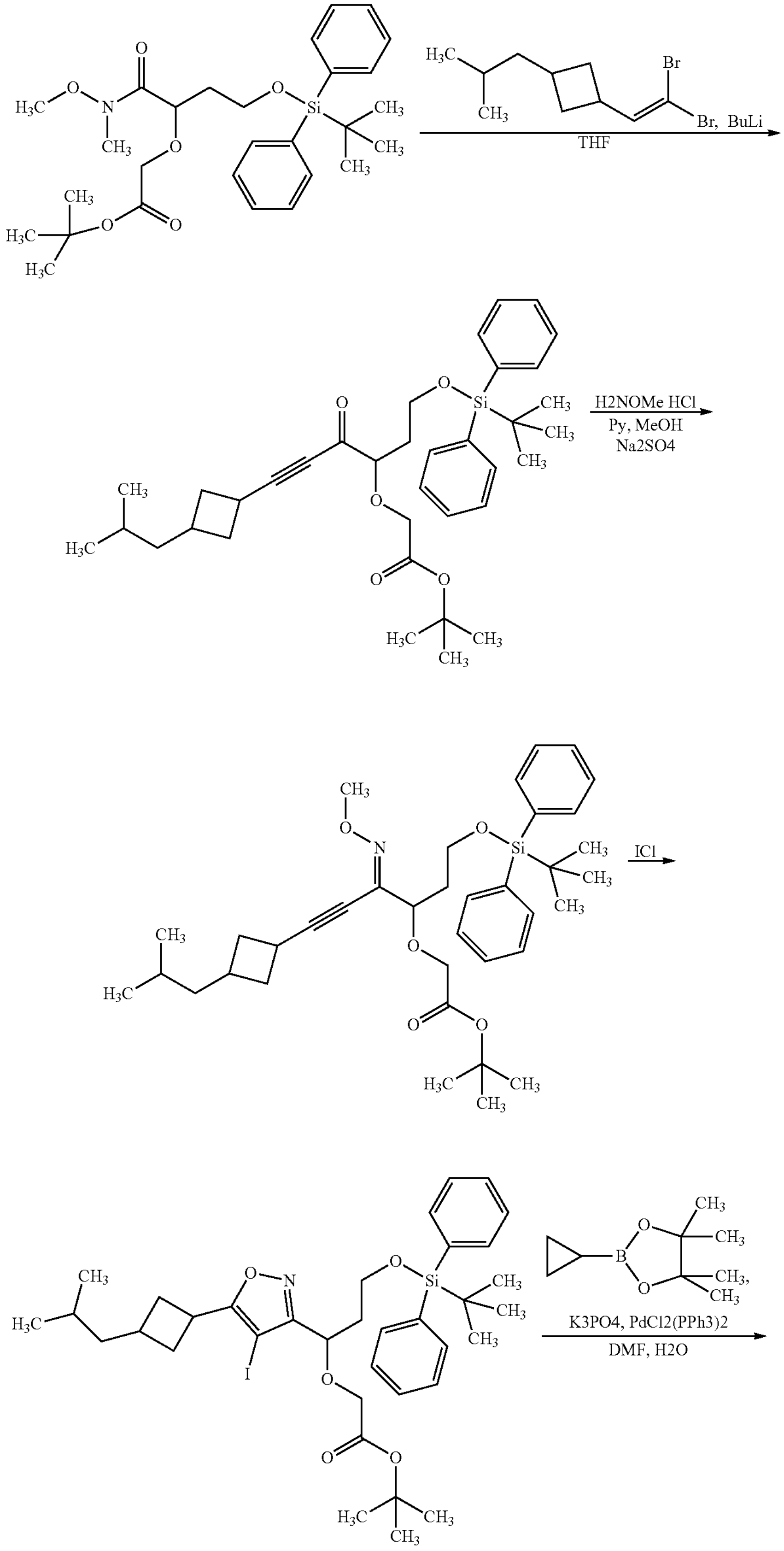

-continued
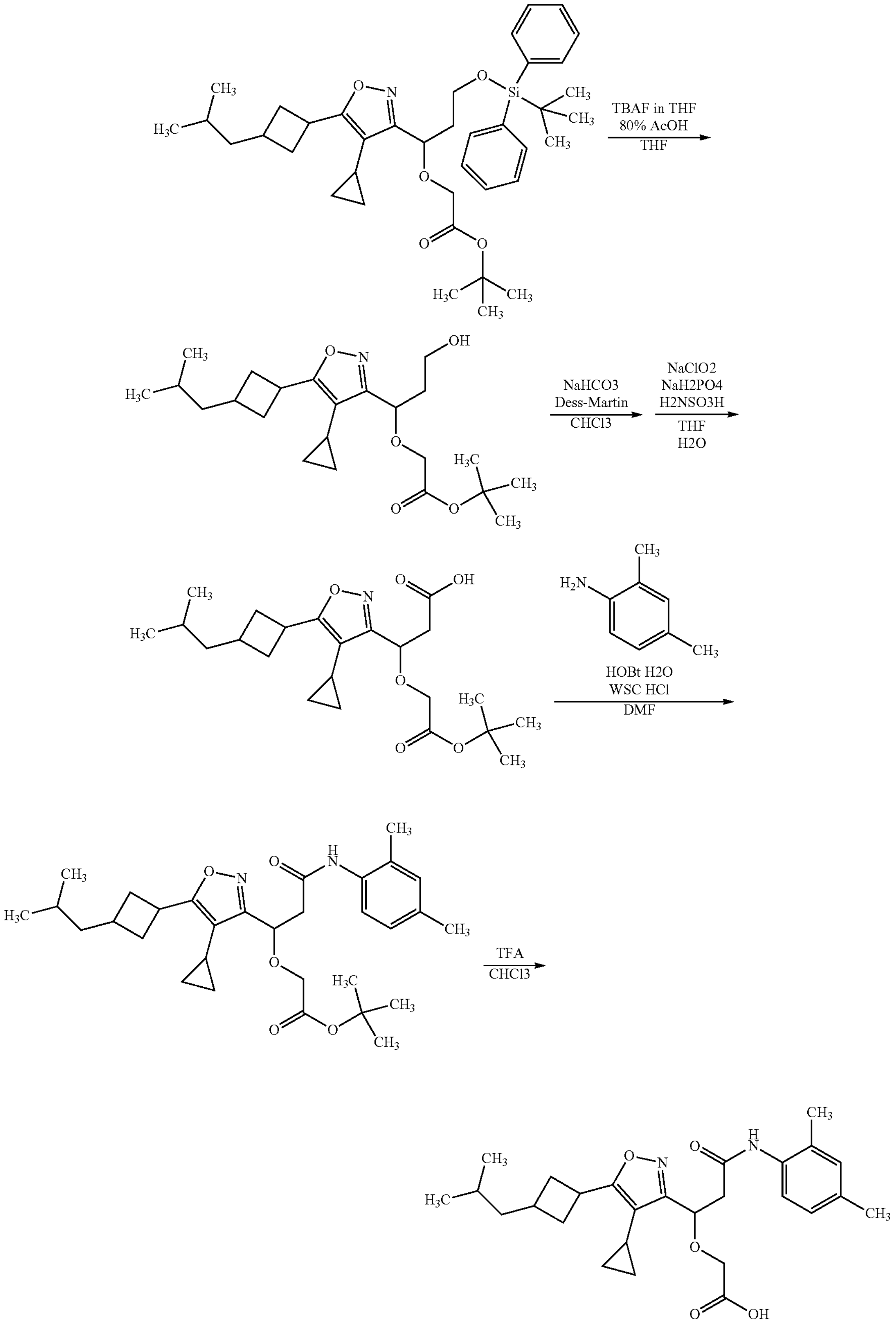

Example A-10
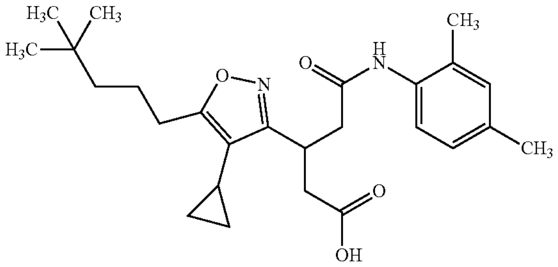
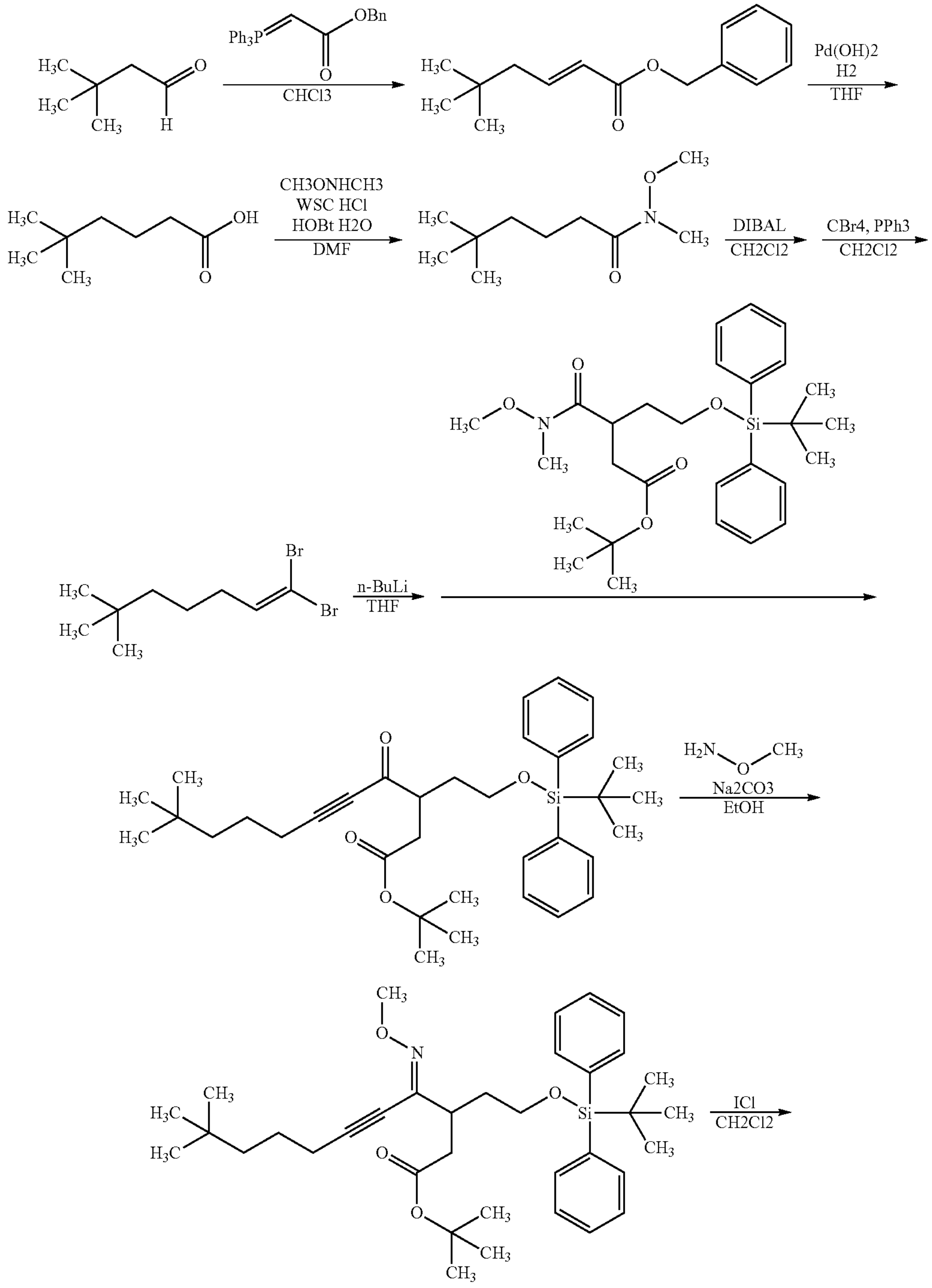

-continued
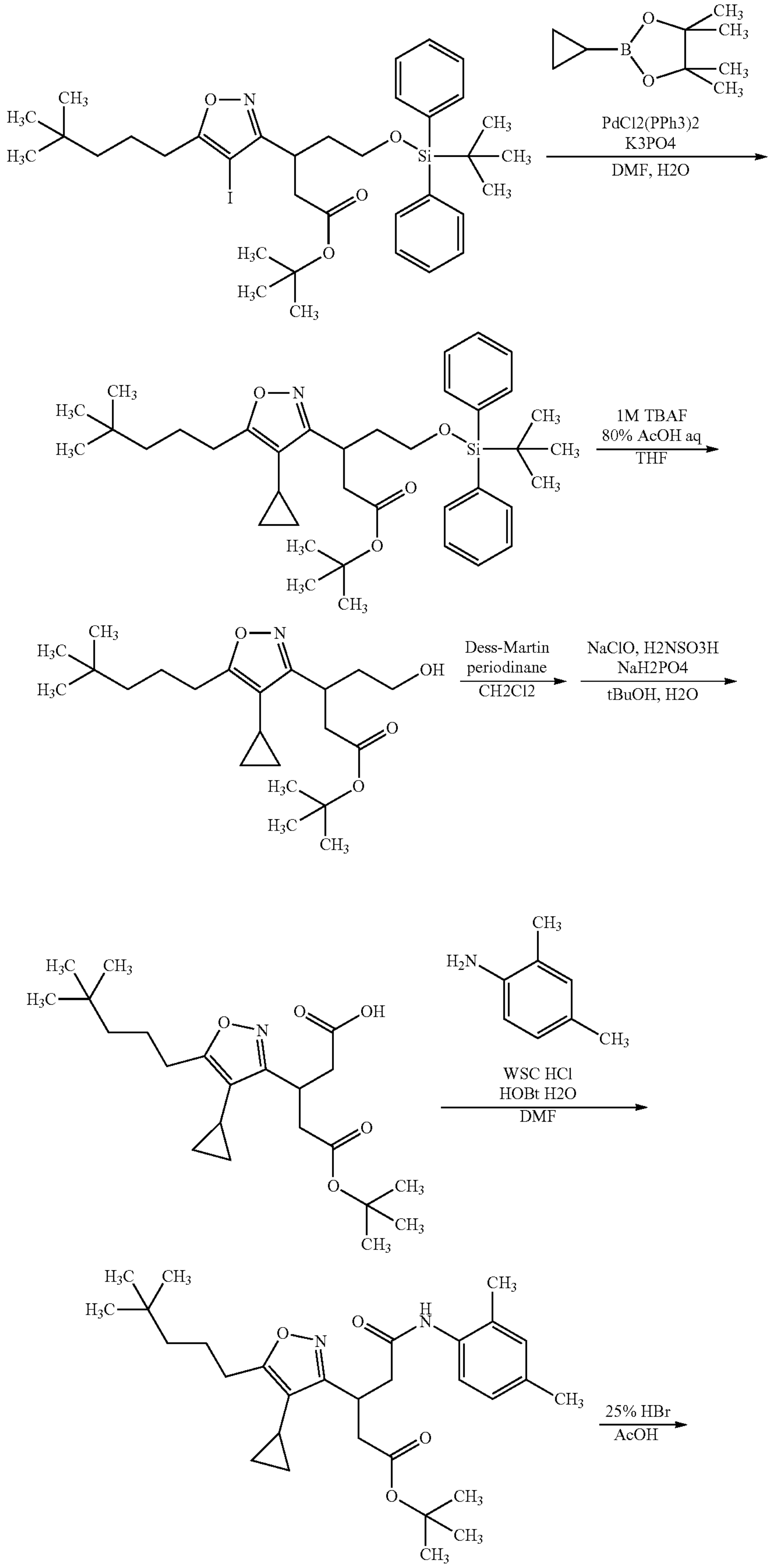

-continued
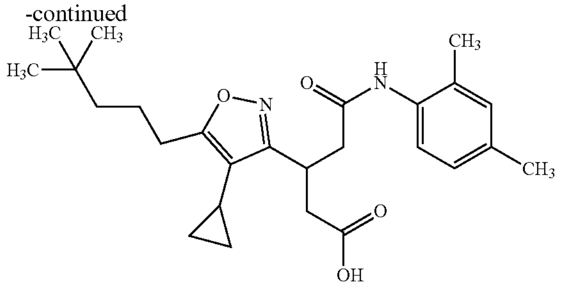
Example A-32
The compound is a typical example of compounds wherein $Y^c$ is $C_{1-6}$ alkylene group which may be substituted with the same or different 1 to 5 substituents selected from Group A, for example, $C_{1-6}$ alkylene group substituted with methyl group.
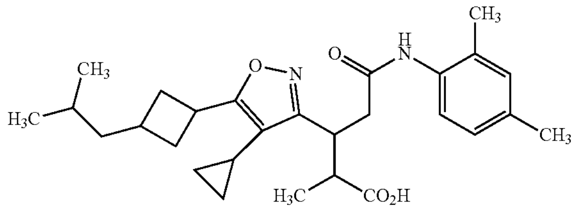
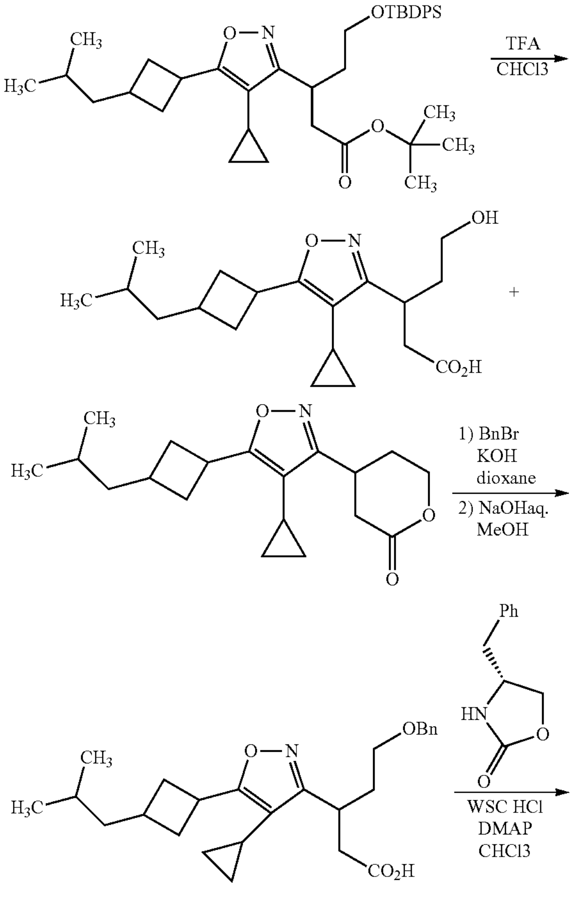
-continued
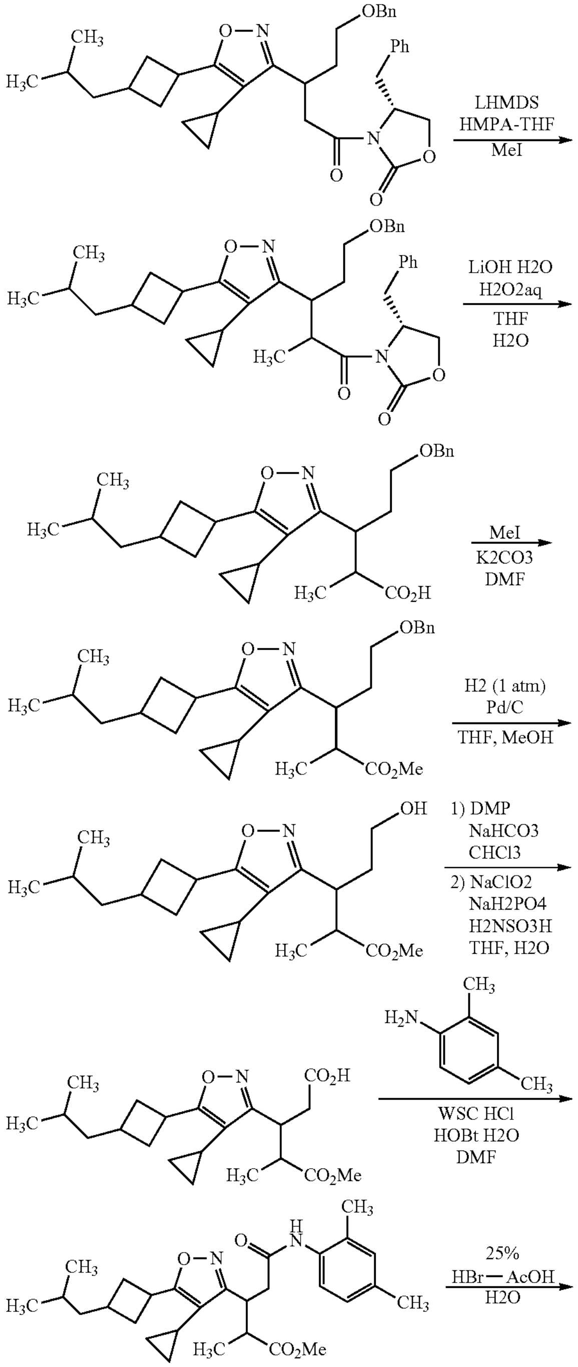

-continued
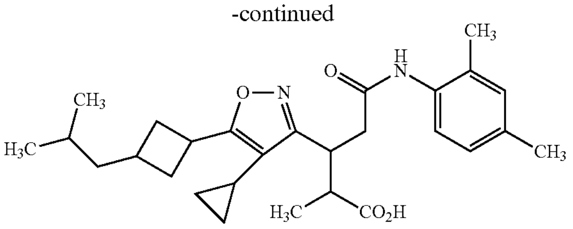
Example A-52
The compound is another typical example of compounds wherein $Y^c$ is $C_{1-6}$ alkylene group which may be substituted with the same or different 1 to 5 substituents selected from Group A, for example, $C_{1-6}$ alkylene group substituted with methyl group.
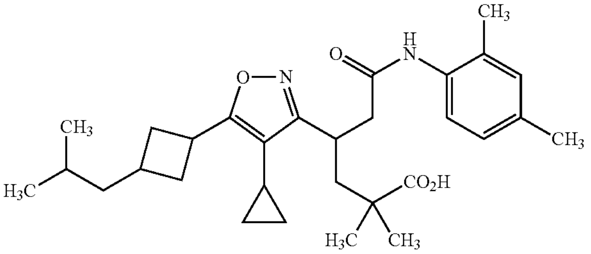
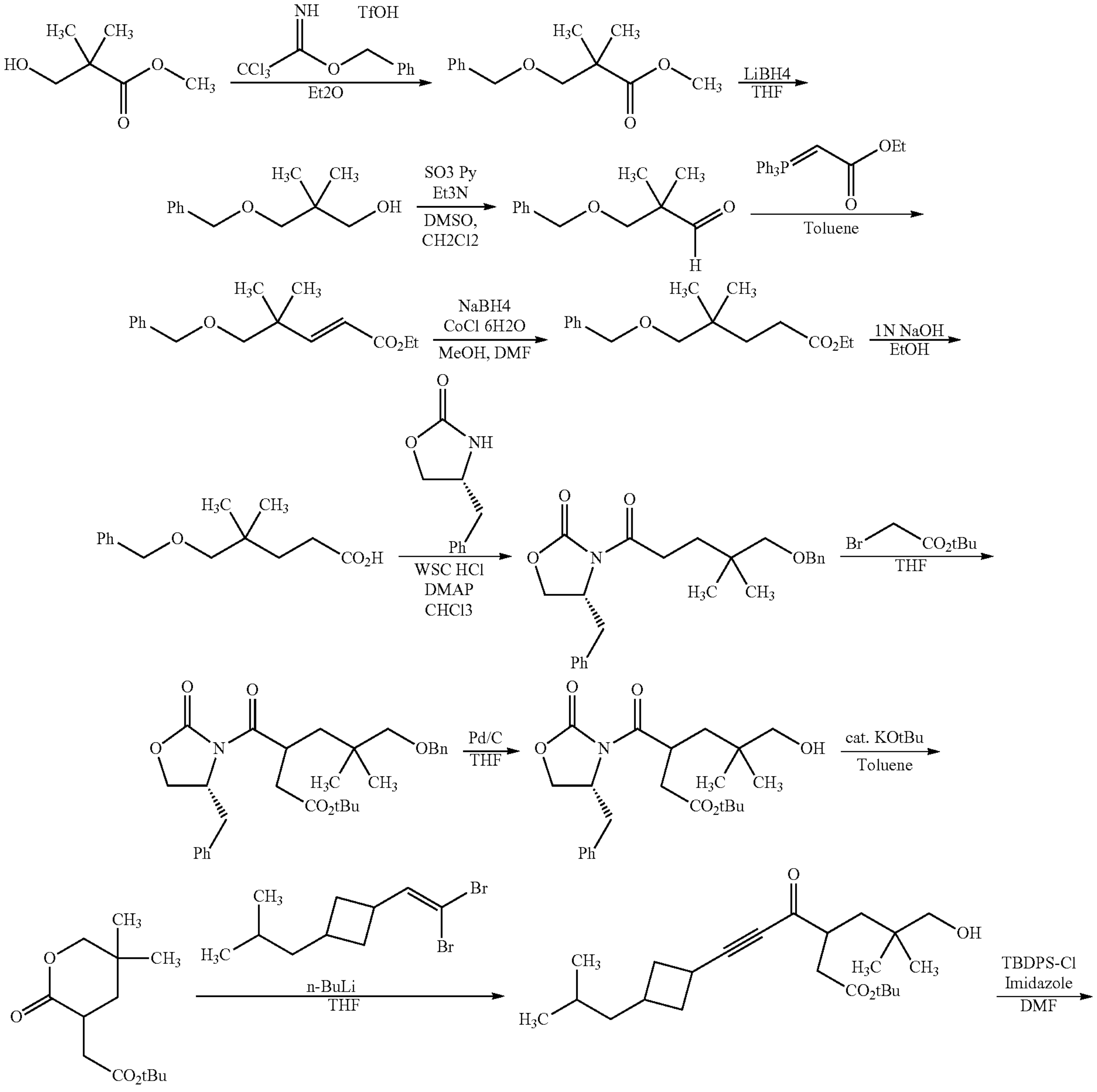

-continued
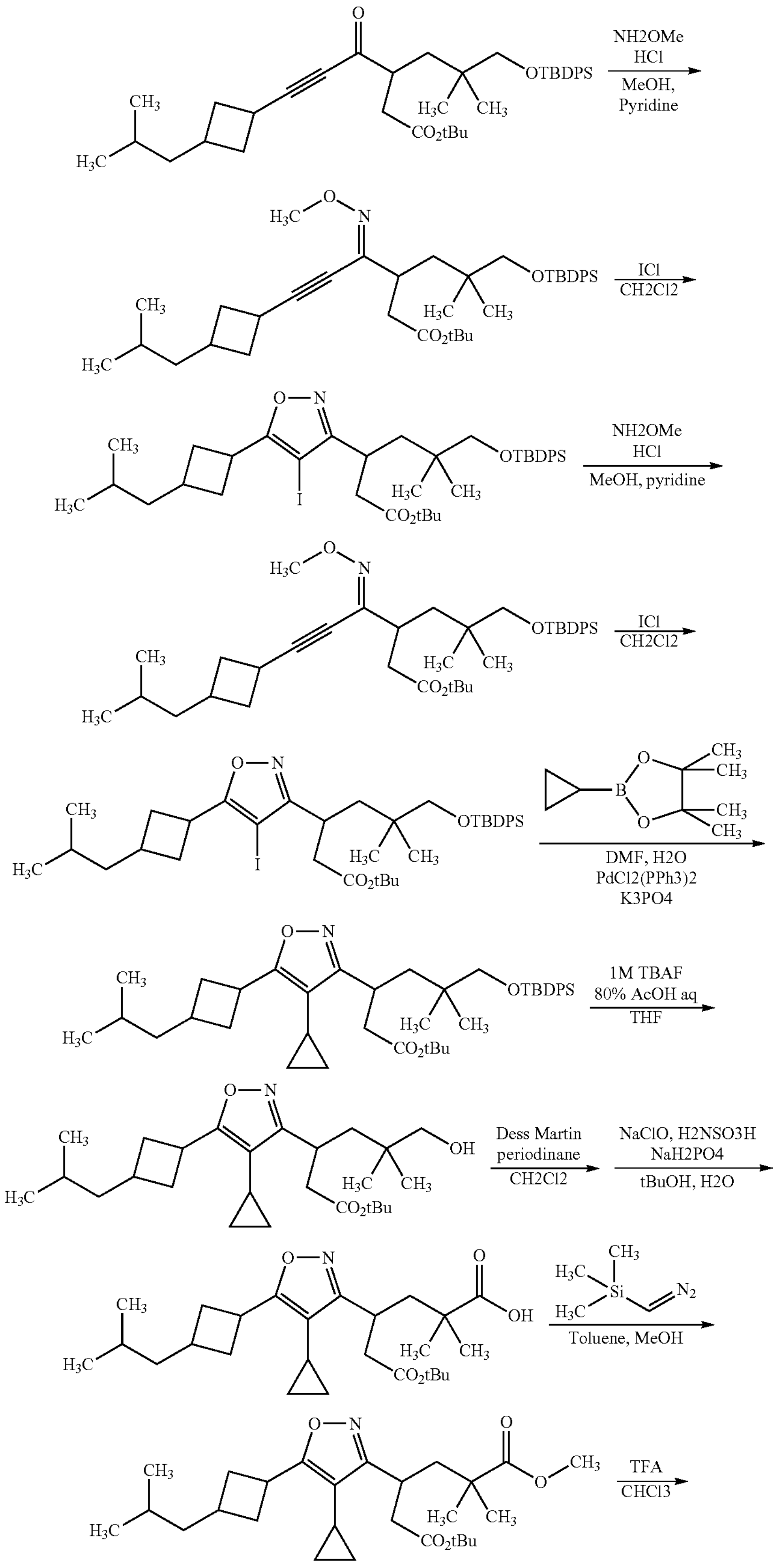

-continued
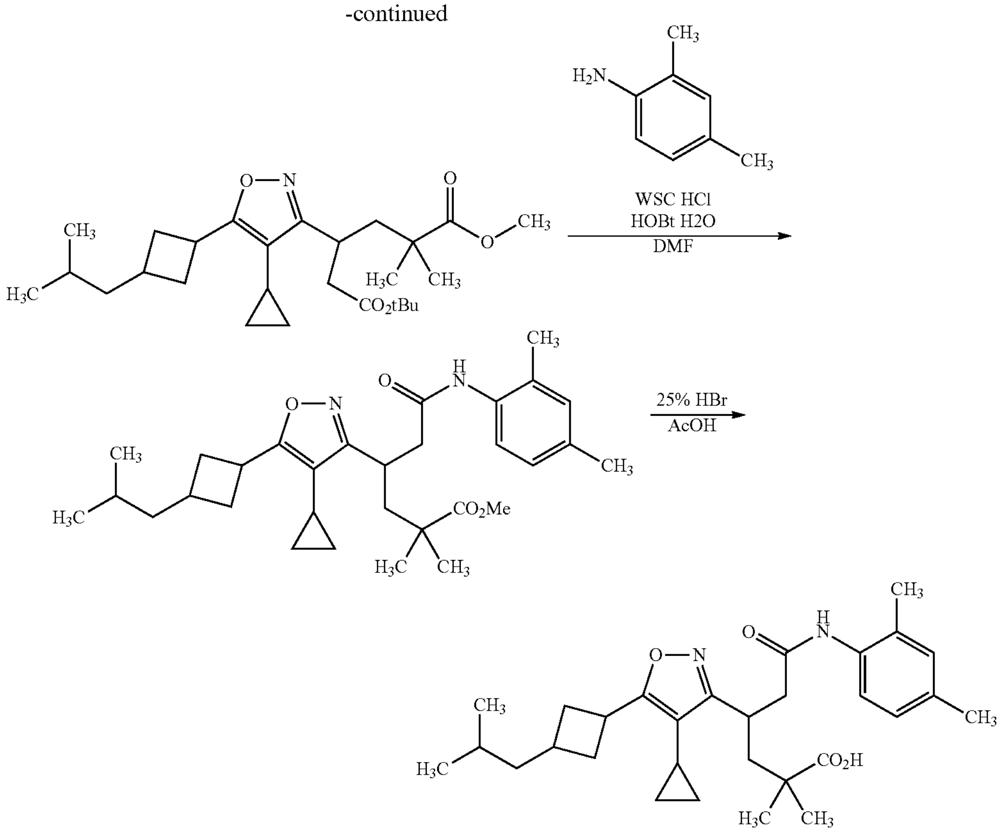
Example A-9
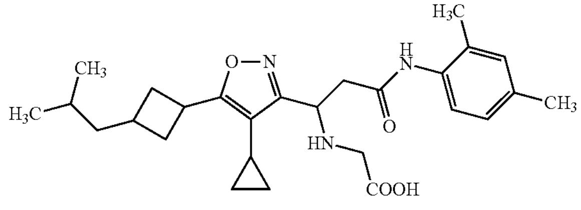
HCl
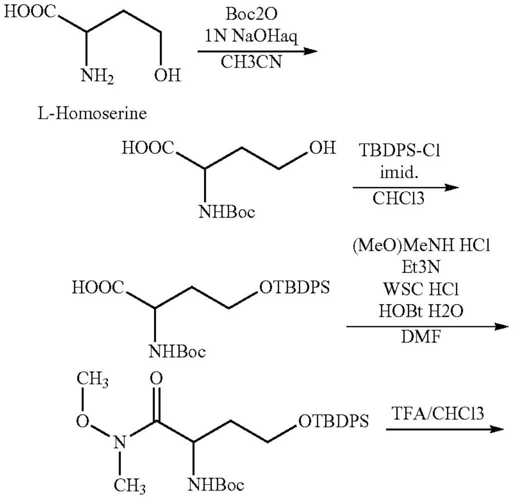
-continued
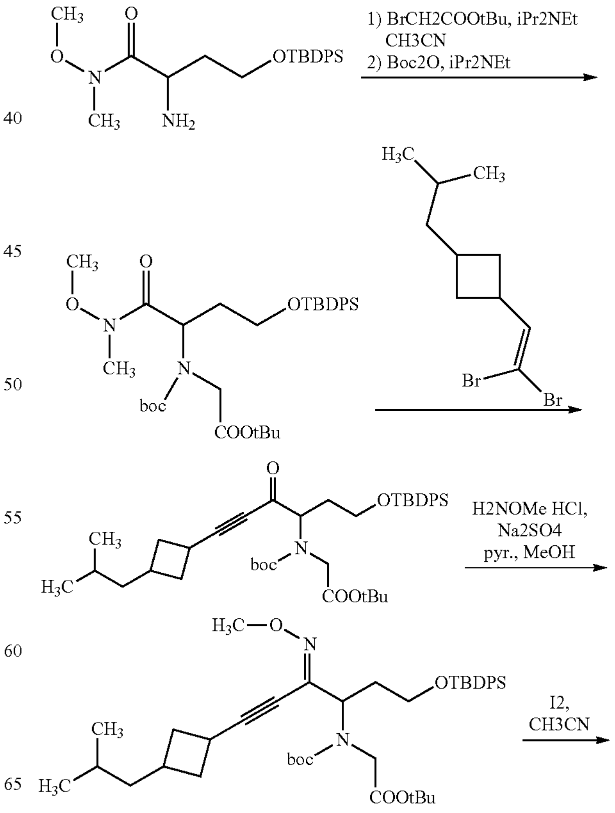

-continued
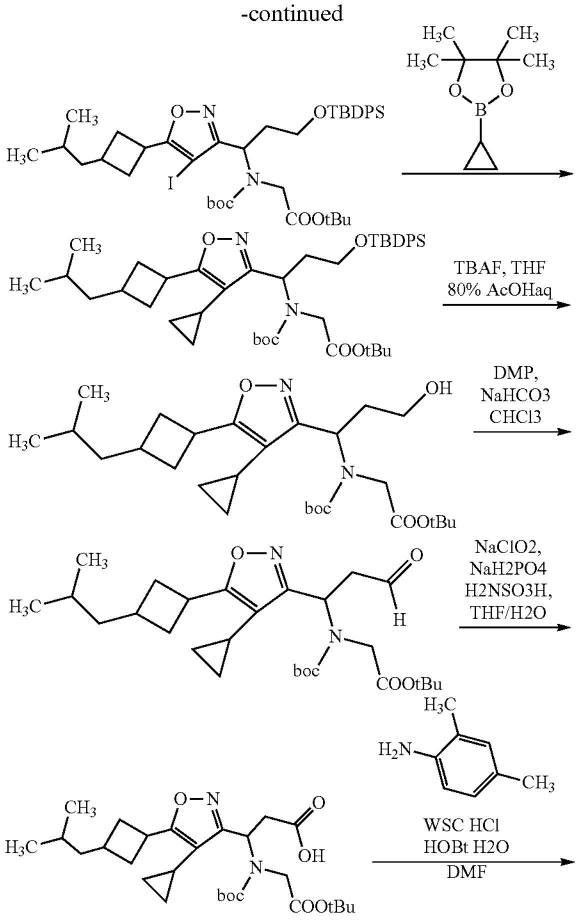
-continued
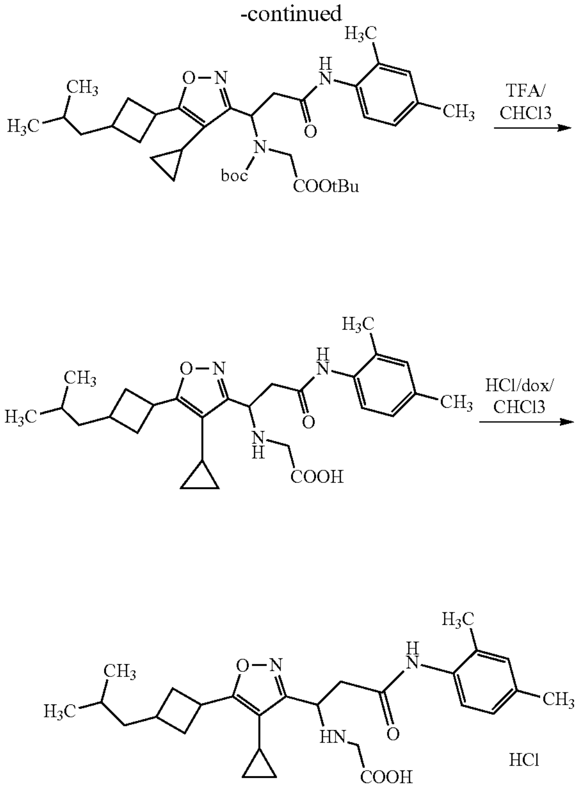
Preparation of Example A-86, A-87, A-88, and A-89
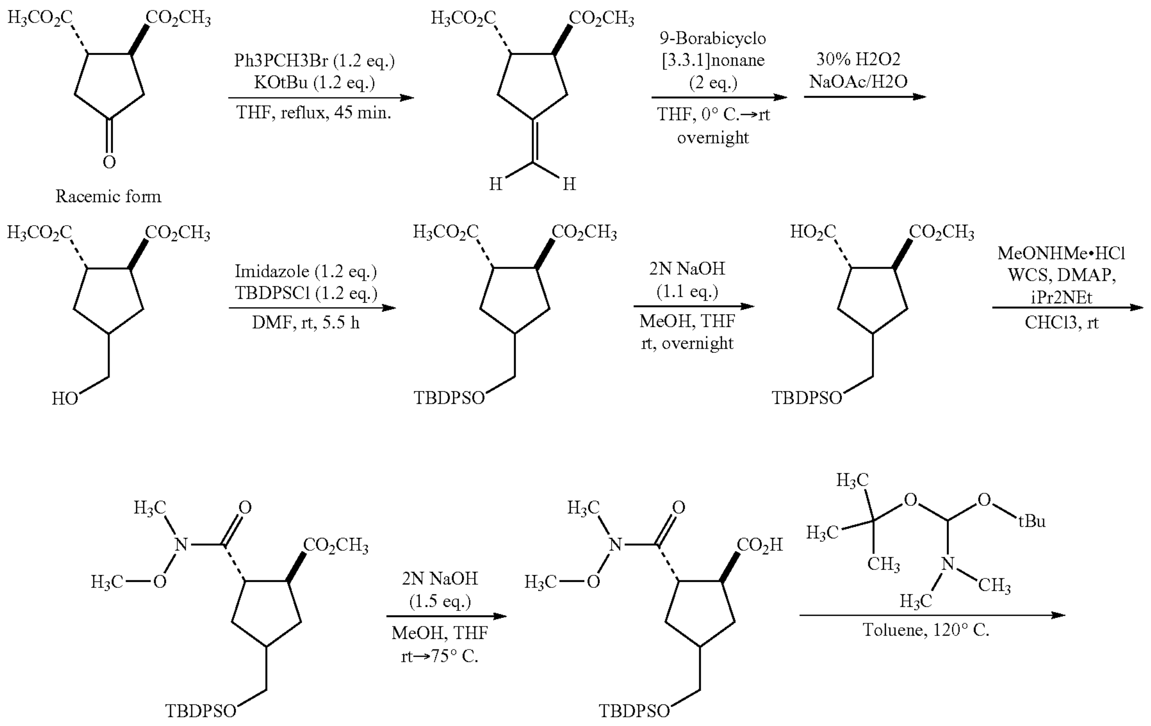

-continued
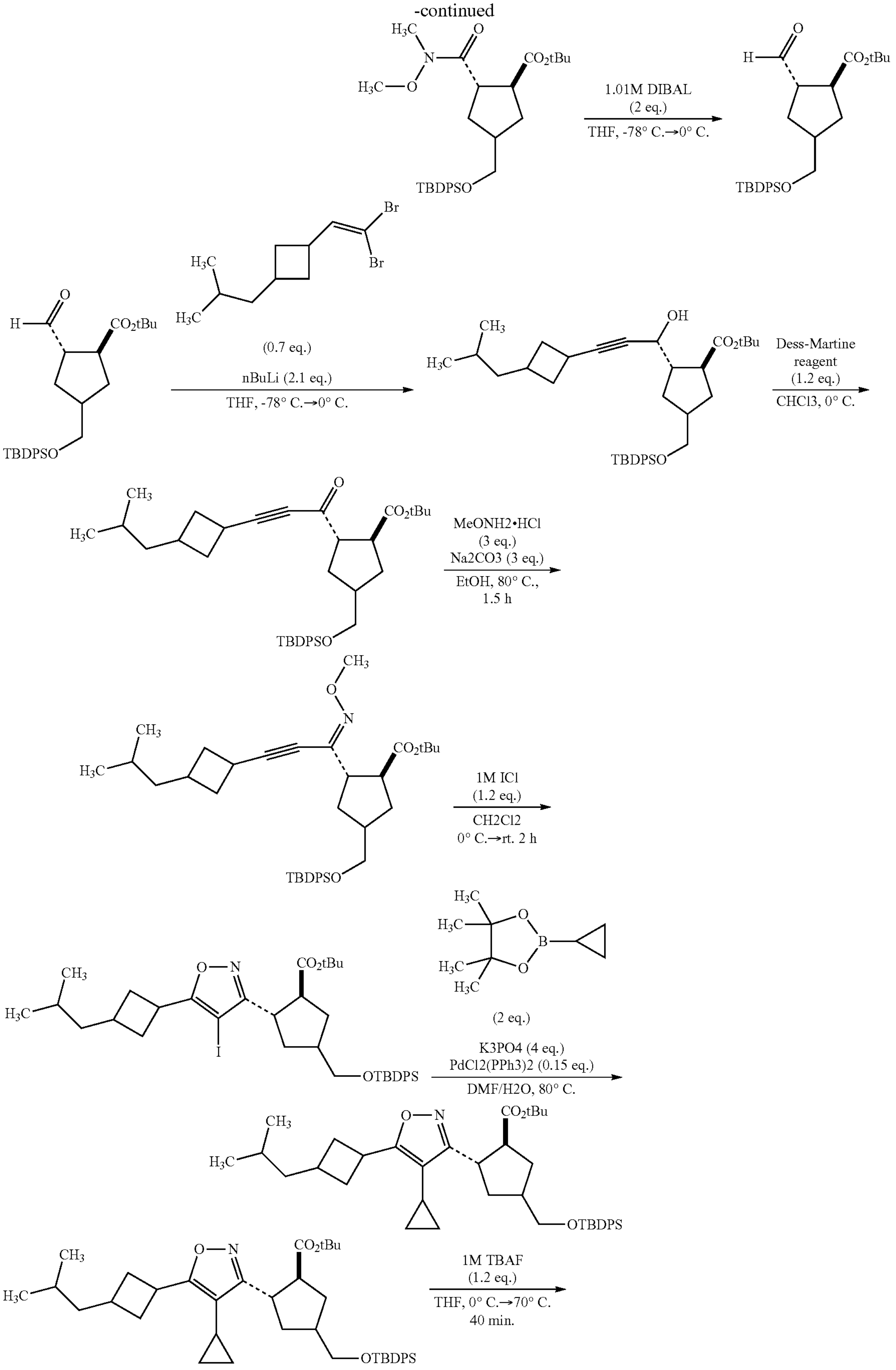

-continued
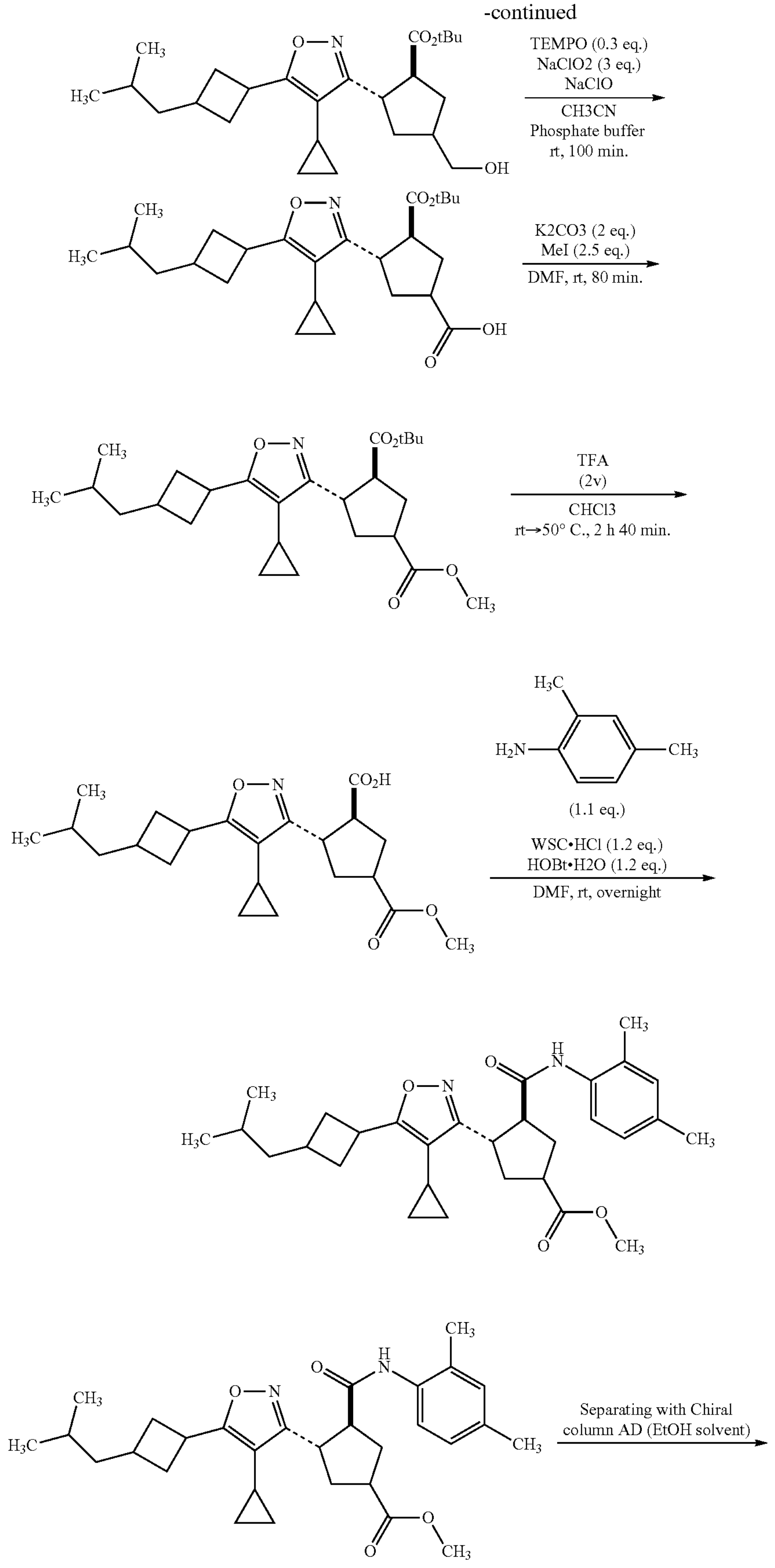

-continued

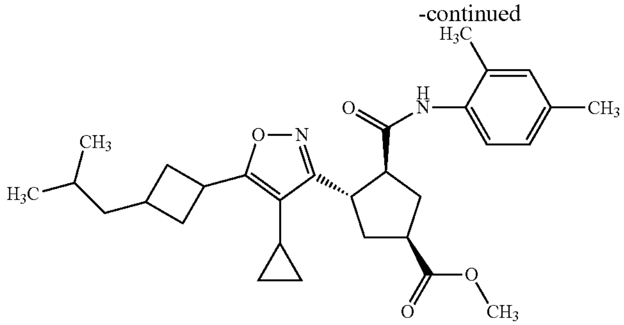

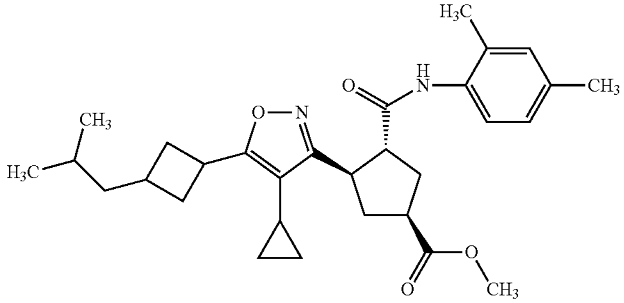

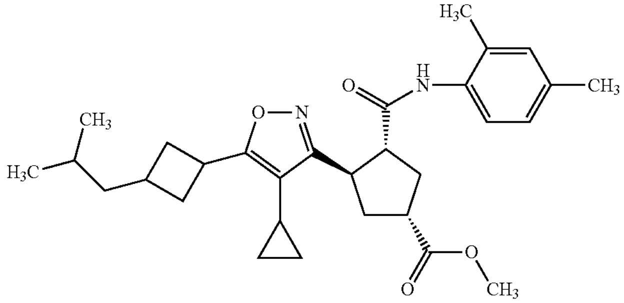

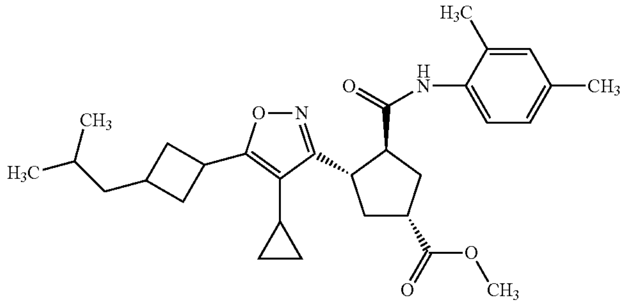

The above 4 stereoisomers were isolated and purified by recycle preparative HPLC (EA-86, EA-87, EA-88, EA-89 in the order of retention time from shortest to longest).

The condition for the purification was as follows:

Instrument: recycle preparative HPLC LC908 type (Japan Analytical Industry)

Column: DAICEL CHIRALPAK AD 2 cmφ×25 cm

Mobile phase: ethanol

Flow rate: 7.0 mL/minutes

Detection: UV (254 nm)

Each of the isolated and purified stereoisomers was analyzed by using a chiral column. The retention time of EA-86 (a methyl ester of Example A-86) was 11.7 minutes. The retention time of compound EA-87 (a methyl ester of Example A-87 ) was 12.0 minutes. The retention time of compound EA-88 (a methyl ester of Example A-88) was 14.5 minutes. The retention time of EA-89 (a methyl ester of Example A-89) is 15.7 minutes.

The condition for the analysis using the chiral column was as follows:

Instrument: HPLC System Shimadzu High performance liquid chromatography Prominence Column: DAICEL CHIRALPAK AD 0.46 cmφ×25 cm Column temperature: 30° C.

Mobile phase: ethanol

Flow rate: 0.5 mL/minutes

Detection: UV (254 nm)

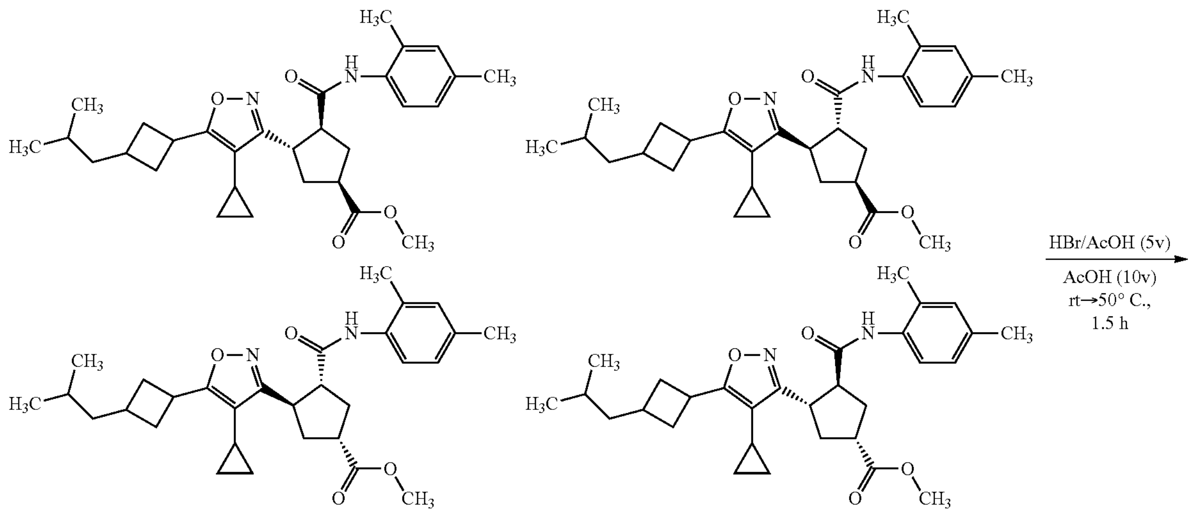

(Compound EA-86, EA-87, EA-88, EA-89)

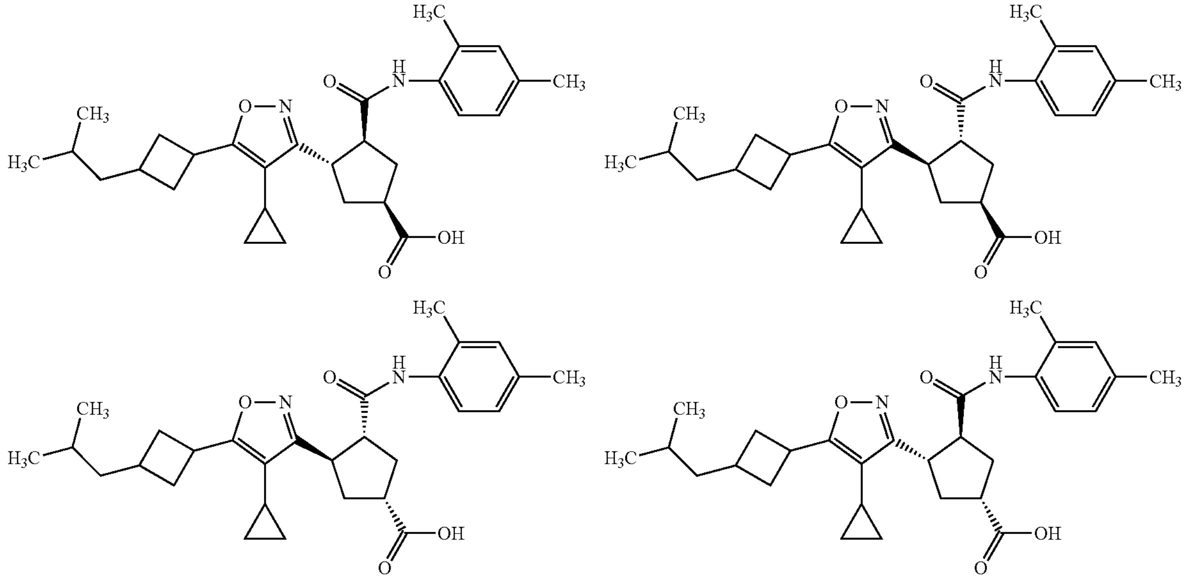

(Compound A-86, A-87, A-88, A-89)

EA-86, EA-87, EA-88, and EA-89 were hydrolyzed to give carboxylic acids A-86, A-87, A-88, and A-89, respectively. The resulting carboxylic acids were analyzed by using a chiral column. The retention time of carboxylic acids A-86, A-87, A-88, and A-89 was 8.0 minutes, 7.0 minutes, 7.9 minutes, and 11.2 minutes, respectively. The optical purity thereof was >99.5% ee, 71% ee, >99.5% ee, and 89% ee, respectively.

The condition for the analysis using the chiral column was as follows:

Instrument: HPLC System Shimadzu High performance liquid chromatography Prominence Column: DAICEL CHIRALPAK AD-3R 0.46 cm ϕ×15 cm Column temperature: 40° C.

Mobile phase: (A solution) 10 mM phosphate buffer (pH=2.6), (B solution) acetonitrile Composition of Mobile phase: A solution:B solution=30:70

Flow rate: 0.5 mL/min

Detection: UV (220 nm)

Preparation of Example A-112, A-113, and A-118

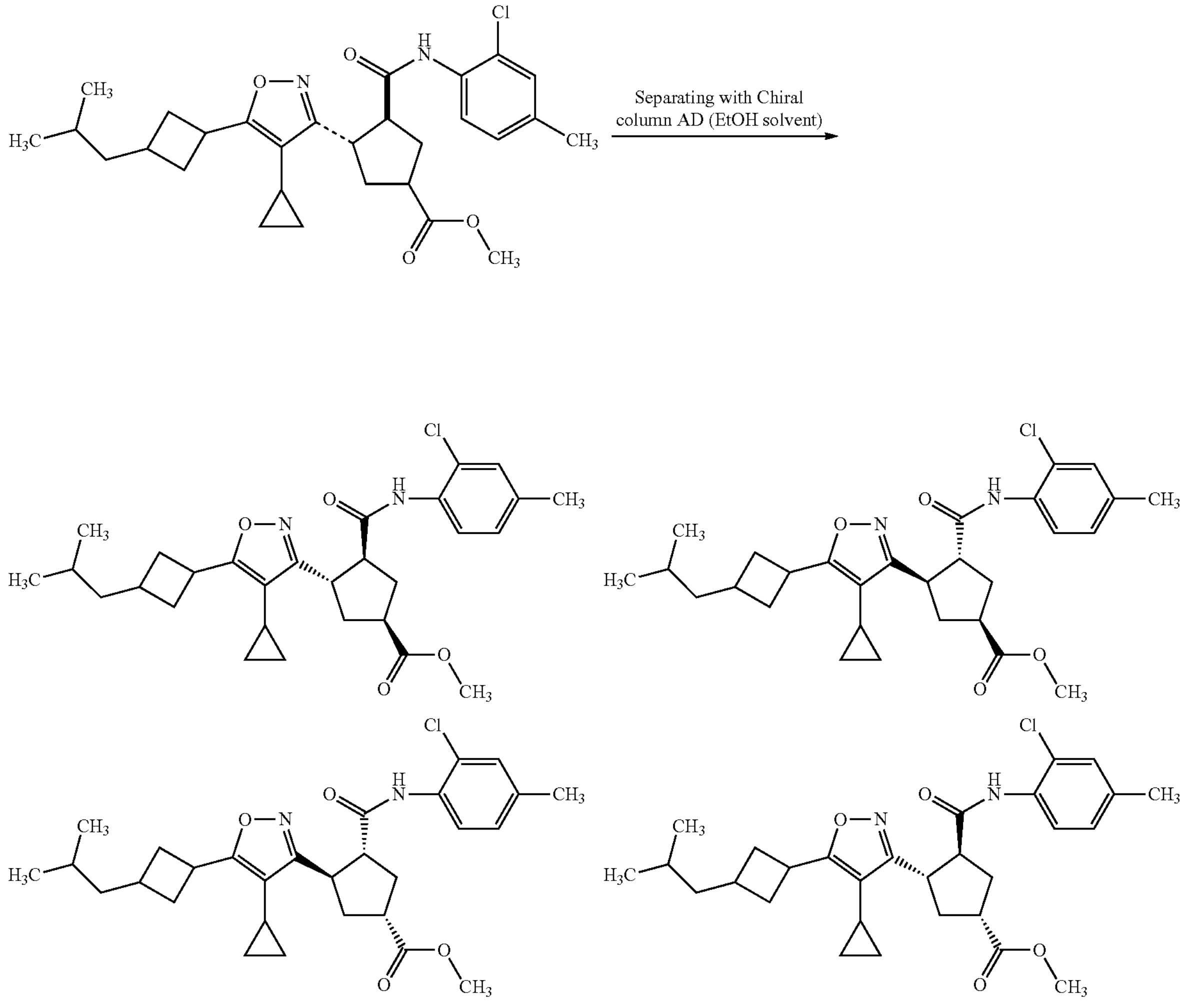

A purification procedure by recycle preparative HPLC gave EA-112, EA-113, and EA-118 which is a mixture of enantiomer(s) of EA-112 and enantiomer(s) of EA-113.

The condition for the purification was as follows:

Instrument: recycle preparative HPLC LC908 type (Japan Analytical Industry)

Column: DAICEL CHIRALPAK AD 2 cmϕ×25 cm

Mobile phase: ethanol

Flow rate: 7.0 mL/min

Detection: UV (254 nm)

Each compound was analyzed by using a chiral column.

The retention time of EA-112 (a methyl ester of Example A-112) was 14.9 minutes. The retention time of EA-113 (a methyl ester of Example A-113) was 16.2 minutes. The retention time of EA-118 (a methyl ester of Example A-118) was 19.4 minutes.

The condition for the analysis using the chiral column was as follows:

Instrument: HPLC System Shimadzu High performance liquid chromatography Prominence Column: DAICEL CHIRALPAK AD 0.46 cmϕ×25 cm Column temperature: 30° C.

Mobile phase: ethanol

Flow rate: 0.5 mL/min

Detection: UV (254 nm)

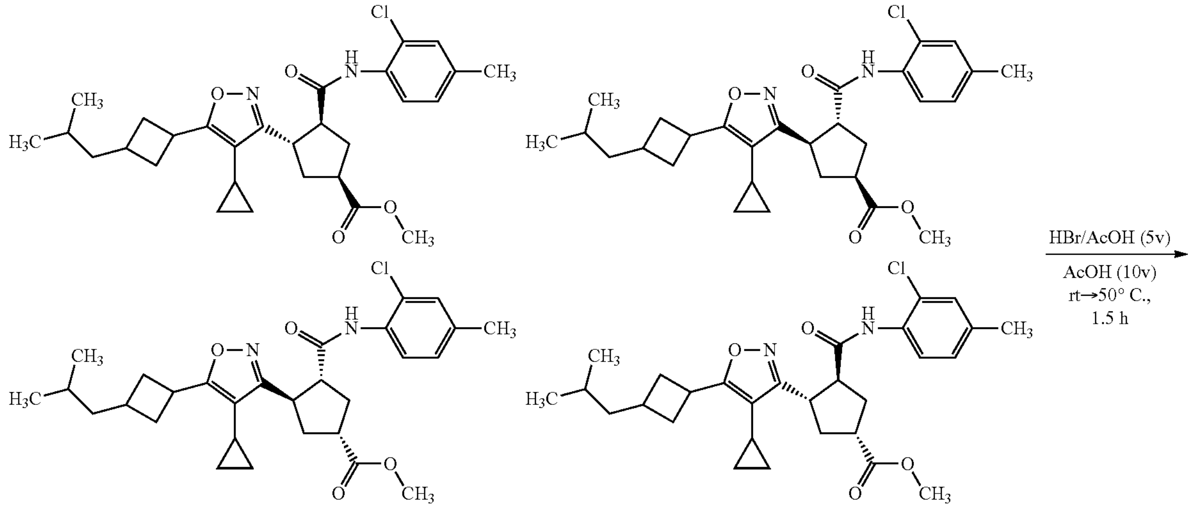
(Compound EA-112, EA-113, EA-118)
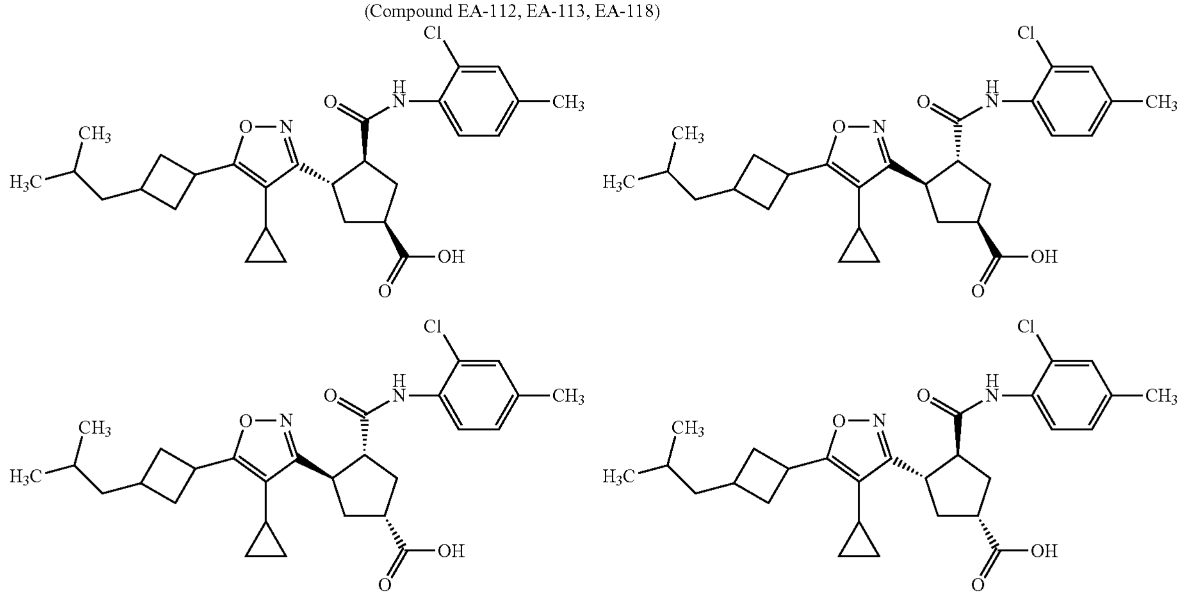
(Carboxylic acids A-112, A-113, and A-118 Which is a Mixture of Enantiomer(s) of A-112 and Enantiomer(s) of A-113)
Compound EA-112, EA-113, and EA-118 were hydrolyzed to give carboxylic acids A-112, A-113, and A-118 which is a mixture of enantiomer(s) of A-112 and enantiomer(s) of A-113, respectively.
Preparation Method of Example C Series
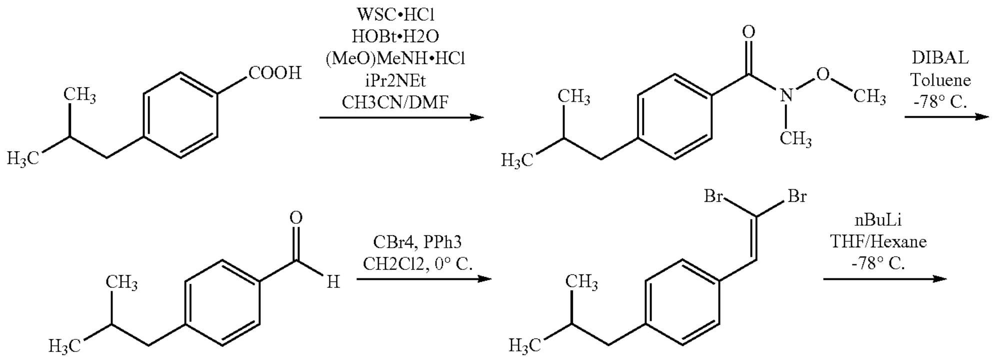

-continued
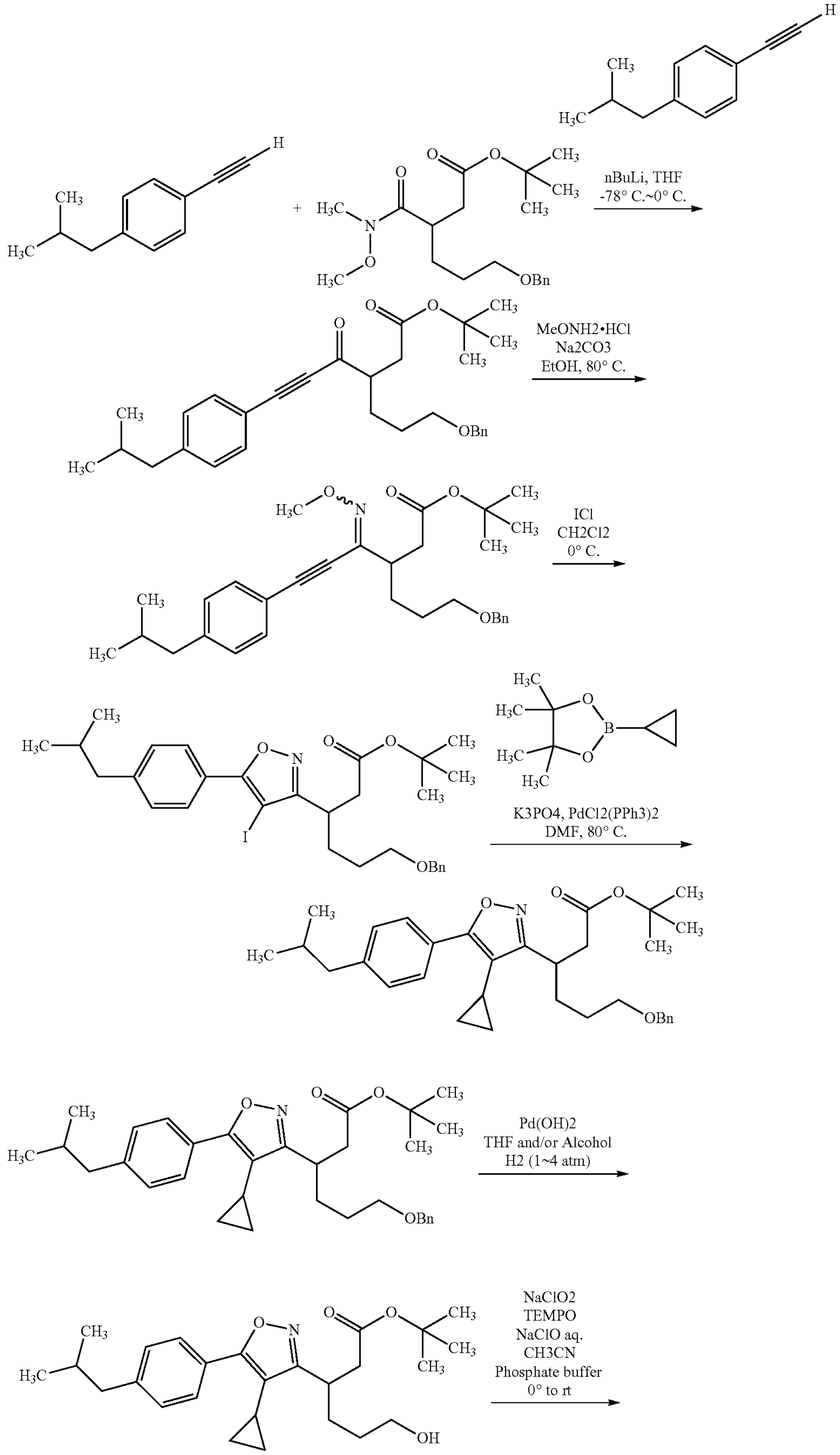

-continued
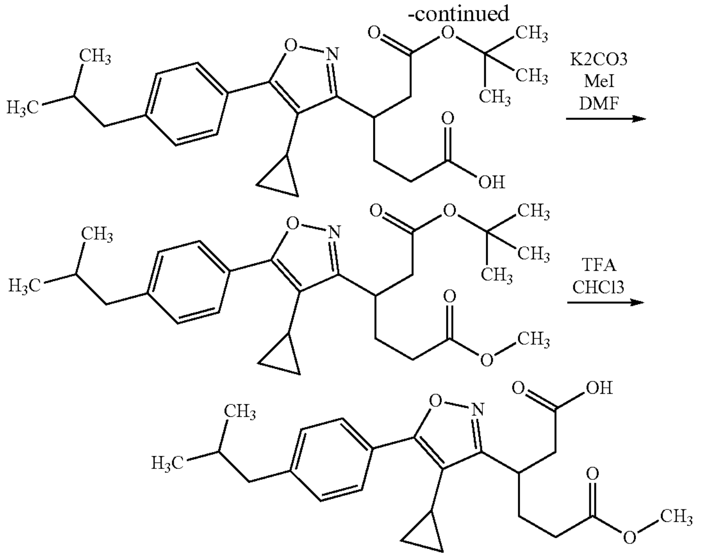
Example C-1
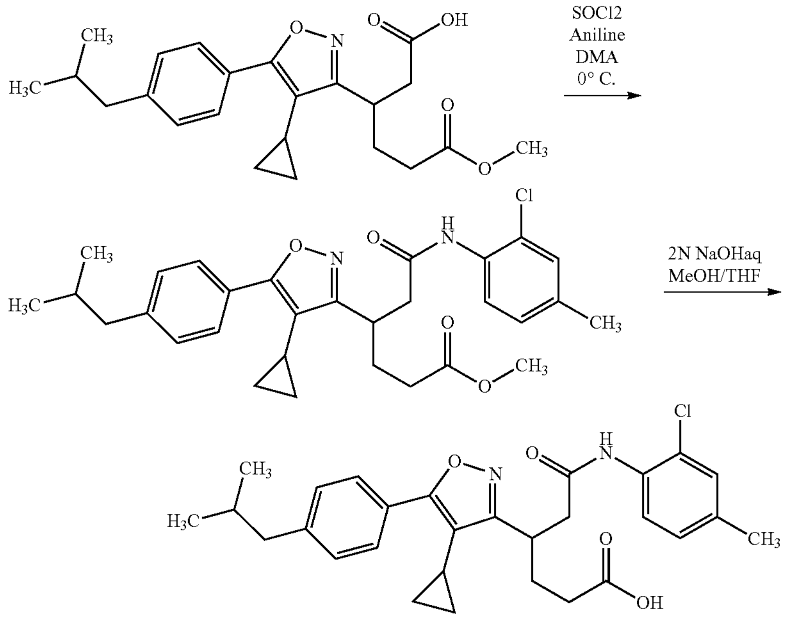
Example C-2
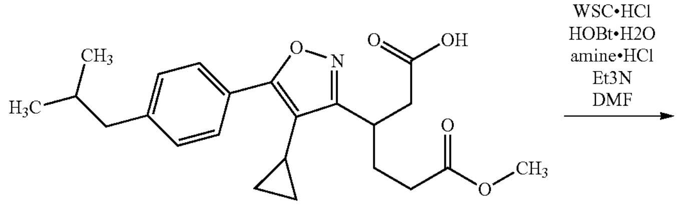

-continued
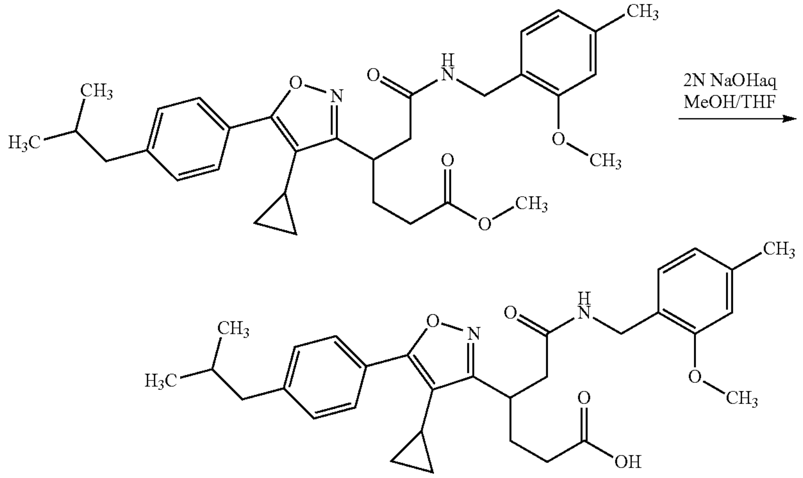
Example D-1, D-3
Preparation Method for Example D Series
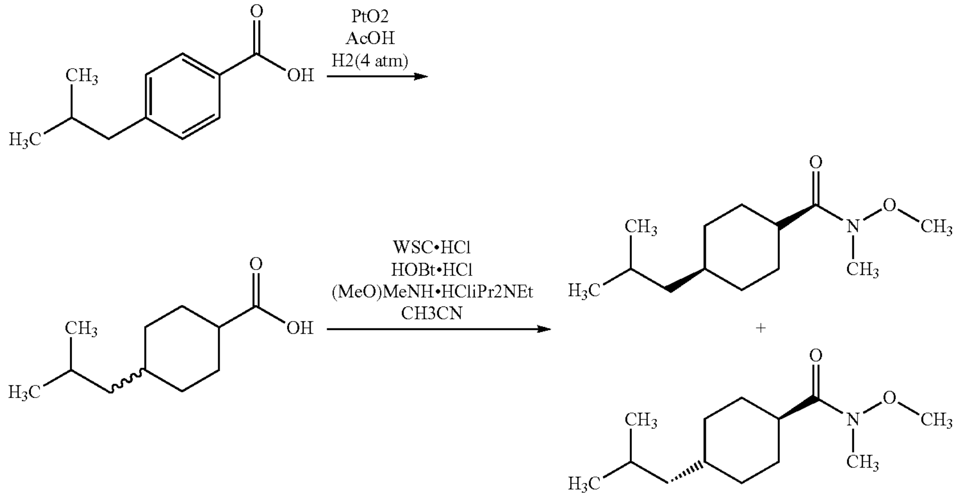
A mixture of the Weinreb amide intermediates as showed below was separated into cis-isomer and trans-isomer thereof through the purification by silica gel column chromatography.
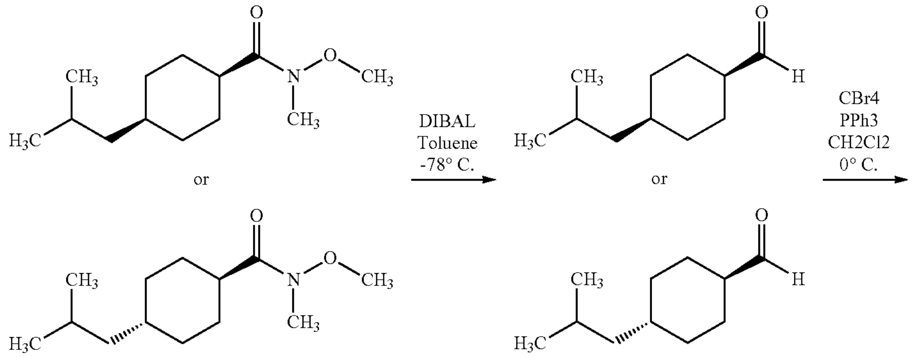

-continued
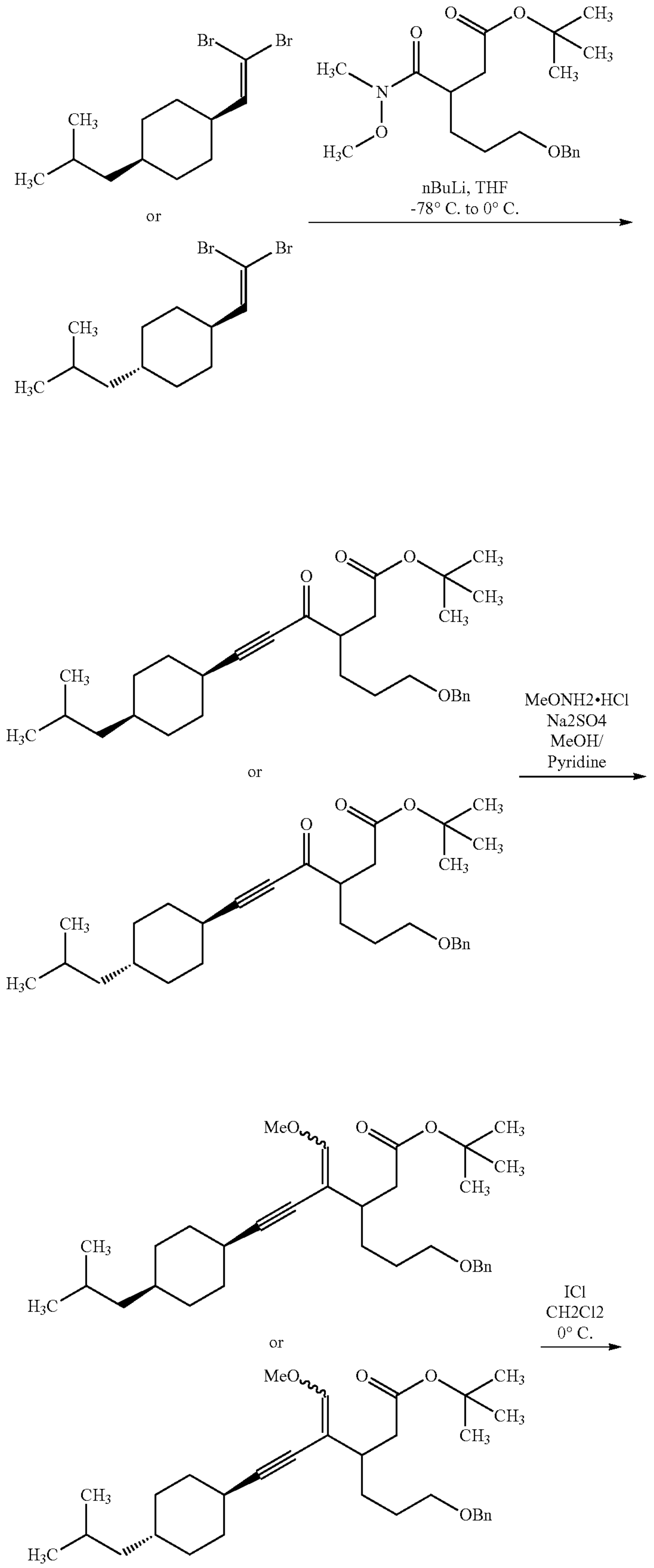

-continued
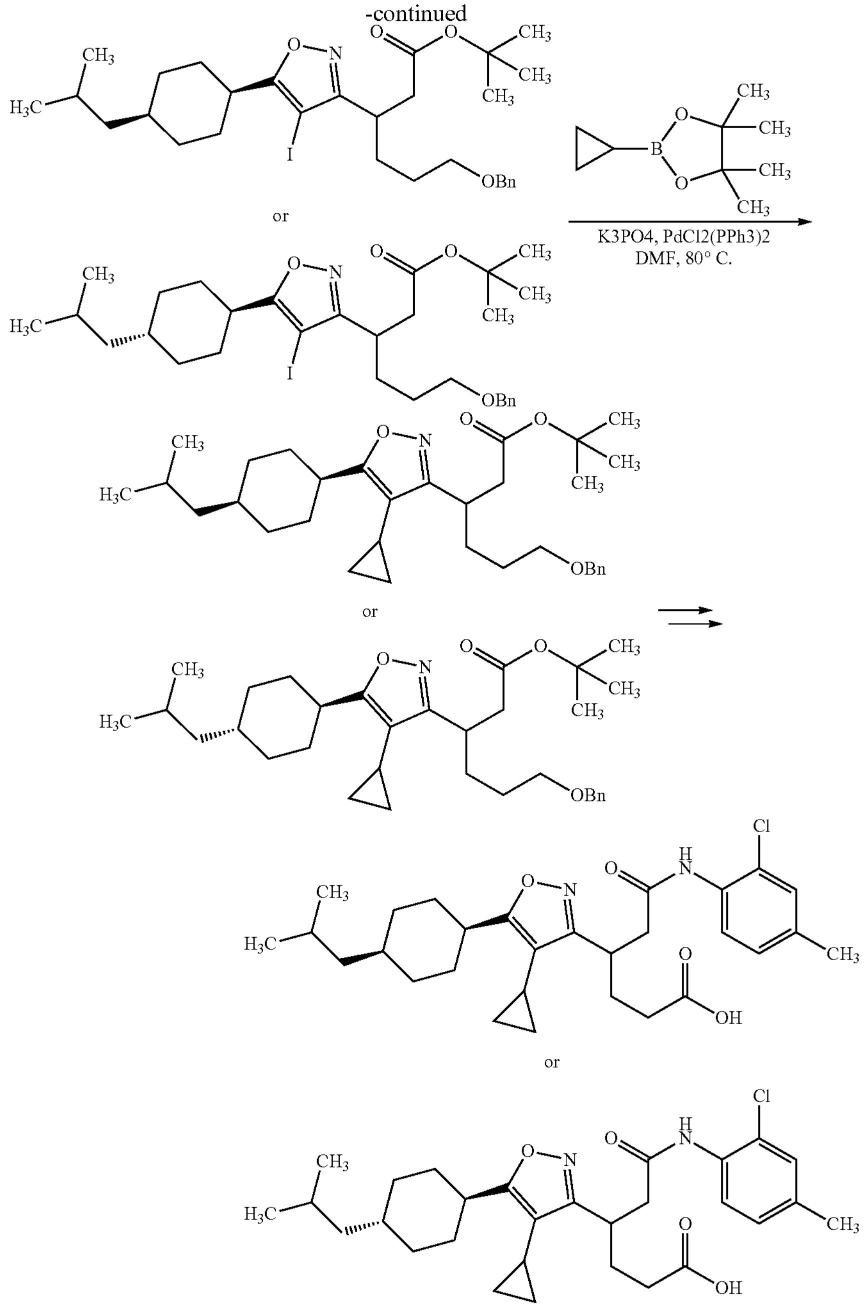
Preparation of Example A-106 and A-105
Example A-106
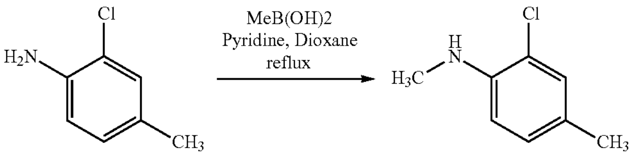

-continued
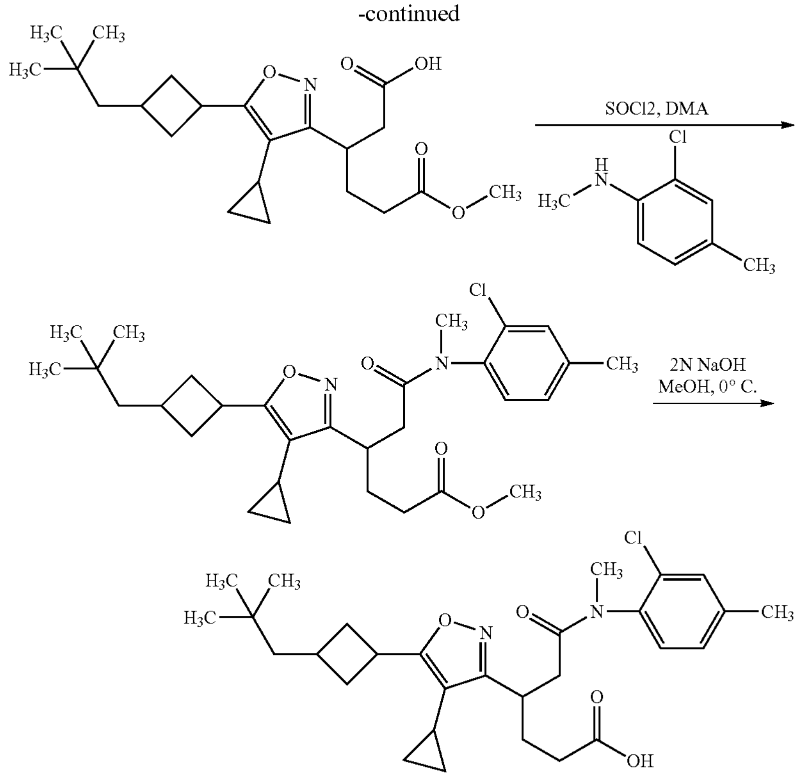
Preparation of Example A-105
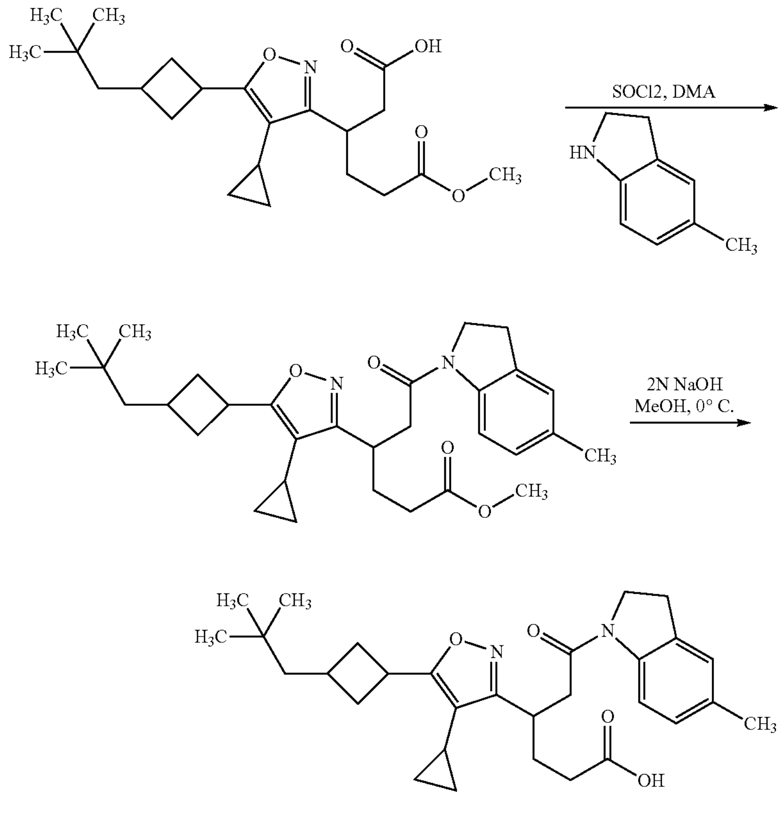

Preparation of Example A-110

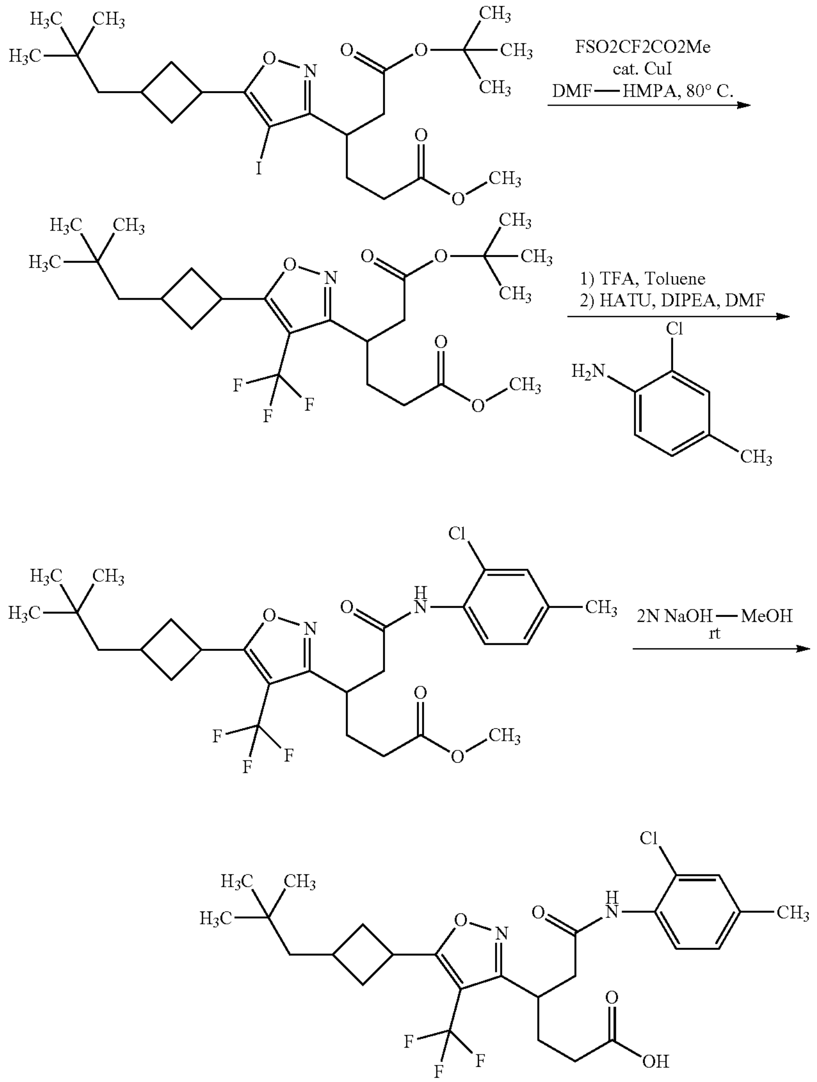

Formulation examples of the present invention include for example the following, but which should not be construed as limitative.

Formulation Example 1

Preparation of Capsule

| | |
|---|---|
| (1) Compound of Example A-1 | 30 mg |
| (2) Microcrystalline cellulose | 10 mg |
| (3) Lactose | 19 mg |
| (4) Magnesium stearate | 1 mg |

(1), (2), (3) and (4) are mixed and filled in a gelatin capsule.

Formulation Example 2

Preparation of Tablet

| | |
|---|---|
| (1) Compound of Example A-1 | 10 g |
| (2) Lactose | 50 g |
| (3) Corn starch | 15 g |
| (4) Carmellose calcium | 44 g |
| (5) Magnesium stearate | 1 g |

The entire amounts of (1), (2) and (3) and 30 g of (4) are mixed with water and dried in vacuo and then granulated. The granulated powder is mixed with 14 g of (4) and 1 g of (5) and tableted by a tableting machine. In this way, 1000 tablets can be obtained, each of which contains 10 mg of Compound of Example A-1.

Biological Assay1

Pharmacological effects of the typical compounds of the present invention were observed.

In Vitro Assay of Inhibitory Effect Against RORγ Transcriptional Activity

Inhibitory effect of test article on transcriptional activity of RORγ was measured by means of the following luciferase reporter gene assay.

A cDNA encoding human and mouse RORγ ligand binding domain (LBD) were obtained based on the reported sequences (Genebank asseccion number and sequence: human, NM_005060.3 and from Ser253 to Lys518; mouse, NM_011281.2 and from Ile251 to Lys516).

The cDNA of human RORγ or mouse RORγ was inserted into pFA-CMV vector (Strategene), which expresses GAL4-DNA binding domain fusion protein.

The resulting plasmids are hereinafter referred to as GAL4-hRORγ plasmid and GAL4-mRORγ plasmid, respectively.

Human or mouse GAL4-RORγ plasmid was transiently co-transfected into Chinese hamster ovary cells (CHO cells) with pGL5-Luc plasmid, a reporter plasmid expressing firefly luciferase depending on GAL4.

TransIT CHO transfection reagent (Mirus) was used to co-transfect human or mouse GAL4-RORγ plasmid into CHO cells with pGL5-Luc plasmid.

One day before the assay, CHO cells were suspended in HAM F-12 Nutrient medium containing 10 v/v % fetal bovine serum and seeded at $6\times10^6$ cells per 175 $cm^2$ cell culture flask.

Fifty four micro liters of Transit-CHO reagent was added into a 15 ml tube containing 1.16 ml of HAM F-12 Nutrient medium without fetal bovine serum and incubated at room temperature for 10 min.

A total 36 uL plasmid solution containing the GAL4-hRORγ plasmid (400 ng), pGL-Luc plasmid (9000 ng) and pcDNA3 plasmid (8600 ng) were added into the tube and mixed gently.

In case of mouse assay, the GAL4-mRORγ plasmid (250 ng), pGL-Luc plasmid (9000 ng) and pcDNA3 plasmid (8750 ng) were added.

The mixture was incubated at room temperature for 10 min.

Nine micro liters of CHO Mojo Reagent was then added into each tube and mixed gently. The mixture was incubated at room temperature for 10 min.

The resultant transfection reagent was applied to the cell culture.

After incubation at 37° C., 5% $CO_2$ for 4 hr, the transfected CHO cells were harvested by a trypsin treatment.

The collected cells were resuspended in HAM F-12 Nutrient medium supplemented with 10 v/v % fetal bovine serum and plated into a 384-well-white plate at 8,000 cells/50 uL/well.

The plate was incubated at room temperature for 1 hour and then further incubated at 37° C., 5% $CO_2$ for 3 hours.

The test articles were dissolved in dimethylsulfoxide (DMSO) to obtain a concentration of 10 mmol/L. The resulting solution was diluted with the medium just before use and added to the cells in the plate to prepare 8 different concentrations of the test article.

The final concentration of DMSO was 0.1 v/v %. After the addition of the test articles, the cells were incubated at 37° C., 5% $CO_2$ for 2 days.

Cell viability was tested by a fluorescence method using Resazurin (invitrogen).

Two days after the addition of the test article, Resazurin was diluted with culture medium to make the 20 umol/L resazurin solution.

10 uL of the diluted resazurin solution was added into the 384-well-plate.

Then, the fluorescence was measured immediately at 615 nm with the excitation wavelength of 570 nm (0 hr reading). After incubation at 37° C., 5% $CO_2$ for 2 hr, the fluorescence was measured at 615 nm with the excitation wavelength of 570 nm again (2 hr reading).

The fluorescence counts (2 hr−0 hr) were calculated by subtracting the 0 hr readings from the 2 hr readings.

The luminescence count in the cells treated with 0.1% DMSO alone was defined as 100%, and the cell viability in the test article was calculated as a percentage (%-of-control) based on the value of 0.1% DMSO alone.

When the cell viability is 70% or less, it was judged that the test article has cytotoxicity.

RORγ transcriptional activity was detected as the intracellular luciferase activity using SteadyLite HTS Reporter Gene Assay System (Perkin Elmer).

StedyLite Reagent was diluted five-fold into a solution containing 10 mM Tricine, 0.2% w/v BSA, 0.02% v/v Tween-20 to obtain the luciferase substrate solution.

After the measurement of the cell viability using Resazurin, the culture media in the 384 well-plate were removed. Then the Luc substrate solution was added into each well.

After the incubation at room temperature for 10 minutes, luminescence of each well was measured by a microplate reader.

The luciferase activity derived from the luminescence count in the vehicle-control well treated with 0.1% DMSO alone was defined as 100%, and the luciferase activity in the test article was calculated as a percentage (%-of-control) based on the value of the vehicle-control.

EC50 value of test article was calculated by curve fitting with GraphPad Prism.

The luminescence counts at the concentration of the test article where the cytotoxicity was observed were excluded from the data analysis.

The results are shown in FIGS. 42-48.

In FIGS. 42-48, the values with % is the activity of the test article which was calculated as a percentage (%-of-control) based on the value of the vehicle-control treated with 0.1% DMSO alone (100%).

The activities of Examples A-34 and A-41 in human which were calculated as a percentage (%-of-control) based on the value of the vehicle-control treated with 0.1% DMSO alone (100%) were 50% and 78%, respectively.

INDUSTRIAL APPLICABILITY

The present invention is useful in treating or preventing autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes; allergic disease such as asthma; dry eye; fibrosis such as pulmonary fibrosis and primary biliary cirrhosis; and metabolic disease such as diabetes.

The invention claimed is:

1. A compound of formula [III]:

[III]

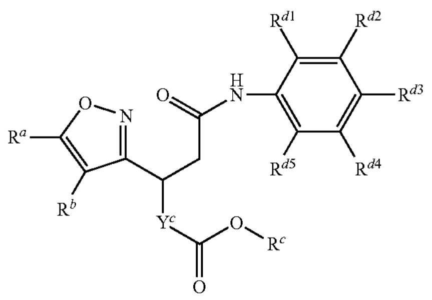

wherein $R^a$ is (1) $C_{5-12}$ alkyl group which may be substituted with the same or different 1 to 5 substituents selected from Group A, or (2)

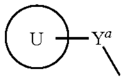

wherein $Y^a$ is (i) single bond, or (ii) $C_{1-6}$ alkylene group, and cyclic moiety U is (i) $C_{3-7}$ cycloalkyl group which may be substituted with the same or different 1 to 5 substituents selected from Group A, (ii) $C_{5-11}$ spirocyclic cycloalkyl group which may be substituted with the same or different 1 to 5 substituents selected from Group A, or (iii) $C_{6-10}$ aryl group which may be substituted with the same or different 1 to 5 substituents selected from Group A;

$R^b$ is a group selected from the following (1) to (3):

(1) $C_{1-3}$ alkyl group which may be substituted with the same or different 1 to 5 substituents selected from Group A, (2) $C_{2-3}$ alkenyl group which may be substituted with the same or different 1 to 5 substituents selected from Group A, (3) $C_{3-7}$ cycloalkyl group which may be substituted with the same or different 1 to 5 substituents selected from Group A;

$R^c$ is (1) hydrogen atom, or (2) $C_{1-6}$ alkyl group;

$Y^c$ is a $C_{1-6}$ alkylene group which may be substituted with the same or different 1 to 5 substituents selected from Group A, $R^{d1}$, $R^{d2}$, $R^{d3}$, $R^{d4}$, and $R^{d5}$ are the same or different group selected from the following (1) to (7):

(1) hydrogen atom (2) halogen atom, (3) $C_{1-6}$ alkyl group which may be substituted with the same or different 1 to 5 substituents selected from Group A, (4) —$OR^{d10}$ wherein $R^{d10}$ is hydrogen atom or $C_{1-6}$ alkyl group which may be substituted with the same or different 1 to 5 substituents selected from Group A, (5) —$COOR^{d11}$ wherein $R^{d11}$ is hydrogen atom or $C_{1-6}$ alkyl group, (6) $C_{3-7}$ cycloalkyl group which may be substituted with the same or different 1 to 5 substituents selected from Group A, (7) cyano group, or alternatively $R^{d1}$ and $R^{d2}$, or $R^{d2}$ and $R^{d3}$ can be taken together to form a $C_{6-10}$ aryl ring fused to the benzene ring to which they are all attached wherein the $C_{6-10}$ aryl ring may be substituted with the same or different 1 to 4 substituents selected from Group A; and Group A is (a) $C_{1-6}$ alkyl group, (b) halogen atom, and (c) —$OR^{A1}$ wherein $R^{A1}$ is hydrogen atom or $C_{1-6}$ alkyl group, or a pharmaceutically acceptable salt thereof.

2. The compound according to claim 1, wherein the compound is of formula [IV]:

[IV]

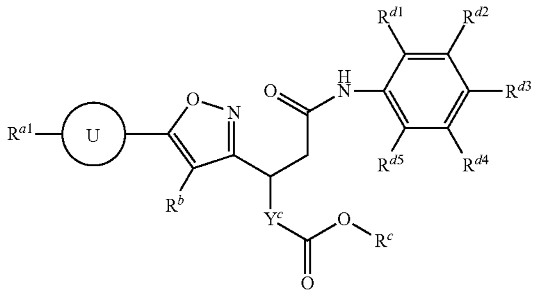

wherein $R^{a1}$ is $C_{1-6}$ alkyl group, or a pharmaceutically acceptable salt thereof.

3. The compound according to claim 1, which is selected from the group consisting of the following formulas or a pharmaceutically acceptable salt thereof:

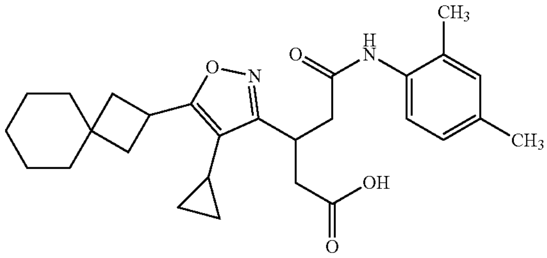

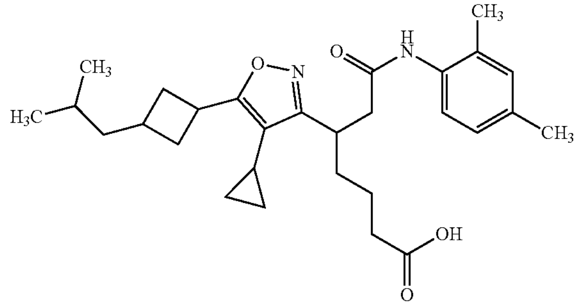

-continued
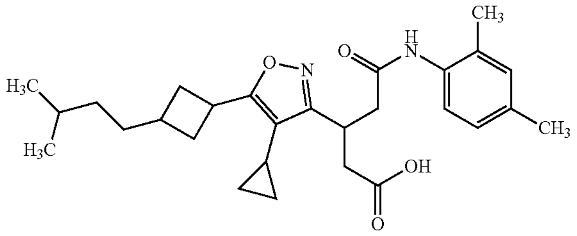
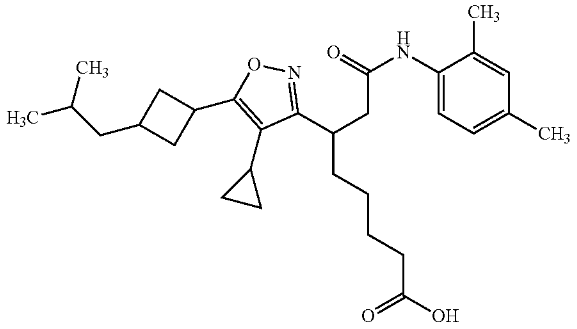
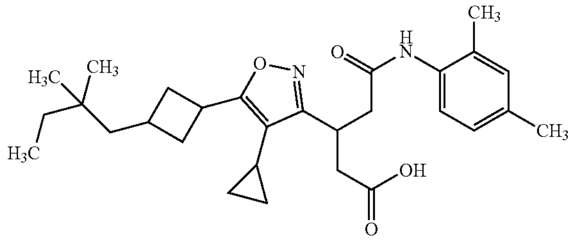
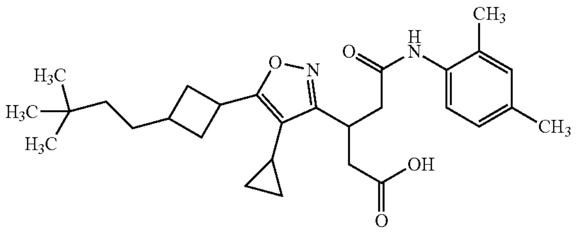
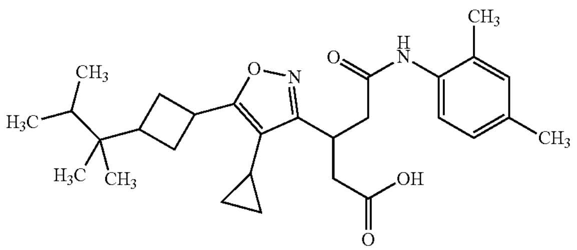
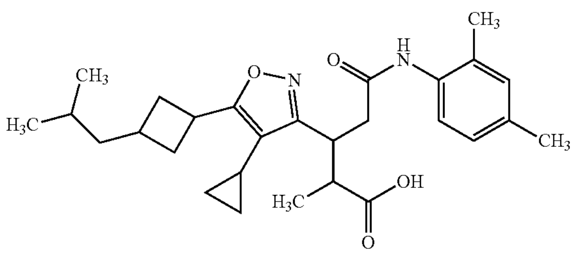
-continued
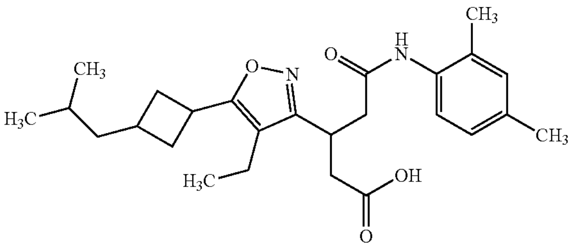
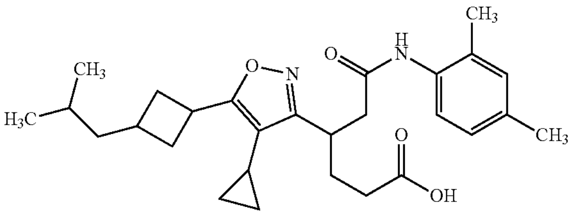
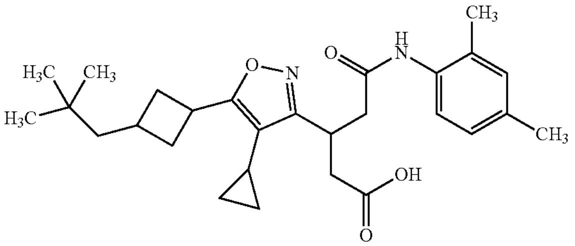
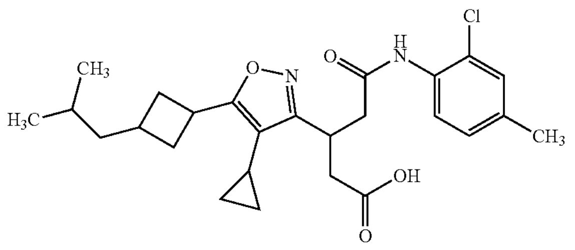
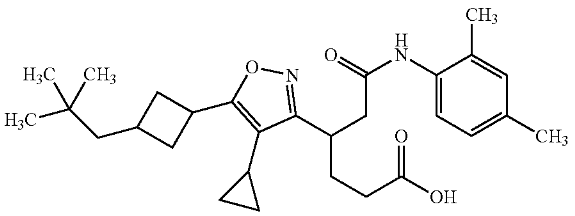
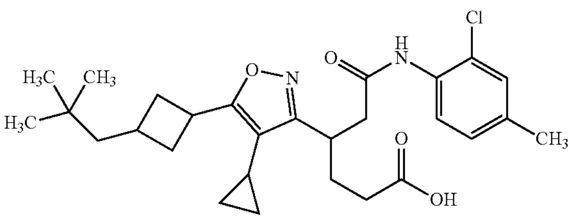
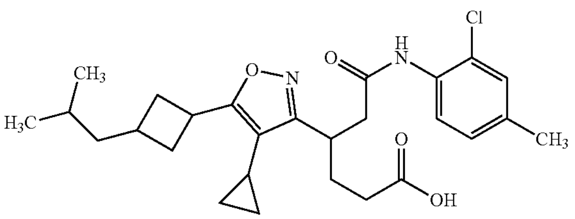

-continued
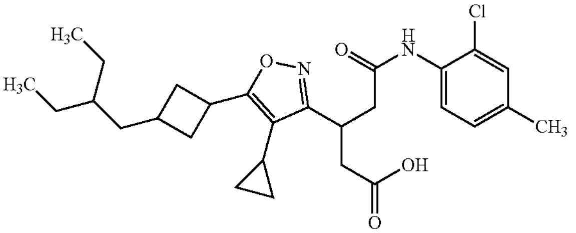
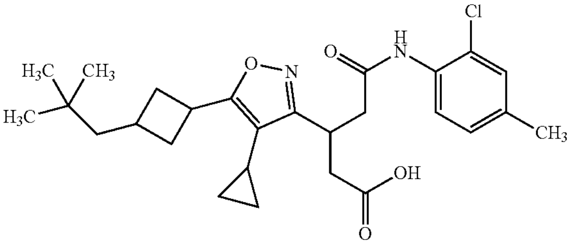
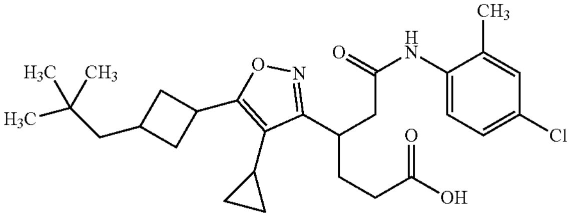
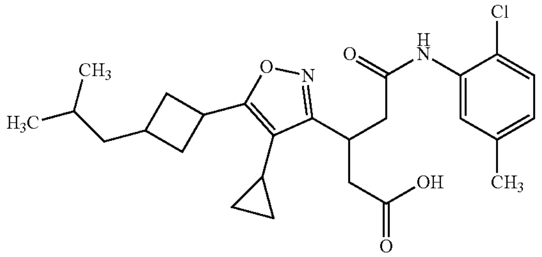
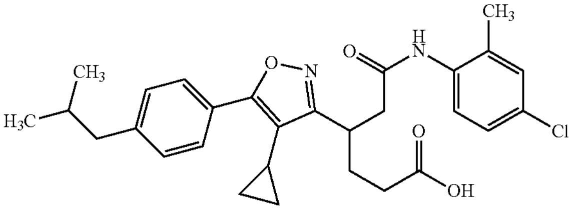
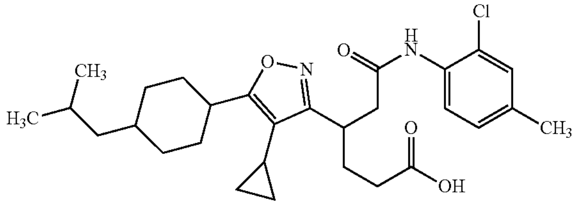
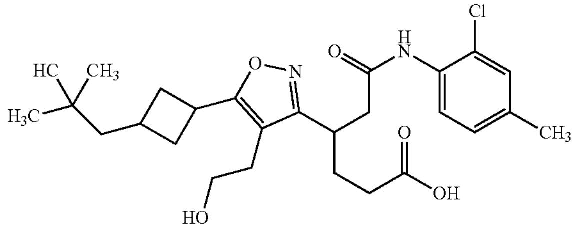
-continued
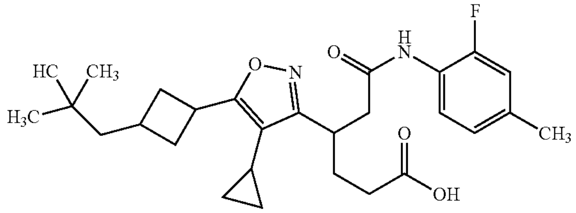
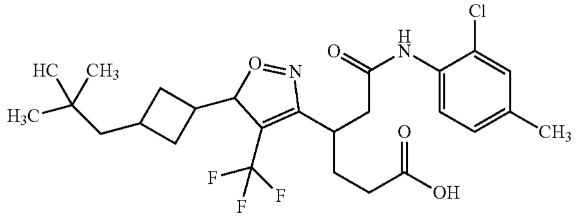
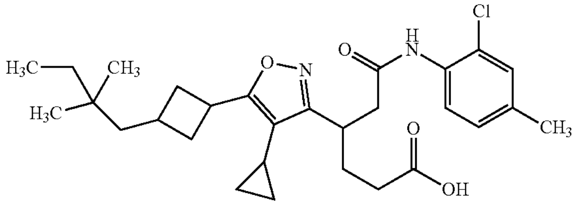
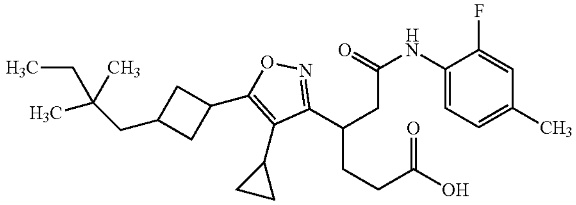
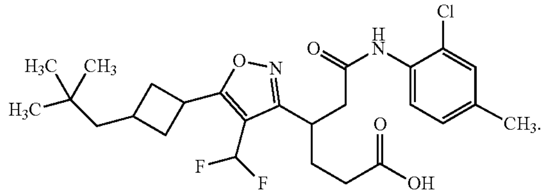 [SMILES: Cc1ccc(NC(=O)CC(CCC(=O)O)c2noc(C3CC(CC(C)(C)C)C3)c2C(F)F)c(Cl)c1]
4. The compound according to claim 1, which is
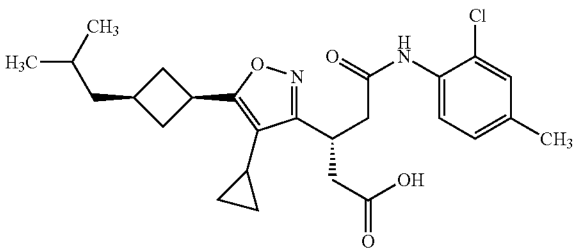 [SMILES: Cc1ccc(NC(=O)C[C@H](CC(=O)O)c2noc([C@H]3C[C@@H](CC(C)C)C3)c2C2CC2)c(Cl)c1]
or a pharmaceutically acceptable salt thereof.

5. The compound according to claim 1, which is

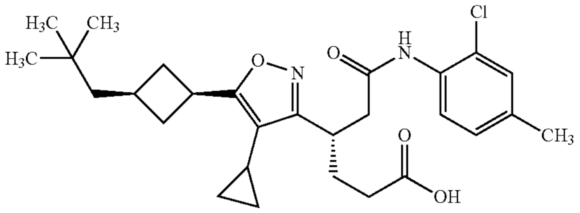 [SMILES: Cc1ccc(NC(=O)C[C@H](CCC(=O)O)c2noc([C@H]3C[C@@H](CC(C)(C)C)C3)c2C2CC2)c(Cl)c1]

or a pharmaceutically acceptable salt thereof.

6. The compound according to claim 1, which is

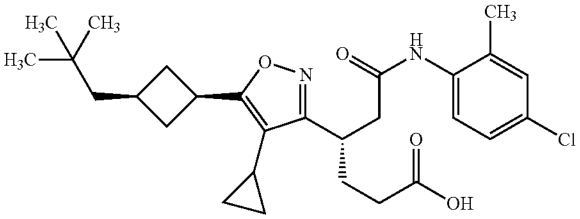 [SMILES: Cc1cc(Cl)ccc1NC(=O)C[C@H](CCC(=O)O)c1noc([C@H]2C[C@@H](CC(C)(C)C)C2)c1C1CC1]

or a pharmaceutically acceptable salt thereof.

7. The compound according to claim 1, which is

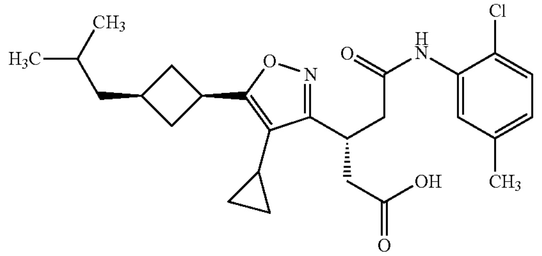 [SMILES: Cc1ccc(Cl)c(NC(=O)C[C@H](CC(=O)O)c2noc([C@H]3C[C@@H](CC(C)C)C3)c2C2CC2)c1]

or a pharmaceutically acceptable salt thereof.

8. The compound according to claim 1, which is

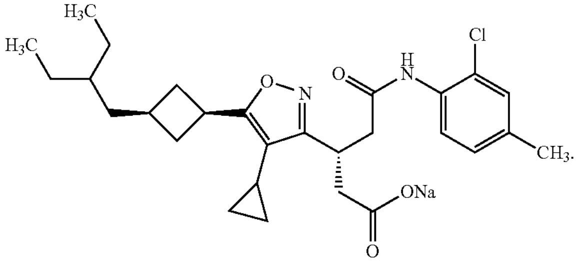

9. The compound according to claim 1, which is

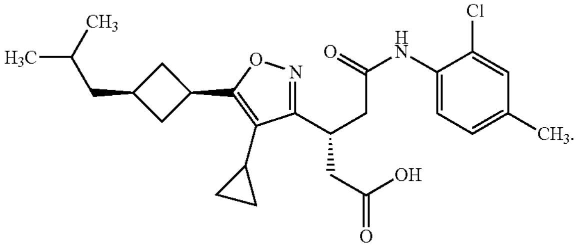 [SMILES: Cc1ccc(NC(=O)C[C@H](CC(=O)O)c2noc([C@H]3C[C@@H](CC(C)C)C3)c2C2CC2)c(Cl)c1]

10. The compound according to claim 1, which is

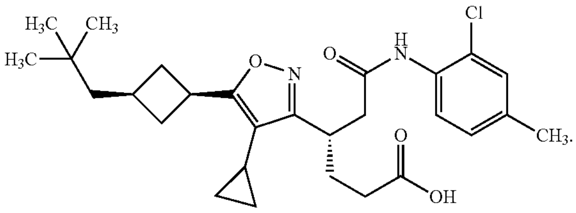 [SMILES: Cc1ccc(NC(=O)C[C@H](CCC(=O)O)c2noc([C@H]3C[C@@H](CC(C)(C)C)C3)c2C2CC2)c(Cl)c1]

11. The compound according to claim 1, which is

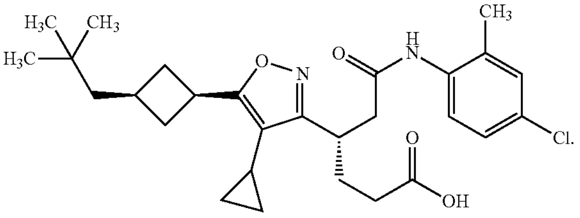 [SMILES: Cc1cc(Cl)ccc1NC(=O)C[C@H](CCC(=O)O)c1noc([C@H]2C[C@@H](CC(C)(C)C)C2)c1C1CC1]

12. The compound according to claim 1, which is

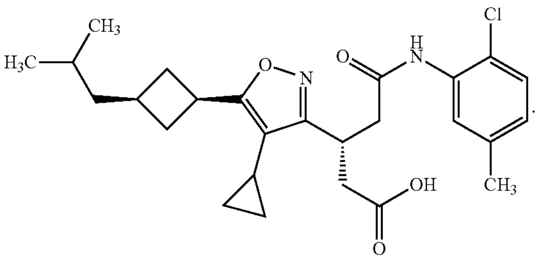 [SMILES: Cc1ccc(Cl)c(NC(=O)C[C@H](CC(=O)O)c2noc([C@H]3C[C@@H](CC(C)C)C3)c2C2CC2)c1]

13. The compound according to claim 2, wherein the compound is of formula [IV-D1]:

[IV-D1]

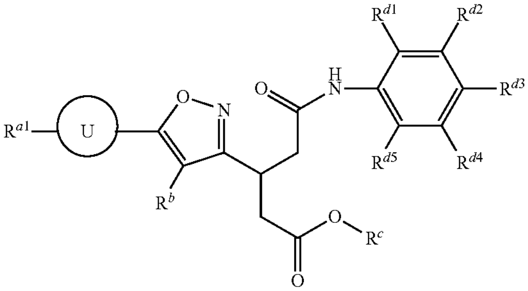

or a pharmaceutically acceptable salt thereof.

14. The compound according to claim 2, wherein the compound is of formula [IV-D2]:

[IV-D2]

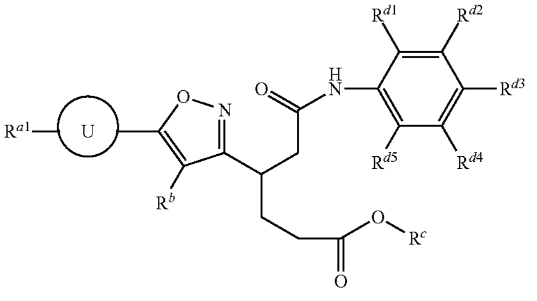

or a pharmaceutically acceptable salt thereof.

15. The compound according to claim 2, wherein the compound is of formula [IV-D3]:

[IV-D3]

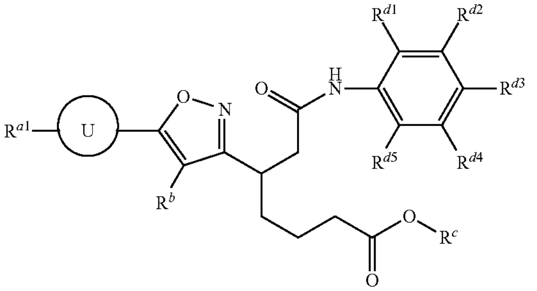

or a pharmaceutically acceptable salt thereof.

16. The compound according to claim 2, wherein the compound is of formula [IV-D4]:

[IV-D4]

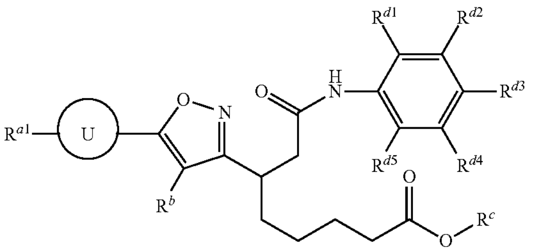

or a pharmaceutically acceptable salt thereof.

17. The compound according to any one of claims 1, 2, and 13-16, wherein:

$R^b$ is $C_{3-7}$ cycloalkyl group which may be substituted with the same or different 1 to 5 substituents selected from Group A, or a pharmaceutically acceptable salt thereof.

18. The compound according to any one of claims 1, 2, and 13-16, wherein:

$R^b$ is cyclopropyl group, or a pharmaceutically acceptable salt thereof.

19. The compound according to any one of claims 1, 2, and 13-16, wherein:

the cyclic moiety U is $C_{3-7}$ cycloalkyl group which may be substituted with the same or different 1 to 5 substituents selected from Group A, or a pharmaceutically acceptable salt thereof.

20. The compound according to any one of claims 1, 2, and 13-16, wherein:

the cyclic moiety U is cyclobutyl group which may be substituted with the same or different 1 to 5 substituents selected from Group A, or a pharmaceutically acceptable salt thereof.

21. A pharmaceutical composition comprising (a) the compound according to any one of claims 1 and 4-7 or a pharmaceutically acceptable salt thereof and (b) a pharmaceutically acceptable carrier.

22. A pharmaceutical composition comprising (a) the compound according to any one of claims 8-12 and (b) a pharmaceutically acceptable carrier.

23. A method of inhibiting RORγ in a mammal, comprising administering to said mammal a therapeutically effective amount of the compound according to any one of claims 1 and 4-7 or a pharmaceutically acceptable salt thereof, thereby inhibiting RORγ in said mammal.

24. A method of treating an allergic disease, dry eye, or fibrosis in a mammal, comprising administering to said mammal a therapeutically effective amount of the compound according to any one of claims 1 and 4-7 or a pharmaceutically acceptable salt thereof, thereby treating the allergic disease, dry eye, or fibrosis in said mammal.

25. A method of treating rheumatoid arthritis, psoriasis, inflammatory bowel disease, multiple sclerosis, systemic lupus erythematosus, ankylosing spondylitis, uveitis, polymyalgia rheumatica, or type I diabetes in a mammal, comprising administering to said mammal a therapeutically effective amount of the compound according to any one of claims 1 and 4-7 or a pharmaceutically acceptable salt thereof, thereby treating the rheumatoid arthritis, psoriasis, inflammatory bowel disease, multiple sclerosis, systemic lupus erythematosus, ankylosing spondylitis, uveitis, polymyalgia rheumatica, or type I diabetes in said mammal.

26. The method according to claim 25, wherein the autoimmune disease is selected from the group consisting of rheumatoid arthritis, psoriasis, inflammatory bowel disease, multiple sclerosis, systemic lupus erythematosus, ankylosing spondylitis, uveitis, polymyalgia rheumatica, and type I diabetes.

27. The method according to claim 25, wherein the inflammatory bowel disease is Crohn's disease or ulcerative colitis.

28. A method of treating an allergic disease in a mammal, comprising administering to said mammal a therapeutically effective amount of the compound according to any one of claims 1 and 4-7 or a pharmaceutically acceptable salt thereof, thereby treating the allergic disease in said mammal.

29. The method according to claim 28, wherein the allergic disease is asthma.

30. A method of treating dry eye in a mammal, comprising administering to said mammal a therapeutically effective amount of the compound according to any one of claims 1 and 4-7 or a pharmaceutically acceptable salt thereof, thereby treating dry eye in said mammal.

31. A method of treating fibrosis in a mammal, comprising administering to said mammal a therapeutically effective amount of the compound according to any one of claims 1 and 4-7 or a pharmaceutically acceptable salt thereof, thereby treating fibrosis in said mammal.

32. The method according to claim 31, wherein the fibrosis is pulmonary fibrosis or primary biliary cirrhosis.

33. A method of treating diabetes in a mammal, comprising administering to said mammal a therapeutically effective amount of the compound according to any one of claims 1 and 4-7 or a pharmaceutically acceptable salt thereof, thereby treating diabetes in said mammal.

34. The method according to claim 33, wherein the metabolic disease is diabetes.

35. The method according to claim 33, wherein the diabetes is type I diabetes.

36. The method according to claim 33, wherein the diabetes is type II diabetes.

37. A method of inhibiting RORγ in a mammal, comprising administering to said mammal a therapeutically effective amount of the compound according to any one of claims 8-12, thereby inhibiting RORγ in said mammal.

38. A method of treating an allergic disease, dry eye, or fibrosis in a mammal, comprising administering to said mammal a therapeutically effective amount of the compound according to any one of claims 8-12, thereby treating the allergic disease, dry eye, or fibrosis in said mammal.

39. A method of treating rheumatoid arthritis, psoriasis, inflammatory bowel disease, multiple sclerosis, systemic lupus erythematosus, ankylosing spondylitis, uveitis, polymyalgia rheumatica, or type I diabetes in a mammal, comprising administering to said mammal a therapeutically effective amount of the compound according to any one of claims 8-12, thereby treating the rheumatoid arthritis, psoriasis, inflammatory bowel disease, multiple sclerosis, systemic lupus erythematosus, ankylosing spondylitis, uveitis, polymyalgia rheumatica, or type I diabetes in said mammal.

40. The method according to claim 39, wherein the autoimmune disease is selected from the group consisting of rheumatoid arthritis, psoriasis, inflammatory bowel disease, multiple sclerosis, systemic lupus erythematosus, ankylosing spondylitis, uveitis, polymyalgia rheumatica, and type I diabetes.

41. The method according to claim 39, wherein the inflammatory bowel disease is Crohn's disease or ulcerative colitis.

42. A method of treating an allergic disease in a mammal, comprising administering to said mammal a therapeutically effective amount of the compound according to any one of claims 8-12, thereby treating the allergic disease in said mammal.

43. The method according to claim 42, wherein the allergic disease is asthma.

44. A method of treating dry eye in a mammal, comprising administering to said mammal a therapeutically effective amount of the compound according to any one of claims 8-12, thereby treating dry eye in said mammal.

45. A method of treating fibrosis in a mammal, comprising administering to said mammal a therapeutically effective amount of the compound according to any one of claims 8-12, thereby treating fibrosis in said mammal.

46. The method according to claim 45, wherein the fibrosis is pulmonary fibrosis or primary biliary cirrhosis.

47. A method of treating diabetes in a mammal, comprising administering to said mammal a therapeutically effective amount of the compound according to any one of claims 8-12, thereby treating diabetes in said mammal.

48. The method according to claim 47, wherein the metabolic disease is diabetes.

49. The method according to claim 47, wherein the diabetes is type I diabetes.

50. The method according to claim 47, wherein the diabetes is type II diabetes.

* * * * *

UNITED STATES PATENT AND TRADEMARK OFFICE

CERTIFICATE OF CORRECTION

PATENT NO. : 8,604,069 B2
APPLICATION NO. : 13/457844
DATED : December 10, 2013
INVENTOR(S) : Maeba et al.

It is certified that error appears in the above-identified patent and that said Letters Patent is hereby corrected as shown below:

On the Title Page, below Abstract “50 Claims, 48 Drawing Sheets” is corrected to read -- 46 Claims, 48 Drawing Sheets --.

IN THE CLAIMS

Column 227, line 25, claim 1, “(2)” should be aligned to the left side.

Column 232, line 47, claim 3, the “.” should be on the right side and below the figure.

Column 233, line 49, claim 8, the “.” should be on the right side and below the figure.

Column 233, line 62, claim 9, the “.” should be on the right side and below the figure.

Column 234, line 9, claim 10, the “.” should be on the right side and below the figure.

Column 234, line 25, claim 11, the “.” should be on the right side and below the figure.

Column 234, line 40, claim 12, the “.” should be on the right side and below the figure.

Column 236, lines 43-48, delete claim 26.

Column 237, lines 8-9, delete claim 34.

Column 237, line 33 – column 238, line 4, delete claim 40.

Column 238, lines 28-29, delete claim 48.

Signed and Sealed this
Second Day of September, 2014

Michelle K. Lee
*Deputy Director of the United States Patent and Trademark Office*